(12) United States Patent
Aljuri et al.

(10) Patent No.: US 11,213,313 B2
(45) Date of Patent: Jan. 4, 2022

(54) TISSUE RESECTION AND TREATMENT WITH SHEDDING PULSES

(71) Applicant: PROCEPT BIOROBOTICS CORPORATION, Redwood City, CA (US)

(72) Inventors: Nikolai Aljuri, Hillsborough, CA (US); Surag Mantri, Sunnyvale, CA (US); Luis Baez, Mountain View, CA (US); George Surjan, Redwood City, CA (US); Michael W. Sasnett, Los Altos, CA (US); Jonathan Foote, San Francisco, CA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 988 days.

(21) Appl. No.: 15/825,040

(22) Filed: Nov. 28, 2017

(65) Prior Publication Data
US 2018/0263647 A1    Sep. 20, 2018

Related U.S. Application Data

(63) Continuation of application No. 14/708,910, filed on May 11, 2015, now Pat. No. 9,848,904, which is a
(Continued)

(51) Int. Cl.
*A61B 17/3203* (2006.01)
*A61B 18/14* (2006.01)
(Continued)

(52) U.S. Cl.
CPC .......... *A61B 17/3203* (2013.01); *A61B 8/12* (2013.01); *A61B 18/12* (2013.01); *A61B 18/148* (2013.01);
(Continued)

(58) Field of Classification Search
CPC ...... A61B 17/3203; A61B 2017/32032; A61B 2018/00404–00422
See application file for complete search history.

(56) References Cited

U.S. PATENT DOCUMENTS 3,818,913 A    6/1974 Wallach
3,821,510 A    6/1974 Muncheryan
(Continued)

FOREIGN PATENT DOCUMENTS

CN    101460101 A    6/2009
CN    102271595 A    12/2011
(Continued)

OTHER PUBLICATIONS

Notice of Allowance dated Sep. 13, 2017 for U.S. Appl. No. 14/708,910.
(Continued)

*Primary Examiner* — Jaymi E Della
(74) *Attorney, Agent, or Firm* — Fisherbroyles LLP; John Shimmick

(57) ABSTRACT

A fluid stream is directed toward tissue to generate a plurality of shedding clouds. The fluid stream can be scanned such that the plurality of shedding clouds arrive a different overlapping locations. Each of the plurality of shedding clouds can remove a portion of the tissue. In many embodiments, an apparatus to ablate tissue comprises a source of pressurized fluid, and a nozzle coupled to the source of pressurized fluid to release a fluid stream, in which the fluid stream generates a plurality of shedding clouds.

16 Claims, 92 Drawing Sheets

Related U.S. Application Data continuation of application No. PCT/US2014/054412, filed on Sep. 5, 2014.

(60) Provisional application No. 62/019,305, filed on Jun. 30, 2014, provisional application No. 61/972,730, filed on Mar. 31, 2014, provisional application No. 61/874,849, filed on Sep. 6, 2013.

(51) Int. Cl.
*A61B 8/12* (2006.01)
*A61B 34/10* (2016.01)
*A61B 18/12* (2006.01)
*A61B 18/00* (2006.01)
*A61B 18/24* (2006.01)
*A61B 17/00* (2006.01)
*A61B 90/00* (2016.01)
*A61B 34/00* (2016.01)
*A61B 17/34* (2006.01)
*A61B 18/22* (2006.01)

(52) U.S. Cl.
CPC ...... *A61B 18/1482* (2013.01); *A61B 18/1485* (2013.01); *A61B 34/10* (2016.02); *A61B 18/24* (2013.01); *A61B 90/36* (2016.02); *A61B 2017/00274* (2013.01); *A61B 2017/32032* (2013.01); *A61B 2017/3486* (2013.01); *A61B 2018/00166* (2013.01); *A61B 2018/00285* (2013.01); *A61B 2018/00517* (2013.01); *A61B 2018/00547* (2013.01); *A61B 2018/00577* (2013.01); *A61B 2018/00589* (2013.01); *A61B 2018/00636* (2013.01); *A61B 2018/00916* (2013.01); *A61B 2018/00982* (2013.01); *A61B 2018/00994* (2013.01); *A61B 2018/141* (2013.01); *A61B 2018/1405* (2013.01); *A61B 2018/1472* (2013.01); *A61B 2018/2272* (2013.01); *A61B 2018/2288* (2013.01); *A61B 2034/254* (2016.02); *A61B 2090/378* (2016.02); *A61B 2217/005* (2013.01); *A61B 2217/007* (2013.01); *A61B 2218/001* (2013.01); *A61B 2218/002* (2013.01); *A61B 2218/007* (2013.01)

(56) References Cited

U.S. PATENT DOCUMENTS

| | | |
|---|---|---|
| 3,847,988 A | 11/1974 | Gold |
| 3,875,229 A | 4/1975 | Gold |
| 3,930,505 A * | 1/1976 | Wallach ............ A61F 9/00736 604/22 |
| 4,097,578 A | 6/1978 | Perronnet |
| 4,220,735 A | 9/1980 | Dieck |
| 4,239,776 A | 12/1980 | Bayles |
| 4,377,584 A | 3/1983 | Rasmusson |
| 4,386,080 A | 5/1983 | Crossley |
| 4,461,283 A | 7/1984 | Doi |
| 4,474,251 A * | 10/1984 | Johnson, Jr. ............ B05B 17/06 175/67 |
| 4,560,373 A | 12/1985 | Sugino |
| 4,636,505 A | 1/1987 | Tucker |
| 4,672,963 A | 6/1987 | Barken |
| 4,760,071 A | 7/1988 | Rasmusson |
| 4,776,349 A | 10/1988 | Nashef |
| 4,913,698 A | 4/1990 | Ito |
| 5,037,431 A | 8/1991 | Summers |
| 5,116,615 A | 5/1992 | Gokcen |
| 5,135,482 A * | 8/1992 | Neracher ......... A61B 17/32037 604/22 |
| 5,207,672 A | 5/1993 | Roth |
| 5,257,991 A | 11/1993 | Fletcher |
| 5,267,341 A | 11/1993 | Shearin |
| 5,269,785 A | 12/1993 | Bonutti |
| 5,322,503 A | 6/1994 | Desai |
| 5,322,504 A | 6/1994 | Doherty |
| 5,454,782 A | 10/1995 | Perkins |
| 5,496,267 A | 3/1996 | Drasler |
| 5,505,729 A | 4/1996 | Rau |
| 5,514,669 A | 5/1996 | Selman |
| 5,527,330 A | 6/1996 | Tovey |
| 5,558,634 A | 9/1996 | Mitchell |
| 5,562,703 A | 10/1996 | Desai |
| 5,582,190 A * | 12/1996 | Slavin ............... A61B 1/015 128/898 |
| 5,620,414 A | 4/1997 | Campbell, Jr. |
| 5,630,794 A | 5/1997 | Lax |
| 5,649,923 A | 7/1997 | Gregory |
| 5,672,153 A | 9/1997 | Lax |
| 5,672,171 A | 9/1997 | Andrus |
| 5,753,641 A | 5/1998 | Gormley |
| 5,770,603 A | 6/1998 | Gibson |
| 5,772,657 A | 6/1998 | Hmelar |
| 5,773,791 A | 6/1998 | Kuykendal |
| 5,782,848 A | 7/1998 | Lennox |
| 5,785,521 A | 7/1998 | Rizoiu |
| 5,817,649 A | 10/1998 | Labrie |
| 5,833,701 A | 11/1998 | Gordon |
| 5,836,941 A | 11/1998 | Yoshihara |
| 5,861,002 A | 1/1999 | Desai |
| 5,871,462 A * | 2/1999 | Yoder ............... A61B 17/1644 604/22 |
| 5,872,150 A | 2/1999 | Elbrecht |
| 5,902,499 A | 5/1999 | Richerzhagen |
| 5,994,362 A | 11/1999 | Gormley |
| 6,022,860 A | 2/2000 | Engel |
| 6,066,130 A | 5/2000 | Gregory |
| 6,071,284 A | 6/2000 | Fox |
| 6,117,128 A | 9/2000 | Gregory |
| 6,142,991 A | 11/2000 | Schatzberger |
| 6,179,831 B1 | 1/2001 | Bliweis |
| 6,200,573 B1 | 3/2001 | Locke |
| 6,217,543 B1 | 4/2001 | Anis |
| 6,217,860 B1 | 4/2001 | Woo |
| 6,228,046 B1 | 5/2001 | Brisken |
| 6,231,591 B1 | 5/2001 | Desai |
| 6,254,597 B1 | 7/2001 | Rizoiu |
| 6,296,639 B1 | 10/2001 | Truckai |
| 6,375,635 B1 | 4/2002 | Moutafis |
| 6,378,525 B1 | 4/2002 | Beyar |
| 6,413,256 B1 | 7/2002 | Truckai |
| 6,425,877 B1 | 7/2002 | Edwards |
| 6,440,105 B1 | 8/2002 | Menne |
| 6,451,017 B1 | 9/2002 | Moutafis |
| 6,565,555 B1 | 5/2003 | Ryan |
| 6,572,578 B1 | 6/2003 | Blanchard |
| 6,607,524 B1 | 8/2003 | Labudde |
| 6,720,745 B2 | 4/2004 | Lys |
| 6,814,731 B2 | 11/2004 | Swanson |
| 6,821,275 B2 | 11/2004 | Truckai |
| 6,890,332 B2 | 5/2005 | Truckai |
| 6,953,461 B2 | 10/2005 | McClurken |
| 6,960,182 B2 | 11/2005 | Moutafis |
| 6,986,764 B2 | 1/2006 | Davenport |
| 7,008,421 B2 | 3/2006 | Daniel |
| 7,015,253 B2 | 3/2006 | Escandon |
| 7,115,100 B2 | 10/2006 | McRury |
| 7,122,017 B2 | 10/2006 | Moutafis |
| 7,163,875 B2 | 1/2007 | Richerzhagen |
| 7,326,054 B2 | 2/2008 | Todd |
| 7,882,841 B2 | 2/2011 | Perkins et al. |
| 8,092,507 B2 | 1/2012 | Tomasello et al. |
| 8,419,723 B2 | 4/2013 | Shadduck |
| 8,795,194 B2 | 8/2014 | Howard |
| 8,814,921 B2 | 8/2014 | Aljuri et al. |
| 9,232,959 B2 | 1/2016 | Aljuri |
| 9,232,960 B2 | 1/2016 | Aljuri |
| 9,237,902 B2 | 1/2016 | Aljuri |
| 9,364,250 B2 | 6/2016 | Aljuri |
| 9,364,251 B2 | 6/2016 | Aljuri et al. |
| 9,510,853 B2 | 12/2016 | Aljuri et al. |

(56) References Cited

U.S. PATENT DOCUMENTS

| | | |
|---|---|---|
| 9,848,904 B2 | 12/2017 | Aljuri et al. |
| 9,867,635 B2 | 1/2018 | Alvarez |
| 9,931,445 B2 | 4/2018 | Pustilnik |
| 10,448,966 B2 | 10/2019 | Aljuri |
| 2001/0002562 A1 | 6/2001 | Moutafis et al. |
| 2001/0048942 A1 | 12/2001 | Weisman |
| 2002/0010502 A1 | 1/2002 | Trachtenberg |
| 2002/0022869 A1 | 2/2002 | Hareyama et al. |
| 2002/0040220 A1 | 4/2002 | Zvuloni |
| 2002/0045911 A1 | 4/2002 | Fletcher |
| 2002/0111617 A1 | 8/2002 | Cosman |
| 2002/0128637 A1 | 9/2002 | von der Heide |
| 2003/0036768 A1 | 2/2003 | Hutchins et al. |
| 2003/0060819 A1 | 3/2003 | McGovern |
| 2003/0065321 A1 | 4/2003 | Carmel |
| 2003/0073902 A1 | 4/2003 | Hauschild |
| 2003/0135205 A1 | 7/2003 | Davenport |
| 2003/0139041 A1 | 7/2003 | Leclair |
| 2003/0161816 A1 | 8/2003 | Fraser |
| 2003/0216722 A1 | 11/2003 | Swanson |
| 2004/0097829 A1 | 5/2004 | McRury |
| 2004/0133254 A1 | 7/2004 | Sterzer |
| 2004/0143269 A1 | 7/2004 | Pude |
| 2005/0004516 A1 | 1/2005 | Vanney |
| 2005/0256517 A1 | 11/2005 | Boutoussov |
| 2006/0030787 A1 | 2/2006 | Quay |
| 2006/0089626 A1 | 4/2006 | Vlegele et al. |
| 2006/0149193 A1 | 7/2006 | Hall |
| 2007/0230757 A1 | 10/2007 | Trachtenberg et al. |
| 2007/0239153 A1 | 10/2007 | Hodorek et al. |
| 2008/0178654 A1 | 7/2008 | Hochmitz |
| 2008/0253527 A1 | 10/2008 | Boyden |
| 2009/0018533 A1 | 1/2009 | Perkins et al. |
| 2009/0088775 A1 | 4/2009 | Swarup et al. |
| 2009/0227998 A1 | 9/2009 | Aljuri et al. |
| 2010/0076269 A1 | 3/2010 | Makower et al. |
| 2010/0145254 A1 | 6/2010 | Shadduck et al. |
| 2010/0179522 A1 | 7/2010 | Companion et al. |
| 2010/0179528 A1 | 7/2010 | Shadduck |
| 2011/0104800 A1 | 5/2011 | Kensy |
| 2011/0184291 A1 | 7/2011 | Okamura et al. |
| 2011/0184391 A1 | 7/2011 | Aljuri et al. |
| 2012/0065656 A1 | 3/2012 | Karwei |
| 2012/0157841 A1 | 6/2012 | Glaenzer et al. |
| 2013/0158534 A1 | 6/2013 | Hoey |
| 2013/0165944 A1 | 6/2013 | Gal et al. |
| 2013/0253484 A1 | 9/2013 | Aljuri |
| 2013/0253488 A1 | 9/2013 | Aljuri et al. |
| 2013/0261540 A1 | 10/2013 | Crank |
| 2013/0267889 A1 | 10/2013 | Aljuri et al. |
| 2014/0058361 A1 | 2/2014 | Gordon |
| 2014/0193833 A1 | 7/2014 | Srivastava |
| 2014/0309649 A1 | 10/2014 | Alvarez |
| 2015/0025539 A1 | 1/2015 | Alvarez |
| 2015/0045777 A1 | 2/2015 | Aljuri et al. |
| 2015/0057646 A1 | 2/2015 | Aljuri et al. |
| 2015/0088107 A1 | 3/2015 | Aljuri et al. |
| 2015/0088110 A1 | 3/2015 | Aljuri et al. |
| 2015/0313666 A1 | 11/2015 | Aljuri |
| 2015/0335344 A1 | 11/2015 | Aljuri |
| 2016/0074059 A1 | 3/2016 | Aljuri |
| 2016/0228141 A1 | 8/2016 | Aijuri |
| 2017/0172548 A1 | 6/2017 | Aljuri |
| 2017/0172668 A1 | 6/2017 | Aljuri |
| 2017/0231655 A1 | 8/2017 | Aljuri |
| 2019/0105023 A1 | 4/2019 | Aljuri |

FOREIGN PATENT DOCUMENTS

| | | |
|---|---|---|
| CN | 102271602 | 12/2011 |
| CN | 103118611 | 5/2013 |
| CN | 103764056 | 4/2014 |
| EP | 1075853 A2 | 2/2001 |
| EP | 3188667 A1 | 7/2017 |
| JP | 2001046528 A | 2/2001 |
| JP | 2004170414 A | 6/2004 |
| JP | 2007020837 A | 2/2007 |
| JP | 2010532178 A | 10/2010 |
| JP | 2012508068 A | 4/2012 |
| JP | 2012523253 A | 10/2012 |
| JP | 2013518684 A | 5/2013 |
| WO | WO-03088833 A1 | 10/2003 |
| WO | 2004028592 A1 | 4/2004 |
| WO | WO-2004080529 A2 | 9/2004 |
| WO | 2006089426 A1 | 8/2006 |
| WO | WO-2007101015 A1 | 9/2007 |
| WO | WO-2007114917 A2 | 10/2007 |
| WO | 2008083407 | 7/2008 |
| WO | WO-2008083407 A1 | 7/2008 |
| WO | 2009029461 A1 | 3/2009 |
| WO | 2009111736 | 9/2009 |
| WO | WO-2009111736 A1 | 9/2009 |
| WO | WO-2009152613 A1 | 12/2009 |
| WO | WO-2010054220 A1 | 5/2010 |
| WO | WO-2010144419 A2 | 12/2010 |
| WO | 2011097505 | 8/2011 |
| WO | WO-2011097505 A1 | 8/2011 |
| WO | WO-2011100753 A2 | 8/2011 |
| WO | WO-2011141775 A1 | 11/2011 |
| WO | 2013130895 | 9/2013 |
| WO | WO-2013129657 A1 | 9/2013 |
| WO | WO-2013130895 A1 | 9/2013 |
| WO | 2014127242 | 8/2014 |
| WO | 2014165703 | 10/2014 |
| WO | 2015035249 A2 | 3/2015 |
| WO | 2015200538 A1 | 12/2015 |
| WO | 2016004071 A1 | 1/2016 |
| WO | 2016037132 A1 | 3/2016 |

OTHER PUBLICATIONS

Notice of Allowance dated Sep. 20, 2017 for U.S. Appl. No. 14/708,910.

Notice of Allowance dated Oct. 13, 2017 for U.S. Appl. No. 14/708,910.

"Office action dated Jan. 25, 2016 for U.S. Appl. No. 14/708,910."

Office action dated Apr. 27, 2016 for U.S. Appl. No. 14/708,910.

Botto et al., "Electrovaporization of the Prostate with the Gyrus Device," J. Endourol. (Apr. 2001) 15(3):313-316.

Hillegersberg et al., "Water-jet-cooled Nd:YAG laser coagulation: selective destruction of rat liver metastases," Lasers Surg Med. 1991; 11(5)445-454. [Abstract Only].

International search report and written opinion dated Apr. 24, 2009 for PCT/US2009/036390.

International search report and written opinion dated Jul. 11, 2014 for PCT/US2014/016491.

International search report and written opinion dated Jun. 27, 2013 for PCT/US2013/028441.

International search report and written opinion dated Mar. 31, 2011 for PCT/US2011/023781.

International search report and written opinion dated May 20, 2008 for PCT/US2008/050051.

International Search Report dated Jan. 21, 2016 for International Application No. PCT/US2015/048695.

International Search Report dated Oct. 1, 2015 for International Patent Application No. PCT/US2015/038605.

Jian, et al. The Development ofthe Water Jet Scalpel With Air Pressure. Trans. ASME (Jun. 2001) 123(2):246-248.

Prajapati, et al., Pluripotent Stem Cell within the Prostate could be Responsible for Benign Prostate Hyperplasia in Human, J Stem Cell Res Ther2014, 4:1.

Prajapati, et al., Prostate Stem Cells in the Development of Benign Prostate Hyperplasia and Prostate Cancer: Emerging Role and Concepts, Biomed Res Int 2013; 2013:107954.

Richerzhagen et al., "Water Jet Guided Laser Cutting: a Powerful Hybrid Technology for Fine Cutting and Grooving," Proceedings ofthe 2004 Advanced Laser Applications Conference and Exposition, Ann Arbor, Michigan, Sep. 20-22, 2004, ALAC 2004, 2:175-182; retrieved from the Internet <http://www.synova.ch/pdf/ALAC04.pdf>.

(56) References Cited

OTHER PUBLICATIONS

Ruggeri, et al., Activation-independent platelet adhesion and aggregation under elevated shear stress. Blood. Sep. 15, 2006; 108(6):1903-1910.
Sander et al., "The water jet-guided Nd:YAG laser in the treatment of gastroduodenal ulcer with a visible vessel. A randomized controlled and prospective study," Endoscopy. Sep. 1989; 21(5):217-220. [Abstract Only].
Sander et al., "Welter jet guided Nd:YAG laser coagulation—its application in the field of gastroenterology," Endosc Surg Allied Technol. Aug. 1993; 1(4):233-238. [Abstract Only].
Stalder et al., "Repetitive Plasma Discharges in Saline Solutions," Appl. Phys. Lett. (Dec. 2001), 79(27):4503-4505.
Woloszko et al., "Plasma Characteristics of Repetitively-Pulsed Electrical Discharges in Saline Solutions Used for Surgical Procedures," (2002) IEEE Trans. Plasma Sci. 30(3):1376-1383.
"European search report and opinion dated Sep. 11, 2015 for EP Application No. 13754453.2."
European Search Report dated Mar. 15, 2017 for EP Application No. 14841517.7.
"Extended European search report and opinion dated Jan. 25, 2016 for EP Application No. 13754453.2."
International search report and written opinion dated Mar. 10, 2015 for PCT Application No. US2014/054412.
Nishimura, et al. Similarity Law on Shedding Frequency of Cavitation Cloud Induced by a Cavitating Jet. Journal of Fluid Science and Technology, vol. 7, No. 3, 2012, pp. 405-420.
Nishimura, Staoshi, et al. "Similarity Law on Shedding Frequency of Cavitation Cloud Induced by a Cavitating Jet*." Journal of Fluid Science and Technology, 2012, pp. 405-420.
Notice of allowance dated Aug. 8, 2016 for U.S. Appl. No. 14/816,747.
"Office action dated Feb. 3, 2016 for U.S. Appl. No. 14/816,747."
Wright, et al. Cavitation of a submerged jet. Exp Fluids (2013) 54:1541.

* cited by examiner

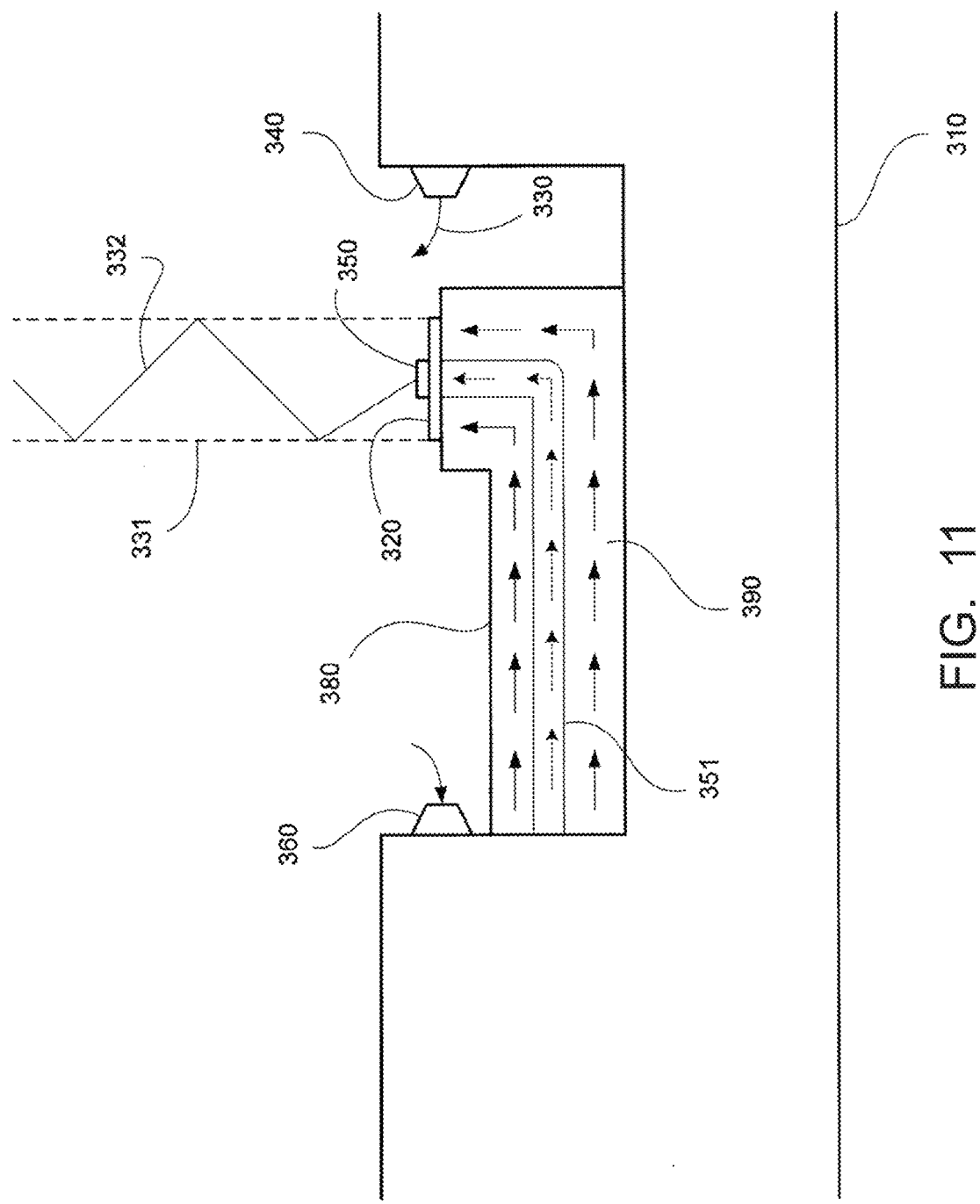

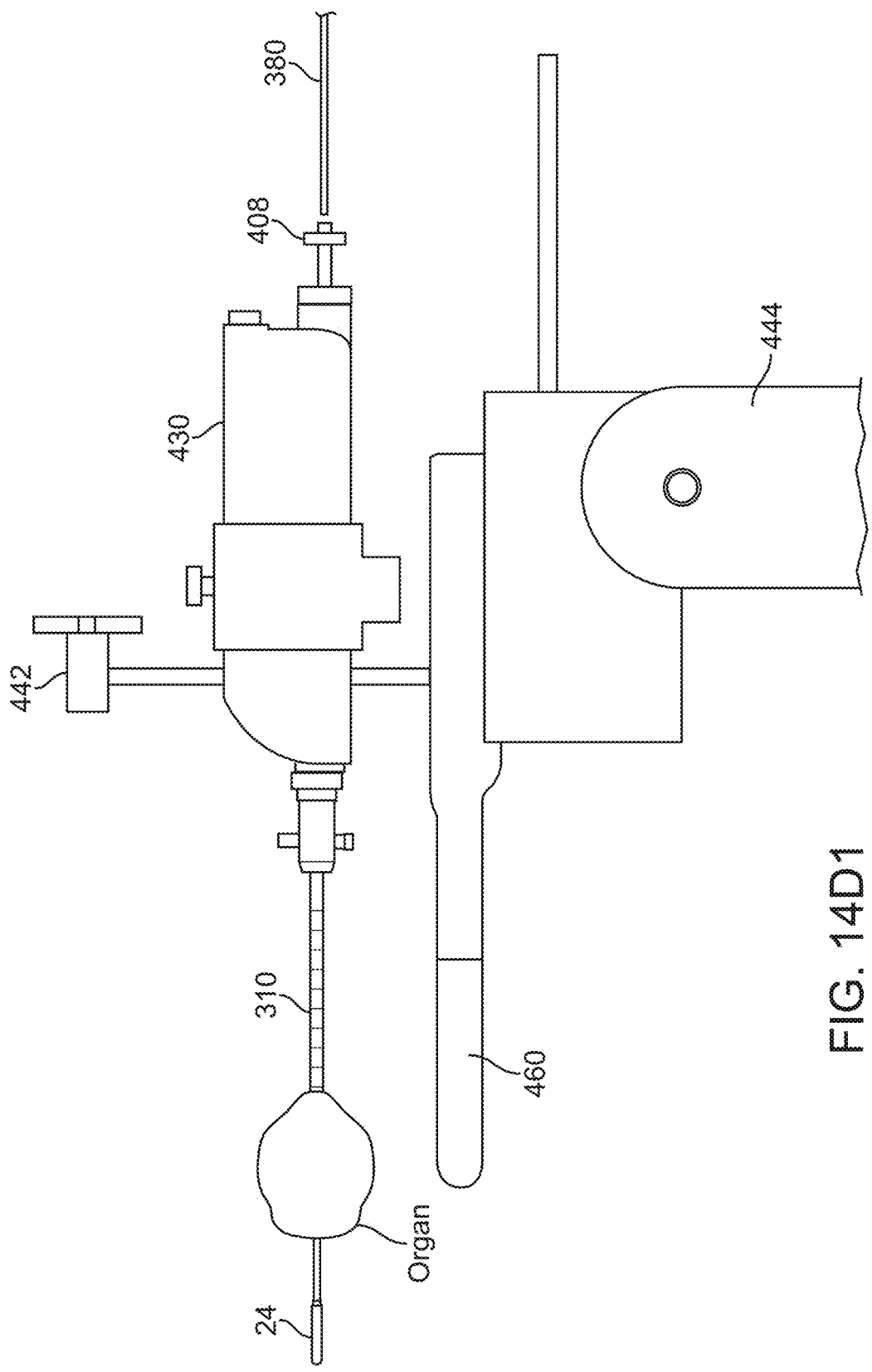
FIG. 14D1

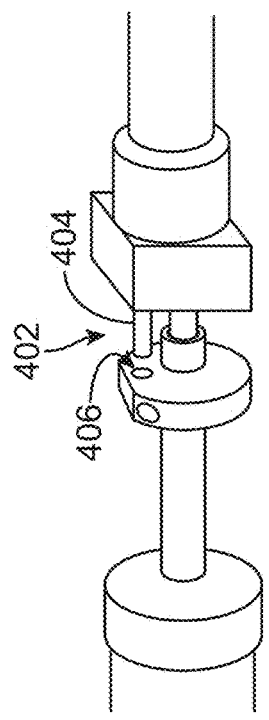
FIG. 14D3
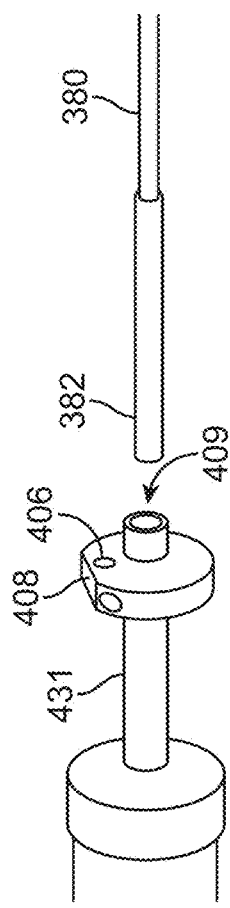
FIG. 14D2
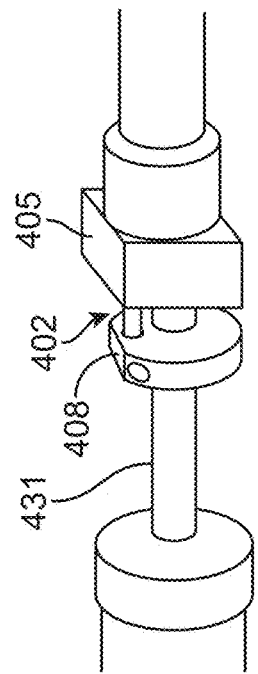
FIG. 14D4

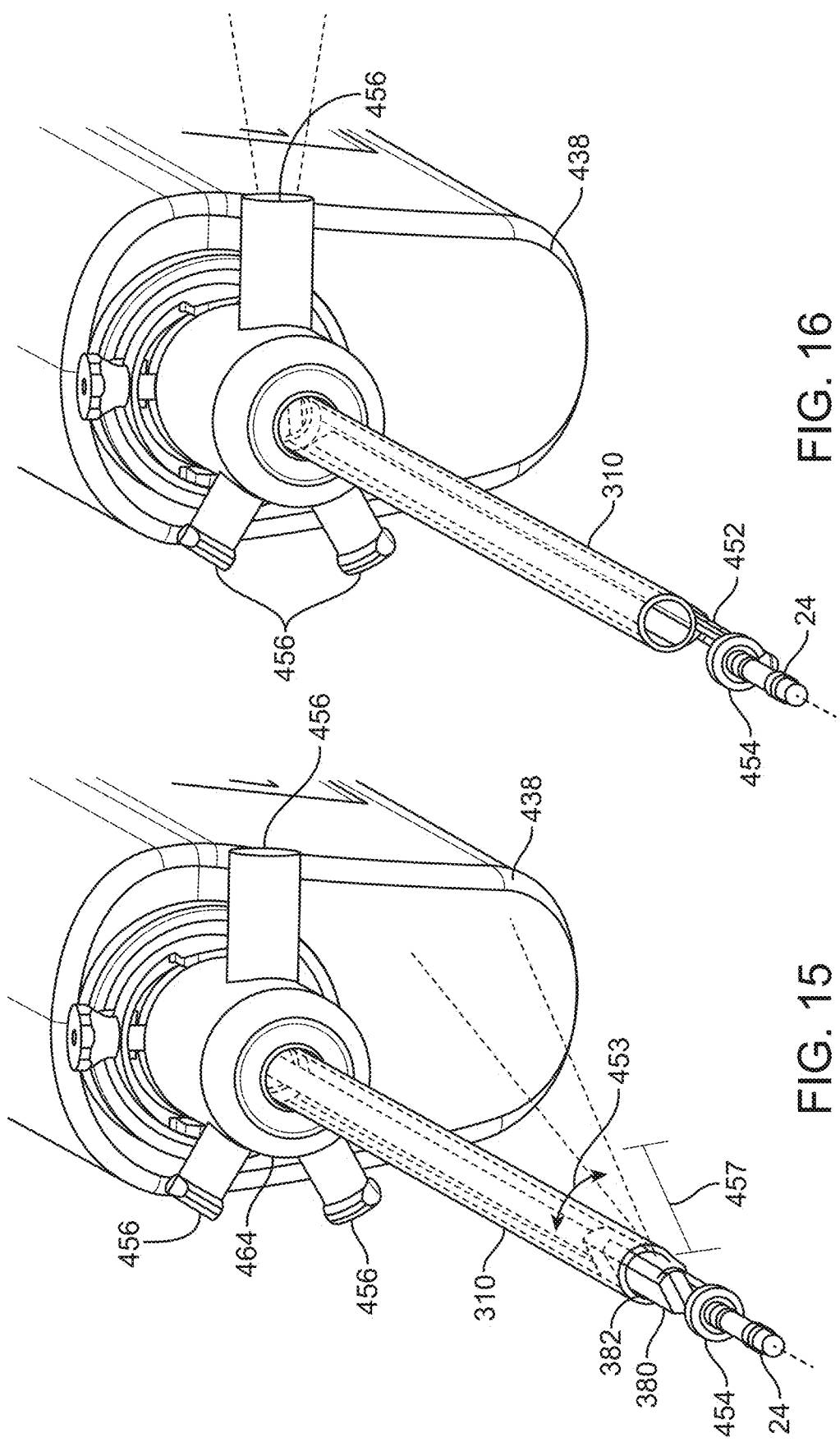

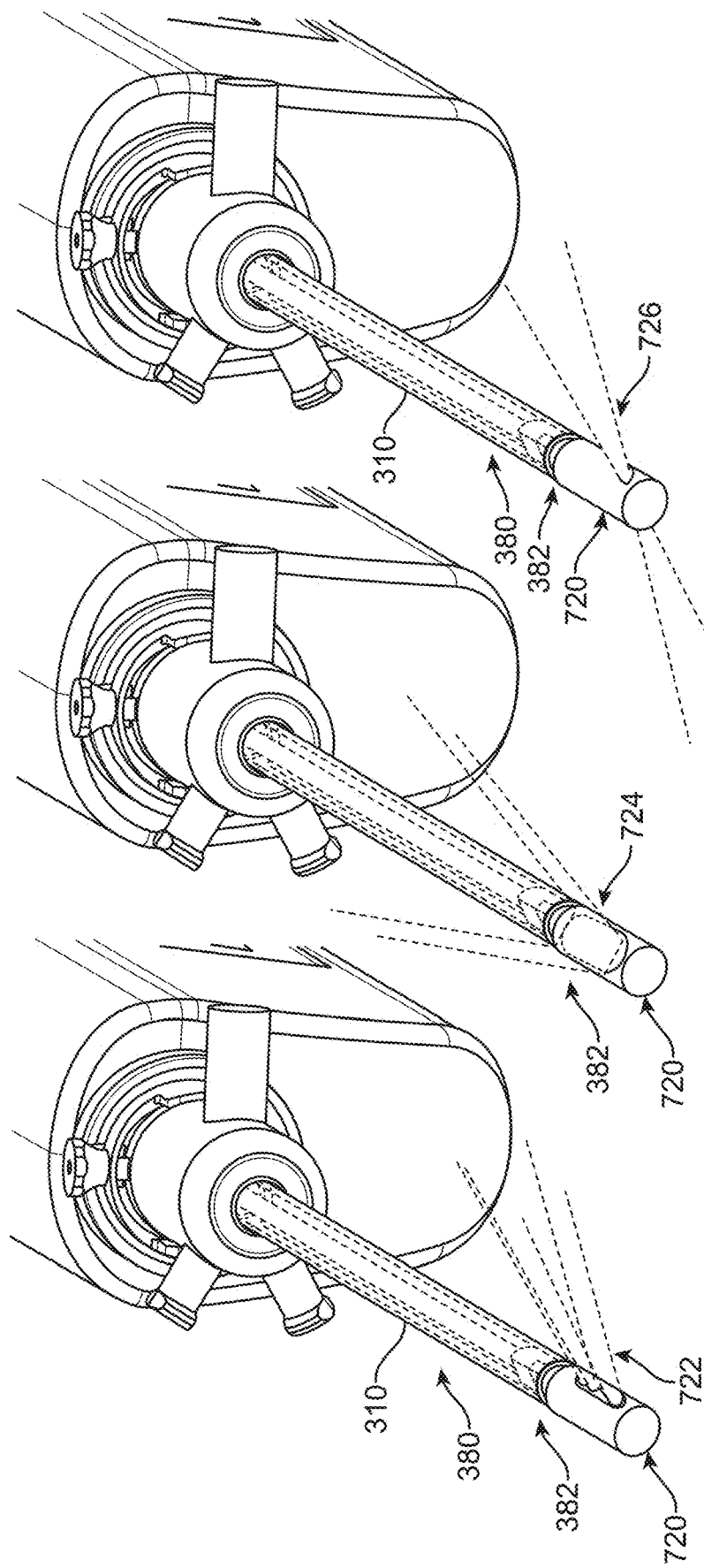

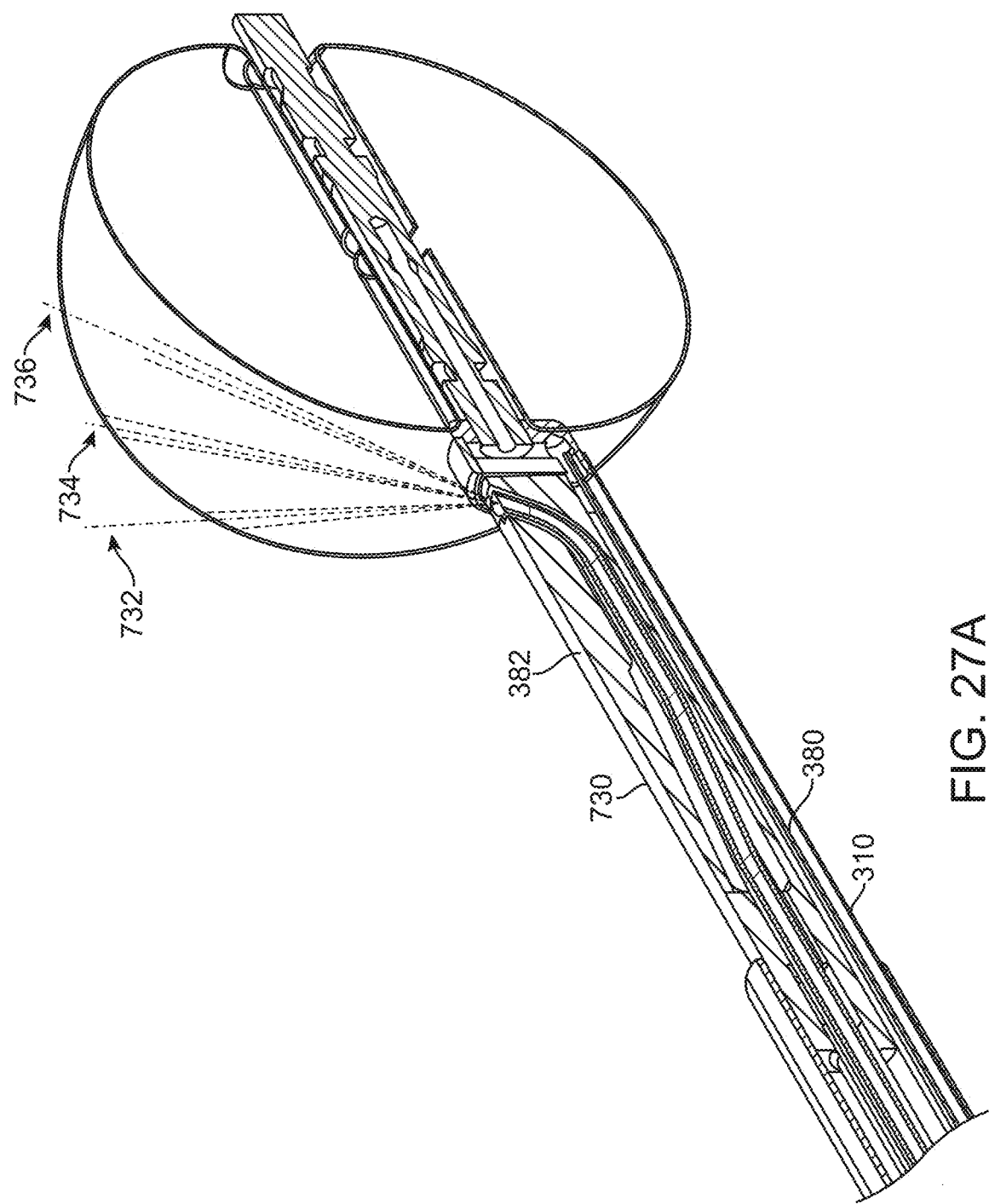

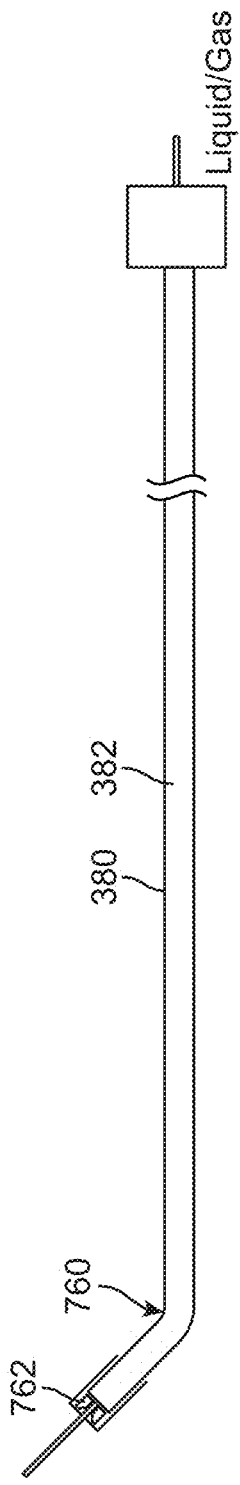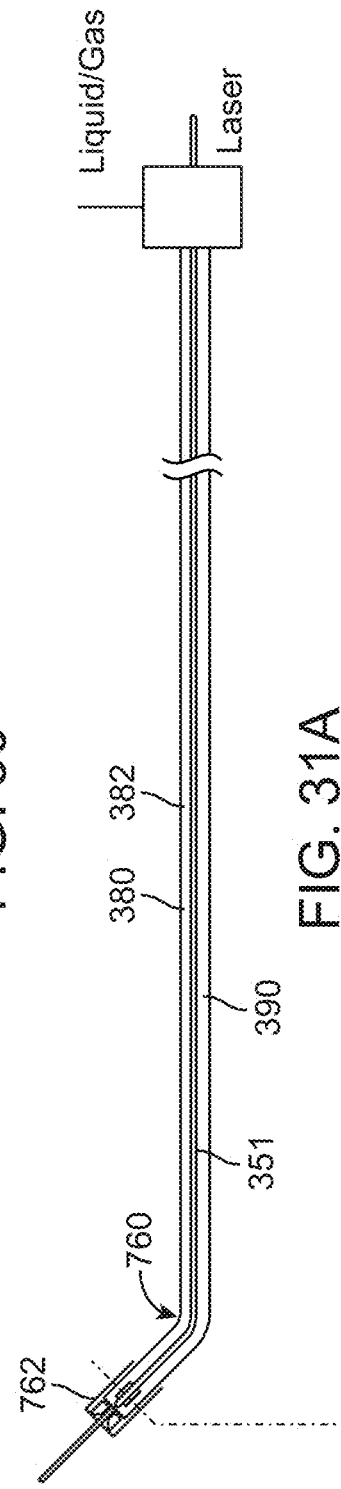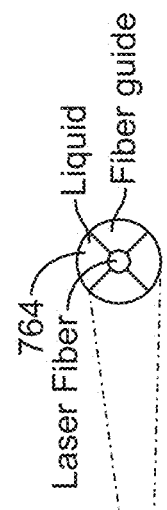

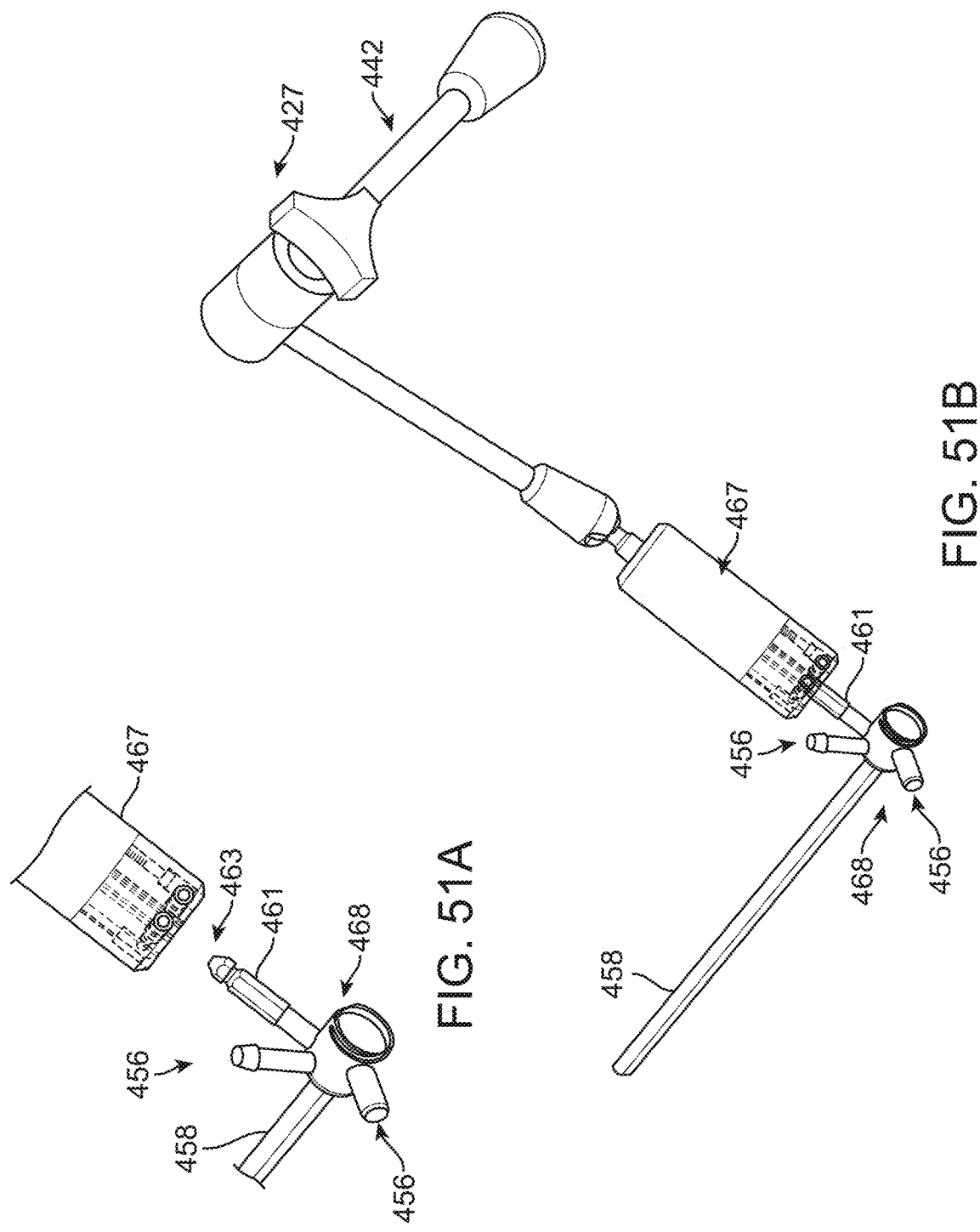

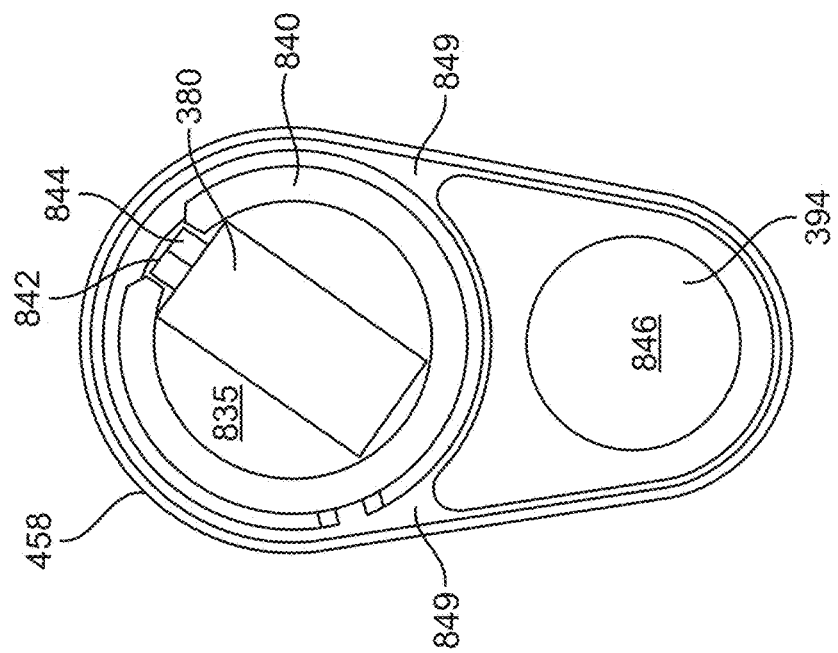
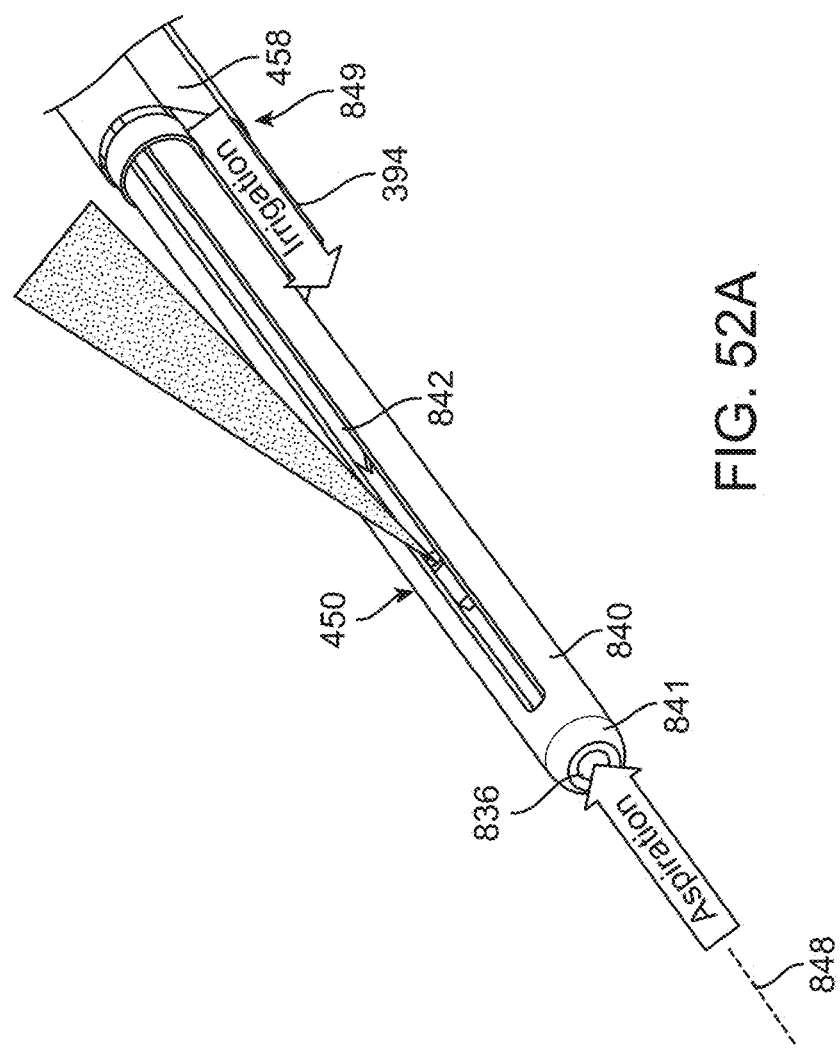
FIG. 52B
FIG. 52A

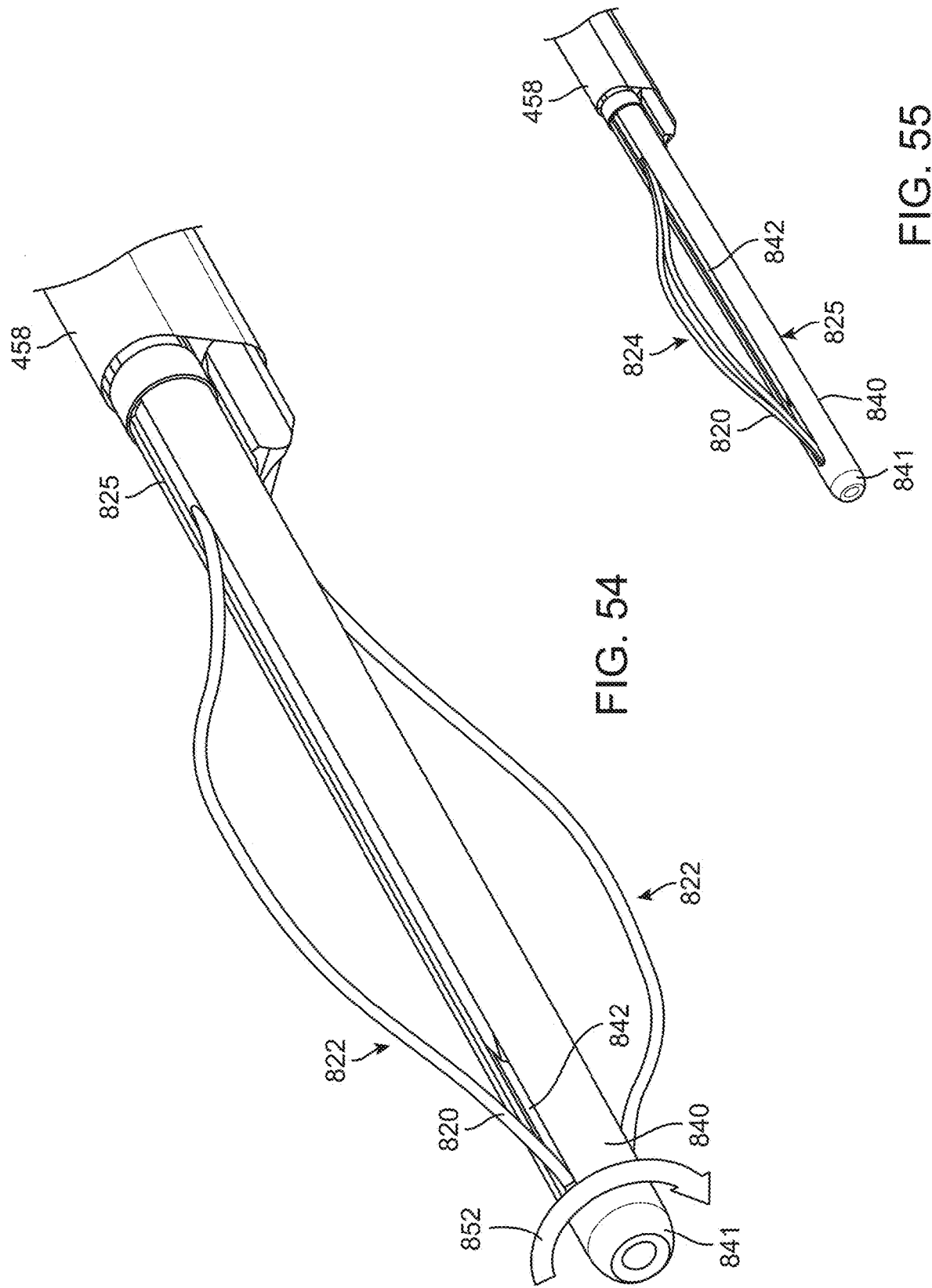

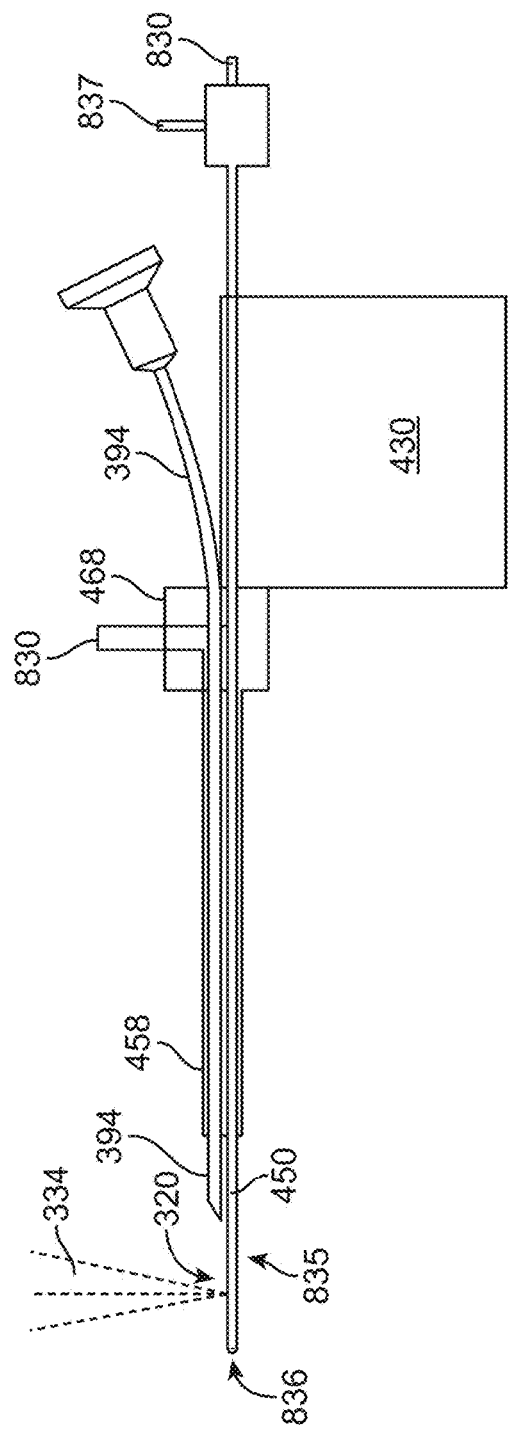
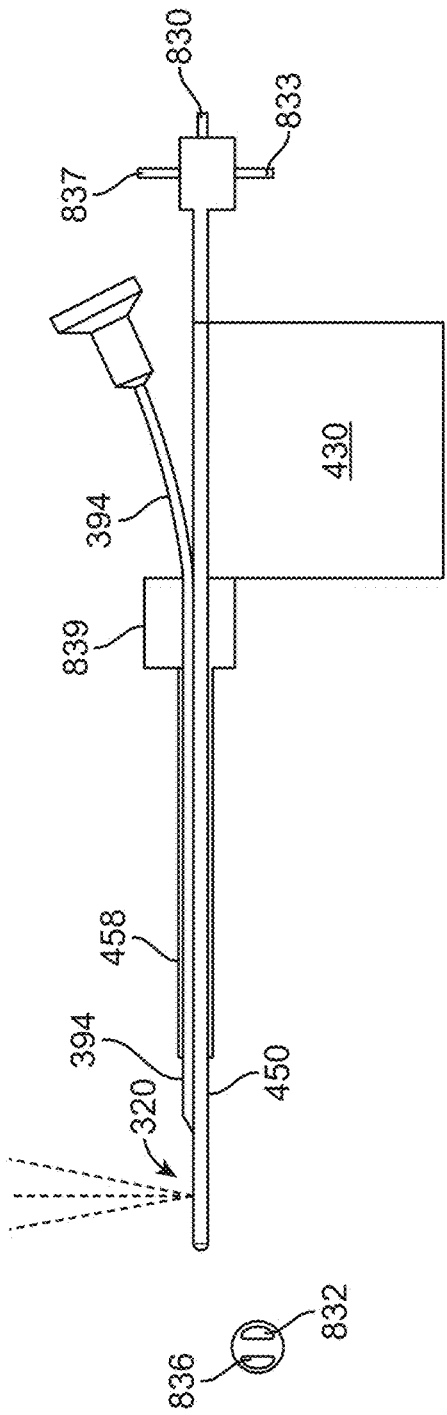
FIG. 57
FIG. 58

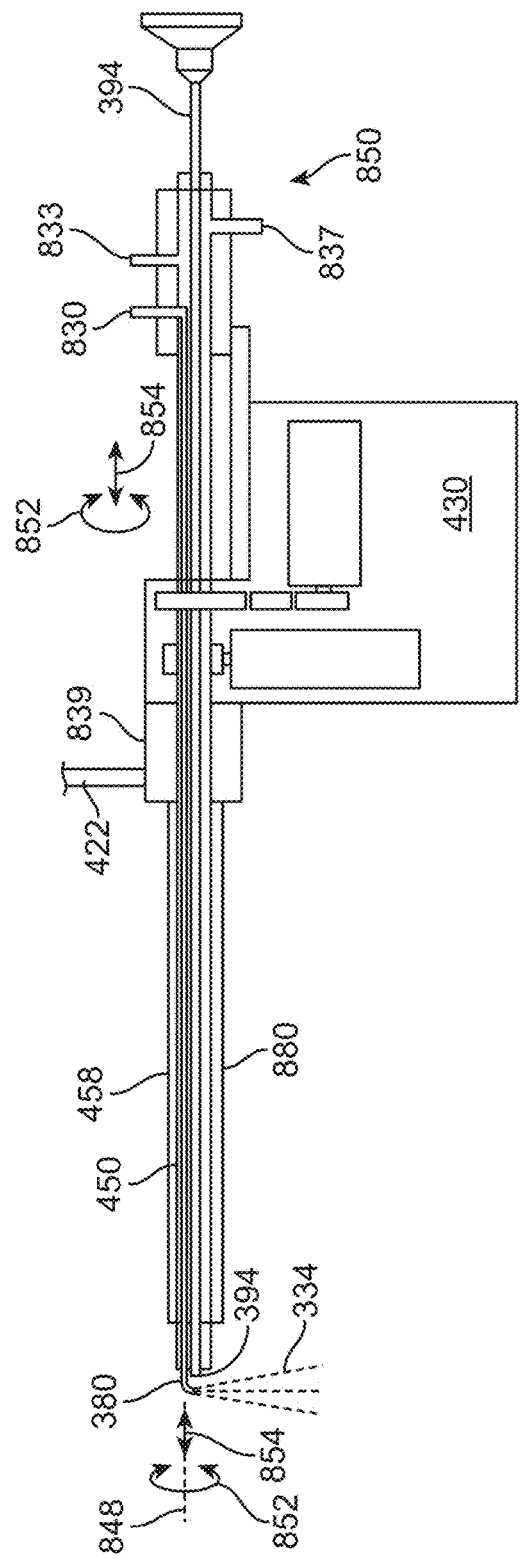
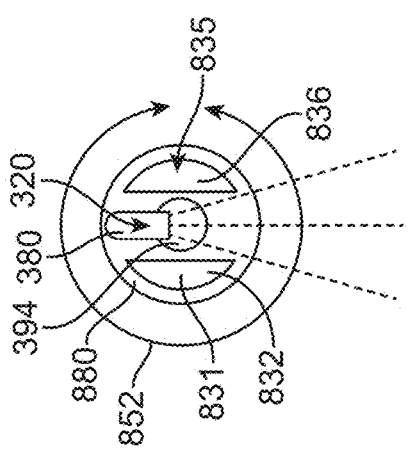
FIG. 62
FIG. 63

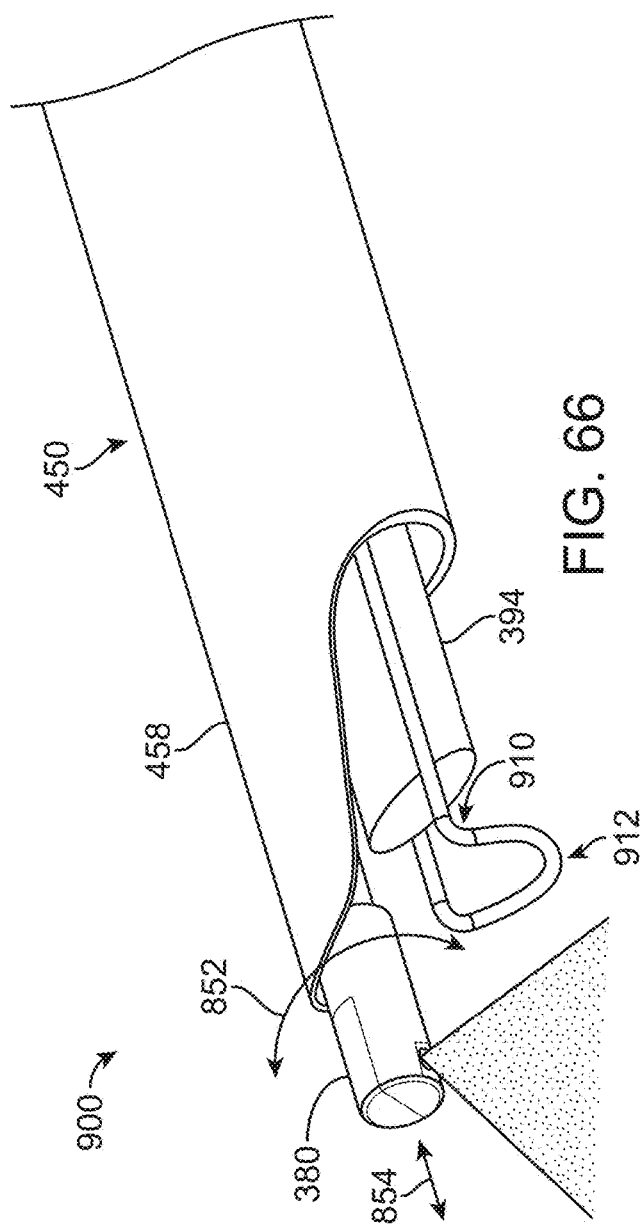
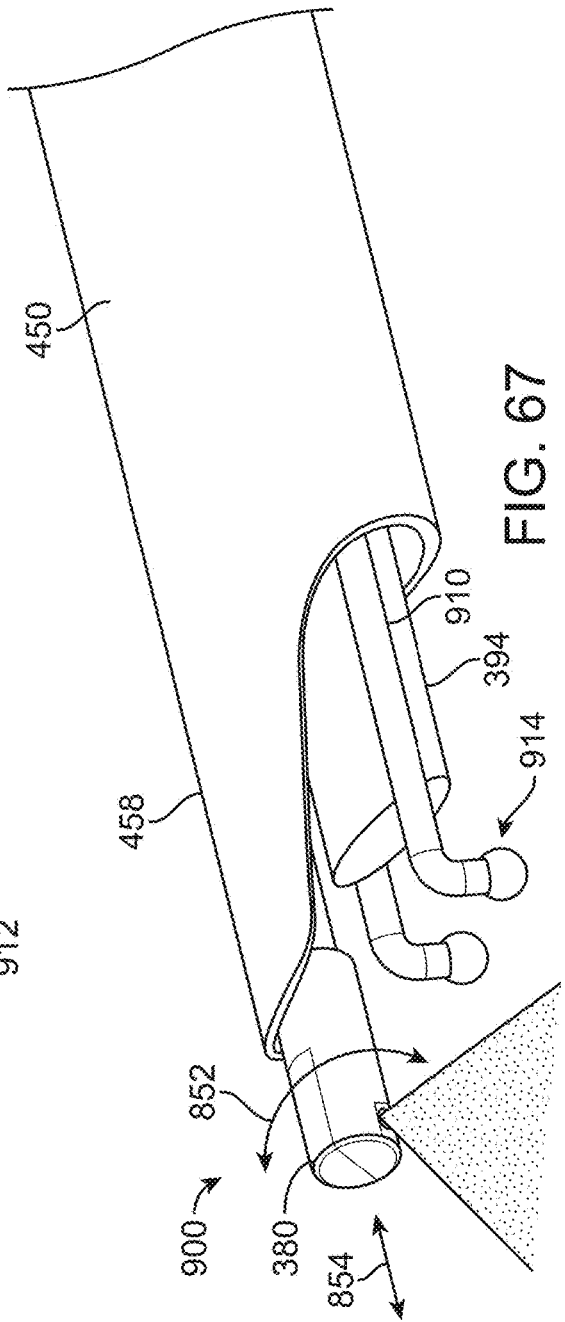

ent application Ser. No. 14/708,910, filed May 11, 2016, entitled "TISSUE RESECTION AND TREATMENT WITH SHEDDING PULSES", now U.S. Pat. No. 9,848,904, issued Dec. 26, 2017, which is a continuation of International Application No. PCT/US2014/054412, filed Sep. 5, 2014, published as WO 2015/035249 on Mar. 12, 2015, entitled "AUTOMATED IMAGE-GUIDED TISSUE RESECTION AND TREATMENT", which application claims priority to U.S. Provisional Patent Application No. 62/019,305, filed Jun. 30, 2014, entitled "AUTOMATED IMAGE-GUIDED TISSUE RESECTION AND TREATMENT", U.S. Provisional Patent Application No. 61/972,730, filed Mar. 31, 2014, entitled "AUTOMATED IMAGE-GUIDED TISSUE RESECTION AND TREATMENT", and U.S. Provisional Patent Application No. 61/874,849, filed Sep. 6, 2013, entitled "AUTOMATED IMAGE-GUIDED TISSUE RESECTION AND TREATMENT", the entire disclosures of which are incorporated herein by reference.

The subject matter of this application is related to International Application No. PCT/US2013/028441, filed Feb. 28, 2013, published as WO 2013/130895 on Sep. 6, 2013, entitled "AUTOMATED IMAGE-GUIDED TISSUE RESECTION AND TREATMENT"; and U.S. Patent Application No. 61/604,932, filed Feb. 29, 2012, entitled "AUTOMATED IMAGE-GUIDED INTRA-ORGAN RESECTION AND TREATMENT"; U.S. patent application Ser. No. 12/399,585, filed Mar. 6, 2009, entitled "TISSUE ABLATION AND CAUTERY WITH OPTICAL ENERGY CARRIED IN FLUID STREAM", now U.S. Pat. No. 8,814,921, issued Aug. 26, 2014; U.S. application Ser. No. 12/700,568, filed Feb. 4, 2010, entitled "MULTI FLUID TISSUE RESECTION METHODS AND DEVICES", now U.S. Pat. No. 9,232,959, issued Jan. 12, 2016; and U.S. patent application Ser. No. 11/968,445, filed Jan. 2, 2008, now U.S. Pat. No. 7,882,841, issued Feb. 8, 2011, entitled "MINIMALLY INVASIVE METHODS AND DEVICES FOR THE TREATMENT OF PROSTATE DISEASES"; International Application No. PCT/US2011/023781, filed Apr. 8, 2007, published as WO 2011/097505 on Nov. 8, 2011, entitled "MULTI FLUID TISSUE RESECTION METHODS AND DEVICES", the full disclosures of which are incorporated herein by reference.

BACKGROUND

The field of the present invention is related to the treatment of tissue with energy, and more specifically to the treatment of an organ such as the prostate with fluid stream energy.

Prior methods and apparatus of treating subjects such as patients can result in less than ideal removal in at least some instances. For example, prior methods of prostate surgery can result in longer healing time and less than desirable outcome than would be ideal in at least some instances.

Prior methods and apparatus of imaging tissue can be less than ideal for imaging a treated tissue. For example, prior ultrasound methods and apparatus may not be well suited to view the treatment sight during treatment, and alignment of diagnostic images with treatment images can be less than ideal. Also, at least some of the prior treatment methods and apparatus of treating tissue may not be well suited from combination with imaging systems of the prior art. In at least some instances, it would be helpful to provide improved imaging of tissue during surgery, for example to provide real time imaging of tissue that would allow a user to adjust the treatment based on real time images of the tissue. At least some of the prior methods and apparatus to image tissue during surgery can be somewhat cumbersome to use, and can result in delays in the patient treatment.

Prior methods and apparatus to treat an organ such as the prostate may provide a user interface that is somewhat cumbersome for the user, and can provide less than ideal planning of the surgery. Also, at least some of the prior methods and apparatus to treat tissue such as the prostate tissue can be somewhat less accurate than would be ideal. In at least some instances, the prior methods and apparatus may provide a less than ideal user experience. Also, at least some of the prior interfaces may provide less than ideal coupling of the treatment apparatus with tissue structures.

Improved methods for tissue resection are described in U.S. Pat. No. 7,882,841 and pending applications U.S. Ser. No. 12/700,568 and U.S. Ser. No. 12/399,585. The methods and systems described in this patent and these patent applications rely on the positioning of a probe such as a urethral probe, which directs a fluid stream radially outwardly for controlled resection of tissue such as the prostate and luminal tissues. Optionally, the fluid stream may be used to deliver light, electrical, heat or other energy sources to aid in resection and/or to cauterize the treated tissue.

Work in relation to embodiments suggest that in at least some instances treatment of diseased tissue can be less than ideal. For example, diseased tissue may not provide fluid flow similar to healthy tissue, and work in relation to embodiments suggest that diseased tissue can be related to distension and stretching with small variations in fluid delivery and removal. Consequently, recovery and healing, while an improvement over the prior art, can take somewhat longer than would be ideal in at least some instances.

In addition, it would be helpful to have improved monitoring of surgical procedures that could be readily implemented in a cost effective manner so that many people could benefit from the advances in surgical robotics. In at least some instances it would be helpful to have improved imaging of the surgical site. Also, it would be helpful to determine when treatment may exceed a desired limit, such as the capsule of the prostate, and to provide measurement apparatus with the treatment device to inhibit cutting tissue too deeply and perforation of tissue such as the capsule of the prostate, for example. Although ultrasound imaging can be helpful, it would be desirable to have improved alignment of ultrasound probes with treatment probes.

While these methods are very effective and represent a significant advance over prior luminal tissue treatment protocols, it would be desirable to provide improvements to assist in more accurate tissue removal in both fully automated and physician assisted operating modes. At least some of these objectives will be met by the inventions described hereinafter.

SUMMARY

Embodiments of the present invention provide improved methods and apparatus for performing tissue resection, such as prostate tissue resection, by positioning an energy source within a urethra.

Embodiments of the present invention provide improved methods and apparatus for performing tissue resection, such as prostate tissue resection, by positioning an energy source within a urethra. In many embodiments, a fluid stream is directed toward tissue to generate a plurality of shedding clouds. The fluid stream can be scanned such that the plurality of shedding clouds arrive a different overlapping locations. Each of the plurality of shedding clouds can remove a portion of the tissue. In many embodiments, an apparatus to ablate tissue comprises a source of pressurized fluid, and a nozzle coupled to the source of pressurized fluid to release a fluid stream, in which the fluid stream generates a plurality of shedding clouds.

In a first aspect, embodiments provide a method of ablating tissue. A fluid stream is directed toward the tissue to generate a plurality of shedding clouds. The fluid stream is scanned such that the plurality of shedding clouds arrives at different overlapping locations.

In many embodiments, each of the plurality of shedding clouds removes a portion of the tissue.

In many embodiments, the shedding clouds comprise cavitations visible to a user.

In many embodiments, the fluid stream comprises a first liquid released into a second liquid to generate the shedding clouds.

In many embodiments, the first liquid comprises saline and the second liquid comprises saline.

In many embodiments, the fluid stream is scanned with one or more of a hand held probe or a probe coupled to a linkage.

In another aspect, embodiments provide an apparatus to ablate tissue. The apparatus comprises a source of pressurized fluid, and a nozzle coupled to the source of pressurized fluid to release a fluid stream. The fluid stream generates a plurality of shedding clouds, wherein each of the plurality of shedding clouds removes a portion of the tissue.

In many embodiments, a scanner is coupled to the nozzle to ablate each portion of the tissue with partially overlapping shedding clouds.

In many embodiments, the fluid stream comprises a liquid, the apparatus further comprising an irrigation opening to irrigate the tissue with a second liquid.

In many embodiments, the first liquid comprises saline and the second liquid comprises saline.

In many embodiments, the nozzle comprises a Strouhal number within a range from about 0.02 to about 0.03.

In many embodiments, fluid source comprises a pump having a frequency less than a frequency of the shedding pulses.

In many embodiments, the shedding pulses comprise a frequency within a range from about 1 k Hz to about 10 kHz.

In many embodiments, tissue resection is performed with an opening to aspirate ablated material on the distal end of the probe in order to promote removal of fluid from the bladder neck and inhibit excessive amounts of fluid from accumulating in the bladder. The opening on the distal end of the probe can be fluidically coupled to the surgical site. In many embodiments, the probe can be provided without a distal anchor on the treatment probe, and improved methods and apparatus are provided for aligning the treatment with the target tissue structure. The probe inserted into the urethra can be provided without an anchor in order to promote movement of fluid from the surgical site toward the bladder neck. A distal opening of the probe can be configured to aspirate fluid with suction from the distal end of the probe toward a source of suction such as a gravity flow line of a siphon or suction pump. The opening on the distal end of the probe can be fluidically coupled to the surgical site, such that fluid can be drawn from the surgical site when the distal end of the probe is placed in the bladder neck during at least an initial portion of the procedure. In many embodiments, the aspiration opening on the distal end of the probe is coupled to a fluid pump configured to remove fluid at a rate determined by the user. The fluid pump may comprise a peristaltic pump, or pump with a diaphragm such that fluid can be accurately removed from the surgical site to inhibit distension of tissue. In many embodiments, the probe can be aligned with reference to anatomical structures of the patient such as the bladder neck and verumontanum, which can be readily viewed with endoscopic visualization. In many embodiments, the display screen visible to the user comprises a reference, and a tissue marker such as the bladder neck is aligned with internal visualization of the patient in order to align a reference structure shown on the display with the anatomical marker of the patient. When the probe is aligned, an arm coupled to the probe can be locked to inhibit unintended movement of the probe.

While embodiments of the present invention are specifically directed at transurethral treatment of the prostate, certain aspects of the invention may also be used to treat and modify other organs such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 11 illustrates a tissue modification device that uses a fluid stream for tissue resection, wherein the fluid stream may optionally act as a conduit for electromagnetic energy;

FIG. 14D1 shows rapid exchange of a carrier when the linkage is coupled to the elongate element anchored to a target location of an organ, in accordance with embodiments;

FIG. 14D2 shows alignment of the distal tip of the carrier with the proximal end of the linkage to insert the carrier tube as in FIG. 14D1;

FIG. 14D3 shows the carrier advanced toward a locking structure on the proximal end of the linkage as in FIG. 14D1;

FIG. 14D4 shows the carrier locked to the linkage as in FIGS. 14D1 and 14D2;

FIGS. 15 and 16 show self cleaning with a fluid jet in accordance with embodiments;

FIGS. 26A, 26B and 26C show jet masking in accordance with embodiments;

FIGS. 27A and 27B show variation of jet angle in accordance with embodiments;

FIGS. 30, 31A and 31B show single tube designs in accordance with embodiments;

FIG. 51A shows a docking structure configured to engage a protrusion of a stiff sheath to hold the stiff sheath in place for the surgery, in accordance with embodiments;

FIG. 51B shows the docking structure engaging the stiff sheath with the docking structure in order to support and inhibit movement of the stiff sheath during treatment, in which the docking structure is coupled to a lockable arm;

FIGS. 52A and 52B show isometric and cross-sectional views, respectively, of a treatment probe comprising a support structure having a dynamic tip, in accordance with embodiments;

FIG. 54 shows a radio frequency (hereinafter "RF") electrode on a cautery probe configured to rotate around an elongate axis of the probe in order to cauterize tissue, in accordance with embodiments;

FIG. 55 shows a bipolar electrode configured to rotate around an elongate axis of a cautery probe in order to cauterize tissue, in accordance with embodiments;

FIG. 57 shows an integrated treatment probe with an opening for fluid suction on a distal end, in which the probe has been place in a stiff sheath with an endoscope to view the treatment;

FIG. 58 shows an integrated treatment probe having an aspiration opening and an irrigation opening on a distal end to aspirate through the aspiration opening and irrigate through the irrigation opening, in which the probe has been placed in a stiff sheath with an endoscope to view the treatment, in accordance with embodiments;

FIGS. 61, 62 and 63 show isometric, side and cross-sectional views, respectively of a treatment probe having a viewing path substantially concentric with rotation of a nozzle of a treatment jet, in accordance with embodiments;

FIG. 66 shows a treatment probe configured for at least partially manual treatment of an electrode and at least partially automated treatment with a water jet, in accordance with embodiments;

FIG. 67 shows a treatment probe configured for at least partially manual treatment with bipolar electrodes and at least partially automated treatment with the liquid jet, in accordance with embodiments;

DETAILED DESCRIPTION

Figure 1:
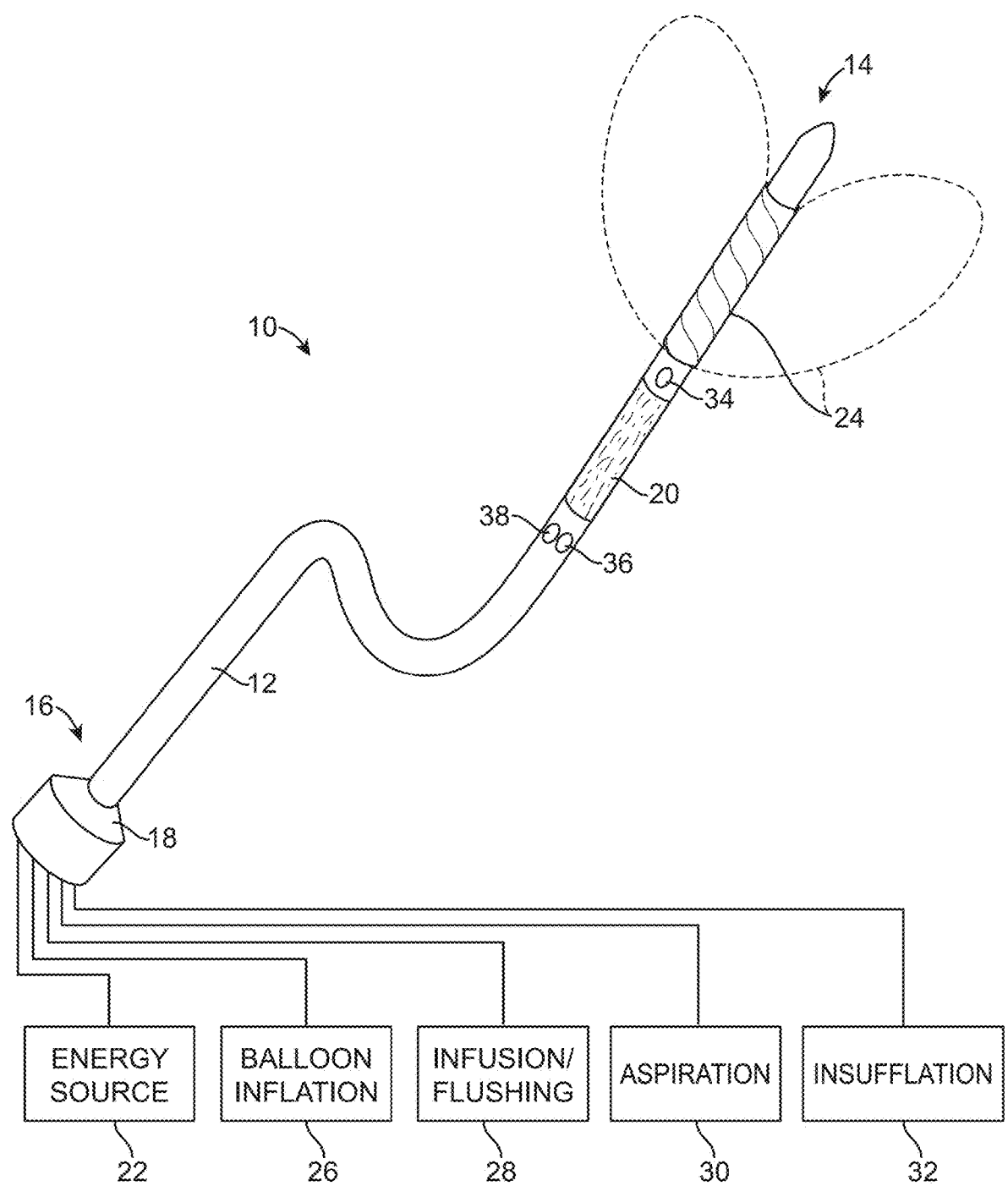
FIG. 1 is a schematic illustration of a device suitable for performing intraurethral prostatic tissue debulking in accordance with the principles of the present invention.

A better understanding of the features and advantages of the present disclosure will be obtained by reference to the following detailed description that sets forth illustrative embodiments, in which the principles of embodiments of the invention are utilized, and the accompanying drawings.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described herein.

The embodiments disclosed herein can be combined in one or more of many ways to provide improved therapy to a patient. The disclosed embodiments can be combined with prior methods and apparatus to provide improved treatment, such as combination with known methods of prostate surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of treatment profiles and volumes as described herein are presented in the context of prostate surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, etc. as well as body lumens and passages such as the sinuses, ureter, colon, esophagus, lung passages, blood vessels and throat.

As used herein, the term Aquablation™ encompasses ablation with water.

As used herein, the words telescope, endoscope and cytoscope are used interchangeably.

As used herein, the terms entrainment region and cavitation region are used interchangeably.

The imaging and treatment probes as described herein can be combined in one or more of many ways, and in many embodiments the images of the patient can be used to define a target volume and a target profile of the volume of tissue removed. The profile of tissue removed can be planned to efficaciously remove tissue. The methods and apparatus for imaging as described herein can be used to beneficially plan for treatment. Alternatively or in combination, the imaging methods and apparatus as described herein can be used to modify the treatment in real time as the patient is treated, for example.

The visible entrainment and cavitation region can be combined with the images of tissue and treatment regions shown on the display, so as to provide confirmation that the correct amount of tissue will be resected. In many embodiments, the distance of the visible entrainment region corresponds to a maximum cut depth, such that the surgeon can select the depth of the cut based on images and with adjustment of treatment parameters such as one or more of flow rate, nozzle diameter, or pressure.

The visible entrainment region as described herein comprises region of cavitation of the fluid stream emitted from the energy source such as a nozzle, and the maximum resection depth corresponds to the distance of the visible entrainment region. By visible entrainment region, it is meant that the user can visualize the entrainment region with imaging sensitive to formation of cavitation pockets, such as visible and ultrasound imaging which scatter waves in response to cavitation pockets being formed.

A plurality of carrier probes can be provided to allow the user to treat one or more of many tissues in a variety of ways. An elongate structural element having a working channel such as a shaft remains positioned in the patient when a first carrier probe is exchanged with one or more carrier probes. In many embodiments, the carrier probes can be rapidly exchanged while a linkage remains fixedly attached to the elongate element anchored to an internal structure of the patient. Each of the carrier probes inserted into the patient can be identified based on a treatment plan, for example.

As used herein a processor encompasses one or more processors, for example a single processor, or a plurality of processors of a distributed processing system for example. A controller or processor as described herein generally comprises a tangible medium to store instructions to implement a steps of a process, and the processor may comprise one or more of a central processing unit, programmable array logic, gate array logic, or a field programmable gate array, for example.

As used herein, the transverse plane of an image may be referred to as the horizontal plane of the image, the axial plane of the image, or transaxial plane of the image. An image along an axial plane may be referred to as an axial image.

As used herein, a probe encompasses an object inserted into a subject such as a patient.

As used herein like characters and numerals identify like elements.

As used herein, real-time a real time image shown on a display encompasses an image shown within a few seconds of the event shown. For example, real time imaging of a tissue structure encompasses providing the real time image on a display within about ten seconds of the image being acquired.

As used herein, the terms distal and proximal refer to locations referenced from the apparatus, and can be opposite of anatomical references. For example a distal location of a probe may correspond to a proximal location of an elongate member of the patient, and a proximal location of the probe may correspond to a distal location of the elongate member of the patient.

Automated robotic control—where movement of the water jet is motorized and under computer control with preselected routines—allows accurate and finely detailed resections not possible with manual control. Advantages include reduced time required for procedures, fewer complications, improved outcomes and less training time needed for surgeons. Many of these improvements arise from reducing or eliminating the need for manual dexterity of the treating physician. Automatic control further allows the cutting power of the nozzle to be increased to levels not achievable with full manual control. The system may be manually controlled during less critical portions of the procedure, e.g. during initial selection of an area to operate on and for touch-ups in cutting and cautery. Even during these less critical phases of the protocols, the increased precision and smoothness provided by the automated control can provide reduction and filtering of hand jitter. Another significant advantage is that automation allows for pretesting or "dry runs" of a procedure. When a cutting routine is selected, the limits of area can be selected using a joystick or other control element to position the laser during a mock the procedure without cutting. Changes can be made before cutting commences, so that errors can be corrected before beginning the actual procedure.

Closed-loop and real-time automation are new capabilities provided by robotic automation include resection volume registration within the organ and in-situ depth and volume measurement. With the ability to input organ geometry data into the control system, e.g., from an ultrasound or other pre-operative or real time image, the cutting region can be precisely registered within the organ. This eliminates the imprecision of manual procedures with respect to important tolerances, such as to how close the resection is to the surface of the capsule and/or to the neurovascular bundle in the prostate. Additionally, the shape of the resected volume itself may be selectable and adjustable from a set of pre-programmed routines, where the details of how to control the cutting motion and pressure have been worked out in advance with extensive engineering knowledge that is then stored in the robotic surgical tool, ready for access at the push of a button by the surgeon. For example, the resected shape of tissue may comprise a pre-defined treatment profile such as one or more of domed, cubic, tear-drop, or directly from a 3D rendering of the target volume as described herein and illustrated below in the two screenshots of FIGS. 21A and 21B, for example. In addition, the surgeon can adjust the cutting parameters in real-time based on the feedback provided by the ultrasound images, which adds another layer of safety to the system.

INCORPORATION BY REFERENCE

The subject matter of FIGS. 1 to 11 and the corresponding text have been incorporated by reference as described in: U.S. application Ser. No. 12/700,568, filed Feb. 4, 2010, entitled "MULTI FLUID TISSUE RESECTION METHODS AND DEVICES", published as US 20110184391; and PCT Application PCT/US2011/023781 filed on Apr. 8, 2007, published as WO2011097505 on Nov. 8, 2011, entitled "MULTI FLUID TISSUE RESECTION METHODS AND DEVICES"; the full disclosures of which have been previously incorporated herein by reference.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized C02 or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheathes, and the like which could be positioned over the shaft 12.

Figure 2A:
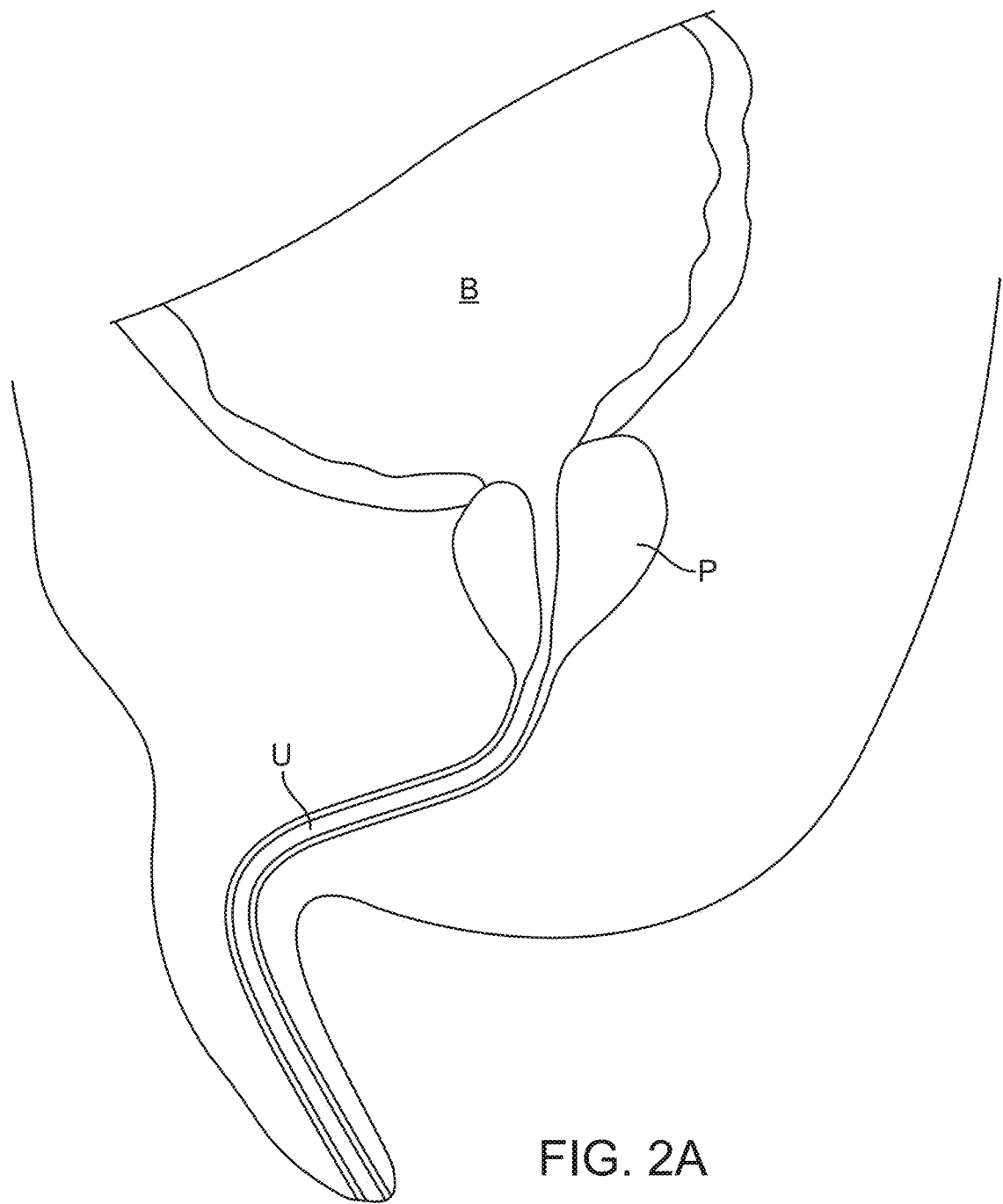
FIGS. 2A, 2B, 2C and 2D illustrate use of the device of FIG. 1 in performing prostatic tissue debulking.
Figure 2B:
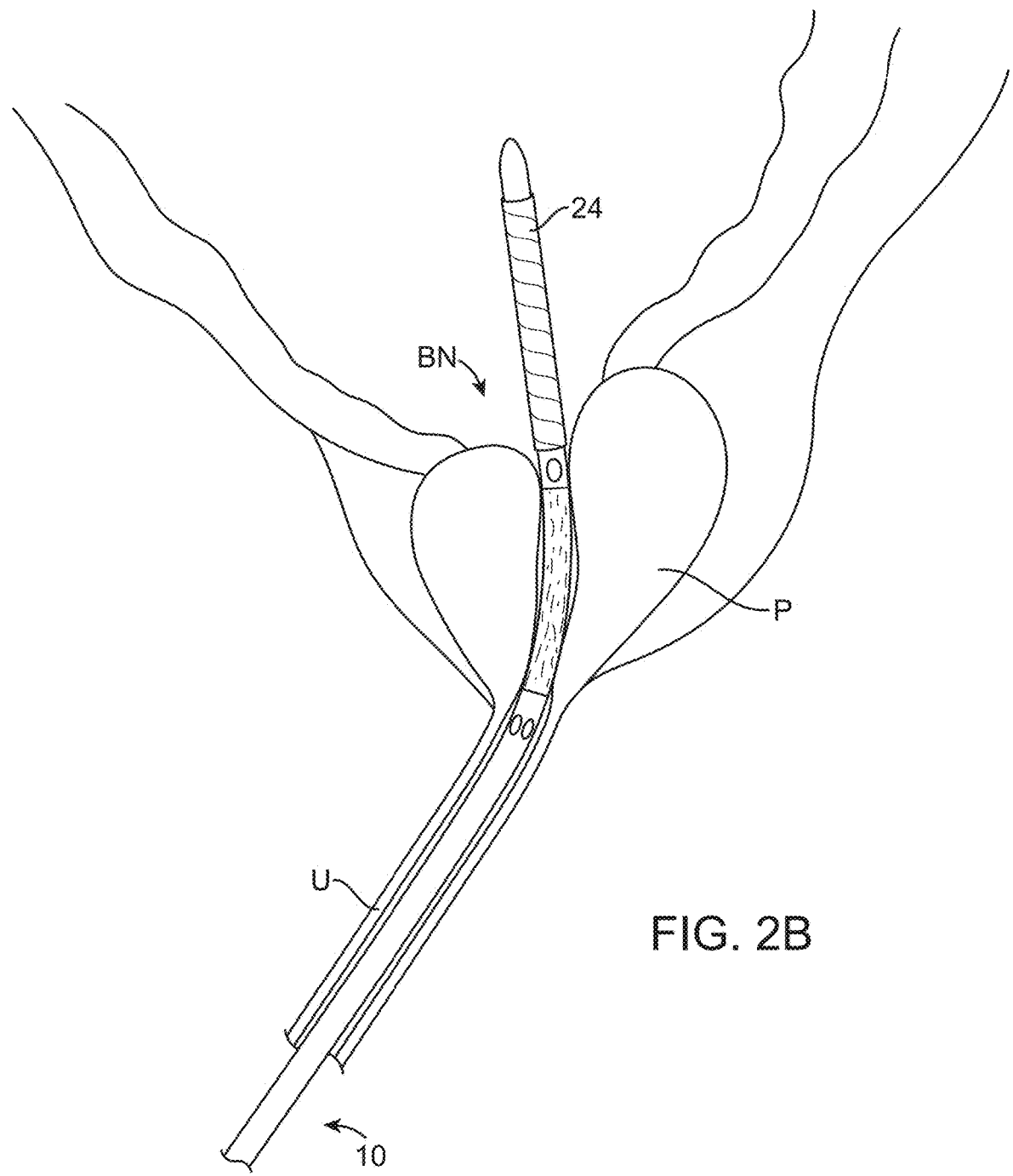
Figure 2C:
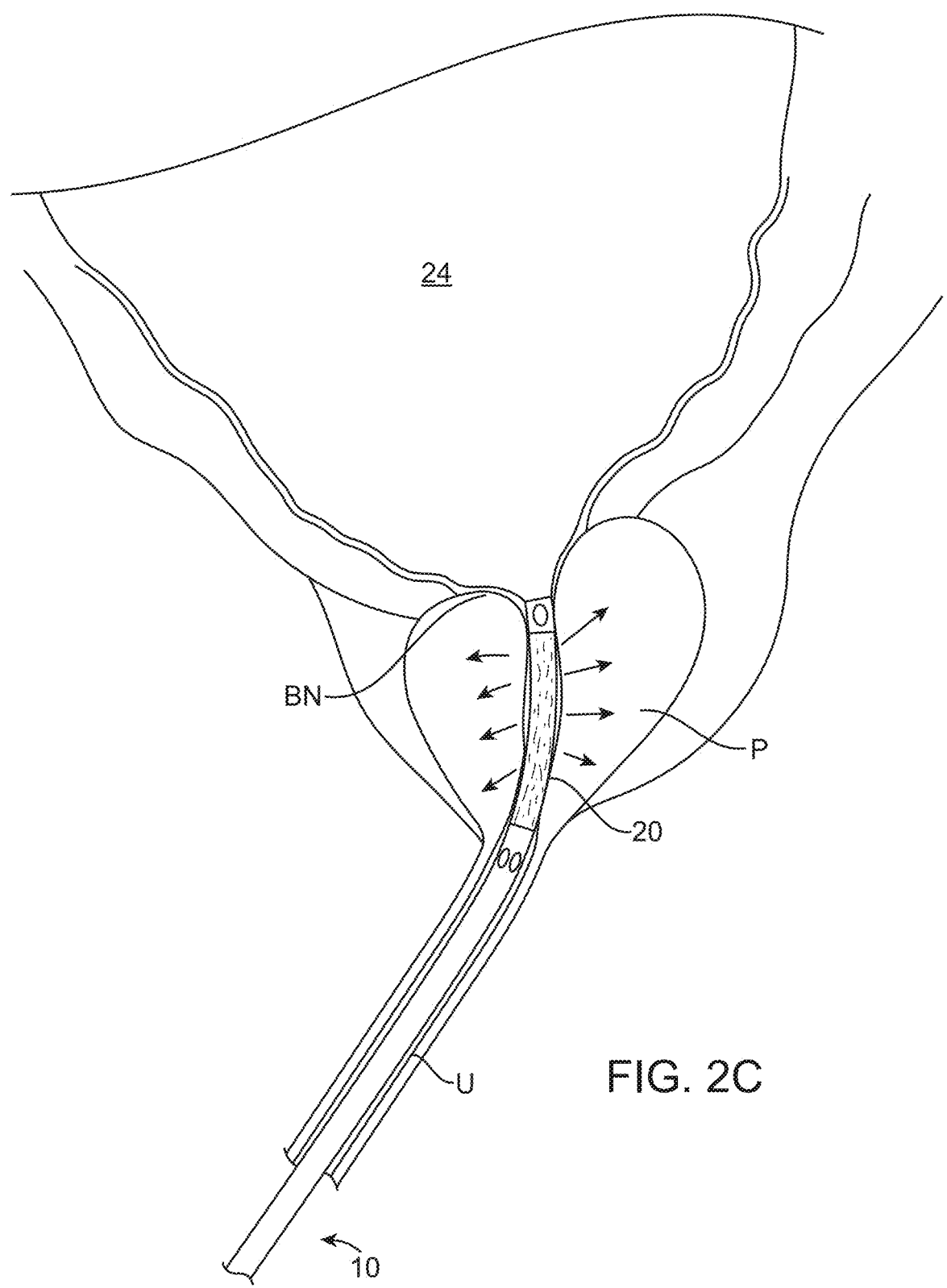
Figure 2D:
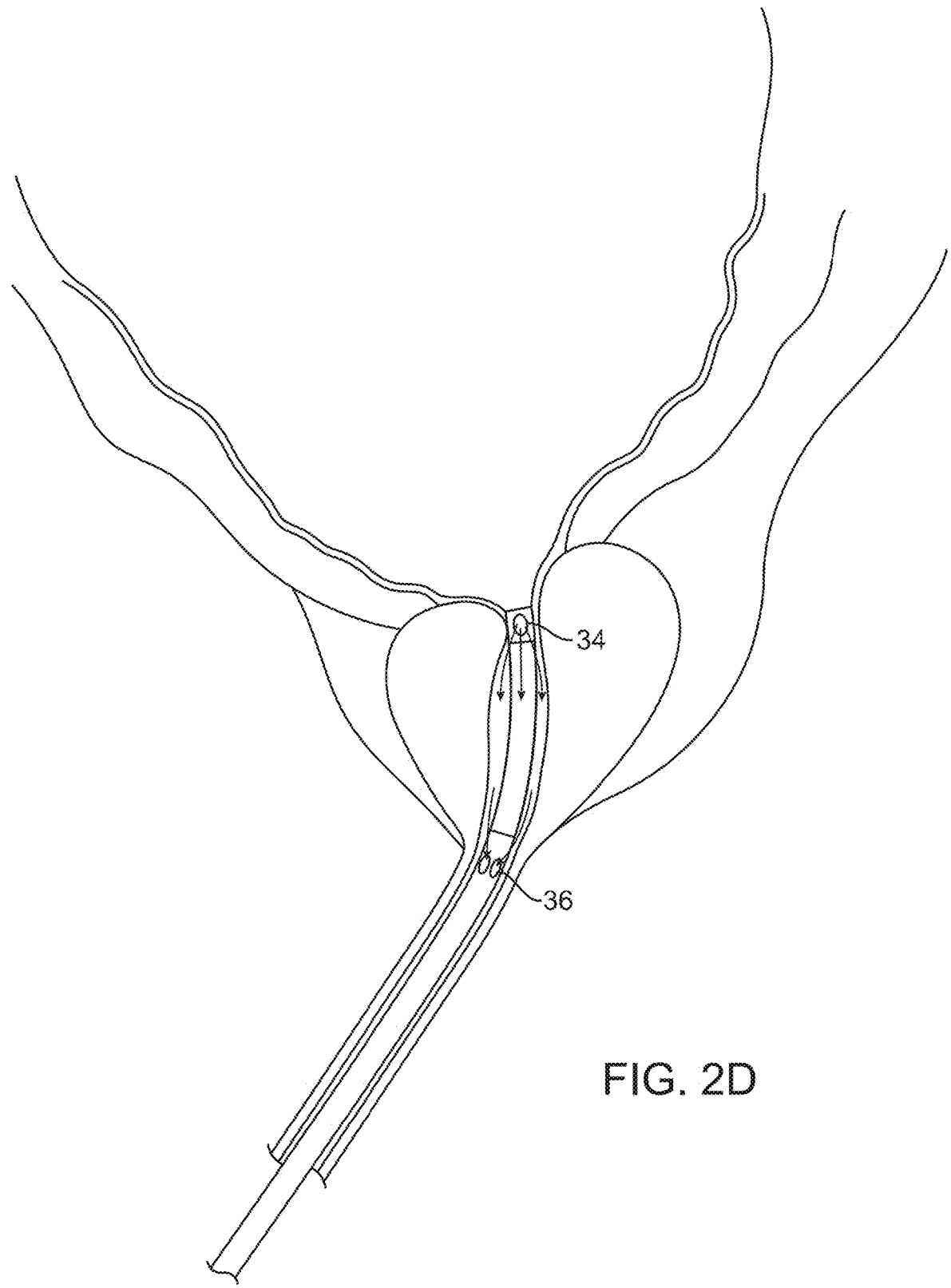

While the present embodiments are described with reference to the human prostate, it is understood that they may be used to treat mammal prostates in general. Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 2. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a modified or separate catheter device.

Figure 3:
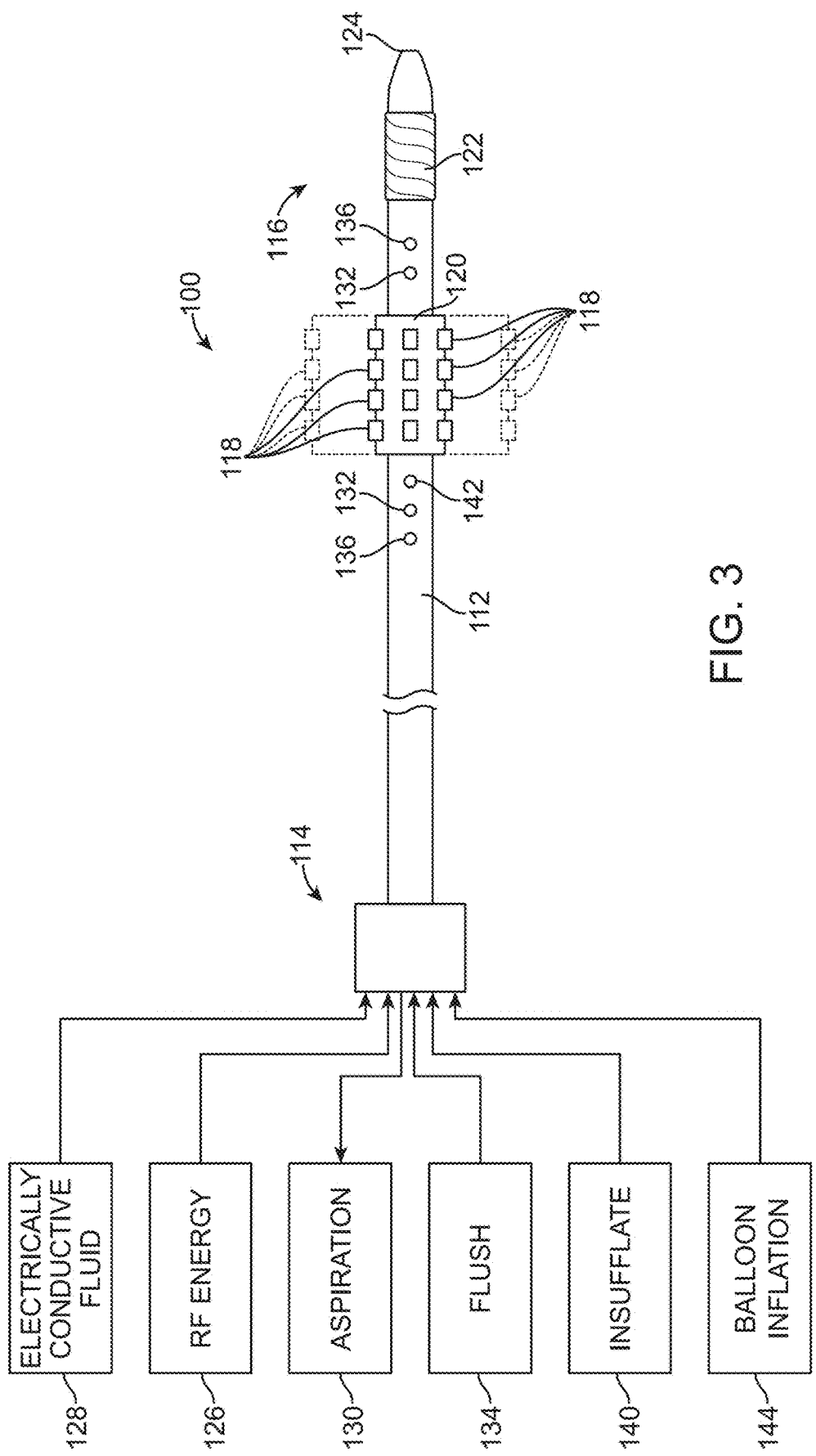
FIG. 3 illustrates a specific prostatic tissue treatment device incorporating the use of a radiofrequency saline plasma for performing prostatic tissue debulking.

Referring now to FIGS. 3-7, a number of representative energy delivery regions will be described. Referring now to FIG. 3, a first exemplary prostate resection device 110 constructed in accordance with the principles of the present invention comprises a shaft 112 having a proximal end 114 and a distal end 116. A plurality of nozzles 118 are mounted on the shaft 112 at a location spaced proximally from the distal end 116 by distance in the range from 1 cm to 5 cm. The nozzles, which are typically ceramic cores capable of generating a plasma or ports capable of directing a radially outward stream of electrically conductive fluid, may be mounted on structure 120, which allows the nozzles 118 to be moved radially outwardly, as shown in broken line in FIG. 3. An anchor 122, shown as an inflatable balloon is mounted on the distal end 116 of the shaft 112 at a location between the nozzles 118 and the distal tip 124. The expandable structure 122 will be capable of being expanded within the bladder to anchor the shaft 112 so that the nozzle array 118 lies within the prostate, as described in more detail below. The shaft 112 will include lumens, passages, electrically conductive wires, and the like, in order to deliver energy and materials from the proximal end 114 to the distal end 116 of the shaft. For example, an RF energy source 126 will be connected to the shaft 112, usually to the nozzles 118, in order to deliver RF energy to an electrically conductive fluid delivered from source 128 to the nozzles 118, typically through a lumen within the shaft 112. Other lumens, channels, or conduits will be provided in order to allow aspiration to a vacuum source 130 which is typically connected to one or more aspiration ports 132. Other conduits may be provided within the shaft 112 in order to permit introduction of a flushing fluid, such as saline, from a source 134 to ports 136. In other instances, it will be possible to connect the aspiration and flushing sources 130 and 134 to a common port so that aspiration and flushing may be conducted sequentially rather than simultaneously. Further optionally, internal lumens, conduits, or the like, may be provided in order to connect a source of insufflation 140 to one or more insufflation ports 142 on the shaft in the region of the array 118. Finally, internal lumens, conduits, or the like, may be provided for connecting balloon 122 to a balloon inflation source 144.

Figure 4:
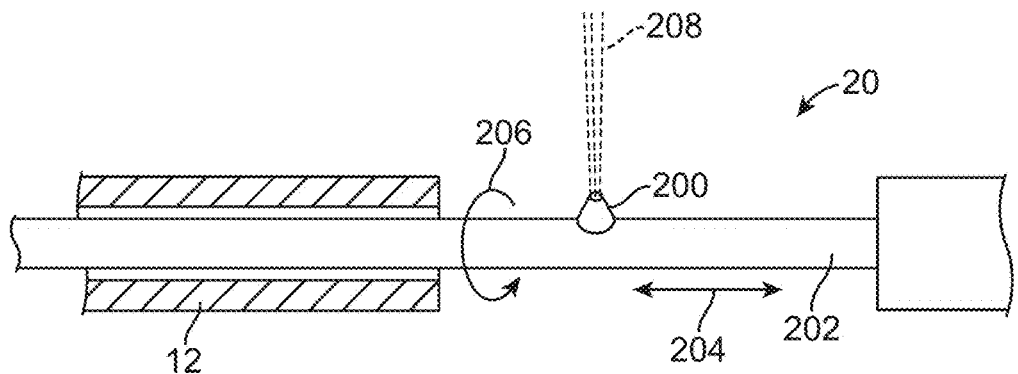
FIG. 4 illustrates an energy source suitable for use in the devices of the present invention, wherein the energy source delivers a fluid stream for tissue resection.

As shown in FIG. 4, an exemplary energy delivery region 20 can be formed by a high pressure nozzle 200 which is carried on a delivery tube 380 which is disposed within the shaft 12. Carrier tube 380 may be axially translated as shown by arrow 204 and/or rotated as shown by arrow 206 so that the fluid stream 208 emanating from the nozzle 200 can be scanned or rastered over all or a selected portion of the urethra within the prostate. Specific pressures and other details for such high pressure water treatment are described, for example, in Jian and Jiajun, supra.

Figure 5:
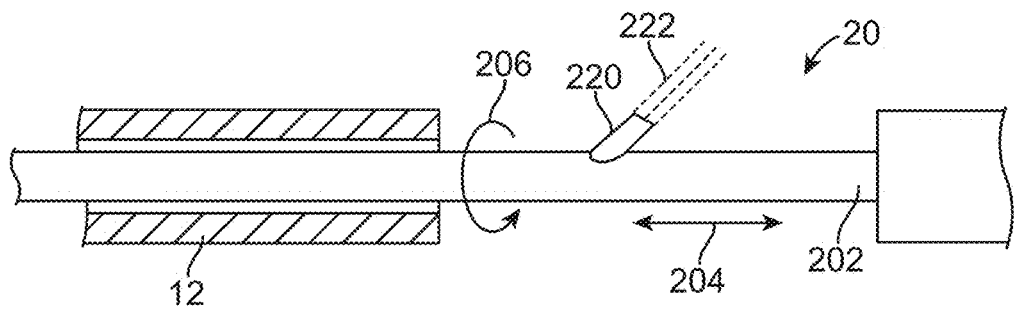
FIG. 5 illustrates an energy source suitable for use in devices of the present invention, wherein the energy source comprises a deflected optical waveguide for delivering laser energy to the prostatic tissue.

Referring now to FIG. 5, the energy source within the energy delivery region 20 may comprise a fiber-optic waveguide or fiber bundle 220 carried on the rotating and translating shaft 380. The optical waveguide 220 transmits laser or other coherent optical energy in a beam 222 which may be scanned or rastered over the urethral wall and prostatic tissue by rotating and/or translating the carrier tube 380.

Figure 6:
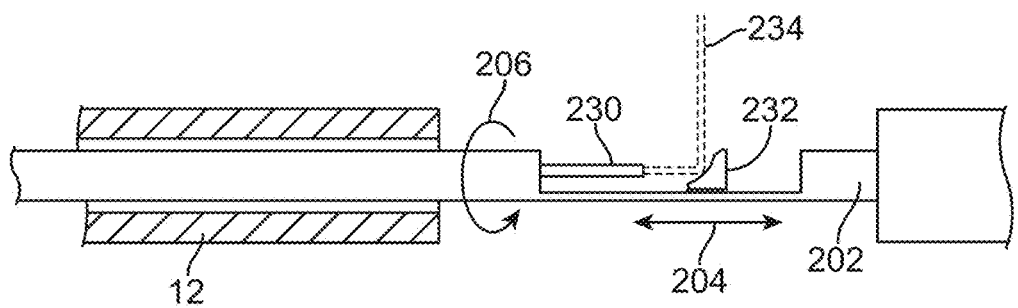
FIG. 6 illustrates a device similar to that shown in FIG. 5, except the optical waveguide directs laser energy at a mirror which laterally deflects the laser energy.

As shown in FIG. 6, laser energy from an optical waveguide or fiber bundle 230 may be directed axially against a mirror 232, where the waveguide and mirror are both carried on the rotating and axially translating carrier tube 380. Again, by rotating and/or translating the carrier tube 380, the emanating beam 234 can be scanned or rastered over the urethral wall.

Figure 7:
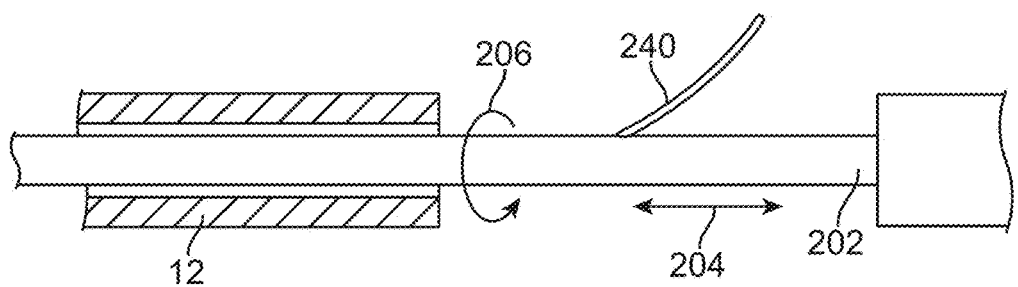
FIG. 7 illustrates an energy source suitable for use in the devices of the present invention, wherein the energy source comprises a laterally projecting electrode which can engage the urethral wall and prostatic tissue to deliver radiofrequency energy for tissue ablation.

Referring now to FIG. 7, in yet another embodiment, the rotating and axially translating tube 380 may carry an electrode 240 which projects laterally from the tube. The electrode 240 will be adapted for connection to a radiofrequency energy source so that, when the electrode contacts the urethral wall and prostatic tissue, radiofrequency energy can be delivered, either in a monopolar or bipolar mode. The radiofrequency energy can thus ablate the tissue over selected volumes and regions of the prostatic tissue. Optionally, by changing the nature of the radiofrequency energy, the electrode 240 could also be used to cauterize the tissue after it has been treated.

In one embodiment of the present invention, the device is configured to selectively resect tissue, causing the removal of some tissue compositions while leaving other tissue compositions intact. For example, the prostate and nearby regions comprise a variety of tissue compositions, including glandular prostate tissue, intra-prostate vessels, fibromuscular stroma, capsular tissue, sphincter muscles, seminal vesicles, etc. When treating BPH or other prostate conditions, it is desirable to remove glandular prostate tissue and leave other tissues, such as vessels and capsular tissue, substantially undamaged.

As referred to herein, the term resection is meant to include any removal of tissue, including removal of one or more conglomerates of tissue cells, removal of fractions of tissue cells, etc.

One advantage of treating BPH by selective tissue resection is the reduced need (or no need) for cauterization, since there is little or no damage to intra-prostate blood vessels and as a result there is limited bleeding. Another advantage is a decreased chance of incontinence or impotence, since selective resection decreases the risk of perforating or otherwise damaging surrounding tissues, such as the prostate capsule, sphincter muscles, seminal vesicles, etc.

When using a fluid stream to resect tissue, selective tissue resection may be accomplished by varying one or more parameters of the fluid stream, such as the pressure within a nozzle or other fluid delivery element, or the flow rate of the fluid in the stream, so that it resects some tissue compositions while leaving other tissue compositions substantially undamaged.

In one embodiment, the fluid stream parameters may be configured to leave non-target tissues substantially undamaged even when those tissues are exposed to the fluid stream for an extended period of time, i.e., typically a period of time that is sufficient to achieve the desired resection. In another embodiment, the fluid stream parameters may be configured to resect the target tissue at a substantially higher rate than the non-target tissue, thereby limiting damage to non-target tissue. Such parameters may be adjusted, depending on the target tissue that is to be selectively resected.

In one embodiment, the rate of resection is configured to be higher for glandular tissue than for non-glandular tissue. The rate of resection may be configured by altering the pressure of the fluid, or by adjusting other fluid parameters, as described above. In particular, the rate of resection for glandular tissue may be configured to be significantly higher than that for non-glandular tissue, such that during the treatment period non-glandular tissue remains effectively undamaged. For example, the rate of resection of glandular tissue may be configured to be at least twice as high as that for non-glandular tissue. As another example, the rate of resection for glandular tissue may be configured to be at least 10 times as high as that for non-glandular tissue.

It is noted that tissue resection has a critical pressure (which is a pressure below which tissue does not resect and above which tissue can be resected) because the removal process involves tearing of the tissue, wherein tissue is stretched on a micro scale to the point where the tissue matrix ruptures or tears. Since tissue is elastic, there will be a critical breaking point. Different types of tissue will have different critical breaking points, and hence different critical pressures associated with them.

Indeed, given a particular fluid delivery element size (such as nozzle diameter), each tissue type typically has a critical pressure of the fluid stream source (hereinafter also referred to as Pcrit) below which the rate of resection approaches zero, and above which the rate of resection generally increases monotonically, and possibly exponentially. Specifically, due to differences in tissue composition, the pressure of the fluid stream source may be configured to selectively resect a particular type of tissue while leaving other tissue types with higher critical pressures generally undamaged.

Figure 8:
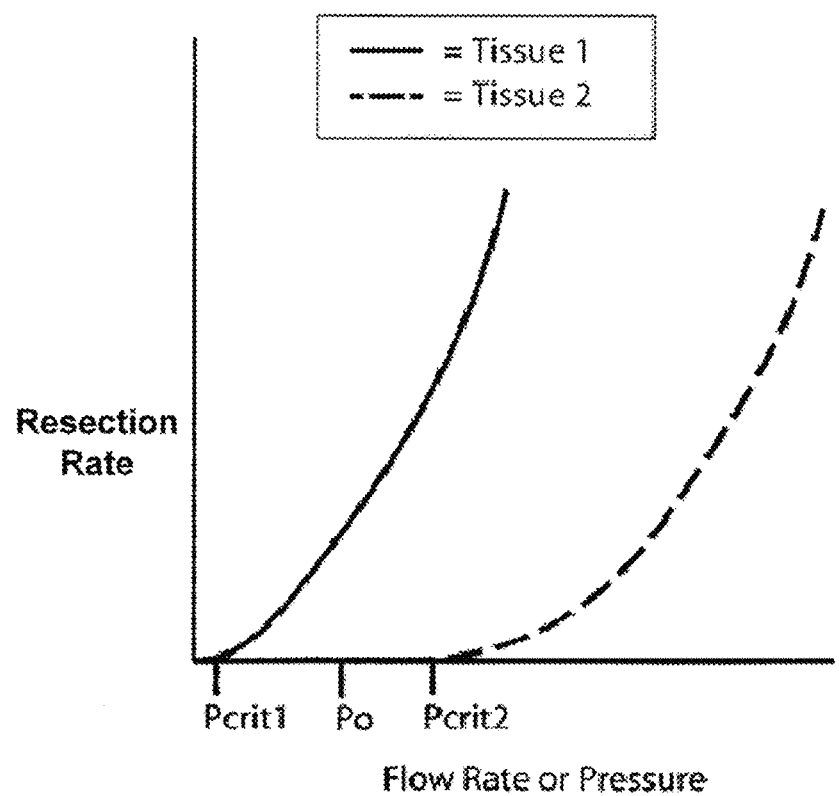
FIG. 8 is a graph of tissue resection rates demonstrating critical pressures.

An important aspect of resecting tissue in a multi-tissue environment according to the present embodiments is that it is possible to operate in a regime where one tissue type is resected and another tissue type remains substantially undamaged. This happens most strongly when operating at a pressure between the critical pressures of the two tissue types. As seen in FIG. 8, the operating pressure p0 of the fluid stream may be configured to be greater than the critical pressure of tissue 1 (/>,, >pcriti) so that tissue 1 experiences a resection rate that is greater than zero, while keeping the pressure p0 less than the critical pressure of tissue 2 (p0<pcrit2) so that tissue 2 experiences a rate of resection that is substantially near zero. In such a configuration, the fluid stream is said to be configured to selectively resect tissue 1 but not tissue 2.

In one embodiment configured to treat BPH, the fluid stream source pressure is configured to be above the critical pressure of glandular prostate tissue but below the critical pressure of non-glandular prostate tissue. In such an embodiment, the pressure is sufficiently high to resect glandular tissue, but too low to substantially resect or damage non-glandular tissue such as intra-prostate blood vessels, fibromuscular stroma, capsular tissue, etc. In one embodiment, the fluid is pressurized to a pressure within the range of about 1-30,000 psi before leaving the fluid delivery element, more preferably to a pressure within the range of about 50-1,500 psi, and most preferably to a pressure within the range of about 100-1,000 psi.

The following example illustrates some tissue critical pressures for fluid stream resection. It is noted that the following configurations are provided as an example and should not be construed as limiting.

EXAMPLE 1: Exemplary Critical Pressures of Different Kidney Tissue Compositions Tissue critical pressures were measured in pig kidneys. Kidney tissue was chosen because its composition is similar to that of the prostate tissue. A columnar fluid stream of approximately 200 microns in diameter was used for tissue resection. The glandular tissue (the pink outer portion of the kidney) is very soft, and easily tears with finger pressure, while the inside of the kidney comprises tougher vascular tissue. The critical pressure for the glandular tissue with this fluid stream was found to be about 80 psi, and about 500 psi for the vascular tissue, as seen in Table 1 below.

Table 1 of Different critical pressures of glandular and vascular tissues in pig kidney.

| Tissue | $P_{crit}$ (psi) |
|---|---|
| Glandular | 80 |
| Vascular | 500 |

For example, experiments show that when resecting pig kidney using a nozzle of approximately 200 microns in diameter with liquid source pressure of about 500 psi, the rate of resection over a 10 cm area is about 1 cm per 30 sec for glandular tissue (i.e., removal of 10 cc per 30 sec), and less than about 0.1 cm per 180 sec for vascular tissue, which is about a sixty-fold difference in resection rates. Thus, within the same resection time period, more glandular tissue will be resected than vascular tissue. Thereby, the resection time period can be configured to allow resection of glandular tissue without substantial damage to vascular tissue. The rate of resection may be adjusted by varying the fluid source pressure and/or the size of the nozzle. For example, the rate of resection for glandular tissue may be adjusted to about 1 cc per min, 5 cc per min, 10 cc per min, 30 cc per min, or other rates. As noted above, it is understood herein that varying the size of the nozzle may necessitate varying the fluid source pressure in order to cause the fluid stream to impinge with sufficient force upon tissue to achieve desired resection rates.

Figure 9A:
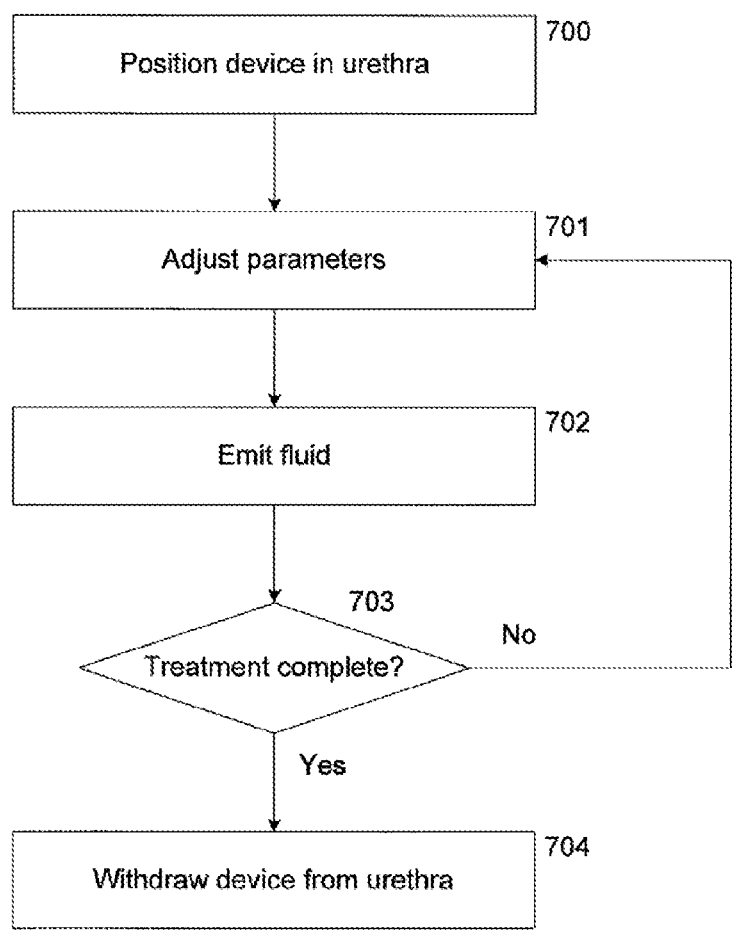
FIG. 9A is a flow diagram illustrating selective and controlled resection.

FIG. 9A is a flow diagram illustrating a method for selective prostate resection, according to one embodiment. At step 700, the device is positioned and anchored in the urethra, as described above. At step 701, various fluid parameters such as the pressure of the fluid source, shape of the fluid stream, etc., are configured to resect a specific tissue type, such as glandular prostate tissue. By configuring the fluid parameters one can control fluid force, rate of resection, treatment time, area of tissue to be resected, etc., in order to achieve controlled and selective resection. After the parameters are configured, at step 702, the device is configured to discharge a fluid stream to resect the target tissue. At step 703, if it is determined that the treatment is complete, the device is withdrawn from the urethra U at step 704.

However, if at step 703 it is determined that the treatment is not yet complete, then the fluid parameters may be re-configured as needed, as described in step 701, and the cycle of steps repeats until treatment is complete. In particular, re-configuration of the fluid parameters is advantageous in an embodiment where it is desired to resect two different types of tissues for a complete treatment. In such an embodiment, the fluid parameters may be adjusted to take into account the change in the type of target tissue that is to be resected.

Typically, after some or all of the glandular tissue has been resected, other tissue types such as vascular or capsular tissue will be exposed to the fluid stream. While the fluid stream parameters are configured to selectively resect glandular tissue, it is also contemplated that the fluid parameters may be dynamically adjusted during the resection procedure to take into account the gradual exposure of non-glandular tissue and to fine-tune the resection selectivity as needed. After the fluid parameters are thusly re-configured at step 701, then at step 702 the re-configured fluid stream is emitted to continue tissue resection, and the operation continues until the treatment is complete.

Specifically, it is noted that when treating the prostate from within the urethra, the urethral wall is interposed between the source of the fluid stream (such as a nozzle or other fluid delivery element) and the target glandular prostate tissue that is to be resected.

Therefore, in one embodiment, the fluid stream parameters are initially configured to resect and penetrate a portion of urethral tissue (e.g., the urethral wall). However, since the composition of glandular prostate tissue is weaker than that of the urethral tissue, it is desirable to avoid resecting glandular tissue with the same fluid stream force as that used to resect the urethral wall. To accomplish this, the fluid stream may be used for a period of time that is sufficient to resect and penetrate the urethral wall, and not longer. Thereafter, a fluid stream of reduced strength may be used to resect glandular prostate tissue.

Figure 9B:
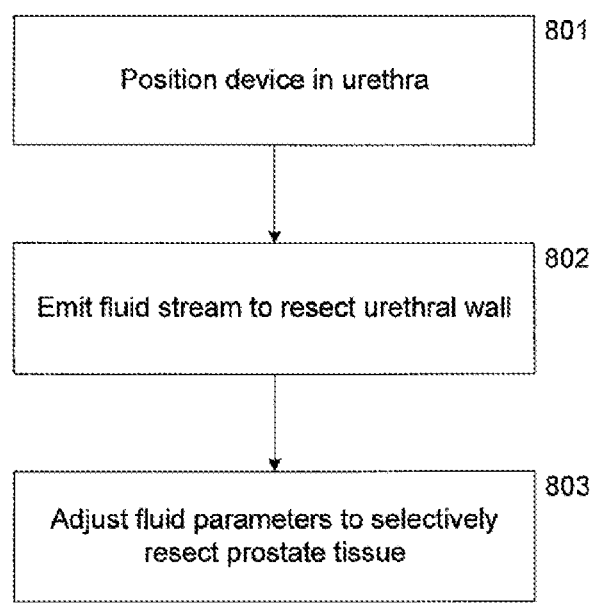
FIG. 9B is a flow diagram illustrating selective resection, wherein the fluid stream is configured to penetrate the urethral wall and resect the prostate tissue.

FIG. 9B is a flow diagram illustrating a method for selective prostate resection, wherein the fluid stream is configured to first penetrate and resect the urethral wall, according to one embodiment. At step 801, the device is positioned and anchored in the urethra, as described above. At step 802, the device is configured to discharge a fluid stream of sufficient force to resect and penetrate the urethral wall. At step 803, after the fluid stream has penetrated the urethral wall, the fluid stream is adjusted to a level that selectively resects the desired prostate tissue while leaving intra-pro state blood vessels, capsules, and other non-glandular tissue substantially undamaged.

In addition, it is contemplated that the shape of the fluid stream also affects selective resection. While the fluid stream is exemplarily shown in FIG. 10A as a columnar fluid stream 333 or diverging fluid stream 334, it is contemplated that the fluid stream may be of any shape or configuration that allows resection according to the present embodiments. In particular, there are numerous advantages to both the columnar fluid stream configuration and the diverging fluid stream configuration, as will be described further below.

In a columnar fluid stream configuration 333, the device emits the fluid stream as a substantially focused rod-like fluid column that has a substantially zero divergence angle. In one embodiment, the columnar fluid stream is configured as a generally straight or non-diverging fluid stream. In such configuration, the device emits the fluid stream substantially as a cylinder or other non-diverging shape, thereby transmitting energy to the tissue over an area or spot size that is largely independent of the tissue distance from the fluid delivery element. Optionally, the fluid stream may be adjusted to converge, for example if the fluid delivery element comprises multiple nozzles or if the fluid contains bubbles, in order to focus the energy delivered to tissue.

Figure 10A:
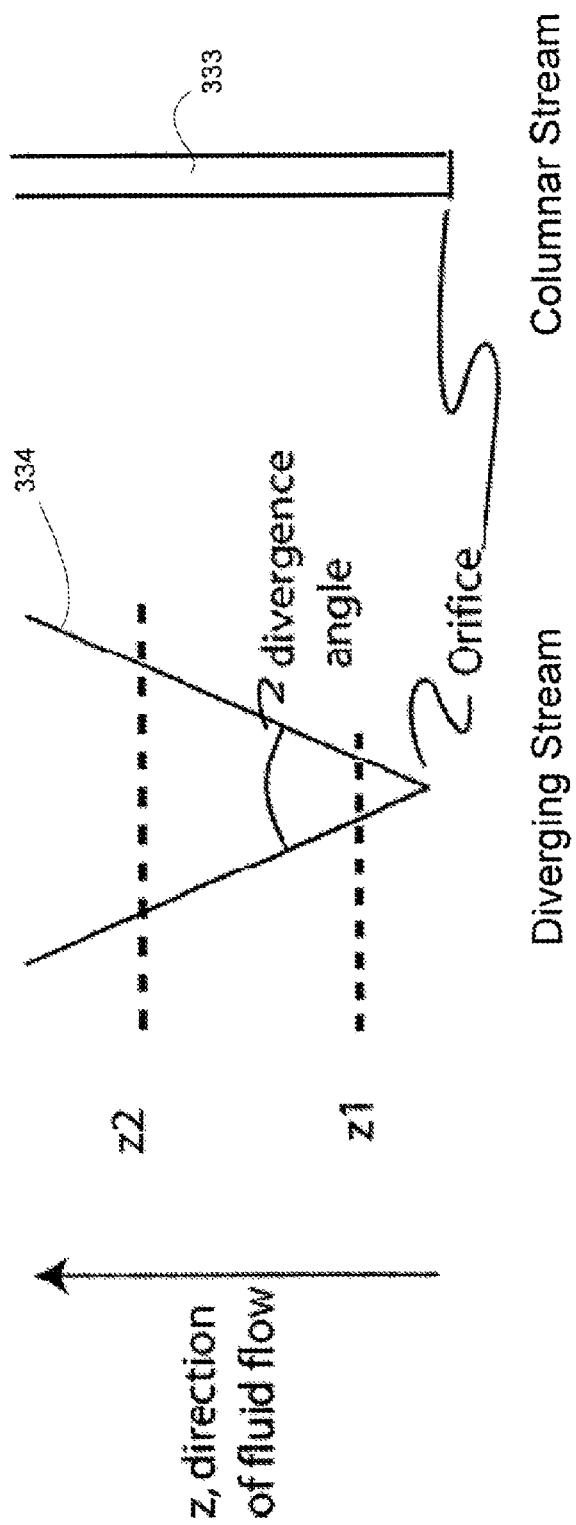
FIG. 10A illustrates a columnar fluid stream and a diverging fluid stream.
Figure 10B:
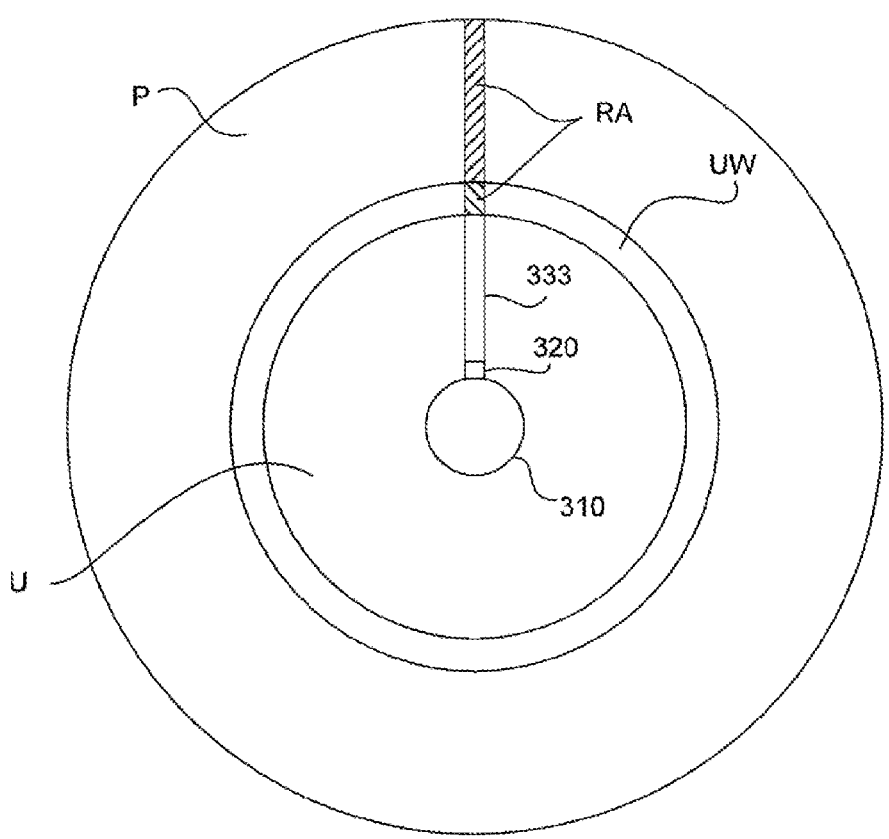
FIG. 10B illustrates a cross-sectional view of a tissue modification device configured to emit a columnar fluid stream.

FIG. 10B shows a cross-sectional view of the device emitting a columnar fluid stream to modify a tissue such as the prostate. An elongate element 310 (such as a shaft, as described above) of the device is disposed within the urethra U. A fluid delivery element 320 disposed on the carrier tube (not shown) within the elongate element 310 is configured to emit a columnar fluid stream 333. As understood herein, the fluid delivery element 320 may comprise a nozzle, as described above, or any other element configured to emit fluid. The columnar fluid stream 333 is configured to resect tissue, such as the urethral wall UW and the prostate tissue P, within a resection area RA.

One characteristic of the columnar fluid stream configuration is that the resection area RA remains substantially constant for some distance from the fluid delivery element 320, since the width of the resection area RA is substantially independent of the fluid distance from the fluid delivery element 320. This is advantageous because the resection area RA remains focused and constant as the fluid stream 333 travels away from the fluid delivery element 320, thereby transmitting energy to the tissue at a focal area. The concentration of energy within a focused resection area RA is particularly advantageous when resecting or penetrating tough tissue, such as the urethral wall UW. In one embodiment, the columnarity of the fluid stream may be varied by introducing pressure fluctuations in the fluid delivery. For example, the columnarity of the fluid stream may be varied by mechanically and controllably introducing a generally solid object in the fluid delivery path, such as behind an aperture of the fluid delivery element 320 or in the path of the fluid stream after it exits an aperture of the fluid delivery element 320. In another example, the columnarity of the fluid stream may be varied by introducing a vibrating element in the fluid pathway, such as a piezoelectric element or the like, to create pressure fluctuations.

In another embodiment, the fluid stream is configured as a diverging fluid stream 334, as seen in FIG. 10A. A diverging fluid stream 334 is one in which the fluid exits a fluid stream source, such as the fluid delivery element 320, and diverges substantially in a cone, wherein the tip of the cone is at the fluid stream source. The rate of resection of a diverging fluid stream 334 can be represented as a function of the distance z from the fluid emitting fluid delivery element 320 to the tissue that is to be resected. As shown in FIG. 10A, z^ is further away from the orifice than z/, and accordingly the rate of resection at z/is higher than the rate of resection at z¯.

The diverging fluid stream 334 may be characterized by the angle of divergence of the fluid stream. In one embodiment, the angle of divergence is configured to be about 0-90 degrees, more preferably about 2-45 degrees, more preferably about 4-20 degrees, and most preferably about 7 degrees, while it is also contemplated that the angle of divergence may be varied as needed.

Additionally, the diverging fluid stream 334 may be characterized by the cross-sectional shape of the fluid stream. Generally, the diverging fluid stream 334 has a cross-sectional area, or spot-size, that increases at distances further from the fluid stream source (e.g., fluid delivery element 320), thereby proportionally reducing the force of the fluid stream per unit area. This increase of spot-size generally results in greater resection rates of tissue closer to the fluid stream source.

In one embodiment, the cross-sectional shape of the diverging fluid stream 334 is configured as a generally narrow rectangle (for a fan-shaped fluid stream). In another embodiment, the cross-sectional shape of the diverging fluid stream 334 is configured as generally a circle (for a conical-shaped fluid stream), wherein the smallest cross-sectional area is at the fluid stream source. It is noted that the cross-sectional shape of the diverging fluid stream 334 may be configured as any shape that encloses a non-zero area (e.g., an ellipse, or an irregular shape).

Figure 10C:
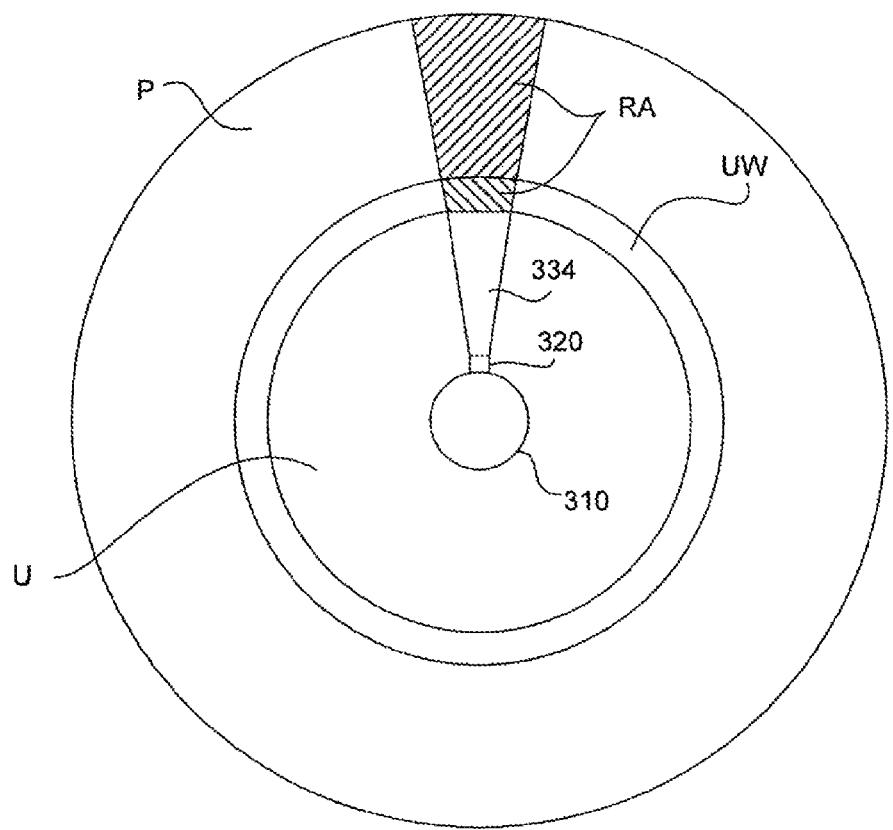
FIG. 10C illustrates a cross-sectional view of a tissue modification device configured to emit a diverging fluid stream.

FIG. 10C shows a cross-sectional view of the device emitting a diverging fluid stream to modify tissue such as the prostate. An elongate element 310 of the device is disposed within the urethra U. A fluid delivery element 320 disposed on the carrier tube (not shown) within the elongate element 310 is configured to emit a diverging fluid stream 334. The diverging fluid stream 334 is configured to resect tissue such as the urethral wall UW and the prostate tissue P within a resection area RA. The resection area RA covered by the diverging fluid stream 334 increases as the fluid stream travels away from the fluid delivery element 320, thereby proportionally reducing the strength of the fluid stream per unit area.

A characteristic of the diverging fluid stream 334 is that the resection width increases as a function of distance from the fluid delivery element 320, while the rate of resection per unit area decreases as a function of distance from the fluid delivery element 320. This is because the total energy delivered in the fluid stream is generally constant (not taking into account any decrease in fluid speed), yet the energy is delivered over a larger area. Thus, the energy delivered per area decreases, which is a key parameter upon which the rate of resection depends. Therefore, the rate of resection per unit area decreases as a function of distance.

Furthermore, in a diverging fluid stream 334 the volumetric rate of resection may be substantially constant as a function of distance. That is, while the rate of resection per unit area decreases, the total area resected increases proportionately, and hence the total resected volume remains substantially constant. It is noted that if the areal rate of resection as a function of areal energy density is non-linear and monotonically increasing with energy, then the volumetric rate of resection will decrease as function of distance from the fluid delivery element 320. It is further noted that any slowing of the fluid stream particles (for example, liquid droplets) will also decrease the volumetric resection rate as a function of distance.

Referring now to FIG. 11, the device comprises an elongate element 310, such as a shaft, configured to be inserted into a body region. The elongate element 310 comprises a window exposing a carrier tube 380 and other components described below. The window reveals a carrier tube 380 and a high pressure fluid delivery element 320 disposed on the carrier tube 380. The fluid delivery element 320 is connected to a fluid source (not shown) via a fluid lumen 390 which delivers fluid from the source to the fluid delivery element 320.

Optionally, when the elongate element 310 is introduced through the urethra, the elongate element 310 may be covered by a sheath or other cover (not shown). When fully covered with the sheath, the window is protected so that it reduces scraping and injury to the urethra as the elongate element 310 is advanced. Once in place, the sheath is retracted, exposing the window. The carrier tube 380 may then be rotated and advanced and/or retracted so that the fluid is delivered through the fluid delivery element 320.

Additionally and optionally, the device may comprise a shield element (not shown) that is positioned to substantially cover the fluid delivery element 320 while maintaining a space between the fluid delivery element 320 and the shield element. This in return effectively maintains that space between the fluid delivery element 320 and any tissue that might impinge on the shield element. In one embodiment, the shield element is a substantially flat sheet-like element positioned over the fluid delivery element 320. The shield element is positioned or shaped such that it allows the carrier tube 380 to move within the elongate element 310 as needed. For example, the shield element may be curved to follow a curvature of the carrier tube 380. The shield element comprises an opening to allow the fluid stream emitted by the fluid delivery element 320 to travel unobstructed through the opening and impinge on the tissue. The opening may be circular, or it may comprise other shapes. One advantage of such a shield element is that it protects the fluid delivery element 320 from being damaged during insertion or removal procedures and/or during treatment. Another advantage of the shield element is that, during or after fluid emission, fluids that are returning back towards the fluid delivery element 320 may travel through the shield element opening (or through other paths around the shield element) and into the space between the shield element and the fluid delivery element 320. Such returned fluids may then be channeled out of that space such that fluid emission is not obstructed or hindered by such returned fluids.

The shield element may further be configured such that the space between the shield element and the fluid delivery element 320 is in continuous communication with a waste disposal lumen via a low-flow-resistance fluid path. This creates a low-flow-resistance path between the fluid delivery element 320 and an external destination of such waste, such that waste and fluids leaving the fluid delivery element 320 may easily leave the region surrounding the fluid delivery element 320. Low resistance in this case is understood to mean a flow resistance that is lower in comparison with a flow resistance of the fluid delivery element 320. This configuration advantageously prevents back-pressure at the fluid delivery element 320, which would otherwise reduce flow, and thereby allows the fluid stream emitted by the fluid delivery element 320 to travel substantially undisturbed by waste and return fluids.

The fluid delivery element 320 may be a single nozzle, a plurality of nozzles, or an array of nozzles of various configurations. The fluid delivery element 320 is configured to emit a fluid radially outwardly as a fluid stream 331, with sufficient force so that upon contact with the tissue the fluid stream 331 resects the tissue. The fluid stream 331 may be perpendicular to the elongate element 310, or it may be configured to be at various angles relative to the elongate element 310.

The carrier tube 380 may be axially translated, rotated, oscillated, or rotationally oscillated relative to the elongate element 310 so that the fluid stream 331 can be scanned or rastered to resect a desired area or volume of the tissue. The desired area or volume may be spherical, cylindrical, or any other predetermined area or volume of arbitrary shape and dimension.

Additionally and optionally, when the device is not being used to resect tissue, the carrier tube 380 may be positioned so that the fluid delivery element 320 and/or any other elements (such as visualization or cauterization elements) are positioned away from the window, thereby reducing the risk of damage to such elements, as well as reducing any risk of unintentional resection of the tissue.

The device further comprises at least one insufflation port 340 disposed on the elongate element 310. The insufflation port 340 is connected via one or more lumens to an insufflation source (not shown), wherein the insufflation source delivers a fluid 330 into the body region through the insufflation port 340 in order to expand the surrounding tissue and create a working space. The device further comprises at least one removal port 360 for the removal of debris products, such as resection products, resection fluid, other waste products, or a mixture thereof. The elongate element 310 may include lumens, passages, electrically conductive wires, and the like, configured to deliver energy and/or materials from the proximal end to the distal end of the elongate element 310 and/or to remove debris and waste products, details of which are described above.

Optionally, in addition to the fluid delivery element 320, the device may comprise an electromagnetic energy delivery port 350 disposed on the carrier tube 380 and positioned near or within the fluid delivery element 320. Electromagnetic energy 332 is delivered to the energy delivery port 350 by means of one or more conduits 351, such as optical fibers or other waveguides within the carrier tube 380 and the elongate element 310, as also described in greater detail above. The electromagnetic energy 332 may be radiofrequency energy, coherent or non-coherent light, or any other modality of electromagnetic energy. The energy delivery port 350 is configured to deliver the energy 332 through the interior of the fluid stream 331 so that the electromagnetic energy 332 may resect the tissue in lieu of, or in combination with, the fluid resection.

Additionally and optionally, the various electromagnetic energy modalities described above may be configured to cauterize the tissue, in combination with tissue resection, or independently thereof. Since selective tissue resection as disclosed herein generally causes little or no damage to remaining tissue such as vascular tissue and therefore causes limited or no bleeding, such cauterization need only be used on a limited basis, if at all. It is contemplated that when electromagnetic energy is delivered to the tissue by the fluid stream 331 for cauterization, the fluid source pressure may be adjusted to be generally below the critical pressure for tissue resection such that no additional tissue is resected.

Alternatively or additionally, cauterization may be achieved using other means, for example using a cauterizing balloon and/or stent placed in contact with tissue using a catheter device, as described above.

Furthermore, the device may comprise optional deflective elements, for example positioned within the interior or the elongate element 310 and away from the window, configured to deflect fluid, emitted by the fluid delivery element 320, back towards the fluid delivery element 320, thereby removing any debris that may have accumulated on the fluid delivery element 320 and/or energy delivery port 350 during tissue resection. Furthermore, the fluid delivery element 320 in combination with the deflective elements may be configured to clean a part of, or substantially the entirety of, the fluid delivery element 320, any visualization or cauterization elements, and/or carrier tube 380. The deflective element may be configured to be substantially flat or concave. Alternatively the deflective element may be configured as any shape or design.

Additionally, the deflective element may act be configured as a protective element for the fluid delivery element. The fluid delivery element may be positioned at a specific location relative to the protective element that protects the prostate from unexpected fluid emissions and protects the fluid delivery element 320 from, for example, clogging or obstruction by tissue, especially during insertion and removal from the body.

The carrier tube 380 comprises a carrier. The carrier may optionally comprise a tubular structure. Although reference is made to a carrier tube 380 in accordance with embodiments, the carrier may comprise a substantially non-tubular cross-section, for example a rectangular cross section, extending along a substantial portion of the carrier as described herein. Therefore, it is to be understood that although the carrier tube shown and described in the drawings, the carrier may comprise a non-circular carrier in each of the drawings and supporting text as described herein.

Figure 12:
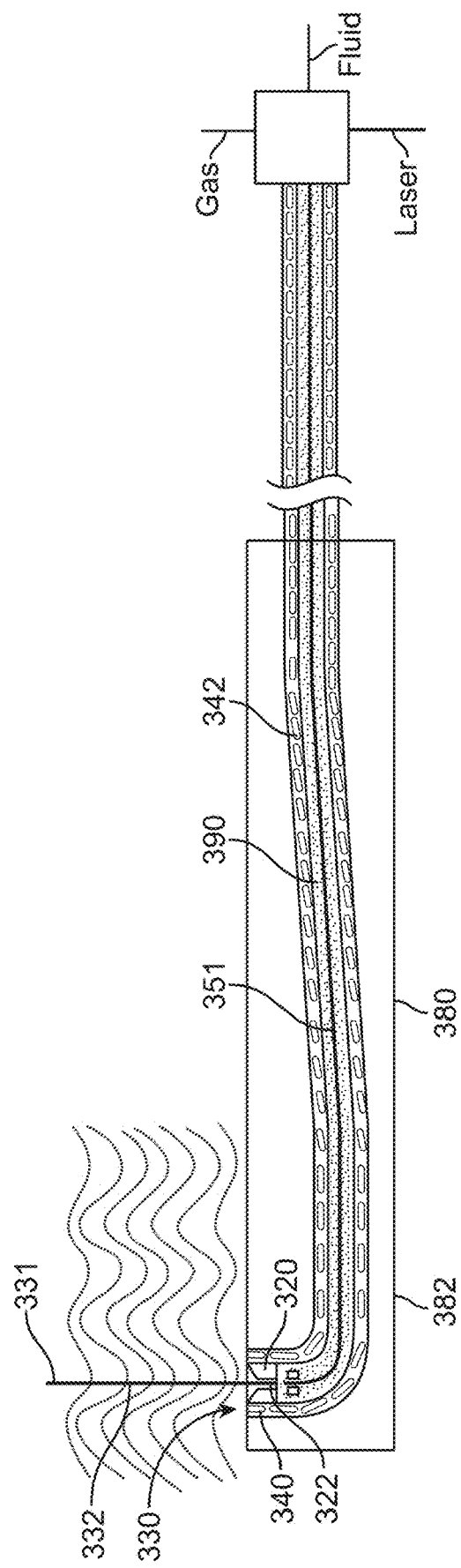
FIG. 12 shows a component of the treatment probe in accordance with embodiments.

FIG. 12 shows a component of treatment probe 350 in accordance with embodiments. A carrier tube 380 comprises a concentric configuration of a first fluid delivery port and a second fluid delivery port. Fluid delivery element 320 releases fluid stream 331. Fluid stream 331 defines an axis extending from the fluid delivery element 320 outward. The fluid stream 331 may comprise a diverging stream 334 or a columnar stream 333 as described herein. Fluid delivery element 320 comprises a nozzle 322. Nozzle 322 may comprise a substantially circular cross section. The nozzle 322 may comprise an internal channel having the circular cross section in which the internal channel extends cylindrically. The internal channel extends along an axis corresponding to the axis of the fluid stream 331.

Concentrically disposed around the fluid delivery element 320 is a port 340. The port 340 comprises a substantially annular channel extending circumferentially around fluid delivery element 320 and nozzle 322. Port 340 may comprise an insufflation port as described herein. Port 340 releases fluid 330 in a substantially concentric arrangement with fluid stream 331. The substantially concentric arrangement has the advantage of providing a protective jacket around fluid stream 331 with first fluid 330 extending outward from port 340 so as to beneficially direct the treatment stream toward the tissue. Energy conduit 351 extends from a source of energy such as a laser toward fluid delivery element 320. The energy conduit may comprise an optical fiber or a plurality of optical fibers coupled to a laser, for example. The optical fiber can extend toward nozzle 322 and can be concentrically aligned with the axis defined by nozzle 322 so as to provide efficient energy transmission of the light energy emitted from the optical fiber through the nozzle 322. A structure can be provided near the distal end of the optical fiber in order to align the optical fiber with the channel of nozzle 322. The concentric alignment of the optical fiber, the nozzle and the port 340 can provide therapeutic treatment of the patient that allows visualization and treatment of the patient. The fluid release from port 340 may comprise a liquid, for example saline, or a gas, for example $CO2$. The fluid delivered through port 340 can be user selectable with the interface as described herein.

The fluid stream 331 can provide an optical wave guide directed toward the tissue. In many embodiments the fluid stream 331 comprises an index of refraction greater than the fluid released through port 340. The wave guide media can be a liquid or gas and the jacketing media released from port 340 can be a liquid or gas. An intermediate media can be located between the probe and the target tissue. The intermediate media can be a liquid or gas, for example, one or more of saline, air or carbon dioxide. In many embodiments the intermediate media comprises a fluid release from nozzle 322 and a fluid release from annular port 340.

Figure 13A:
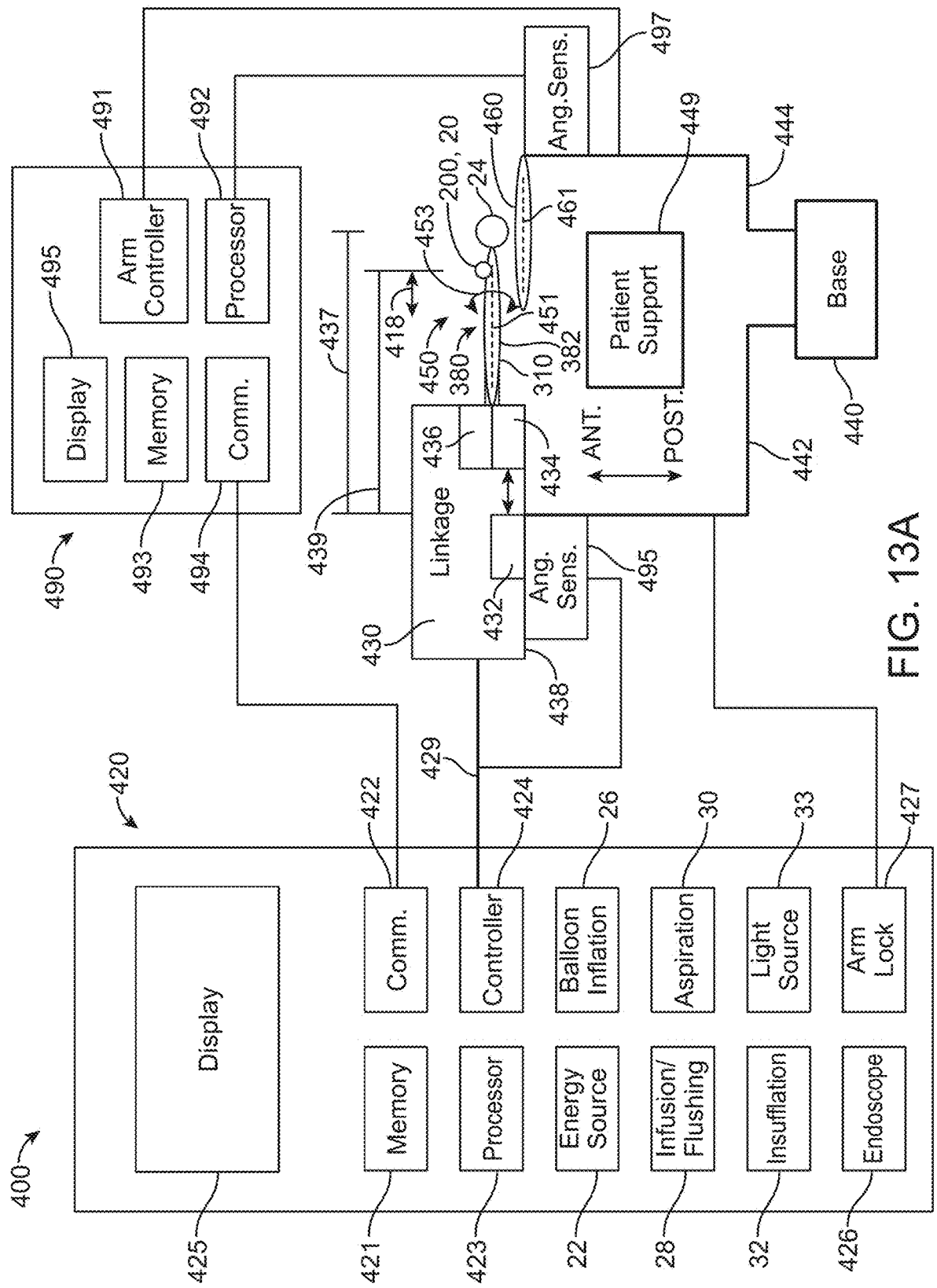
FIGS. 13A and 13B show a system that treat a patient in accordance with embodiments.
Figure 13B:
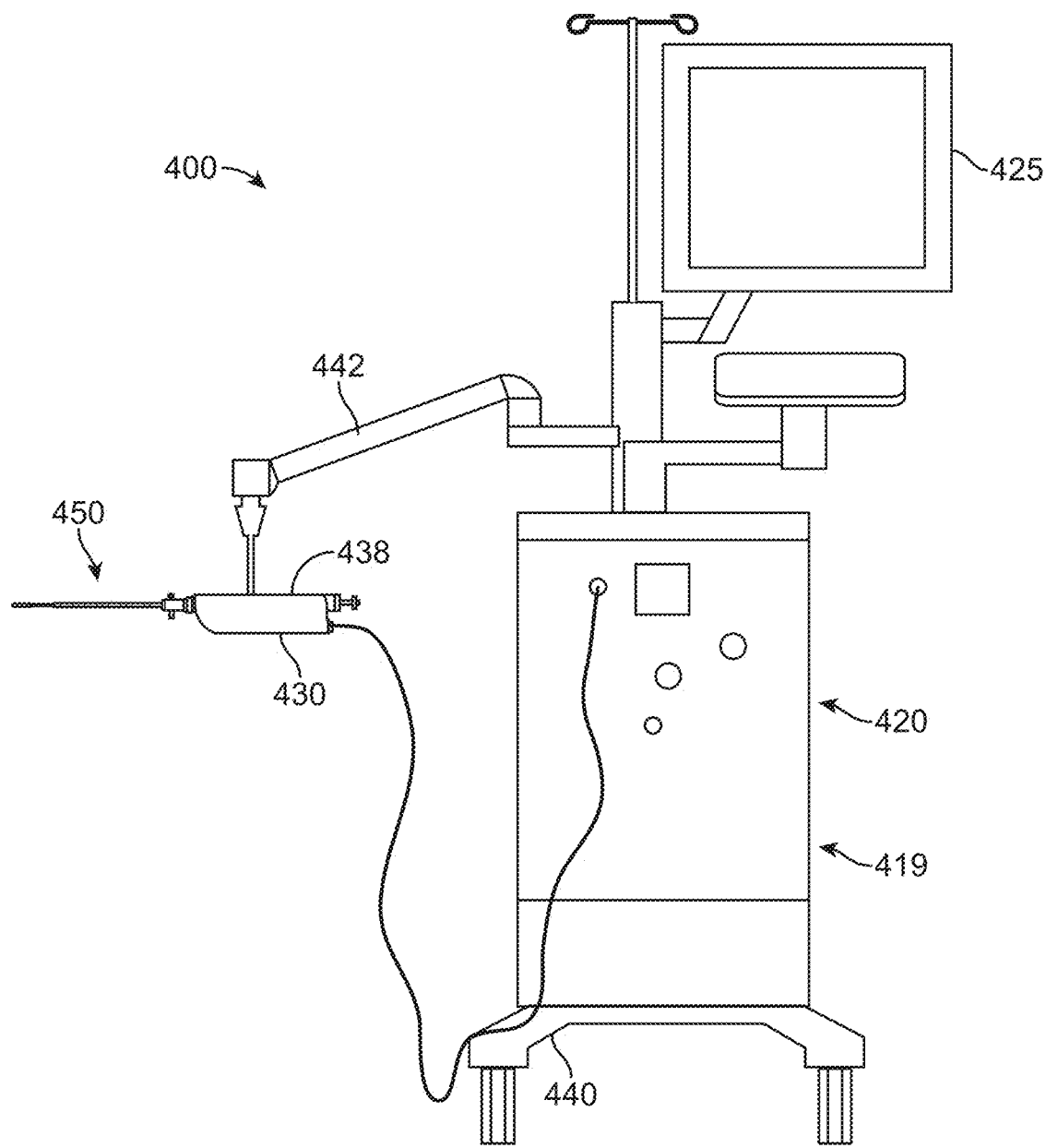

FIGS. 13A and 13B show a system that treat a patient in accordance with embodiments. The system 400 comprises a treatment probe 450 and may optionally comprise an imaging probe 460. The treatment probe 450 is coupled to a console 420 and a linkage 430. The imaging probe 460 is coupled to an imaging console 490. The patient treatment probe 450 and the imaging probe 460 can be coupled to a common base 440. The patient is supported with the patient support 449. The treatment probe 450 is coupled to the base 440 with an arm 442. The imaging probe 460 is coupled to the base 440 with an arm 444.

The patient is placed on the patient support 449, such that the treatment probe 450 and ultrasound probe 460 can be inserted into the patient. The patient can be placed in one or more of many positions such as prone, supine, upright, or inclined, for example. In many embodiments, the patient is placed in a lithotomy position, and stirrups may be used, for example. In many embodiments, the treatment probe 450 is inserted into the patient in a first direction on a first side of the patient, and the imaging probe is inserted into to the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each arm may comprise a substantially unlocked configuration such the probe can be desirably rotated and translated in order to insert the probe into to the patient. When a probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In many embodiments, the treatment probe 450 is coupled to the imaging probe 460. In order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In many embodiments, the arm 442 is a movable and lockable arm such that the treatment probe 450 can be positioned in a desired location in a patient. When the probe 450 has been positioned in the desired location of the patient, the arm 442 can be locked with an arm lock 427. The imaging probe can be coupled to base 440 with arm 444, can be used to adjust the alignment of the probe when the treatment probe is locked in position. The arm 444 may comprise a lockable and movable probe under control of the imaging system or of the console and of the user interface, for example. The movable arm 444 may be micro-actuable so that the imaging probe 440 can be adjusted with small movements, for example a millimeter or so in relation to the treatment probe 450.

In many embodiments the treatment probe 450 and the imaging probe 460 are coupled to angle sensors so that the treatment can be controlled based on the alignment of the imaging probe 460 and the treatment probe 450. An angle sensor 495 is coupled to the imaging probe 450 with a support 438. An angle sensor 497 is coupled to the imaging probe 460. The angle sensors may comprise one or more of many types of angle sensors. For example, the angle sensors may comprise goniometers, accelerometers and combinations thereof. In many embodiments, angle sensor 495 comprises a 3-dimensional accelerometer to determine an orientation of the treatment probe 450 in three dimensions. In many embodiments, the angle sensor 497 comprises a 3-dimensional accelerometer to determine an orientation of the imaging probe 460 in three dimensions. Alternatively or in combination, the angle sensor 495 may comprise a goniometer to determine an angle of treatment probe 450 along an elongate axis of the treatment probe. Angle sensor 497 may comprise a goniometer to determine an angle of the imaging probe 460 along an elongate axis of the imaging probe 460. The angle sensor 495 is coupled to a controller 424. The angle sensor 497 of the imaging probe is coupled to a processor 492 of the imaging system 490. Alternatively, the angle sensor 497 can be coupled to the controller 424 and also in combination.

The console 420 comprises a display 425 coupled to a processor system in components that are used to control treatment probe 450. The console 420 comprises a processor 423 having a memory 421. Communication circuitry 422 is coupled to processor 423 and controller 422. Communication circuitry 422 is coupled to the imaging system 490. The console 420 comprises components of an endoscope 35 is coupled to anchor 24. Infusion flashing control 28 is coupled to probe 450 to control infusion and flushing. Aspiration control 30 is coupled to probe 450 to control aspiration. Endoscope 426 can be components of console 420 and an endoscope insertable with probe 450 to treat the patient. Arm lock 427 of console 420 is coupled to arm 422 to lock the arm 422 or to allow the arm 422 to be freely movable to insert probe 450 into the patient.

The console 420 may comprise a pump 419 coupled to the carrier and nozzle as described herein.

The processor, controller and control electronics and circuitry can include one or more of many suitable components, such as one or more processor, one or more field-programmable gate array (FPGA), and one or more memory storage devices. In many embodiments, the control electronics controls the control panel of the graphic user interface (hereinafter "GUI") to provide for pre-procedure planning according to user specified treatment parameters as well as to provide user control over the surgery procedure.

The treatment probe 450 comprises an anchor 24. The anchor 24 anchors the distal end of the probe 450 while energy is delivered to energy delivery region 20 with the probe 450. The probe 450 may comprise a nozzle 200 as described herein. The probe 450 is coupled to the arm 422 with a linkage 430.

The linkage 430 comprises components to move energy delivery region 20 to a desired target location of the patient, for example, based on images of the patient. The linkage 430 comprises a first portion 432 and a second portion 434 and a third portion 436. The first portion 432 comprises a substantially fixed anchoring portion. The substantially fixed anchoring portion 432 is fixed to support 438. Support 438 may comprise a reference frame of linkage 430. Support 438 may comprise a rigid chassis or frame or housing to rigidly and stiffly couple arm 442 to treatment probe 450. The first portion 432 remains substantially fixed, while the second portion 434 and third portion 436 move to direct energy from the probe 450 to the patient. The first portion 432 is fixed to the substantially constant distance 438 to the anchor 434. The substantially fixed distance 438 between the anchor 24 and the fixed first portion 432 of the linkage allows the treatment to be accurately placed. The first portion 434 may comprise the linear actuator to accurately position the high pressure nozzle in treatment region 20 at a desired axial position along an elongate axis of probe 450.

The elongate axis of probe 450 generally extends between a proximal portion of probe 450 near linkage 430 to a distal end having anchor 24 attached thereto. The third portion 436 controls a rotation angle around the elongate axis. During treatment of the patient, a distance 439 between the treatment region 20 and the fixed portion of the linkage varies with a reference distance 439. The distance 439 adjusts in response to computer control to set a target location along the elongate axis of the treatment probe referenced to anchor 24. The first portion of the linkage remains fixed, while the second portion 434 adjust the position of the treatment region along the axis. The third portion of the linkage 436 adjusts the angle around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging system 490, a memory 493, communication circuitry 494 and processor 492. The processor 492 in corresponding circuitry is coupled to the imaging probe 460. An arm controller 491 is coupled to arm 444 to precisely position imaging probe 460.

Figure 14A:
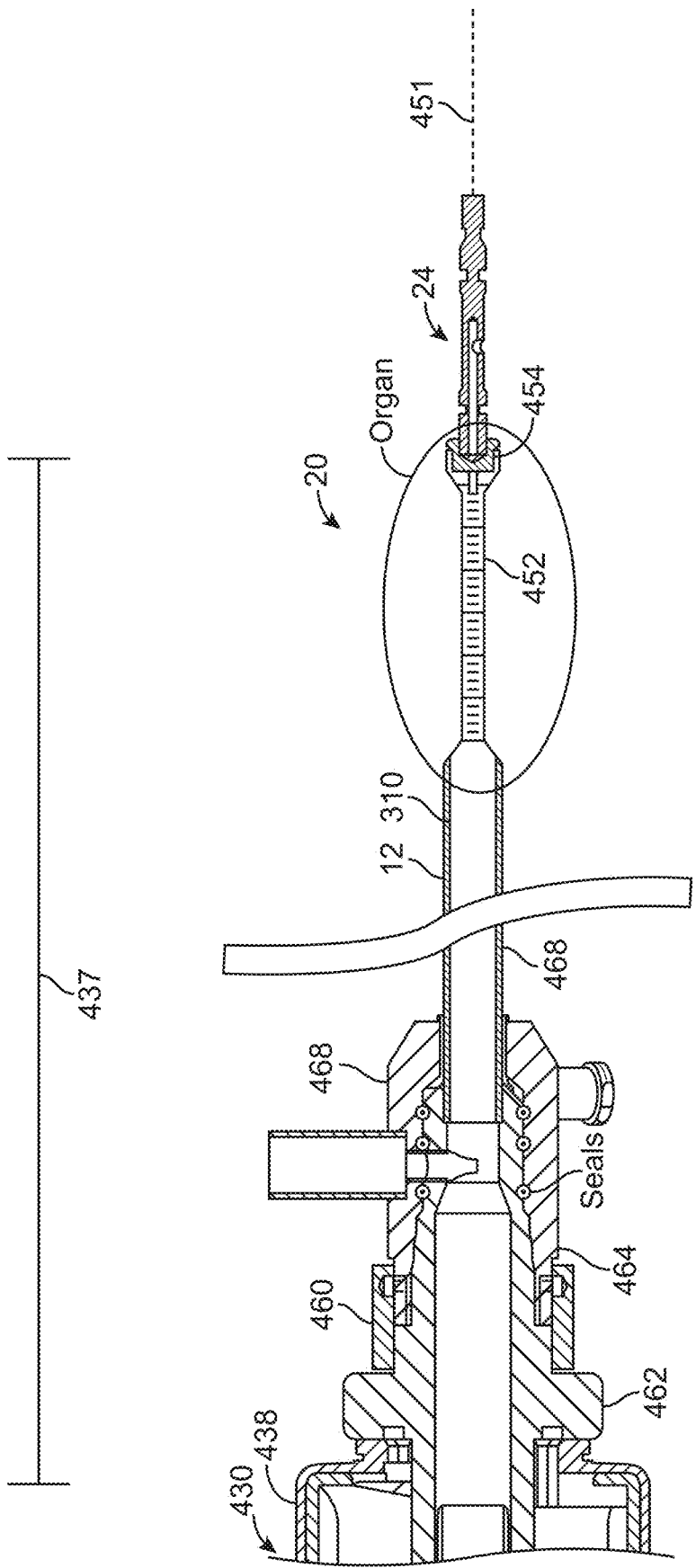
FIG. 14A shows a multipurpose sheath and manifold in accordance with embodiments.

FIG. 14A shows a multipurpose sheath and manifold in accordance with embodiments. A manifold 468 is configured to transmit a plurality of fluids to and from the working site. Manifold 468 is rigidly coupled, for example affixed, to the spine 452. A sheath 458 is located around spine 452 and can extend inward toward the manifold 468. The manifold 468 is coupled with a locking element 460 to support 438 in linkage 430. Manifold 468 can be decoupled from the linkage 430 and the support 438 so as to remove the linkage 430 and support 438 to permit additional components to be inserted into the working channel. For example, an endoscope can be inserted into the working channel to extend toward the working area of the organ, for example, the prostate. A structure 462 comprising a nose portion extends toward manifold 468. Structure 462 is shaped to engage manifold 468 and allow removal of structure 462, linkage 430 and support 438 when locking element 460 is disengaged. Manifold 468 comprises a structure 464 to engage in nose portion of structure 462. A plurality of seals are arranged on manifold 468 to allow removal of structure 462. When structure 462 has been removed an endoscope or other surgical tool can be inserted into the working space and advance toward the treatment site. For example an endoscope can be advanced toward the treatment site to be the treatment area. The manifold comprises a plurality of ports that are coupled to the treatment site to allow fluid to be transmitted and removed from the treatment site. For example when an endoscope has been placed at the treatment site. The locking element and manifold allow for removal of the linkage and treatment probes such that the manifold 468 remains coupled to sheath 458 and spine 452 within the patient.

In many embodiments treatment probes and carriers as described herein, for example tubular carriers, can be inserted and removed while the locking element 460 engages the linkage 430 and support 438. This configuration of the linkage, locking element and support allow probes to be rapidly and easily removed and reinserted to provide beneficial treatments.

The multipurpose sheath and manifold as described herein has the benefit of allowing the sheath, manifold, spine and anchor to remain attached to the patient while additional surgical tools are employed. The locking element interfaces with multiple instruments allowing for placement, visualization, and Aquablation™ and aquabeam operations, without reintroduction or movement with respect to the tissue. Multiple sealed conduits allow for sheath ports to be used to transmit flow or pressure of varying fluids within or parallel to the working channel. The working channel may be used for visualization access to anatomy via existing rigid or flexible endoscope technology. The working channel has a large bore to accommodate many types of tools and allow for free flow of tissue and fluids. Alternate energy delivery devices may be used within the sheath or working channel as described herein.

In many embodiments the working channel is sized to allow a plurality of carriers within the working channel. For example, an endoscope carrier within the working channel and a treatment probe carrier as described herein within the working channel so as to allow visualization of the treatment site while the treatment probe performsAquablation™ and aqua beam operations as described herein.

Figure 14B:
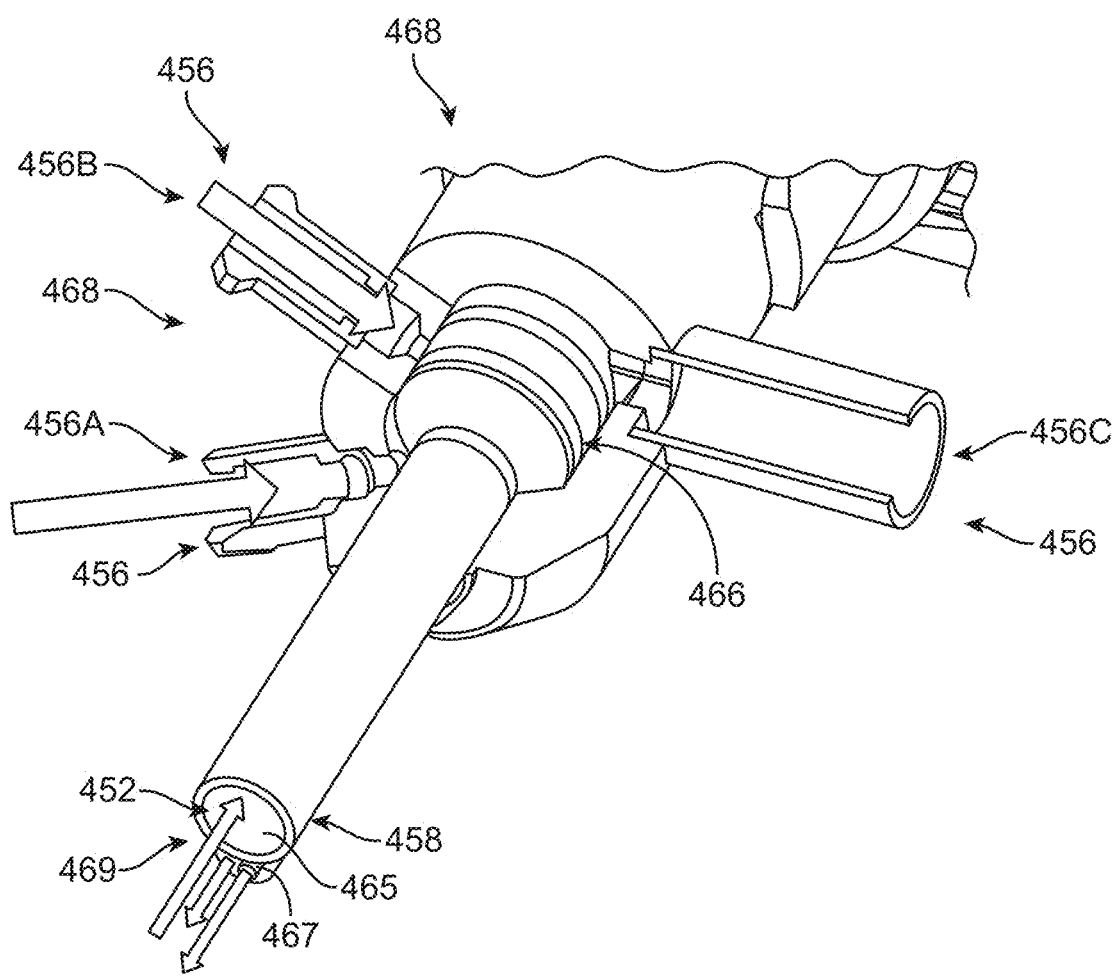
FIG. 14B shows manifold conduits of the manifold as in FIG. 14A configured for transmit and reception of multiple fluids while the manifold remains coupled to the patient in accordance with embodiments.

FIG. 14B shows manifold conduits of the manifold configured for transmitting and receiving multiple fluids while the manifold remains coupled to the patient. The manifold is coupled to a plurality of ports 456. The plurality of ports 456 may comprise an auxiliary fluid port 456A, a balloon pressure port 456B and a tissue removal port 456C. A sheath 458 extends circumferentially around spine 452. The spine 452 and sheath 458 can be rigidly coupled to the manifold portion and provide connections and channels coupled to the manifold portion. A channel 467, for example a tubular channel, is connected to port 456B to allow for inflation of the balloon. A channel 469 can be defined with sheath 458. Channel 469 can be coupled to port 456A to provide an auxiliary fluid to the treatment site. Port 456C to allow removal of tissue can be coupled to the main working channel 465. The main working channel 465 can extend from port 456C to the treatment site. A plurality of seals 466 are arranged to separate the treatment ports and channels as described herein. The manifold 468 can be decoupled from the linkage 430 and support 438 and allow balloon inflation pressure to be applied through port 456B. An auxiliary fluid can be provided through port 456A, for example, so as to flush the working channel 465. This configuration of the manifold allows the spine 452 and anchor 24 to remain in place when other instruments have been inserted into the working channel.

The plurality of manifold conduits as described herein allow tissue collection to be routed through the large bore working channel 469 to reduce flow obstructions. Balloon pressure can be transmitted from a lure fitting to the distal tip of the anchor with small diameter tubing, for example, tubing defining channel 467. An auxiliary fluid is transmitted between the sheath and spine to the treatment area with channel 469.

Figure 14C:
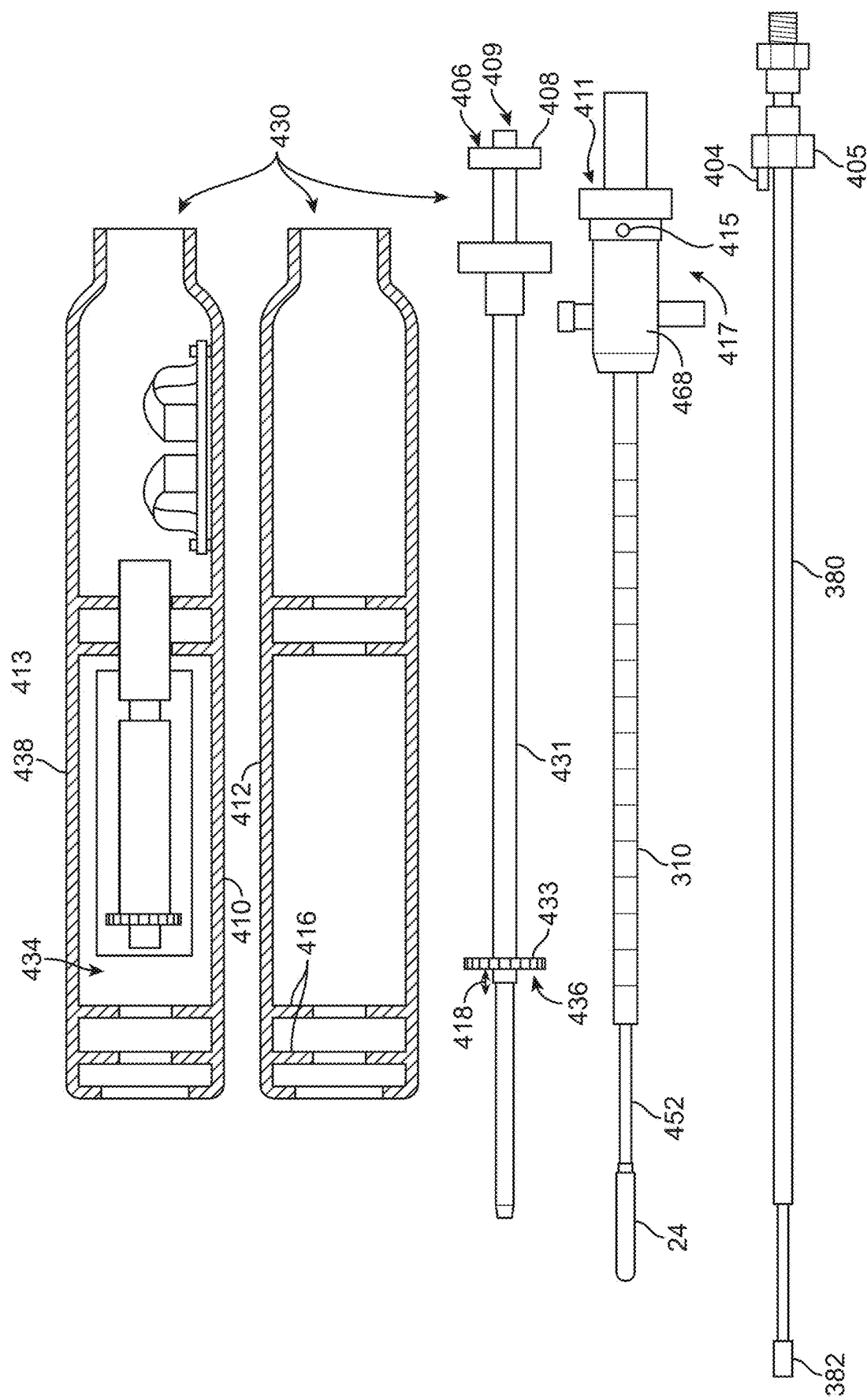
FIG. 14C shows components of treatment probe and linkage in accordance with embodiments.

FIG. 14C shows components of treatment probe and linkage disassembled prior to use. The linkage 430 comprises a casing 410 and a cover 412. The cover 412 can be placed on the lower portion of the casing 410. The cover and casing may comprise rigid materials to add stiffness. The casing and cover can be sized so as to comprise a handpiece containing the linkage 430. The linkage 430 comprises an elongate tubular structure comprising a gear 433 to engage another gear 434 of the linkage. The gear 434 can be positioned on a movable carriage 413. The elongate tubular structure may comprise second movable portion 436 of the linkage. The casing 410 may comprise the support 438 of the linkage. The gear 433 remains connected to the elongate tubular structure 431 when the linkage is disassembled. The movables portion of the linkage 430 may comprise gear 433, gear 434 and movable carriage 413 so as to advance the elongate structure 431 distally when connected to the second movable portion 436 as shown with arrows 418. The cover 412 comprises flanges 416. When the cover is placed on the casing, the elongate structure can be locked into position 431 on the linkage.

The elongate element 310 comprises a spine 452 as described herein and is shown covered with a sheath 458. The sheath 458 comprises a channel to receive the elongate element 310. The elongate element 310 comprises the working channel and can inserted into the sheath 458 such that the elongate element is covered with sheath 458. The sheath 458 and elongate element 310 are shown connected to manifold 468 as described herein.

The sheath 458 can be inserted into the patient prior to insertion of elongate element 310. In many embodiments, sheath 458 is coupled to manifold 468 when inserted into the patient.

The elongate element 310 is configured to slide into the sheath 458 such that the elongate element 310 and sheath comprise a locked configuration. The elongate element 310 comprises structure 411 configured to engage the housing 410 of the linkage, such that the elongate element 310 and housing 410 remain substantially fixed when the elongate structure 431 moves as described herein.

In many embodiments, casing 410 comprises support 438. The support 438 may comprise a substantially non-moving portion of the linkage 430 as described herein. The linkage 430 may comprise moving carriage 433 to move the carrier 382 when the casing 410 comprising support 438 remains locked to the arm and substantially non-moving as described herein.

In many embodiments, the structure 411 of the elongate element 310 comprises locking structure to form a locked joint with the casing 410 and cover 412.

In many embodiments, manifold 468 is connected to the sheath 458 and can be affixed to the sheath to inset the sheath 458 into the patient and inflate the balloon anchor 24 with the manifold 468 as described herein. The elongate element 310 comprising spine 452 may then be inserted into sheath 458. The manifold 468 and structure 411 comprises locking structures 417 to lock the manifold to the elongate element 310 when the elongate element 310 has been inserted into the manifold 468 and sheath 458. A release 415 can be pressed by the user to unlock the manifold 468 from the elongate element 310.

The elongate tubular structure 431 of the linkage 430 comprises structures to receive the carrier tube 380. An opening 409 of the elongate tubular structure 431 is sized to receive the carrier tube 380. A connection structure 408 is shown on the proximal end of the linkage, and comprises a locking structure 406 to receive a protrusion 404 of the connection structure 405 of carrier tube 308.

FIG. 14D1 shows rapid exchange of a carrier tube 380 when the linkage 430 is coupled to the elongate element 310 anchored to a target location of an organ. The elongate element 410 can be inserted or removed from the linkage by the user. The elongate element 380 can be advanced into opening 409 near connection structure 405 of the elongate tubular structure 431.

The imaging probe 460 can be mounted on a second linkage and configured to move with the nozzle of carrier 382, so as to image interaction of the energy stream from carrier 382 when tissue is treated. The images of the treatment may comprise axial images and sagittal images from the imaging probe 460. The linkage can be coupled to the controller or processor (or both) as described herein to move the imaging probe 460 synchronously along the axis with the carrier 382 and nozzle of the carrier, for example. The imaging probe 460 may comprise a trans-rectal ultrasound probe and the carrier 482 may comprise a component of the treatment probe 450 as described herein.

FIG. 14D2 shows alignment of the distal tip of the carrier 382 with the opening 409 of proximal end of the elongate tubular structure 431 to insert the carrier tube 380 as in FIG. 14D1.

FIG. 14D3 shows the carrier advanced toward a locking structure 406 on the proximal end of the linkage as in FIG. 14D1. The locking structure 406 is sized to receive protrusion 404 so as to form a locked joint 402.

FIG. 14D4 shows the carrier tube 380 locked to the linkage 430 as in FIGS. 14D1 and 14D2. The protrusion 404 has been inserted into an opening of locking structure 406 so as to form the locked joint. The joint can be unlocked by user manipulation.

Figure 14E:
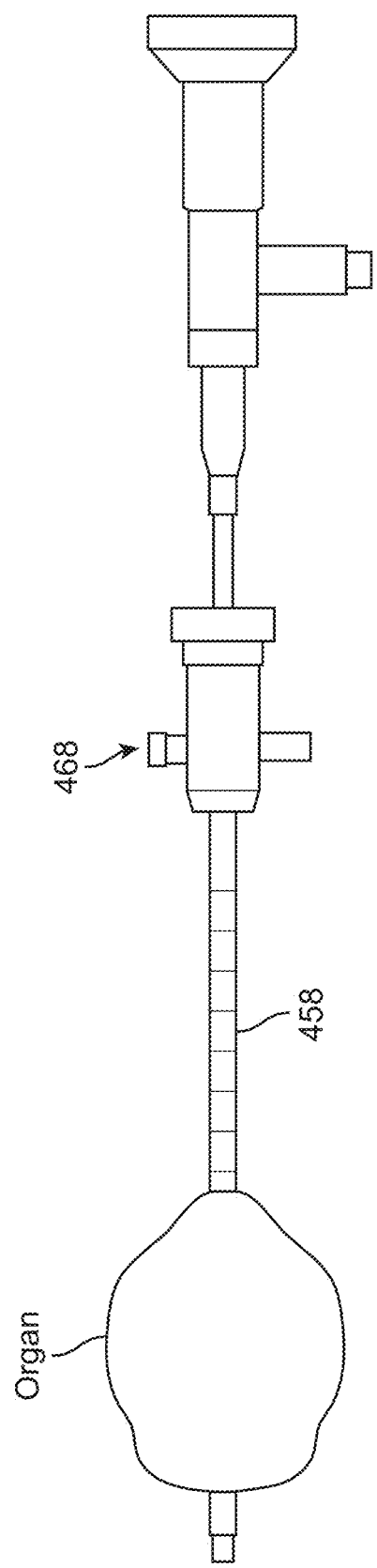
FIG. 14E shows a cytoscope inserted at least partially into an elongate element for advancement toward a bladder neck to view tissue of an organ such as the prostate, in accordance with embodiments.

FIG. 14E shows a cytoscope inserted at least partially into a sheath 458 for advancement toward an anchoring location of an organ. The anchoring location may comprise a bladder neck to view tissue of an organ such as the prostate. The sheath 458 as described herein can be advanced to a target location with visualization from the cytoscope placed within the working channel of the elongate element 310. When positioned, the anchor 24 such as a balloon can be inflated with a port of manifold 468 coupled to the sheath as described herein.

There are at least two forms of visualization possible with the embodiments as described herein. 1) The cystoscope is locked within the sheath 458. The purpose can be to view the prostate and then eventually leave the sheath as a safe channel to guide the elongate element 310 comprising spine 452 into the patient, in many embodiments without having direct visualization. The distal end of the sheath lines up near bladder neck. 2.) Once the elongate element 310 is locked into the sheath 458, ureteroscope can be used to view the patient. The ureteroscope can be inserted inside the same channel that carrier 380 goes into, for example shared channel.

Figure 14F:
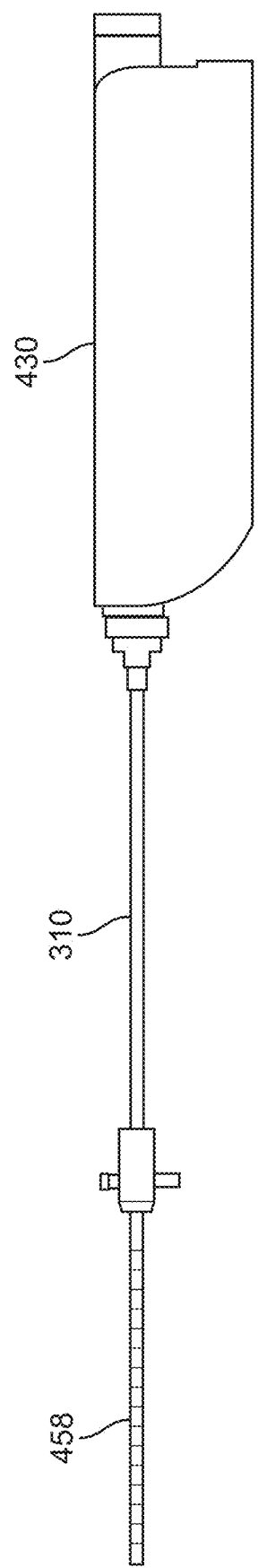
FIG. 14F shows advancement of an elongate element into a sheath.

FIG. 14F shows advancement of an elongate element 310 into a sheath 458. The manifold 468 on the proximal end of the sheath 458 may comprise a locking structure to receive a locking structure on the proximal end of elongate element 310. The elongate element 310 can be advanced into sheath 458 such that the locking elements on the sheath 458 and elongate element 310 engage.

Figure 14G:
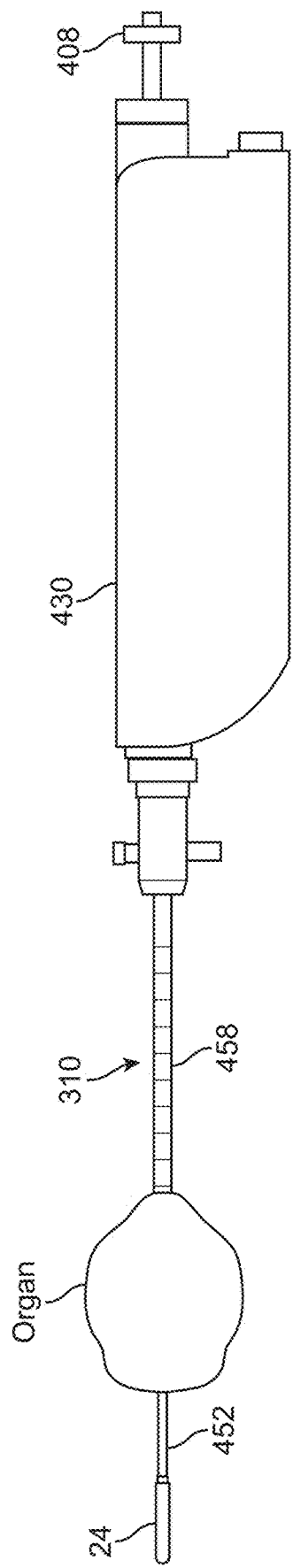
FIG. 14G shows a linkage coupled to an elongate element comprising a spine in accordance with embodiments.

FIG. 14G shows a linkage 430 coupled to an elongate element 310 comprising a spine 452. The linkage is configured to receive carrier 382 and carrier tube 380 as described herein.

Figure 14H:
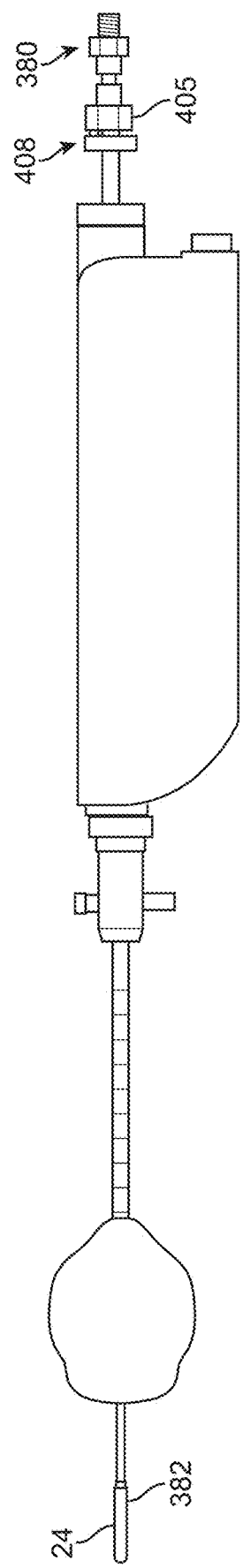
FIG. 14H shows a carrier tube and carrier inserted into the linkage tube in accordance with embodiments.

FIG. 14H shows a carrier tube and carrier inserted into the linkage tube in a locked configuration as described herein.

FIGS. 14A to 14H show a method of treating a patient in accordance with embodiments, and each of these figures shows one or more optional steps of the method.

FIGS. 15 and 16 show self cleaning with a fluid jet as described herein. The fluid jet, for example fluid stream, as described herein, can be utilized to clean the working channel and clear tissue or other ports within the multifunction sheath. The self cleaning can be automated or performed manually. Additionally, water jet intensity can be reduced to clean laser cameras or other accessory devices without having to remove the devices from the working channel. For example an endoscope can be sized to fit within the working channel or alternatively an endoscope can be sized to fit within the working channel with the linkage decoupled and to allow flushing and cleaning of the working channel. Alternatively or in combination the carrier 382 that may comprise carrier tube 380 can be sized to fit within the working channel alongside an endoscope so as to allow cleaning of the endoscope.

In many embodiments the self cleaning can be employed with the probe comprising carrier 382 that may comprise carrier tube 380 positioned within the working channel. The elongated element 310 comprising the sheath and spine can contain the carrier 382 that may comprise carrier tube 380 along a substantial portion of the carrier. The carrier 382 may comprise a rectangular end portion or a tubular end portion and may comprise a portion having a cylindrical and tubular geometry, for example. The fluid stream released from carrier 382 can extend to distance 457 with divergence, for example. Alternatively the fluid stream may comprise a columnar fluid stream. An angle of the fluid stream 453 can be controlled with the linkage so as to rotate the fluid stream during cleaning. The fluid stream can be increased or decreased in terms of pressure.

The fluid jet can be utilized to clean the working channel and clear tissue or other parts within the multifunction sheath. This can be automated or performed manually. Additionally water jet intensity can be reduced to clean the laser camera or other accessory devices without having to remove the devices from the working channel.

Figure 17A:
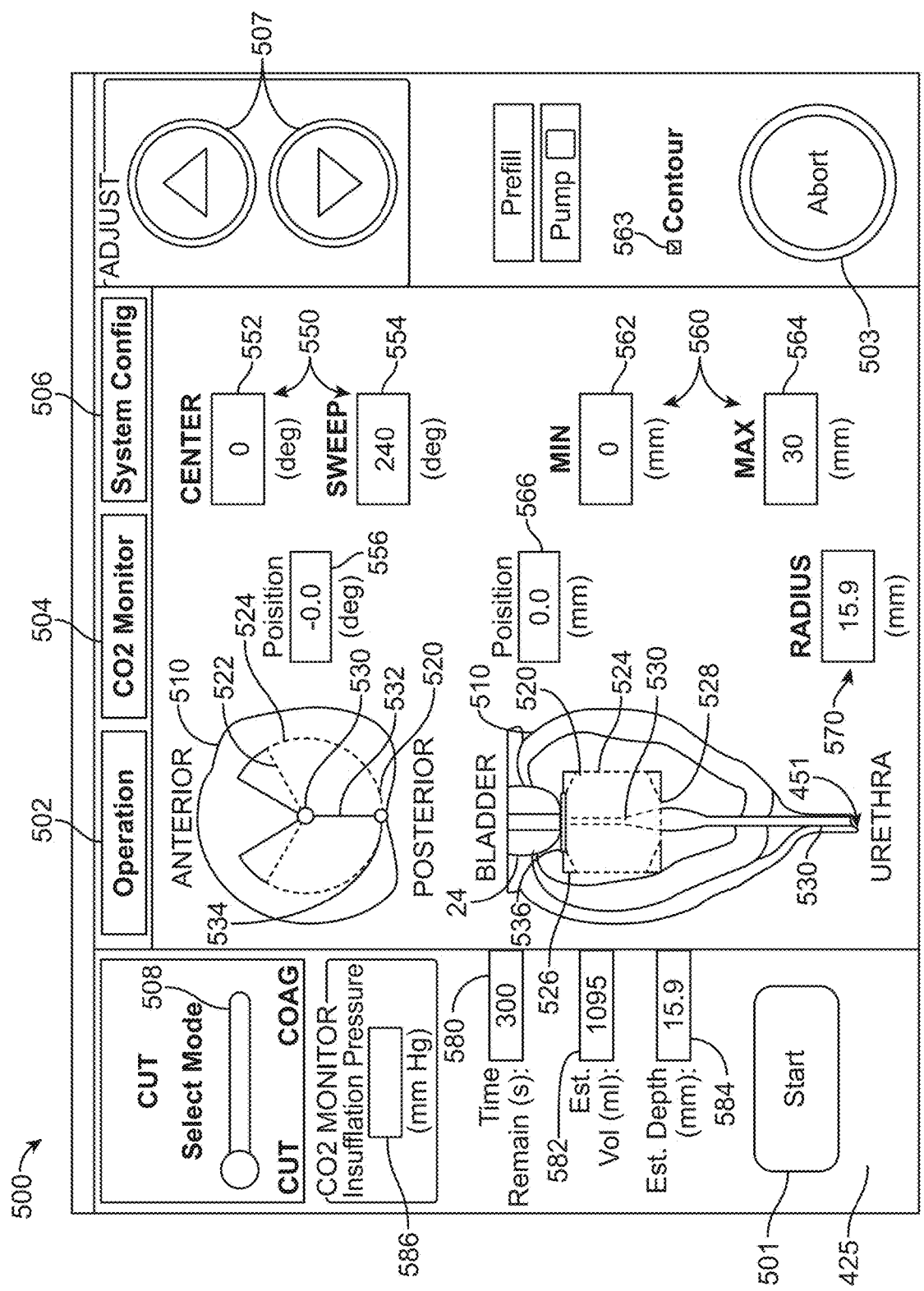
FIG. 17A shows components of user interface on the display of the patient treatment system as in FIG. 13 in accordance with embodiments.

FIG. 17A shows components of user interface 500 on the display 425 of the system 400. The display 425 may comprise a touch screen display, for example, alternatively or in combination, the display 425 can be coupled with a pointing device, a keyboard, and other known user input devices to work with processor systems. The interface 500 comprises an operation tab 502, a $CO_2$ monitor tab 504, and a system configuration tab 506. The user interface 500 includes buttons 507 on the display to adjust up or down values entered into the computer system. An abort button 503 is provided on the user interface for the user to stop treatment of the patient. A start button 501 is provided for the user to initiate treatment of the patient. The user interface 500 comprises an image 510 of an organ such as a prostate. The image 510 shown can be an image of one or more of many organs as described herein. The image 510 may comprise, for example, an image of a prostate from an anatomical image corresponding to a prostate of a patient. The image 510 is shown in an axial transaxial cross-sectional view having an anterior and a posterior orientation, the image 510 is also shown along the longitudinal axis. The sagittal view of the image 510 along the longitudinal axis shows anchor 24 and a lumen such as the urethra. The image 510 may comprise an image of the patient to be treated, for example, an ultrasonic image of the patient. The image 510 can be shown in axial and sagittal views with the ultrasonic image sized so as to correspond with the treatment profiles shown on the display 425.

A treatment profile 520 is shown in the axial and sagittal views. The treatment profile 520 corresponds to a profile of tissue to be removed in the surface remaining subsequent to removal. The treatment profile 520 comprises a radius 522 extending from a central reference location to an outer portion of the cut tissue boundary. The treatment profile 520 comprises an outer component 524 extending circumferentially around an axis of the treatment. The treatment profile 520 extends from a first end 526 proximate the bladder and the anchor to a second end 528 toward the urethra. The treatment profile images shown on the display comprise a plurality of references to align the treatment with the anatomy of the patient. An axis 530 corresponds to a central location of the treatment and extends axially along a lumen of the patient such as the urethra. The treatment axis 530 may correspond to an anatomical reference of the patient such as the urethra or path with which the instrument is introduced to the patient. An angular reference 532 is shown extending from the central axis of the treatment profile to an outer radial boundary of the treatment profile 534. The angular component 532 corresponds to an anterior posterior location on the component of the patient and extends from the anterior to the posterior to location 534 to provide and permit alignment with the patient. As can be seen in the sagittal view, a treatment reference location 536 corresponds to a location adjacent the inflatable anchor such as a balloon 24. Reference location 536 corresponding to the expandable anchor is shown aligned with the end 526 of the treatment profile 20 in which the treatment profile is shown aligned with the axis 451 of the treatment probe.

The user interface 500 comprises a plurality of inputs. The plurality of input may comprise one or more of the following inputs as described herein.

A plurality of angular input parameters 550 may comprise input 552 and input 554, for example. The angular orientation can be set so as to align with an anterior posterior direction of the patient extending between axis 530 and marker 534. The input 552 can be used to adjust the angular orientation of the treatment around the axis 530, for example, when the patient and probe are aligned at slightly different angles. An input 552 aligns the center of the treatment profile in degrees rotationally around the axis. An input 554 provides a sweep angle from one angular extreme to another, for example, a sweep angle may comprise an angle less than 360°, for example, 240°. The sweep angle generally extends around the anterior-posterior treatment axis and extends from the anterior end treatment posterior treatment axis by a distance of approximately half the sweep angle, for example, sweeping 120° in the first direction and sweeping 120° in an opposite direction from the anterior posterior treatment axis. In many embodiments, the sweep angle is limited to less than 360 degrees to avoid sweeping the fluid stream into the spine.

The angular position of the stream can be shown in real time on the display with an output 556 of the angular position in degrees. The output angle can be shown on the display as a moving colored line, for example green, which sweeps around the axis 530.

A plurality of input parameters 560 can be used to determine the extent of the treatment along axis 451 and axis 530. An input 562 determines a location of the treatment profile in relation to expandable anchor 24. An input 564 determines a length of treatment along axis 451 and axis 530. Input 564 may comprise a longitudinal distance of the treatment extending from a first end 524 to a second end 528. An input 570 can determine a radius of the treatment profile around axis 530. Input 570, a radial distance from axis 530 radially outward to an outer boundary of the treatment profile 524. The radius may comprise a radial distance in millimeters such as the distance of 10 mm for example. Alternatively, the radius can be determined with power of a pump which can be set with arbitrary values from 1 to 10, for example.

A select mode input 508 can allow the user to set the interface from a cut mode to a coagulation mode, for example. In the cut mode, many of the inputs for the treatment can be provided so as to determine and align the treatment with the patient. In the cut mode as shown the user is able to visualize the extent of treatment with respect to the anatomy of the patient and to formulate and improve treatment strategy. The user can establish a cut profile having a predetermined profile surface and a predetermined removal volume.

The patient interface comprises additional outputs for the user to determine appropriate treatment, for example, a time remaining in the treatment can allow the user to determine the time of treatment and the time remaining in the treatment, for example, an output 580 shows the time remaining in seconds. An output 582 comprises an estimated volume of tissue removal, the estimated volume of tissue removed can be determined based on the treatment profile. An estimated radial depth of the removal can also be determined and an output 584 can show the estimated radial depth of removal. The estimated depth of removal may comprise the input radius from input 570 alternatively the estimated depth may correspond to an estimated depth from a pump power of input 570. A start button input 501 allows a user to start treatment when the physician is satisfied with the patient treatment. When insufflation is used, for example insufflation with a gas such as CO2 an insufflation pressure can be set with an input 586. Alternatively, if liquid is used as described herein as a second or first fluid in combination with another liquid insufflation pressure may be set to zero or disabled. In many embodiments the insufflation may be set to zero in a first mode such as the cut mode and set to an appropriate value in a second mode such as the coagulation mode.

Figure 17B:
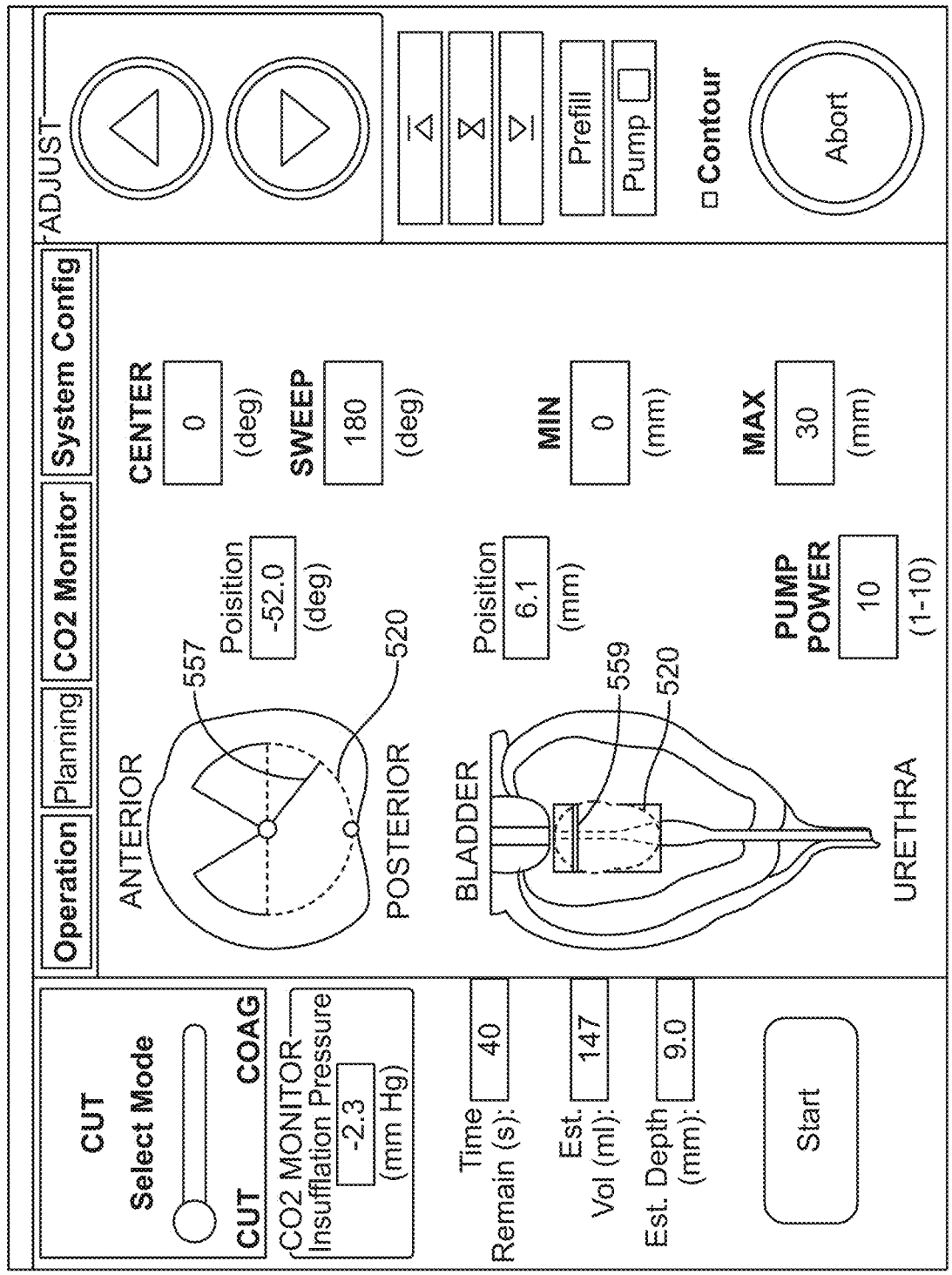
FIGS. 17B and 17C show a marker moving on a plurality of images in which movement of the marker corresponds to the position and orientation of an energy stream in accordance with embodiments.
Figure 17C:
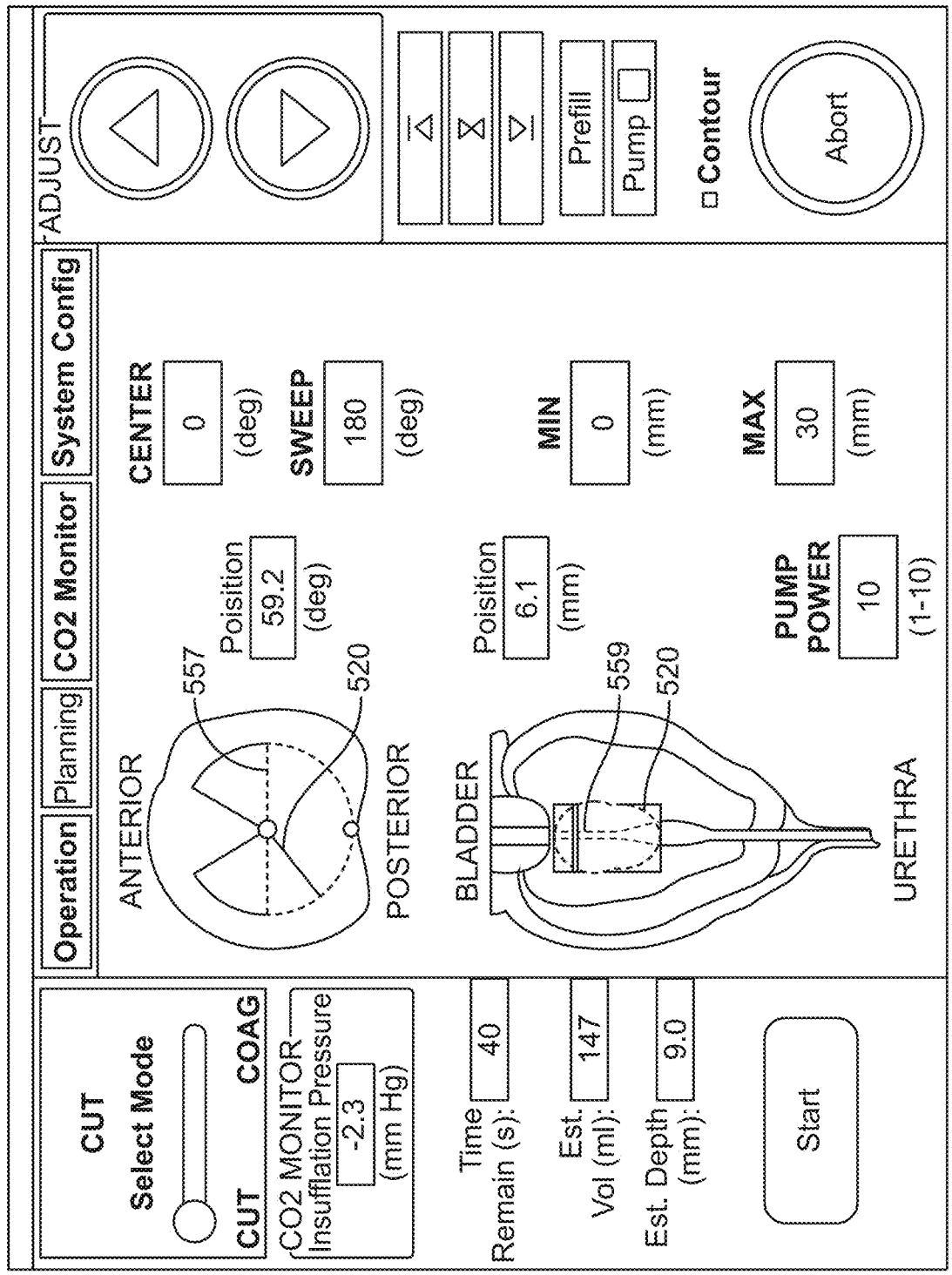

FIGS. 17B and 17C show a marker moving on a plurality of images in which movement of the marker corresponds to the position and orientation of an energy stream. The energy steam may comprise a fluidic stream from the nozzle as described herein. A radial marker 557 is shown on the axial image in relation to the resection profile 520. A longitudinal marker 559 is shown on the sagittal image in relation to resection profile 520. The radial marker 557 is shown at a first angle in FIG. 17B and a second angle in FIG. 17C so as to indicate the angle of the fluid stream from the carrier as described herein, for example. As the treatment progresses, the longitudinal maker 559 can move along the treatment axis of the sagittal image to indicate the longitudinal position of the nozzle on the carrier as the radial marker 557 sweeps rotationally around the axis on the axial image.

Figure 17D:
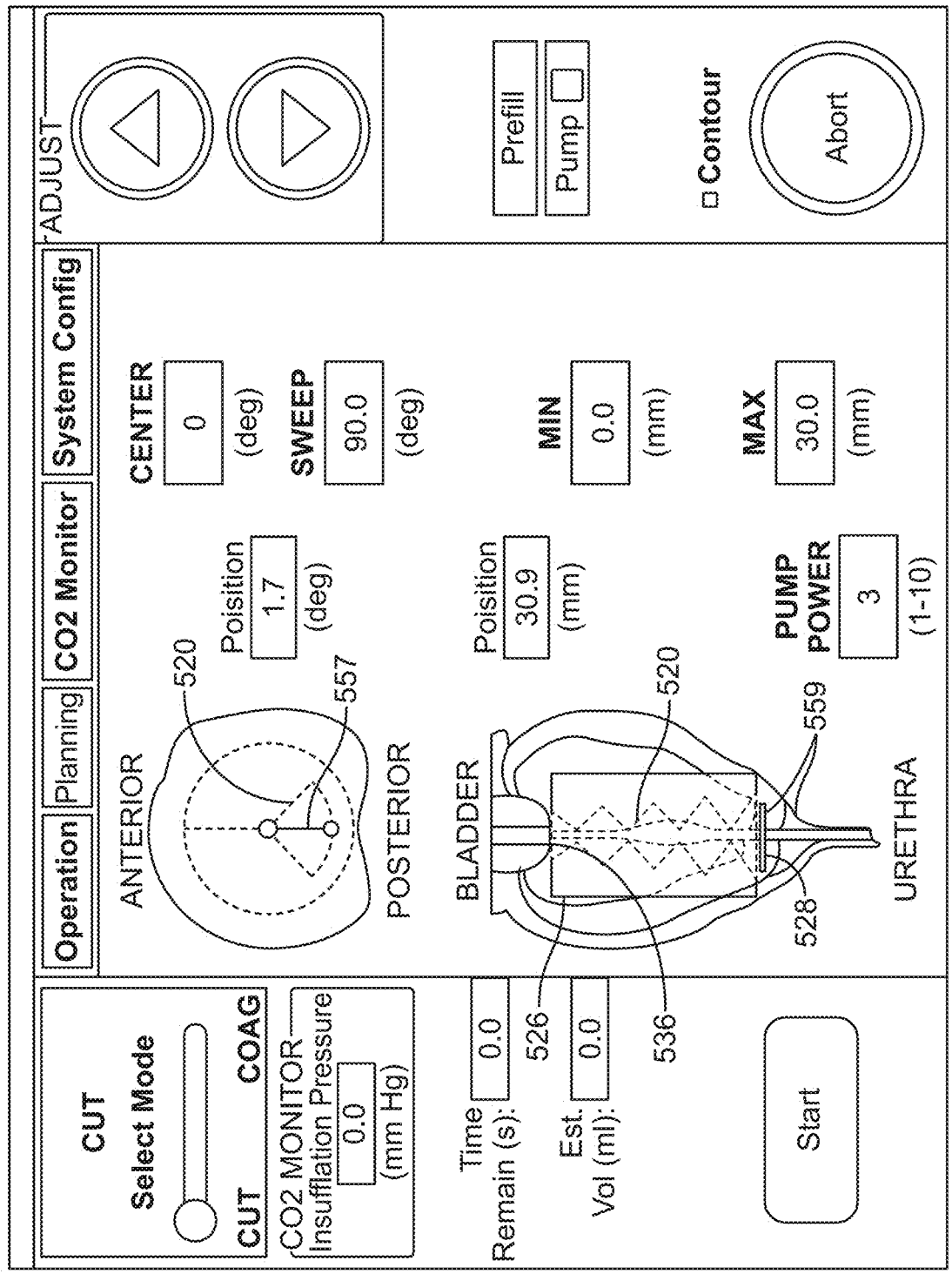
FIG. 17D shows a user defined cut profile in accordance with embodiments.

FIG. 17D shows a user defined resection profile 520. The user interface can be configured with instructions of the processor to allow the user to define a plurality of points of the treatment profile, and interpolate among the points as described herein.

Figure 17E:
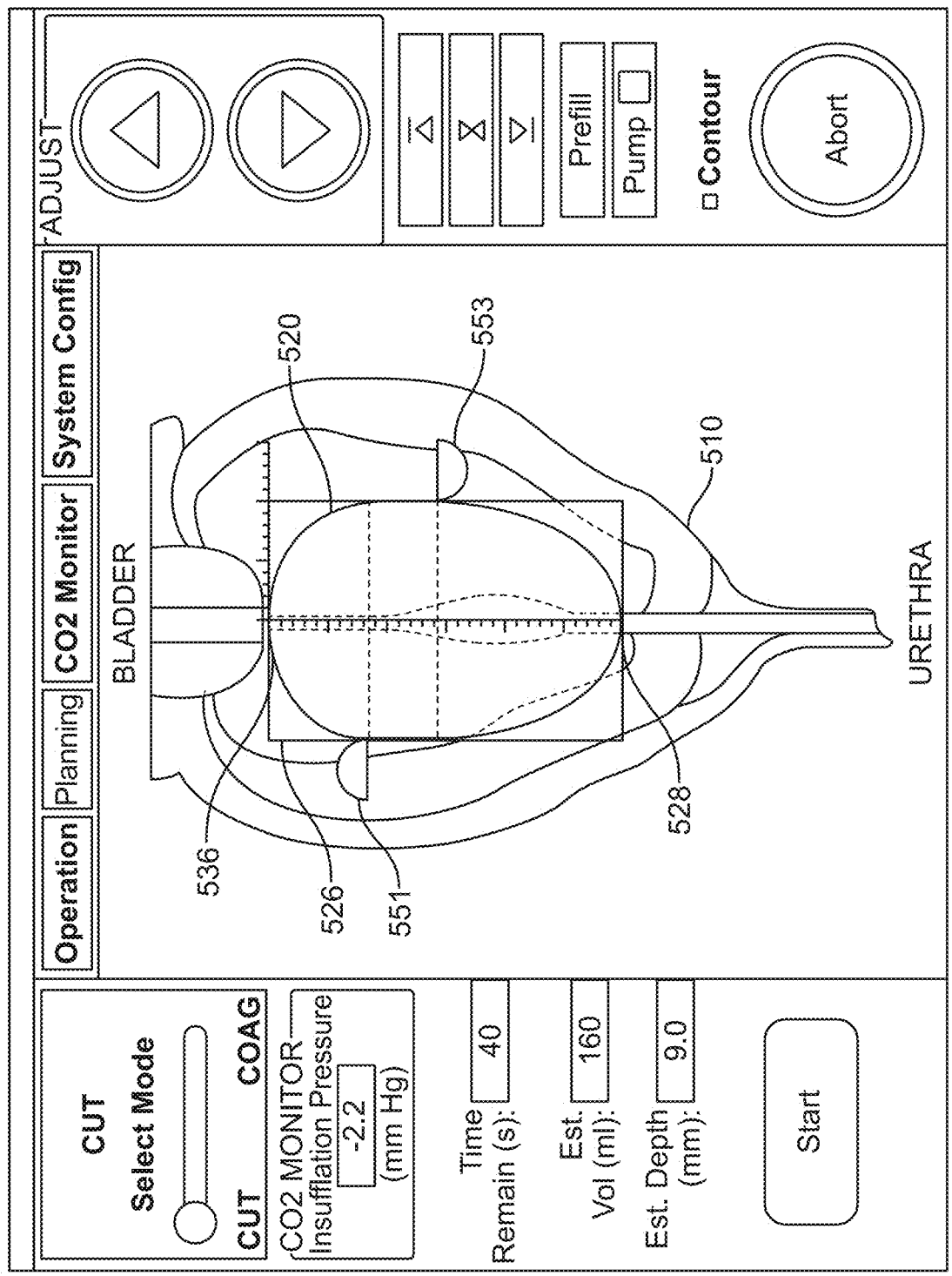
FIGS. 17E and 17F show a user interface to define a plurality of curved portions of a cut profile in accordance with embodiments.
Figure 17F:
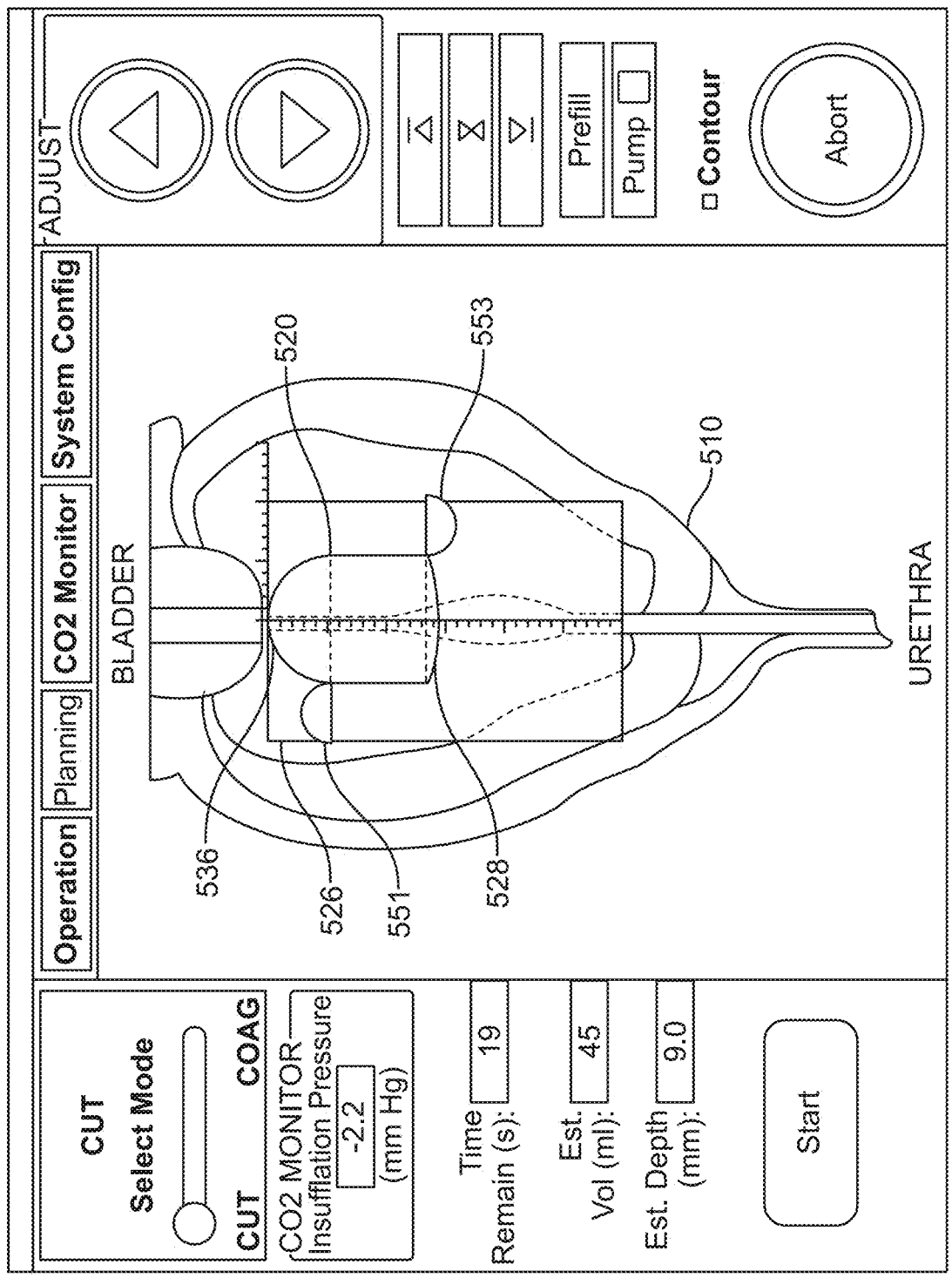

FIGS. 17E and 17F show a user interface to define a plurality of curved portions of a cut profile. A first user movable input 551 can be configured to move along the display to define a first curved portion of the profile 520, and a second user movable input 553 can be configured to move along the display to define a second curved portion of the profile 520, and the instructions of the processor can be configured to interpolate among the first curved portion and the second curved portion to define the profile 529 extending between the first curved portion and the second curved portion, for example. A first end 526 of the treatment profile can be set based on user input and a second end 528 can be set based on user input as described herein. The user can slide the first movable input 551 to determine the curved shape of the first portion based on anchoring of the cut profile with the end 526 and the location of the movable input 551 on the display. For example, the first curved shape may be determined with a spline fit extending from the first input to the end 526 constrained with angles at the end 526 and the movable input 551. The second movable input 553 can be moved similarly to define the second curved shape of the second portion, for example.

Figure 18:
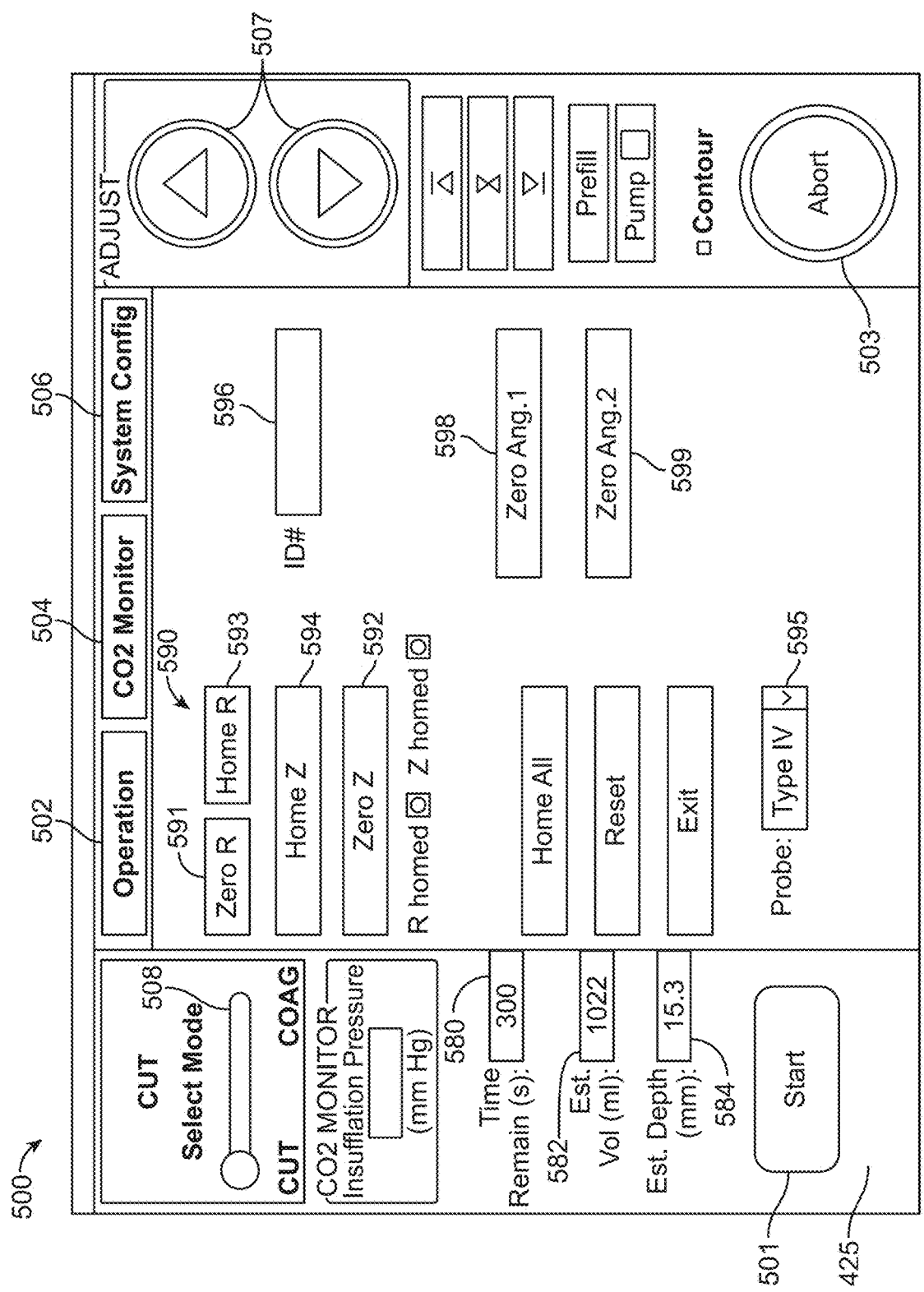
FIG. 18 shows a system configuration mode for the cutting mode input of the user interface as in FIG. 17A.

FIG. 18 shows a system configuration mode 506 for the cutting mode input 508. When the system configuration is set the user can set several parameters for the treatment prior to the treatment or during the treatment so as to align the treatment profile with a patient and to insure that the treatment probe 450 cuts tissue as intended. One or more inputs 590 allows the user to align intended treatment with the probe placed in the patient. One or more inputs 590 may comprise an input 591 to zero the treatment and align the treatment axis with an axis of the patient, for example the intended anterior posterior treatment profile can be aligned in an anterior posterior direction of the patient such that an anterior posterior axis of the treatment profile is aligned with an anterior posterior axis of the patient. Input 591 can be set based on one or more measurements for example an ultrasonic imaging measurement to determine that the probe is properly aligned with the patient. Alternatively or in combination, input 591 can be set based on angle sensors as described herein. One or more inputs 590 may comprise an input 592 to zero the treatment in the axially direction and align the treatment probe with an intended anatomic target of the patient. Input 592 allows alignment of the longitudinal axis with the intended target location of the patient, for example if treatment probe 450 has been placed insufficiently far or too deep the zero z button can be pressed such that input 592 zeros the treatment at the correct anatomical location.

The system configuration mode can also be used to set and calibrate the system. For example, an input 598 can allow the zero angle of a first angle sensor, for example, an angle sensor of the treatment probe 450 to be set to zero and properly aligned. An input 599 can be used to set the imaging probe sensor to an appropriate angle, for example, to calibrate the imaging probe.

An input 595 can allow a user to select a probe type from among a plurality of probe types, for example the probe type may comprise a plurality of nozzle types, for example, a fourth nozzle type may comprise a narrower nozzle diameter to allow treatment at a greater distance radially from the axis of the treatment probe 450. In the system configuration mode for a given profile a user can select a plurality of probe types so as to determine a time remaining, an estimated volume and an estimated depth based on the probe identified and, for example, the size of the nozzle of the probe selected.

By way of example, the input screens and parameters shown in FIGS. 17A and 18 may refer to a divergent cutting screen in which a first fluid comprises a liquid and the second fluid comprises a liquid. Alternatively a gas can be used to provide a protective jacket around a treatment beam in a treatment stream so as to extend the effective cutting distance of the treatment probe 450. The system may comprise instructions so as to perform a portion of the treatment with one configuration of the first fluid and the second fluid and a second configuration of the first fluid and second fluid so as to cut a second portion of the treatment with a gas protecting the treatment stream.

In many embodiments in which the sweep angle is limited to less than 360 degrees to avoid the spine as described herein, a first treatment can be performed at a first angular orientation of the probe about the axis, the probe rotated to move the spine out of the way in order to expose the untreated portion with the stream, and a second treatment performed. The angle of the probe for the first treatment can be measured, and the angle of the probe for the second treatment measured, and the treatment rotated to treat the untreated portion based on the first and second angles. For example, the first treatment may comprise a sweep of 240 degrees, and the second treatment may comprise a sweep of 120 degrees, such that the total treatment extends substantially around the axis of the probe and to a greater angle than would be provided if the spine were not rotated to expose the untreated portion. The probe may be rotated to a second measured angle, for example 70 degrees, and the second treatment performed with a sweep of 120 degrees. The center location can be adjusted with input 552 or software, such that the second treatment is aligned with the untreated portion.

Figure 19:
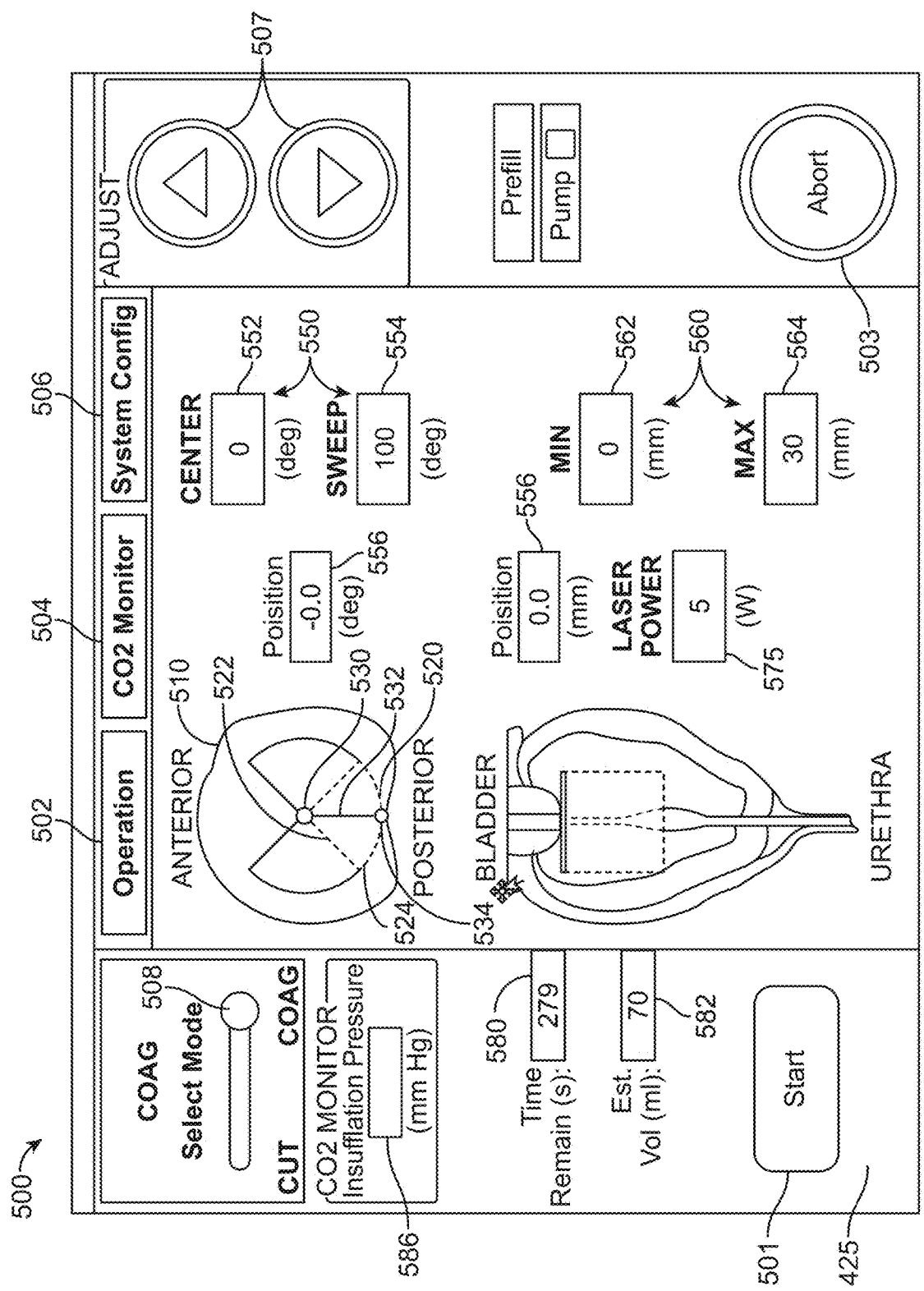
FIG. 19 shows a coagulation mode selected with input of the user interface as in FIG. 17A.

FIG. 19 shows a coagulation mode selected with input 508. With the operation tab selected with input 502, the treatment for coagulation can be set. The coagulation can be provided in many ways, for example, with a divergent stream or a columnar stream and combinations thereof. In many embodiments it may be desirable to treat only a portion of the treatment profile with coagulation. For example, a posterior portion of an organ, for example, the prostate can be selectively treated with coagulation. Work in relation to embodiments suggest that posterior treatment may result in slightly more bleeding potentially and it can be advantageous in some embodiments to selectively treat a posterior portion of a patient's anatomy, for example, the prostate. In the coagulation mode with a laser beam, the treatment input parameters are similar to those described above with respect to cutting. The sweep angle can be set with input 554, for example, to a value of 100° in which the sweep angle for coagulation is less than a sweep angle for cutting. The time of treatment remaining 580 can be shown and the user may also see a volume of treatment, for example, a coagulation volume. The user is allowed to select laser power with an input 575 and also to position the treatment similarly to what was done with the cutting and the angular extent can be lesser and the longitudinal extent can be lesser or greater, for example.

The input treatment profile can be input in one or more of many ways, for example, the image of the organ to be treated, for example, the prostate, can be provided and the user can draw an intended treatment profile on an axial view and a sagittal view of the patient. The image shown may comprise an anatomical image corresponding to anatomy of a generalized population or alternatively the images shown may comprise images of the patient. The processor system comprises instructions to map and transform the reference treatment profile on the image of the patient to the machine coordinate references of the treatment probe 450 and linkage 430 and anchor 24 as described herein. In many embodiments the images shown to the user are scaled to correspond to the treatment profile so that the treatment profile shown on the image of the anatomical organ treated corresponds to and aligns with the treatment dimensions of the image. This allows the user to accurately determine and place the intended treatment profile on the patient.

Figure 20A:
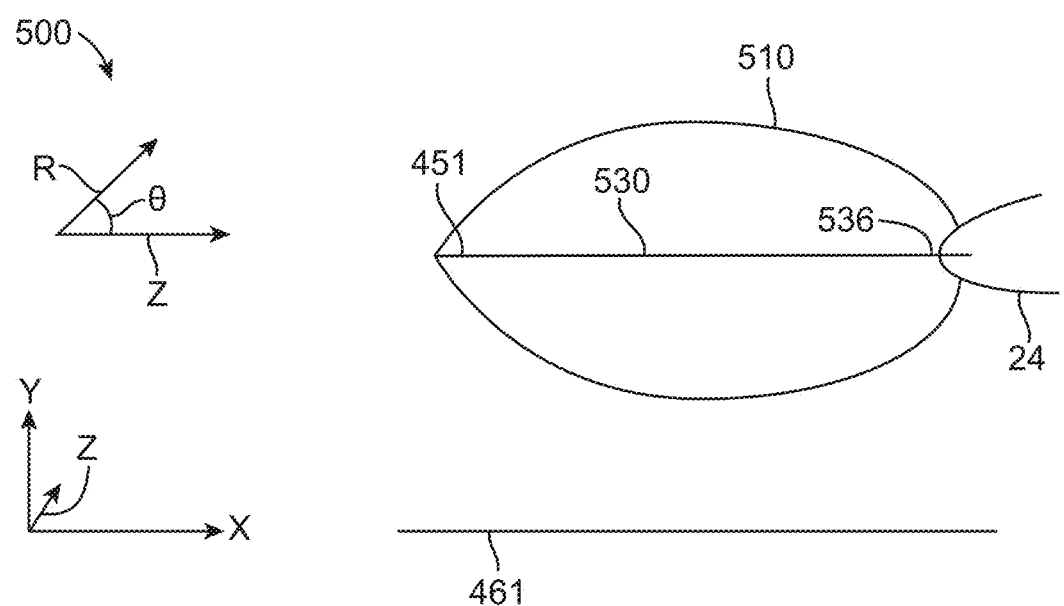
FIG. 20A shows mapping and alignment of an image of the patient with the treatment coordinate reference frame in accordance with embodiments.

FIG. 20A shows mapping and alignment of an image of the patient with the treatment coordinate reference frame. The image 510 of the organ can be obtained in one or more of many ways as described herein. The image may comprise an image reference frame, for example comprising X, Y and Z coordinate references. The treatment probe 450 comprises a treatment reference frame, for example cylindrical coordinate references R, Z, theta. The orientation of the axes of the probes can be determined as described herein. A marker reference 536, such as the anchor of the treatment probe can be identified from the image, in order to align the two images with a common known reference point. The points of the image from the image reference frame can be mapped to the coordinate reference frame and shown on the display, based on the location of the identified reference point and the orientation of the probes. A point in the image having an image coordinate reference of (X1, Y1, Z1) can be mapped to the treatment reference frame to provide treatment reference location (R1, Z1, T1). A three dimensional mapping of the patient tissue can be similarly performed, for example.

Three dimensional mapping of the tissue of the target organ can be performed, and the three dimensional mapping used to provide a three dimensional profile of the target organ. For example, a plurality of sagittal views and plurality of axial views can be provided of the three dimensional profile of the organ, and the user can draw the target treatment profile on each of the plurality of sagittal views and each of the plurality of axial views in order to provide a customized treatment of the patient. In many embodiments, the processor comprises instructions to interpolate the treatment profile among the sagittal an axial views, so as to provide a mapped three dimensional treatment profile. In many embodiments, providing additional treatment of the prostate medially may provide additional tissue removal, and the mapping as described herein can be used to provide additional removal of medial portions of the prostate tissue.

In many embodiments, the user can identify a plurality of points of a treatment profile on the image of the tissue of the patient, and the plurality of points are mapped to the treatment coordinate reference, and shown on the display so that the user can verify that the treatment coordinates of the treatment profile shown on the display treat the targeted tissue as intended by the user.

Figure 20B:
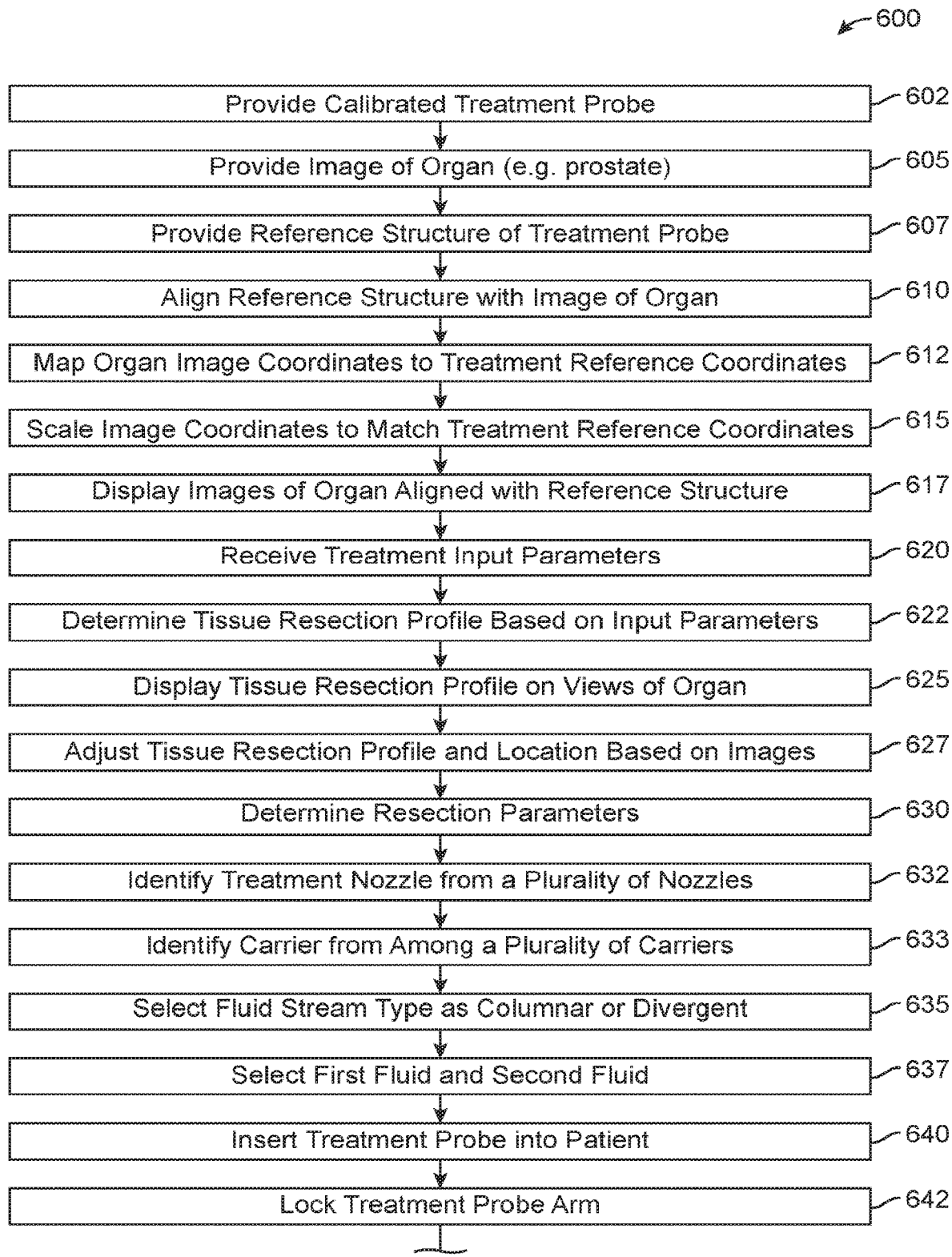
FIGS. 20B and 20C show a method of treating a patient in accordance with embodiments.
Figure 20C:
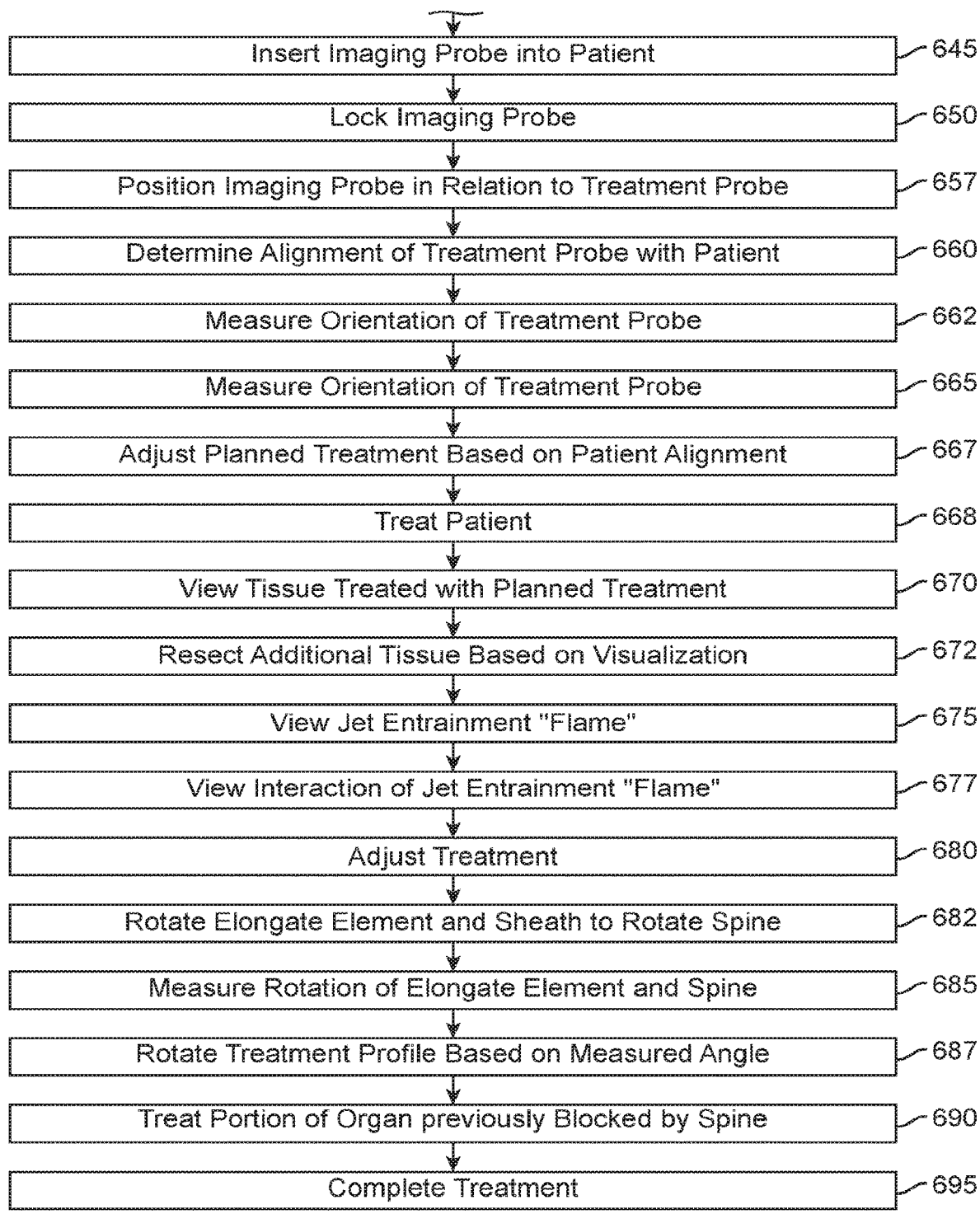

FIGS. 20B and 20C show a method 600 of treating a patient.

At a step 602, a calibrated treatment probe as described herein is provided.

At a step 605, an image of an organ (e.g. prostate) as described herein is provided.

At a step 607, a reference structure of a treatment probe as described herein is provided.

At a step 610, the reference structure is aligned with the image of the organ as described herein.

At a step 612, organ image coordinates are mapped to treatment reference coordinates as described herein.

At a step 615, image coordinates are scaled to match treatment reference coordinates as described herein.

At a step 617, images of the organ aligned with reference structure are displayed as described herein.

At a step 620, treatment input parameters are received as described herein.

At a step 622, the tissue resection profile is determined based on the input parameters as described herein.

At a step 625, the tissue resection profile is displayed on views of the organ as described herein.

At a step 627, the tissue resection profile and location are adjusted based on the images as described herein.

At a step 630, resection parameters are determined as described herein.

At a step 632, a treatment nozzle is identified from among a plurality of treatment nozzles as described herein.

At a step 633, a carrier is identified from among a plurality of carriers as described herein.

At a step 635, a fluid stream type is selected as columnar or divergent as described herein.

At a step 637, a first fluid and a second fluid are selected as described herein.

At a step 640, a treatment probe is inserted into the patient as described herein.

At a step 642, a treatment probe arm is locked as described herein.

At a step 645, an imaging probe is inserted into the patient as described herein.

At a step 650, an imaging probe is locked as described herein.

At a step 657, an imaging probe is moved in relation to the treatment probe as described herein.

At a step 660, alignment of the treatment probe with the patient is determined as described herein.

At a step 662, orientation of treatment probe is measured as described herein.

At a step 665, orientation of a treatment probe is measured as described herein.

At a step 667, the planned treatment is adjusted based on patient alignment as described herein.

At a step 668, the patient is treated as described herein.

At a step 670, tissue treated with the planned treatment is imaged and viewed as described herein.

At a step 672, the jet entrainment "fluid flame" is viewed as described herein.

At a step 675, interaction of the jet entrainment "fluid flame" is viewed as described herein.

At a step 677, additional tissue is resected based on the viewed images as described herein.

At a step 680, treatment is adjusted as described herein.

At a step 682, the elongate element and sheath are rotated amount the elongate axis to rotate the spine as described herein.

At a step 685, an angle of rotation of the elongate element and spine are measured as described herein.

At a step 687, the treatment profile is rotated around the axis based on measured angle. For example, the treatment profile can be rotate around the elongate axis of the treatment profile corresponding to the elongate axis of the elongate element and spine and sheath as described herein as described herein.

At a step 690, a portion of the organ blocked as described herein by the spine is treated.

At a step 695, treatment is completed as described herein.

Although the above steps show method 600 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 600 may be performed with the circuitry as described herein, for example one or more of the processor or logic circuitry such as the programmable array logic for field programmable gate array. The circuitry may be programmed to provide one or more of the steps of method 600, and the program may comprise program instructions stored on a computer readable memory or programmed steps of the logic circuitry such as the programmable array logic or the field programmable gate array, for example.

Figure 21A:
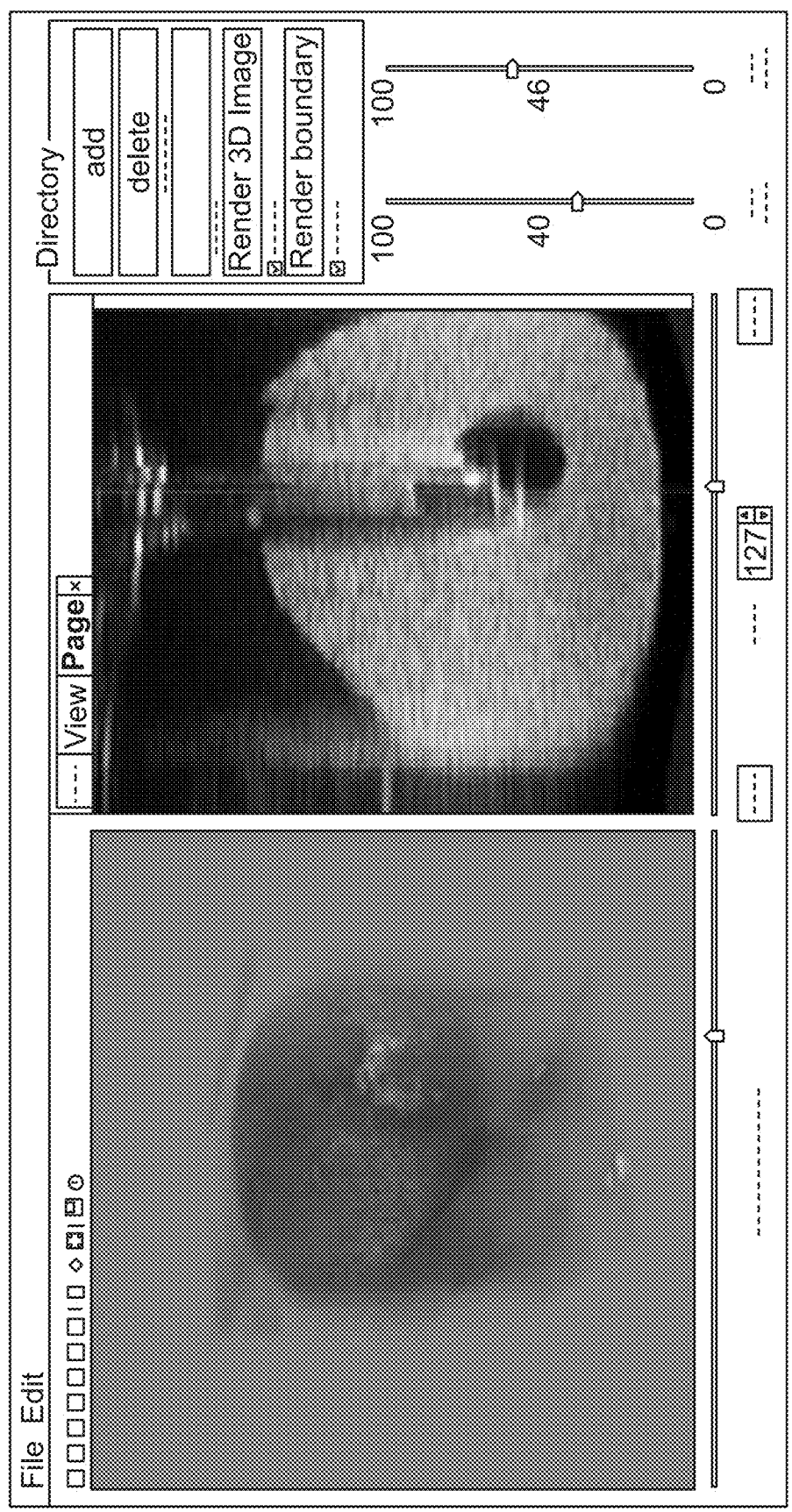
FIGS. 21A and 21B show screenshots of a 3d segmentation image used in accordance with the systems and methods of embodiments.
Figure 21B:
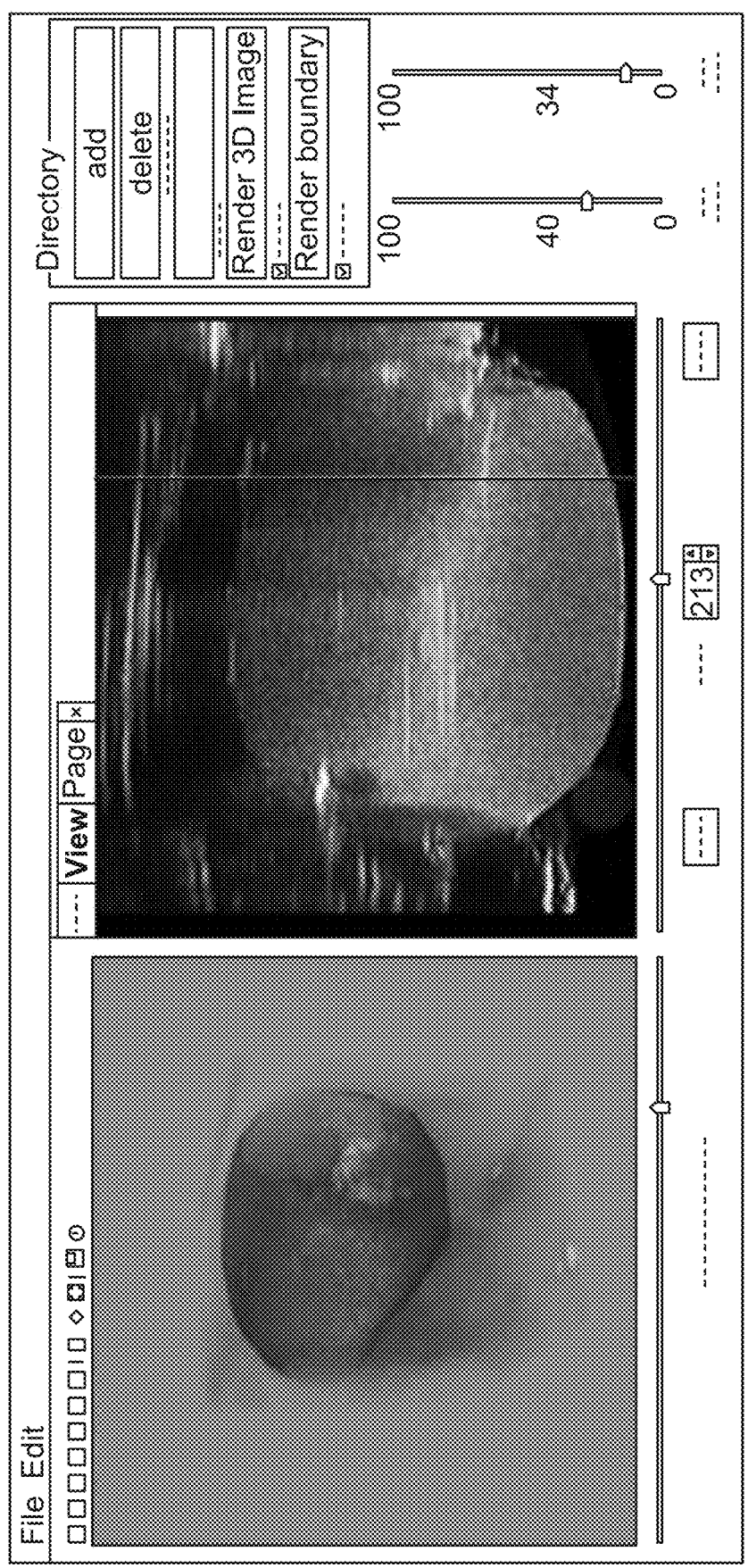
Figure 21D:
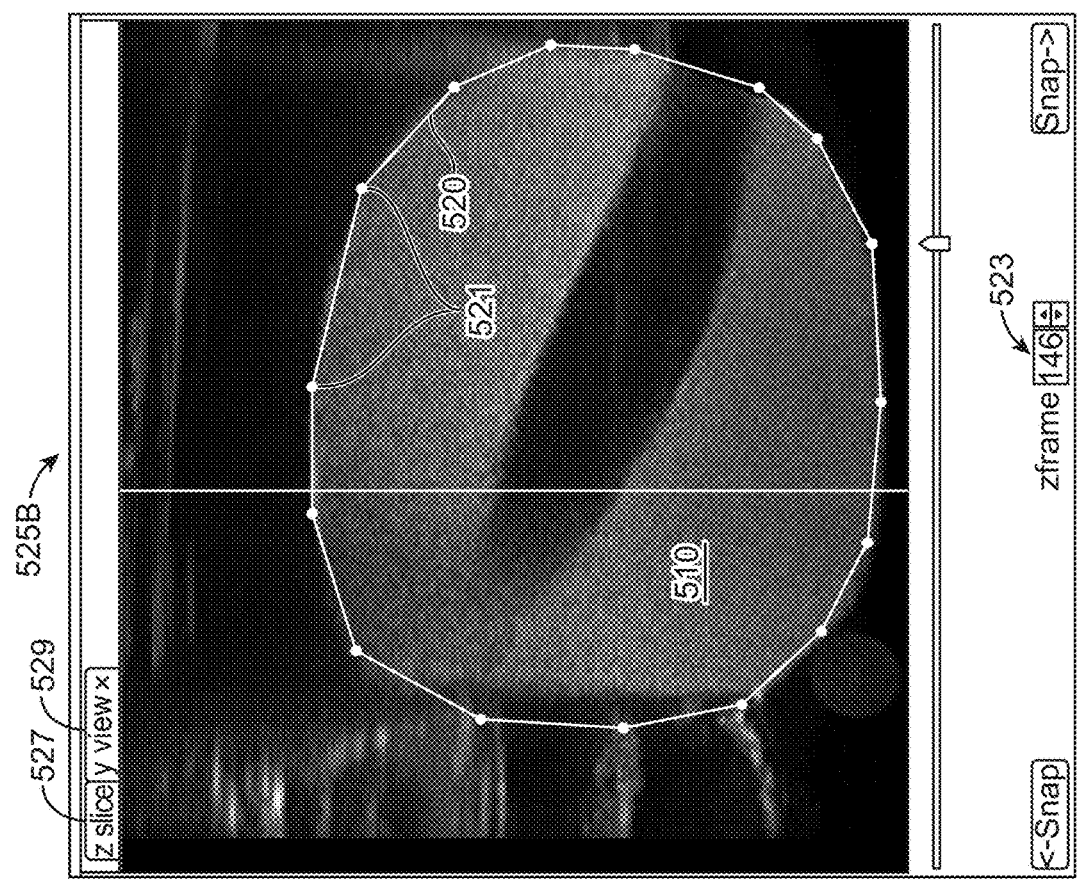
FIGS. 21C, 21D, 21E and 21F show a plurality of sagittal images of a target tissue to define a three dimensional treatment plan and a user defined treatment profile in each of the plurality of images.
Figure 21C:
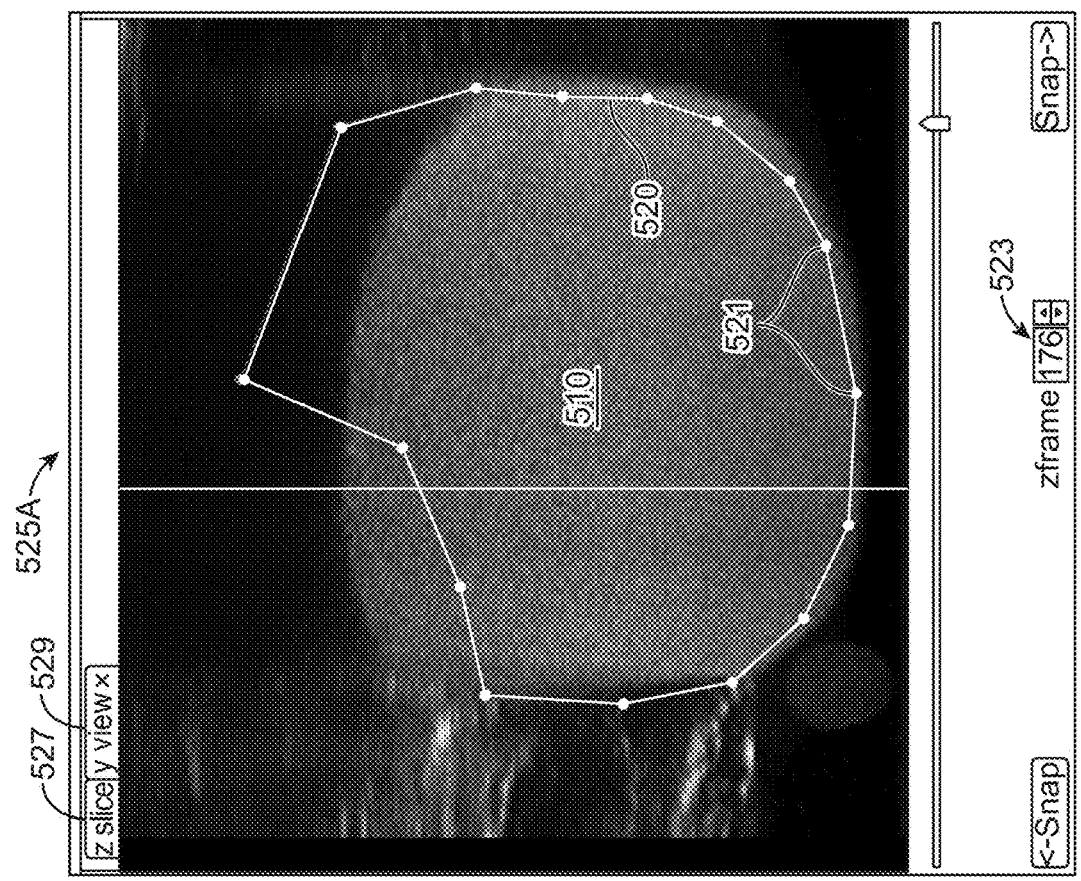
Figure 21E:
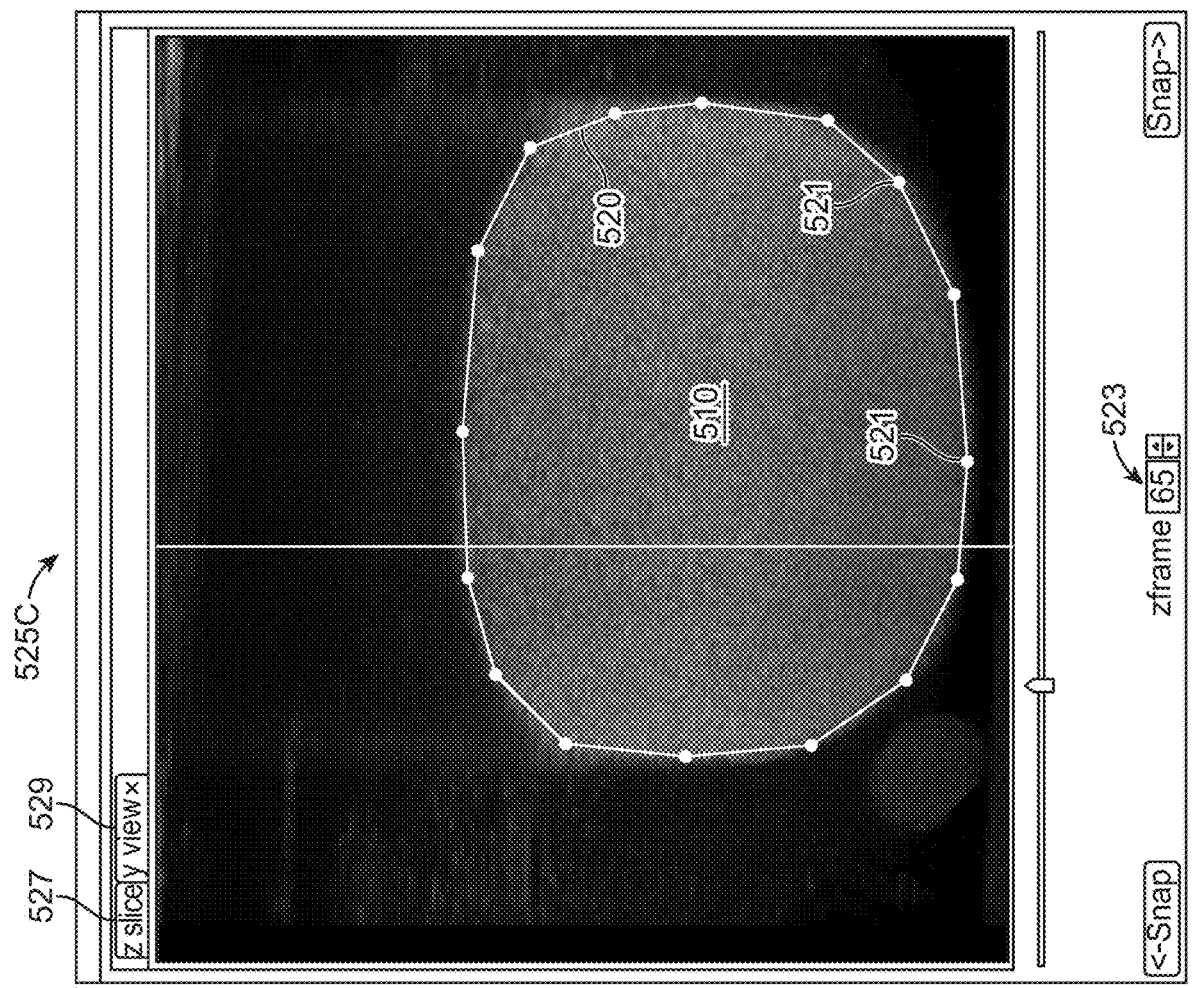
Figure 21F:
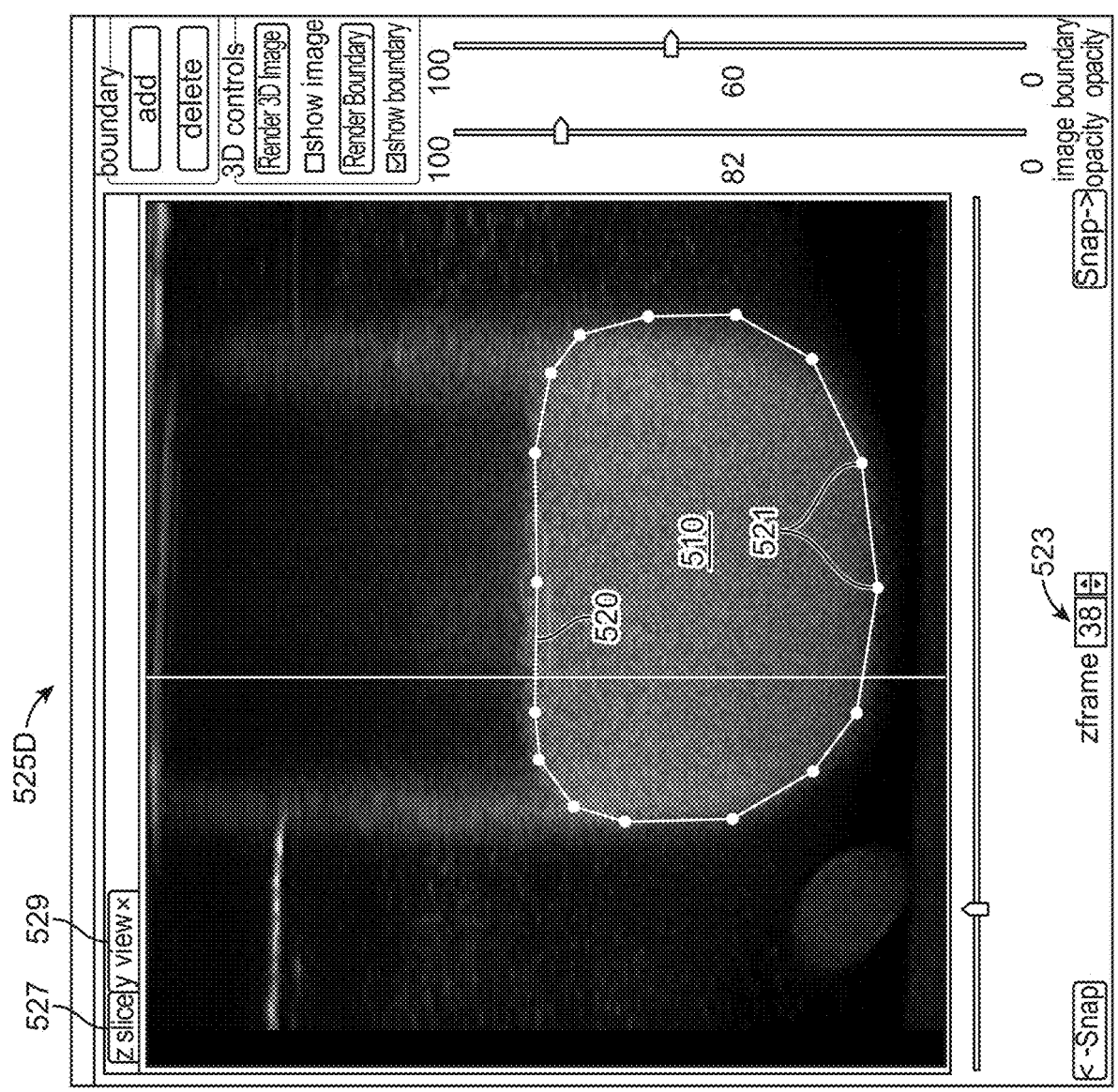

FIGS. 21A and 21B show screenshots of organ images, for example trans-rectal ultrasound prostate images, from 3D segmentation software according to embodiments of the present invention. The two dimensional images shown on the right side of FIGS. 21A and 21B, respectively. Three dimensional images of the prostate are shown on the right left of FIGS. 21A and 21B, respectively. The two dimensional images on the right side of FIGS. 21A and 21B show examples of transverse and sagittal planes, respectively, of the three dimensional prostate representations shown with the images on the left of FIGS. 21A and 21B. The transverse image may also be referred to as horizontal image, axial image, or transaxial image as described herein. Note segmentation of the sagittal plane of the prostate is depicted in light gray color, and the segmentation of the axial plane of the prostate is depicted in light gray color.

These segmented images can be provided on the display for the user to plan the treatment of the organ with images of treatment overlaid on the image of the organ as described herein, such as the treatment profiles overlaid on the image of the prostate.

The images shown in FIGS. 21A and 21B can be provided on the display 425 of interface 500. For example the axial and sagittal images can be provided on the display as described herein.

FIGS. 21C to 21F show a plurality of axial images 525 of a target tissue to define a three dimensional treatment plan and a user defined treatment profile in each of the plurality of images. The user interface comprises a first tab 527 to select a Z-slice view and a second tab 529 to select a Y-view, of a three dimensional representation of a target tissue such as an organ that may comprise the prostate. The Z-slice view may correspond to a sagittal image of the target tissue and the Y-slice view may correspond to an axial view of the target tissue. The plurality of axial images comprises a first image 525A at a first z-frame 523. The z-frame 523 may correspond to a location along an axis of the traversed by the y-slice view, and each z-frame may correspond to a location of the axial image along the z-axis. The first z-frame can be one or more of many frames.

Each image 510 comprises a user input treatment profile 520. The user input treatment profile may comprise a plurality of points that are user adjustable on the image to define the treatment profile. The first plurality of images 525A shows the treatment profile partially positioned by the user, and a plurality of treatment profile marker points 521 have yet to be placed on the target tissue location by the user. The user can adjust the location of the points with the user interface, for example with a pointing device or touch screen display. The processor as described herein comprises instructions to receive the plurality of points input by the user. The plurality of points may comprise small user movable markers such as circles, dots or X's, and the plurality of points can be connected with lines in one or more of many ways, such as with a linear interpolation corresponding to straight lines on the display or splines corresponding to curved lines shown on the display so as to connect the markers, for example.

A second image 525B of the plurality of images at a second depth is shown on the display as described herein. The second image 525B comprises points 521 aligned with the image by the user so as to define the treatment profile 520 at the second location along the z-axis corresponding to the treatment.

A third image 525C of the plurality of images at a third depth is shown on the display as described herein. The third image 525C comprises points 521 aligned with the image by the user so as to define the treatment profile 520 at the third location along the z-axis corresponding to the treatment.

A fourth image 525D of the plurality of images at a fourth depth is shown on the display as described herein. The fourth image 525C comprises points 521 aligned with the image by the user so as to define the treatment profile 520 at the fourth location along the z-axis corresponding to the treatment.

Figure 21H:
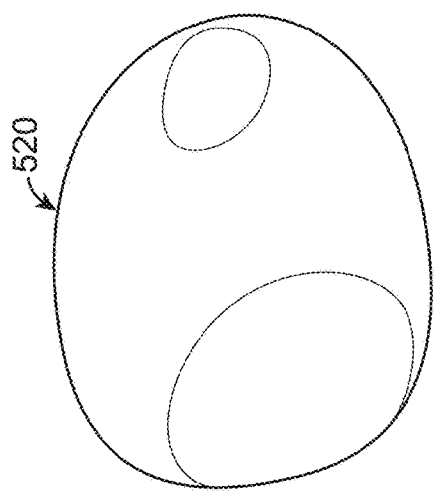
FIG. 21H shows a three dimensional treatment plan based on the plurality of images of FIGS. 21A to 21F.
Figure 21G:
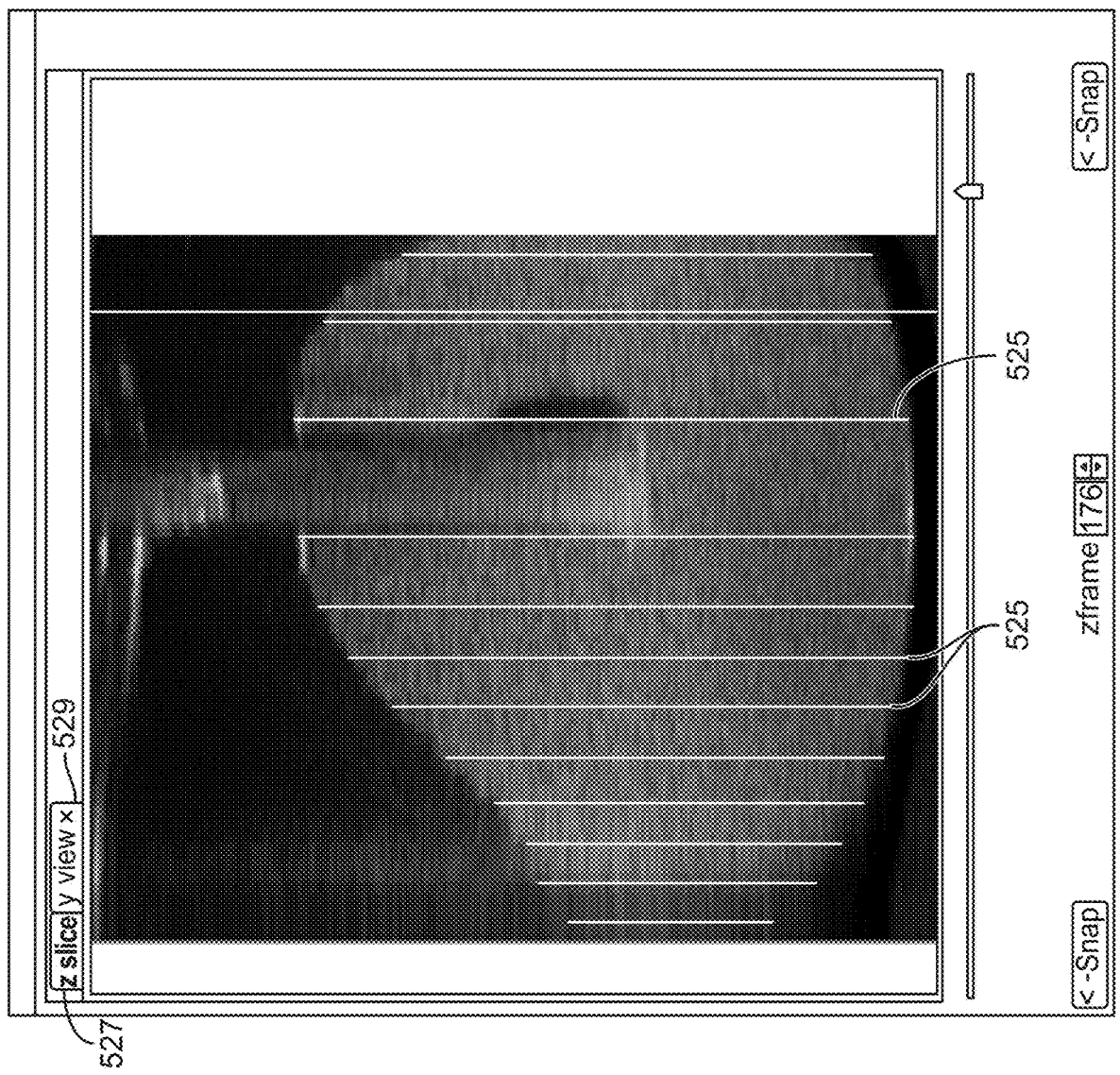
FIG. 21G shows a transverse view of the target tissue and planes of the axial images of FIGS. 21C to 21F.

FIG. 21G shows a sagittal view of the target tissue and planes of the axial images of FIGS. 21C to 21F. The z-slice view can be selected with tab 527, so as to show a sagittal view of the target tissue. The plurality of images 525 are shown as lines extending through the sagittal view.

FIG. 21H shows a three dimensional treatment profile based on the plurality of images of FIGS. 21A to 21F. The three dimensional treatment plan may comprise a three dimensional representation of the three dimensional treatment profile 520. The three dimensional treatment profile 520 can be determined in one or more of many ways. The three dimensional treatment profile may be obtained by interpolation among the plurality of points 521 that define the treatment profile of each image, for example by linear interpolation of splines. Alternatively or in combination, the three dimensional treatment profile can be determined based on polynomial fitting to the surface points 521, for example.

Figure 21I:
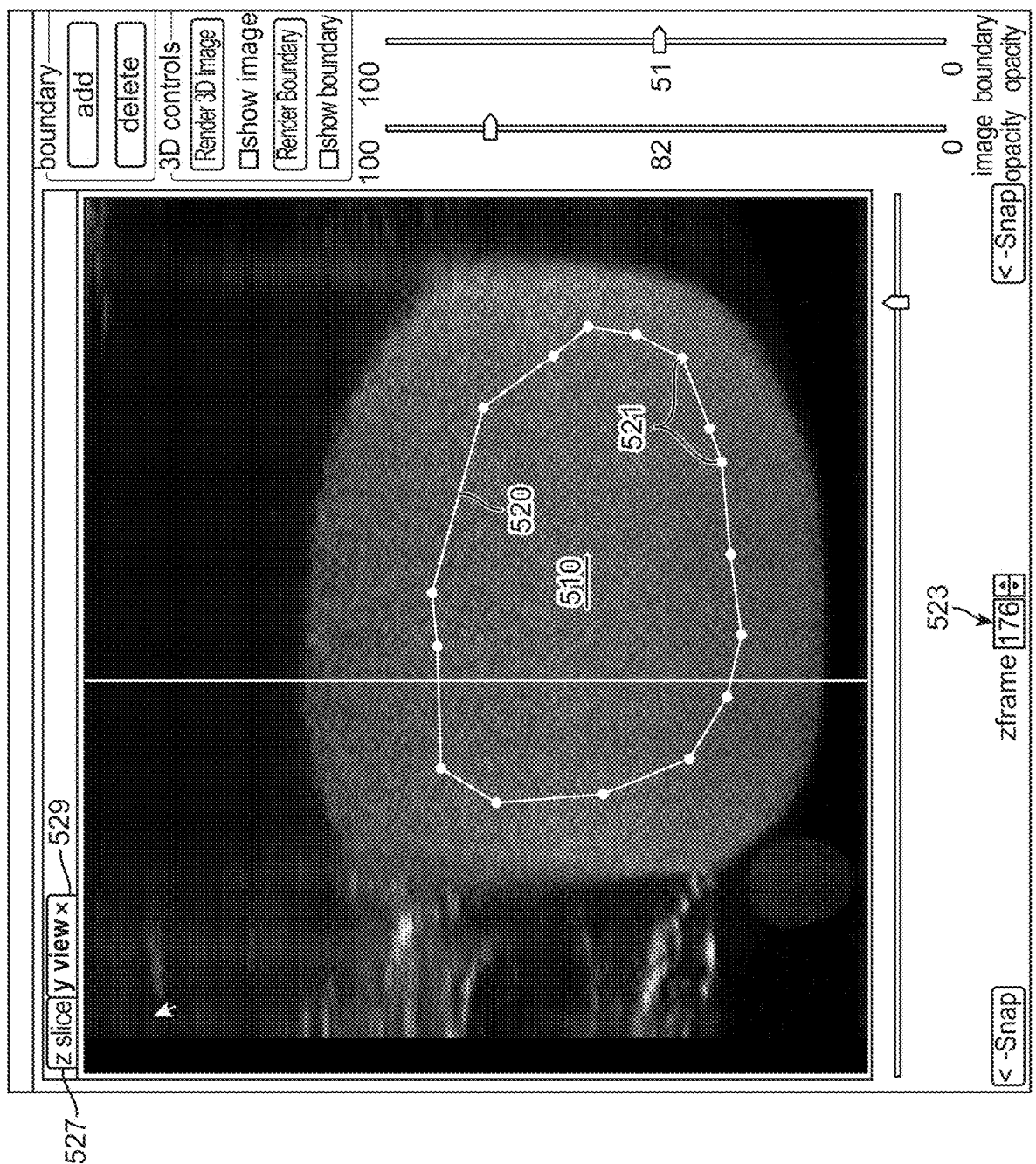
FIG. 21I shows a user input treatment profile of an image among a plurality of images.

FIG. 21I shows a user input treatment profile of an image among a plurality of images as described herein. The user can adjust the plurality of points 521 in one or more of many ways, and the user can determine the treatment profile based on patient need. The treatment profile can be selected so as not to extend to an outer boundary of a tissue structure, for example an outer structure of an organ such as a prostate as shown in FIG. 21I.

Figure 21J:
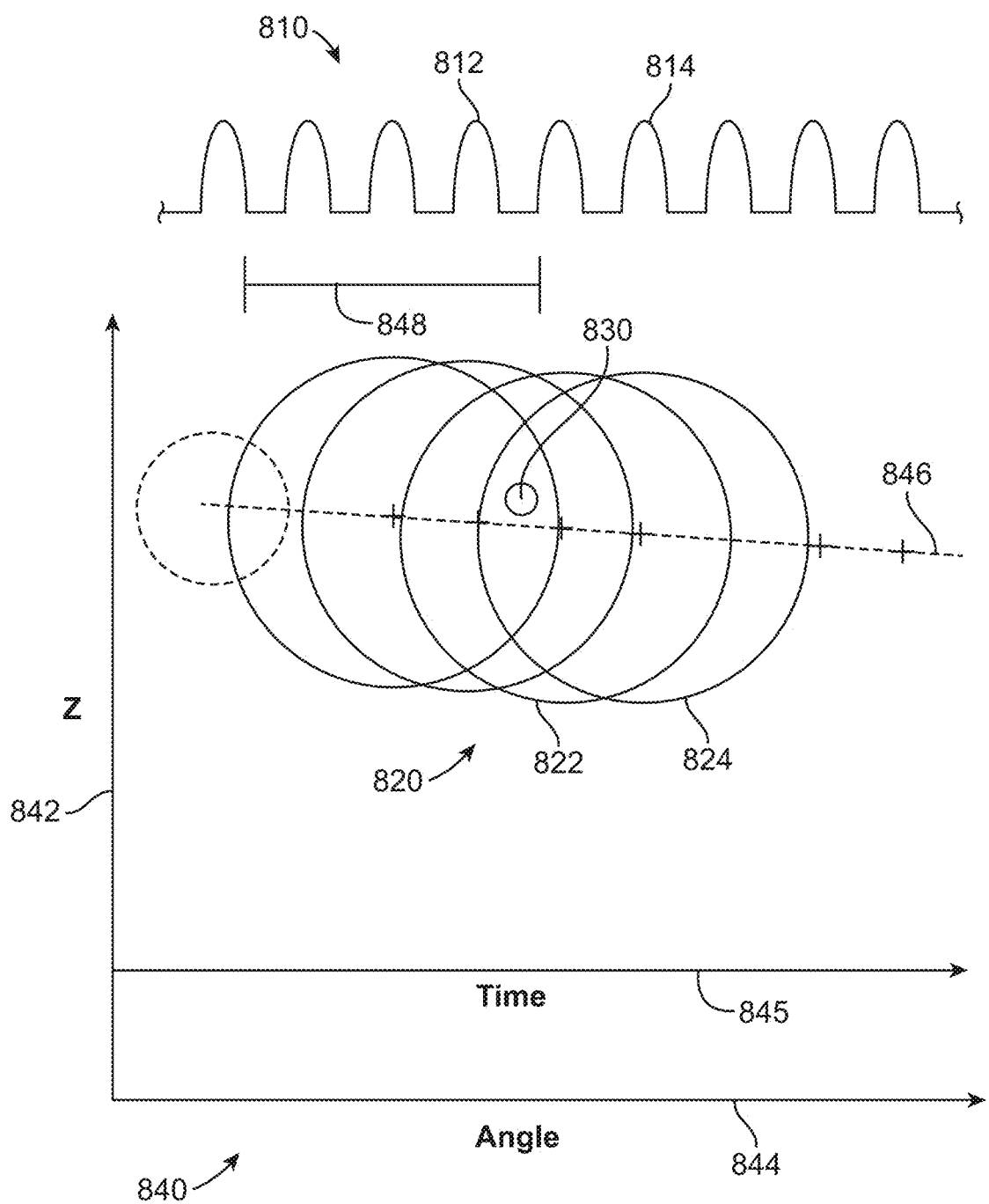
FIG. 21J shows scan patterns of the fluid stream, in accordance with embodiments.

FIG. 21J shows scan patterns of the fluid stream as described herein. The fluid stream may comprise a pulsed or continuous fluid stream. The scan pattern can be based on critical pressures as described herein so as to remove a first tissue and inhibit removal of a second tissue. In many embodiments, the fluid stream comprises a plurality of pulses 810 from a pump such as a piston pump, and the pulses comprise a frequency and duty cycle. In many embodiments, the duty cycle correspond to no more than about 50%. The plurality of pulses 810 comprises a first pulse 812 and a second pulse 814. The fluid flame may comprise an approximate cross sectional size at the location of tissue being scanned. Based on the teachings described herein, a person of ordinary skill in the art will recognize that the fluid flame comprises a maximum cross sectional width at about ½ the length of the fluid flame. At the location where the fluid flame impinges upon tissue, the fluid flame comprises a cross sectional size 848.

The scanning pattern of the fluid stream comprising the fluid flame are along a Z-axis and angle 844. The angle 844 may correspond to time 845, for example when the angular sweep rate remains substantially constant. The fluid flame is scanned along a scan path 846. The scan path 846 may correspond to the velocity of the carrier 382 along the Z-axis and the rotation of the carrier 382 around the Z-axis, for example.

The pulses can be spaced apart such that a plurality of sequential pulses strike a location 830 of tissue. The plurality of sequential pulses can be effective in removing a first type of tissue when removal of a second type of tissue is inhibited.

Alternatively or in combination with the critical pressures as described herein, work in relation to embodiments suggests that the rate of removal can be related to a relaxation time of a targeted tissue. The fluid flame can be configured to dwell on a point 830 of tissue for a duration longer than the relaxation time of the tissue, such that the tissue can be deformed beyond a threshold and removed.

In many embodiments, the plurality of pulses 820 impinge upon the tissue location 830 with a duration between pulses that is less than a tissue relaxation time of elastic deformation of the tissue so as to remove the tissue. In many embodiments, a first tissue to be removed comprises a first relaxation time greater than the time between pulses, and the second tissue for which removal is to be inhibited comprises a second tissue relaxation time less than the time between pulses, so as to inhibit removal of the second tissue.

As the tissue is removed toward the final desired treatment profile, the size of the fluid flame may decrease substantially near the distal tip of the flame, such that the size of the pulsed fluid flame impinging upon the resected profile is decreased substantially tissue removal decreased substantially.

Based on the teachings described herein, a person of ordinary skill in the art can determine the scanning movement of the carrier 382 and nozzle to resect tissue to a target profile with the fluid flame as described herein.

Figure 21K:
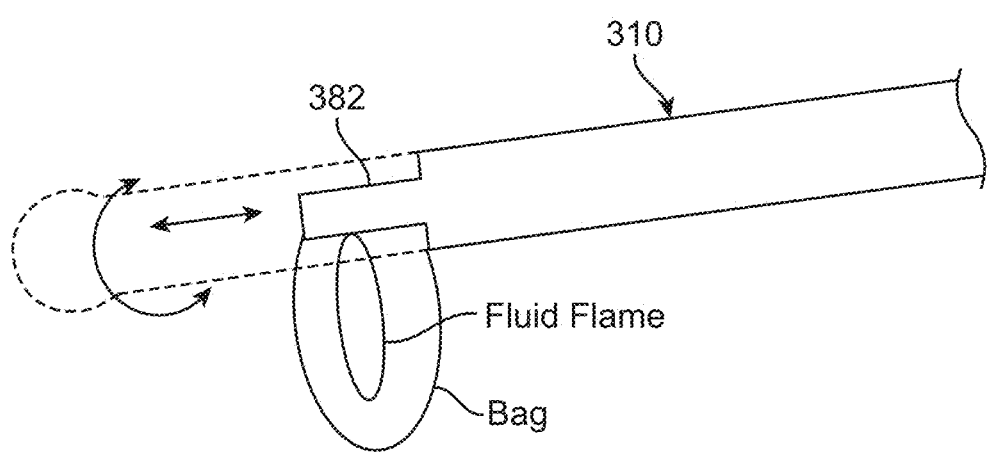
FIG. 21K shows a bag over a fluid stream comprising a water hammer in accordance with embodiments.

FIG. 21K shows a bag over a fluid stream. The fluid stream may comprise the columnar stream or divergent stream as described herein. In many embodiments the bag is placed over a fluid stream comprising a pulsed stream so as to comprise a water hammer. The bag can be made of one or more of many materials and may comprise an elastomer, for example. The interior of the bag can be coupled to the carrier 382, and the exterior of the bag can be coupled to the working channel to remove material. The bag has the advantage of protecting the tissue from the high fluid flow rate and can provide more even pressure. The fragmented tissue can be collect through passive or active means, for example through an outer collection tube or the working channel.

Figure 22A:
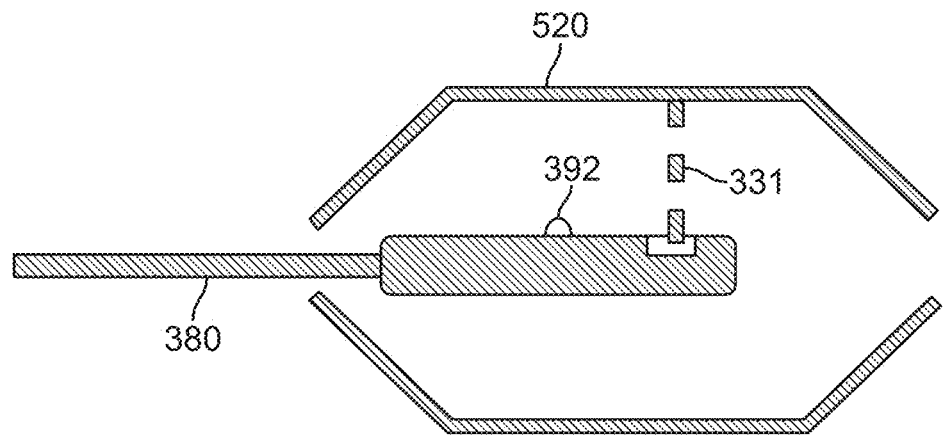
FIGS. 22A and 22B show schematic illustrations of a probe being operated in accordance with the principles of embodiments.
Figure 22B:
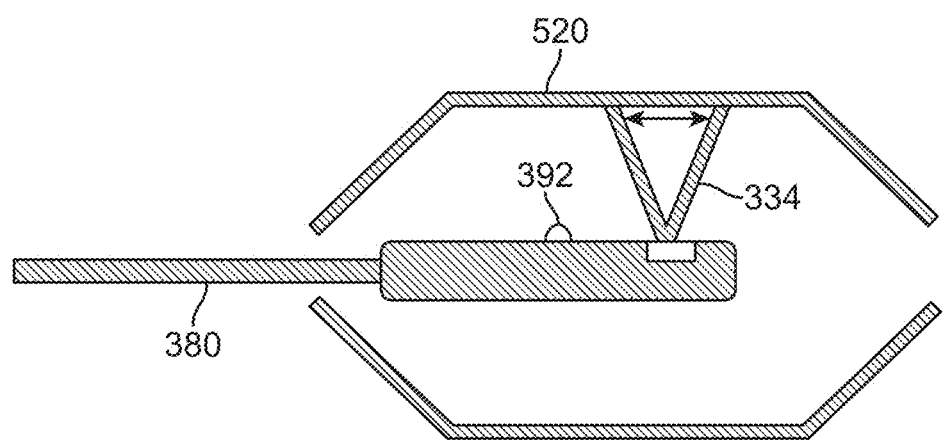

FIGS. 22A and 22B show schematic illustrations of a probe being operated in accordance with the principles of embodiments as described herein, so as to provide a real time determination of the tissue removal profile 520. FIG. 22A shows columnar fluid stream 331 and FIG. 22B shows diverging stream 334, each of which is suitable for combination with the image guided tissue resection as described herein.

Interstitial laser-guided 3D imaging (inside tissue and/or inside an organ with or without fluid and with or without a water jet): employ the spot from the laser on the inner surface of the prostate to determine the depth of a cut. That is, knowing the axial and rotational position of the nozzle, and given that the spot lies on a radius from the nozzle, locating the spot in the image from the camera gives a unique spot-to-nozzle distance. Scanning the laser, and using image processing to find the spot, a full image of the volume inside the prostate can be produced. Combining this with the organ geometrical data, the volume resected can be displayed within the organ in 3D. Alternatively, using the laser to measure the distance between itself and the target surface, an exact three-dimensional replica of the area it has scanned can be recreated.

Acoustic Distance Measurement.

By placing an acoustic transducer in the assembly near the water jet it will be possible to measure distance along the water jet to the tissue plane struck by the jet. Scanning the jet then allows three-dimensional mapping of the cavity. At least one transducer 392 can be provided on the carrier tube 380. Interstitial sound-guided tissue differentiation (inside tissue and/or inside an organ in fluid/gas environments): the audible frequencies produced by the jet-tissue interface can allow for differentiation of tissue. Monitoring the acoustic behavior at this interface may add a depth monitoring feature to the system; this can enhance safety as to prevent the jet from penetrating the prostate's capsule. The sensor could be attached to the tip or anywhere along the probe/ sheath's shaft.

Pulse width modulation of the water column: modulating the frequency at which the water is on and off can allow the user to estimate the distance of nozzle to tissue under camera visualization. The frequency can be fixed to a predetermined column size (e.g. 5 mm) or user could adjust it to match the height between the nozzle and tissue, as shown in FIG. 22A. Alternatively, the diameter of the jet at the jet-tissue interface can determine distance from nozzle assuming the high pressure divergence characteristics of the nozzle is defined as shown in FIG. 22B.

The at least one transducer 392 may comprise an acoustic transducer to receive acoustic signals from the tissue. In some embodiments, at least one transducer 392 transmits acoustic signals for ultrasound imaging. The at least one transducer may comprise a plurality of transducers. A second acoustic transducer can be provided on carrier tube 380 to one or more of receive or transmit acoustic signals for ultrasound imaging from the probe to the tissue. The at least one transducer 392 may comprise an ultrasound array to provide axial and transverse imaging as described herein, for example.

Figure 22C:
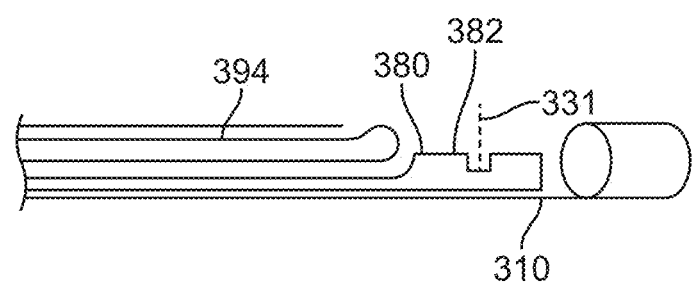
FIG. 22C shows an endoscope placed in the working channel of elongate element with carrier to image tissue when the patient is treated in accordance with embodiments.

FIG. 22C shows an endoscope 394 placed in the working channel of elongate element 310 with carrier 382 to image tissue. The endoscope 394 can be used to image the tissue profile as described herein. For example, a fluid stream can be used to illuminate the tissue with laser pointing with the fluid stream, for example columnar fluid stream 331. The known angle and axial location of the fluid stream can be used with the location of the image from the endoscope to determine the surface profile of the tissue.

Figure 23A:
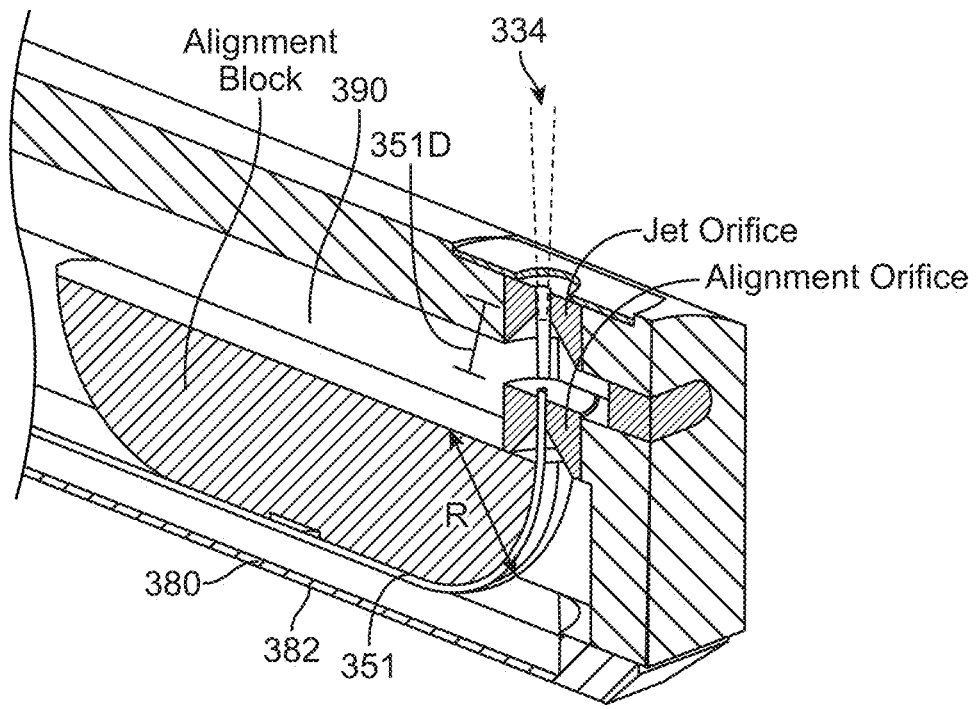
FIGS. 23A and 23B show a carrier configured to provide integrated jet delivery in accordance with embodiments.
Figure 23B:
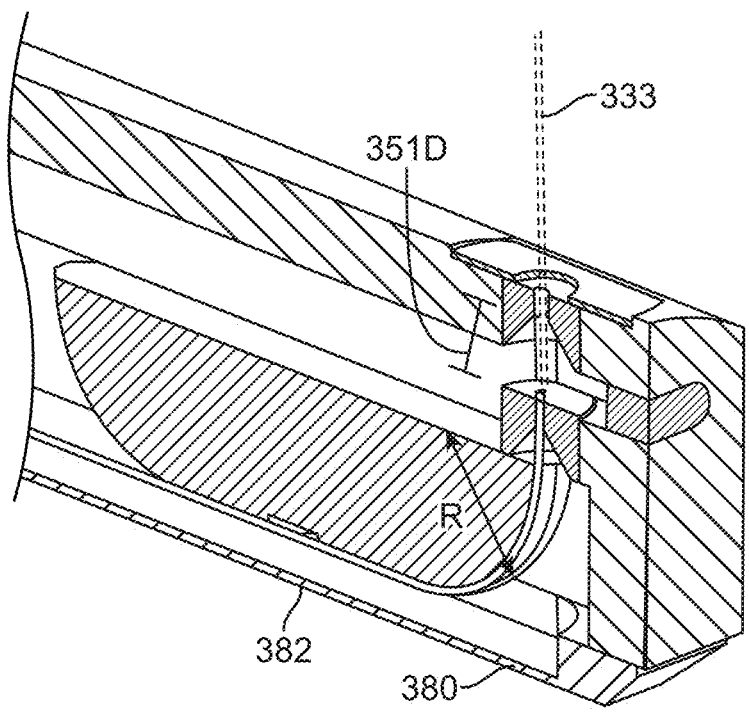

FIGS. 23A and 23B show a carrier configured to provide integrated jet delivery. The carrier 382 that may comprise carrier tube 380 comprises an energy delivery conduit 351, such as an optical fiber. An alignment block is provided to align the optical fiber with the fluid delivery element. The optical fiber can be bent to provide a bend angle suitable for delivery of optical energy to the end of the optical fiber.

The configuration of the optical fiber, jet orifice and alignment orifice provide the integrated jet capability. The jet orifice can be formed in a nozzle that comprises an inverted solid conic section that defines a conic channel to receive the fluid to form the fluid stream and to receive light from the optical fiber. The alignment orifice can be formed in an alignment structure and comprises an inverted solid conic section that defines a conic channel to receive the fiber and the conic channel extends to a cylindrical channel having a diameter sized to receive the optical fiber. In many embodiments, the conic channel comprises of the alignment orifice comprises an angle to receive the fiber such that the fiber can be advanced along the conic channel and through the cylindrical channel without damaging the optical fiber. In many embodiments, the optical fiber, including the cladding, comprises a diameter less than the cylindrical channel of the alignment orifice, such that the optical fiber can be advanced along the cylindrical section without damaging the fiber. The flat section of the alignment block can hold the fiber to inhibit movement of the fiber along the longitudinal axis of the fiber when the tip of the fiber is held in alignment with the cylindrical portion of the jet orifice channel.

The nozzle comprising the jet orifice and the alignment structure comprising the alignment orifice may each comprise a jewel having the conic section and cylindrical section as described herein.

In many embodiments, the cylindrical channel portion of the alignment orifice holds the optical fiber in alignment with a gap extending around at least a portion of the optical fiber. The cylindrical channel portion of the alignment orifice extends along an axis a sufficient distance so as to align the optical fiber with the jet orifice with the gap extending between the fiber and the cylindrical channel portion of the alignment orifice along at least a portion of the fiber and the cylindrical channel portion.

The jet orifice and alignment orifice are spaced apart axially a sufficient distance such that the fluid that passes through the jet orifice can deliver a fluidic stream of energy with predictable flow, for example so as to form the columnar stream with low pressure and the divergent cutting stream with high pressure. In many embodiments, a distance 351D extends between an upper surface of the structure defining the cylindrical channel portion of the alignment orifice and the lower end of the cylindrical channel of the jet orifice. Distance 351D is dimensioned such that the light beam emitted from the optical fiber diverges so as to allow energy transmission of at least about 80% through the jet orifice, for example at least about 90% through the alignment orifice, and such that the predictable flow can be provided. In many embodiments, the distance 351D is within a range from about 200 um to about 2.5 mm, for example within a range from about 0.5 mm to about 2 mm, for example.

An alignment block is coupled to the optical fiber, and the alignment block comprises a surface to engage the optical fiber in which the fiber engaging surface comprises a radius of curvature which can be less than 5 mm, for example no more than 2 mm, so as to allow the cross sectional dimensions of the tip of the carrier 382 to be sized to pass through the working channel with rapid exchange as described herein.

The alignment block can engage the optical fiber so as to retain the optical fiber. The curved engagement surface of the alignment block engages the optical fiber and retains the optical fiber in position. The lower engagement surface of the block also comprises a substantially non-curved elongate channel portion proximal to the curved portion to engage the fiber and fix the location of the fiber within the probe, for example by holding the fiber between the block and an upper surface of the lower portion of the carrier 382.

The fluid jet can be used at high pressure for ablation, for example, a fluid jet, or low pressure, for example, columnar for transmitting an optical beam. The optical fiber can be bent, guided and aligned by positioning the alignment block and alignment orifice to achieve a desired alignment. A short and tight bend radius can be achieved by positioning and fixing the optical fiber in this manner. Cavitation and other fluid jet effects can be altered by varying the relative position and orientation of the jet alignment orifices.

The fluid stream released from the fluid delivery element may comprise a diverging stream 334 as shown in FIG. 23A or a columnar stream 333 as shown in FIG. 23B. The diverging stream 334 can be provided by providing a higher pressure to the delivery element. At high pressure the fluid jet will diverge, for example when the first fluid is a liquid and the second fluid is a liquid. Alternatively a low pressure can be provided to provide the columnar stream 333 as shown. The columnar stream 333 can be provided when the fluid released is a liquid and the liquid is released into a gas, and the liquid can be released with a low pressure within a range from 2 to 100 psi, for example within a range from 5 to 25 psi. At the low pressure the columnar fluid comprising the columnar stream 333 can be used as a pointing device to point the laser beam for alignment. Alternatively or in combination the columnar fluid stream can be used to heat tissue, for example, to heat with one or more of ablation, vaporization, or coagulation, for example.

The diverging stream 334 can be provided by increasing the pressure to the nozzle for tissue removal with the divergent stream as described herein. The optical fiber of the carrier 382 that may comprise carrier tube 380 can be bent to provide a narrow profile configuration of the carrier 382. For example, the optical fiber can be bent with a radius within a range from about 1 to 10 mm, for example, within a range from about 2 to 5 mm. This bending of the optical fiber can allow the light energy to be released and transmitted with high efficiency from a light source to the desired tissue target. Also the terminal end of the optical fiber can be aligned such that light emitted from the optical fiber is substantially directed through the channel defined with the nozzle that delivers the fluid stream. An alignment structure comprising an alignment orifice can be used to align the optical fiber with the jet orifice of the fluid delivery element.

Figure 24:
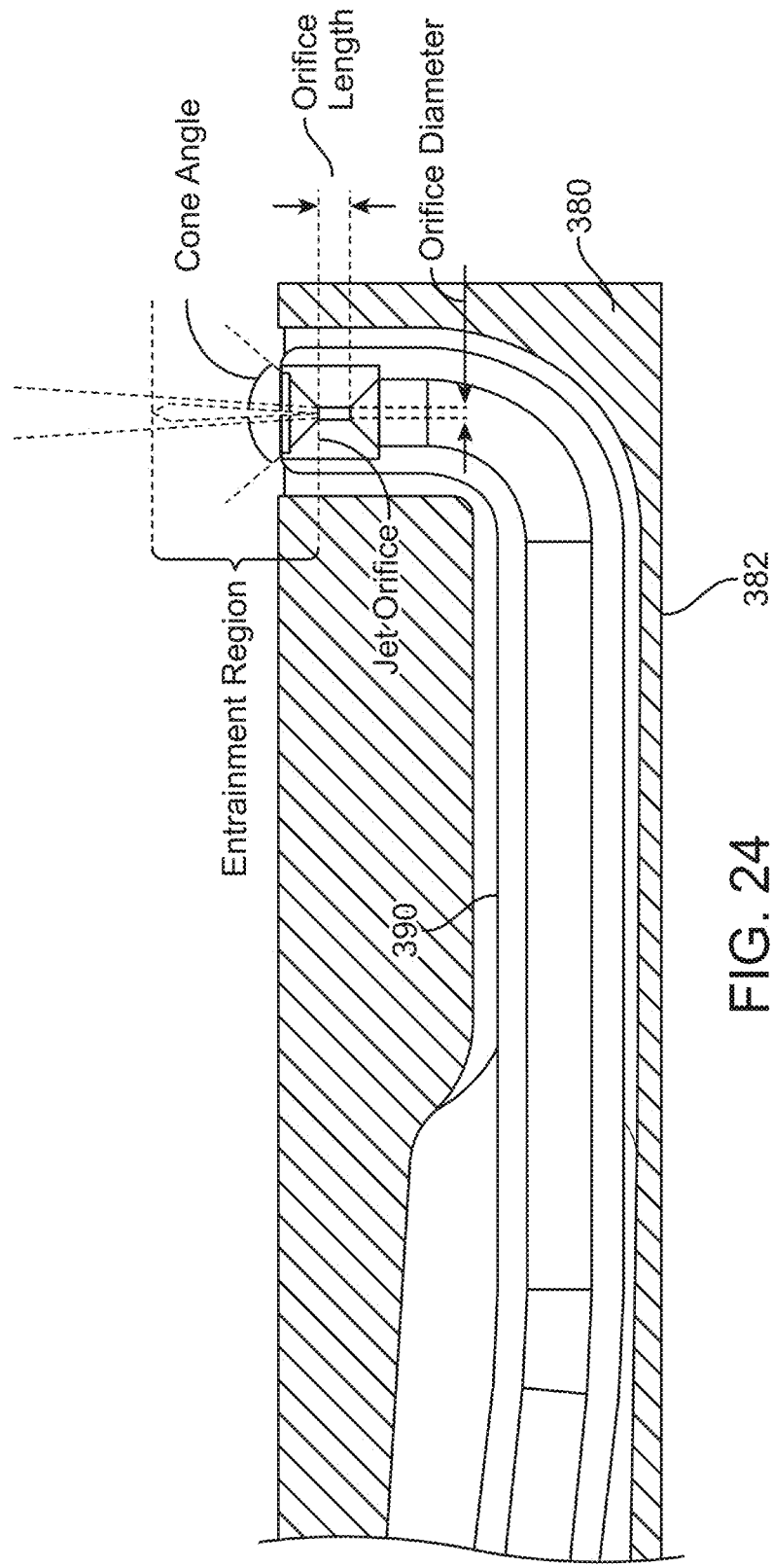
FIG. 24 shows carrier comprising a fluid delivery element and design considerations of the fluid delivery element, in accordance with embodiments.

FIG. 24 shows carrier 382 comprising a fluid delivery element and design considerations of the fluid delivery element. The jet orifice design of the fluid delivery element can be configured in one or more of many ways. Fluid jet ablation characteristics can be varied by varying the jet orifice geometry. For example cone angle variation will result in an increase or decrease in cavitation occurring at the nozzle exit. The jet orifice design may comprise a cone at one or more of the entrance or the exit of the orifice. The cone angle can vary from 0 to 180 degrees, for example. The orifice diameter and orifice length variation can result in a variation in nozzle back pressure and exit speed of the fluid stream. The resulting entrainment region varies with each of these parameters. The entrainment region may comprise a cloud of cavitation bubbles generated by the nozzle. The depth of tissue penetration can be predicted and controlled based on the entrainment region length. In many embodiments the entrainment region can be visualized with ultrasound imaging or optical imaging in combinations thereof. The entrainment region corresponds to a region where cavitation occurs, which allows the entrainment region to be visualized and can be referred to as a fluid flame. The cool cutting of the entrainment region can allow for tissue removal with minimal tissue damage. In many embodiments the cone angles within a range from about 40 degrees to about 80 degrees. A ratio of the orifice length to the inner diameter of the orifice can be within a range from about 1 to 10, for example, within a range from about 4 to 7. A person of ordinary skill in the art can design a jet orifice to treat tissue as described herein based on the teachings provided herein.

Figure 25A:
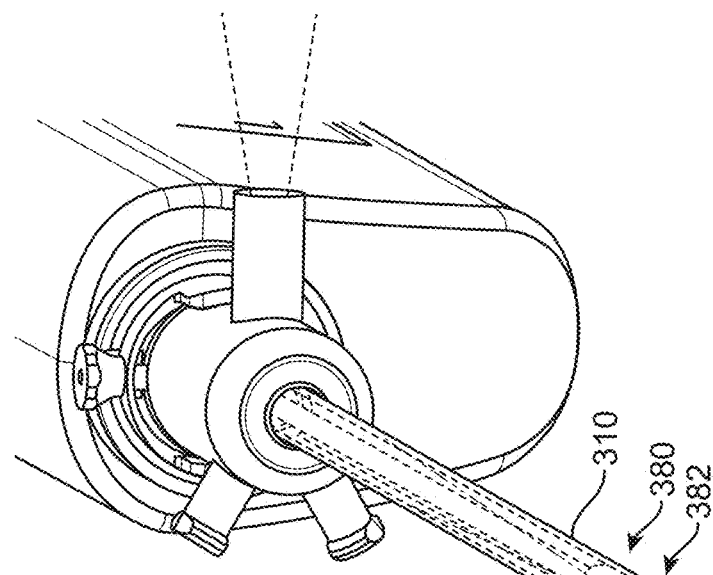
FIGS. 25A, 25B and 25C show jet deflection in accordance with embodiments.
Figure 25B:
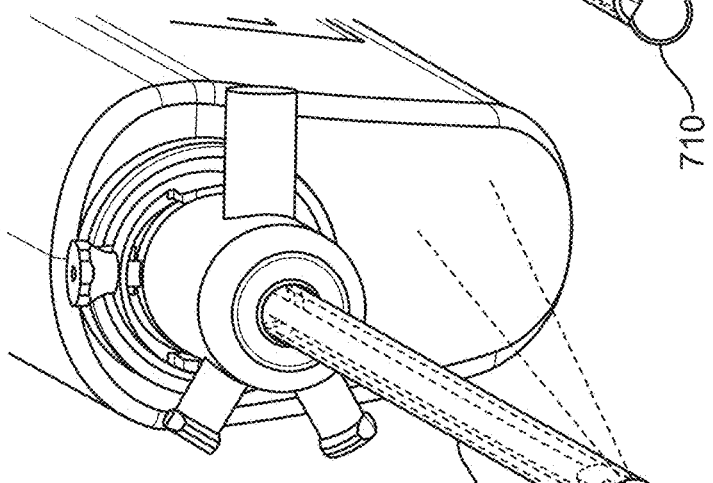
Figure 25C:
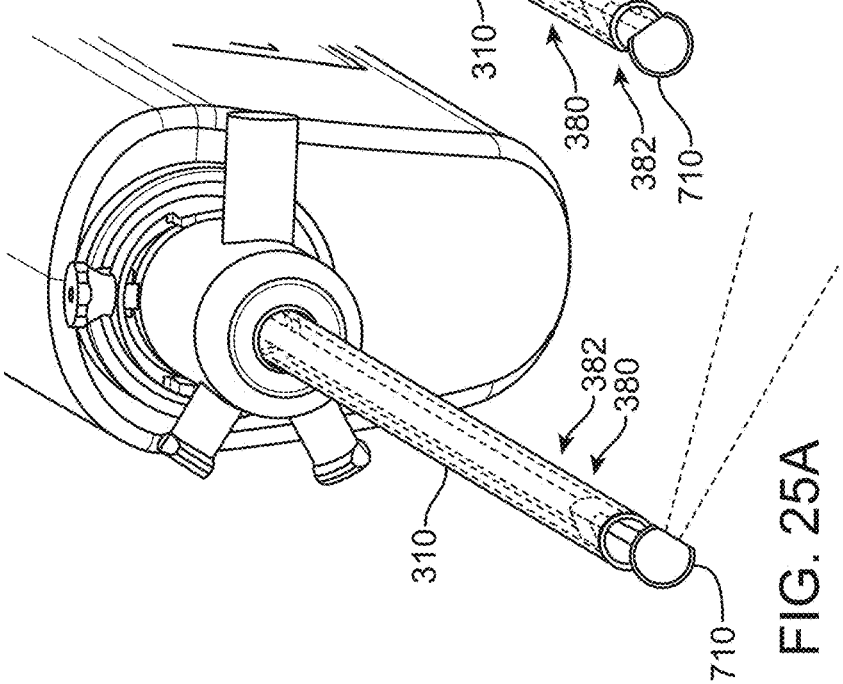

FIGS. 25A through 25C show jet deflection in accordance with embodiments. A deflector 710 can be provided on the distal end of carrier 382. The jet deflection can be achieved in one or more of many ways. The fluid jet can be deflected to achieve different cutting angles, for example. Alternatively or in combination, deflected or diverted fluid jets can be utilized to clean the working channel and auxiliary devices, for example. Deflection of the fluid stream can be actuated manually or robotically via pull wires, pneumatics, hydraulics, mechanical links and other means, for example. The deflector can be moveable under computer control and the deflector may comprise a gimbal to vary deflection of the fluid stream with respect to the longitudinal axis of the carrier 382. FIG. 25A shows deflection of the fluid stream to a first angle in relation to the longitudinal axis. And FIG. 25B shows deflection of the fluid stream at a second angle to the longitudinal axis. FIG. 25C shows rotation of the fluid stream around the longitudinal axis with the fluid stream deflected at the second angle.

FIGS. 26A through 26C show jet masking in accordance with embodiments. Fluid jet masking can be used to achieve different cutting areas, for example in a single location or multiple locations. A masking mechanism can be actuated manually or by robotically via pull wires, pneumatics, hydraulics, mechanical links and other means, for example. In many embodiments a hypo tube extends along carrier 382 so as to allow shaping of the mask on the distal end of the carrier 382. A mask 720 comprises a first configuration 722 as shown in FIG. 26A. As shown in FIG. 26B, mask 720 comprises a second configuration in which the mask has been adjusted to provide a wider angle of the release fluid stream. FIG. 26C shows a third configuration 726 of the mask.

The mask embodiments as described herein can allow rotation of the mask around the longitudinal axis for angles of rotation greater than 360 degrees. For example, a plurality of rotations can be used. The plurality of mask configurations can allow sculpting of the target tissue to a desired intended profile and can allow rapid removal of the tissue with sweep rates that allow a smooth profile to be provided. The shape of the mask can allow for bulk tissue removal with a large divergence angle for tissue proximate to the mask. For tissue farther from the mask the angle may be decreased so as to provide decreased divergence of the jet to reach tissue at a location farther from the mask.

Figure 27B:
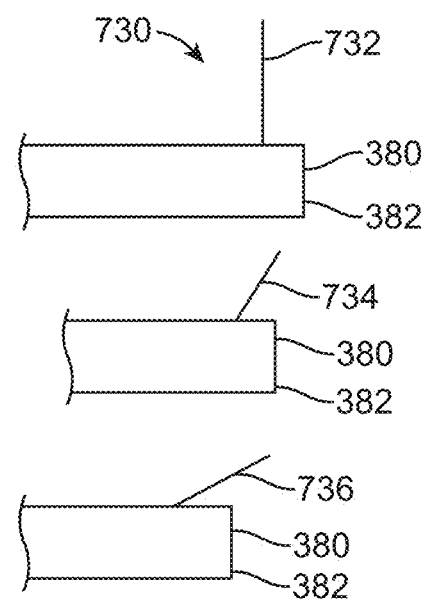

FIGS. 27A and 27B show variation of jet angle in accordance with embodiments. The fluid jet angle and the laser beam can be fixed at different angles to achieve cutting or coagulation. The one or more of cutting or coagulation can be directed to a single location or multiple locations, for example. Angling can assist in targeting tissue near an expandable anchor such as a balloon or reduce risk of incidental contact with unintended tissue. The jet angle can be varied in one or more of many ways. For example, a plurality of carriers 730 can be provided, and each of the carriers may comprise carrier 382 having structures and components for treatment as described herein. Each of the plurality of carriers 730 can provide a different fluid stream angle. For example, a first carrier can provide a first fluid stream at a first angle 732. A second carrier can provide a second fluid stream at second angle 734, and a third carrier can provide a fluid stream at a third angle 736 as shown. The plurality of probes may comprise a set of probes, for example, three or more probes in which each probe is configured to direct one or more of the jet angle or the laser beam at an angle. For example, first angle 732 can extend substantially perpendicular to the elongate axis and third angle 736 can be directed toward a distal end of the probe in order to resect medial tissue, for example tissue of the prostate.

In many embodiments, a plurality of probes can be provided in which one or more jets exits the device axially to target tissue immediately distal of the device.

Figure 28:
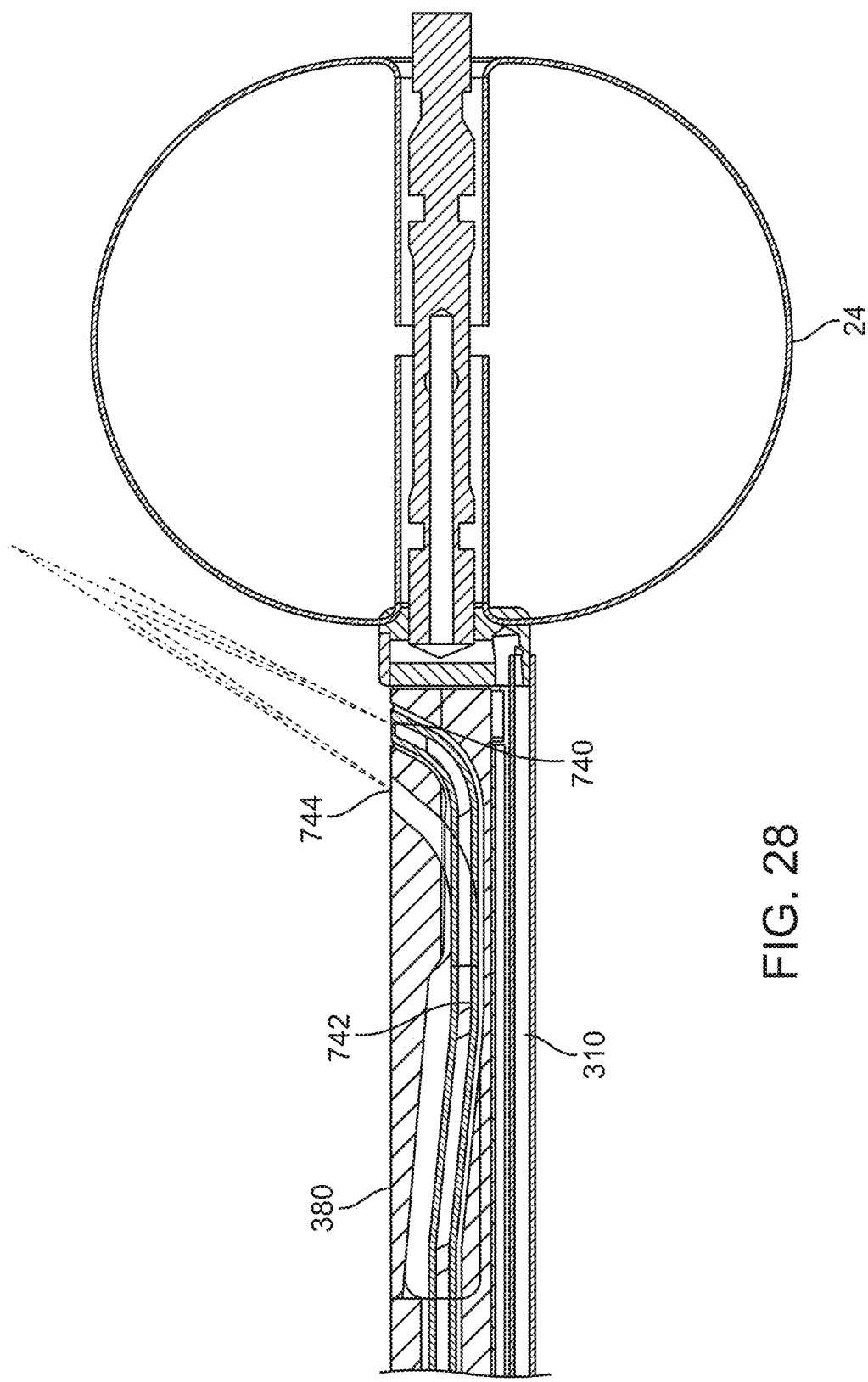
FIG. 28 shows multiple jets delivered simultaneously in accordance with embodiments.

FIG. 28 shows a plurality of jets delivered simultaneously in accordance with embodiments. The plurality of jets of carrier 382 may comprise a primary jet 740 and a secondary jet 744 connected with the supply channel 742. The supply channel 742 may comprise a common supply channel.

Multiple jets can be employed to achieve concurrent ablation and coagulation. This can be achieved through the use of a single supply channel or multiple supply channels. In the case of a single supply channel, a small amount of pressure can be bled off to feed the secondary jet. Additionally, a low power source laser pointer can be utilized for the secondary jet to assist in tissue targeting while using the primary jet for ablation.

In many embodiments, the secondary jet can be used to direct a light beam to coagulate tissue and the primary jet can be used to clear tissue away while the secondary jet is utilized as a wave guide.

In many embodiments, the primary jet can be used to debride tissue while secondary jet is used to coagulate tissue.

Figure 29:
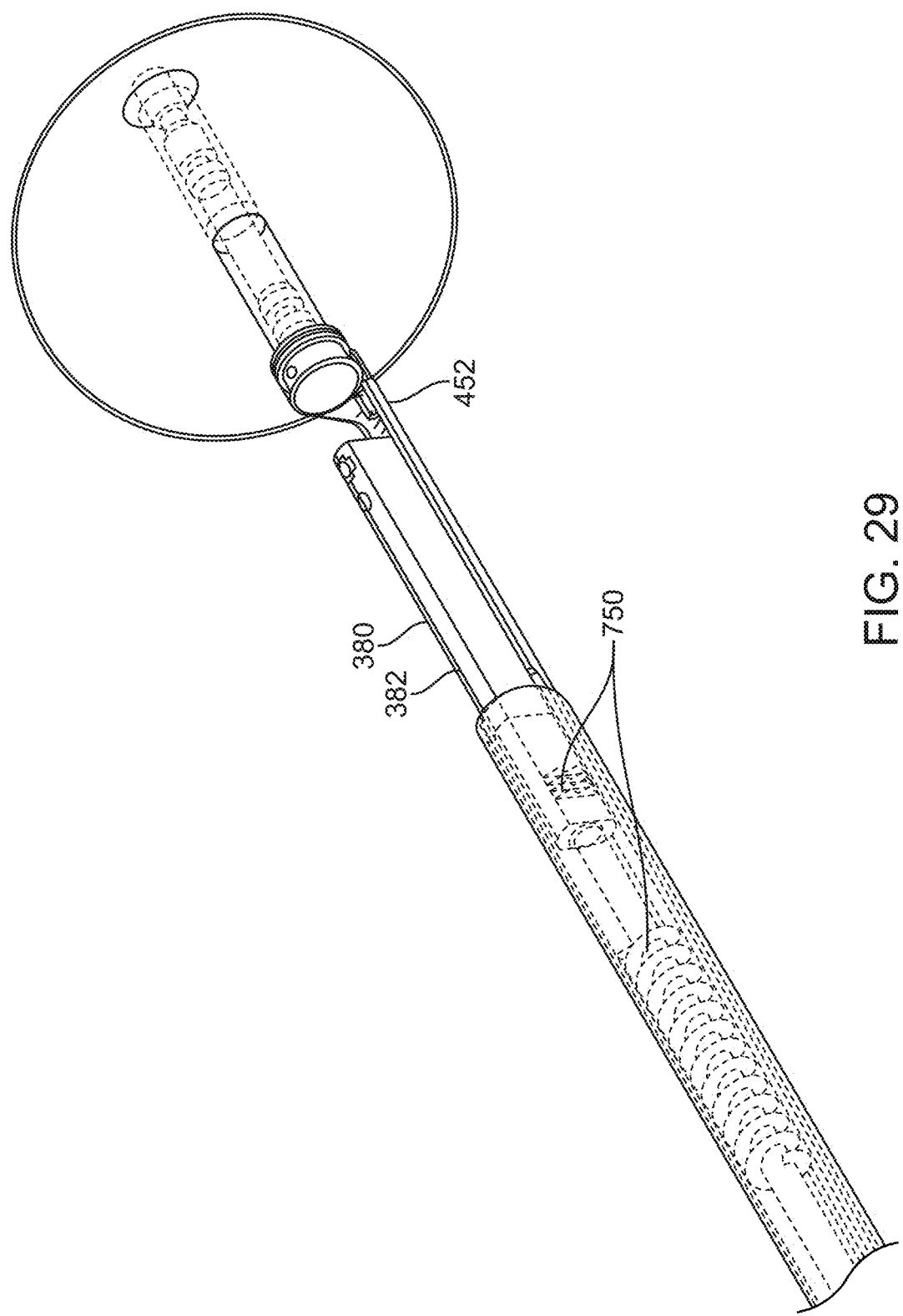
FIG. 29 shows morcellation in accordance with embodiments.

FIG. 29 shows morcellation in accordance with embodiments. In many embodiments, morcellation can be achieved concurrently with ablation with structural features such as blades on the probe or spine for example. If integrated to the probe, morcellation can be automatically driven by the movement of the probe. Vacuum suction can be used alongside or independently with physical morcellation to increase collection flow. The combination of physical morcellation for example with an auger structure and vacuum can be utilized to regulate intraorgan pressure.

Carrier 382 can extend to a distal end portion having one or more jets as described herein. Morcellating features can be provided proximately with respect to the jets and the morcellating features may be contained within the working channel, for example, with an auger shaped structure to remove tissue.

FIG. 30 shows a single tube design in accordance with embodiments. The single tube design may comprise a fluid delivery element such as an orifice jewel 762. A variable bend 760 allows a radius to bend, for example, when the carrier 382 is advanced within the working channels. A fluid is coupled to the orifice on the end of the carrier 382. The fluid may comprise liquid or gas and the orifice on the distal end can be configured in one or more of many ways as described herein. FIGS. 31A and 31B show a single tube design in accordance with embodiments. A fluid such as a liquid or gas can be coupled with a laser as described herein. The laser can emit electromagnetic energy transmitted along an energy conduit 351 such as an optical fiber as described herein. A variable bend 760 can be provided near the fluid delivery element such as an orifice jewel 762 on the distal end. The optical fiber can be aligned with structures as shown in FIG. 31B. For example, a fiber guide can be used to locate the optical fiber coaxially with the orifice of the fluid jet.

The single tube design in accordance with the embodiments of FIGS. 30, 31A and 31B can provide many advantages. For example, package size and complexity can be greatly reduced when utilizing a single tube design. Internal laminar flow characteristics can be improved with a single tube design as the fluid path can be more continuous than with other designs, for example. The orifice jewel can be swaged in place or a small cover can be laser welded to retain the jewel. Optical fiber integration can be achieved through the use of an internal fiber alignment structure. The bend angle and radius can be varied so as to allow for alternate tissue targeting or for manufacturing. Multiple jets can be employed to balance jet reaction courses and cut more than one location concurrently. For example, opposing jets can be used. An additional jet may be added to power rotational motion of the catheter for example.

The small package size can allow the implementation to take the form of a small catheter. This can allow for use with prior commercially available rigid and flexible introducers and scopes. The distal tip shapes can be preformed with a given bend angle to access a tissue volume.

Figure 32:
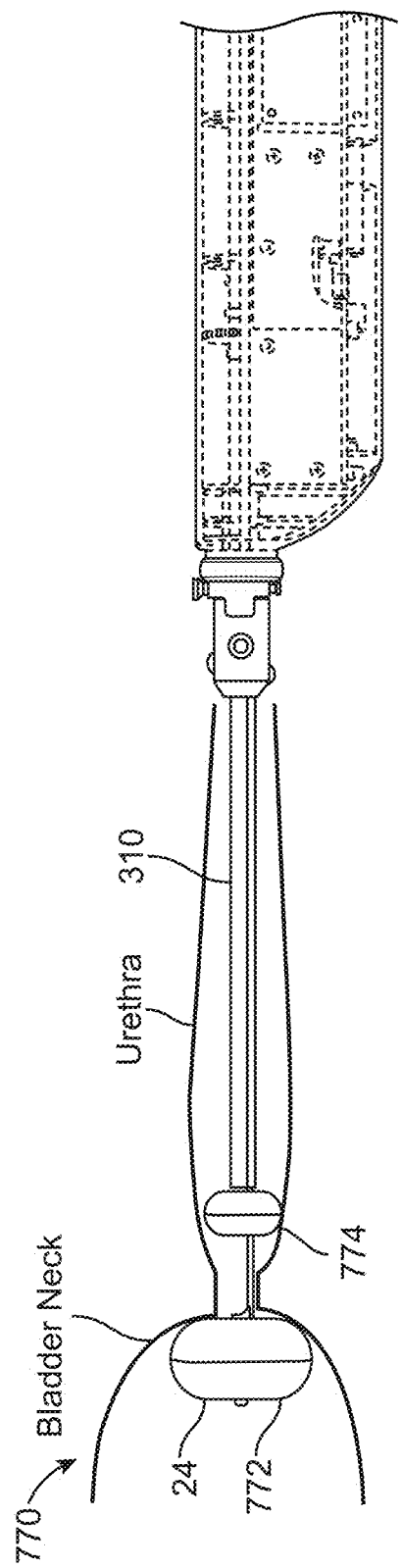
FIG. 32 shows means of registering and locating the treatment system with respect to the human anatomy in accordance with embodiments.

FIG. 32 shows means of registering and locating the treatment system with respect to the human anatomy in accordance with embodiments. A plurality of expandable anchor 770 comprises a first expandable anchor 772 and a second expandable anchor 774. The first expandable anchor 772 may comprise a balloon, for example, and the second expandable anchor 774 may comprise a second balloon, for example. The first expandable structure can be configured to expand in the bladder neck, and the second expandable structure can be configured to expand within the urethra so as to contain movement of the device.

Figure 33:
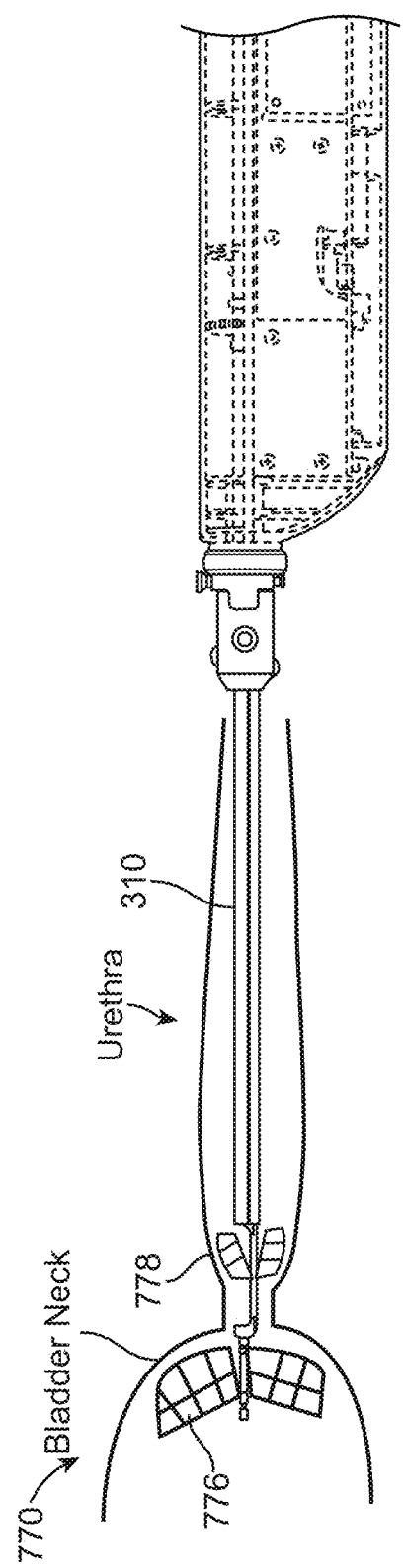
FIG. 33 shows a plurality of expandable structures comprising a first expandable basket and a second expandable basket in accordance with embodiments.

FIG. 33 shows a plurality of expandable structures comprising a first expandable basket 776 and a second expandable basket 778. The expandable basket can be permeable or nonpermeable and can be expanded to allow anchoring. The nonpermeable basket can inhibit fluid flow through the urethra, while the permeable expandable basket can allow fluid flow through the urethra and between the urethra and the bladder.

The plurality of expandable structures can have the benefit of limiting movement of the probe, both from the bladder toward the urethra and also movement from the urethra toward the bladder neck, so as to effectively lock the anchor in place.

Figure 34:
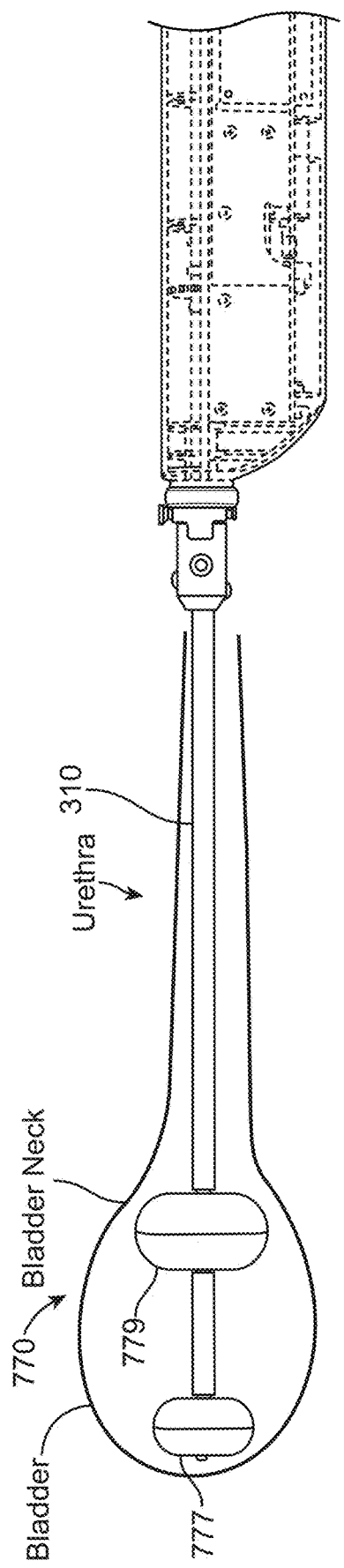
FIG. 34 shows means of registering the system with respect to the human anatomy in accordance with embodiments.

FIG. 34 shows means of registering the system with respect to the human anatomy. For example, a plurality of expandable anchors 770 may comprise a first expandable anchor 777 and a second expandable anchor 779. The first expandable anchor 777 may comprise a balloon or a basket, for example. The expandable anchor 777 is used to position against a posterior wall of the bladder. The second expandable anchor is positioned in the bladder neck. The first expandable anchor and the second expandable anchor can lock the position of the probe so as to inhibit movement. Opposing forces can be applied manually or via robotic control.

In some embodiments, an opposing force can be applied between the first expandable anchor and the second expandable anchor, so as to urge the first expandable anchor toward the bladder wall and the second expandable anchor toward the neck of the bladder.

Additional anchoring op embodiments can be provided in accordance with the teachings described herein. For example, a suction means can be used for anchoring. Alternatively, sensors for patient movement can be used. An arm can be used for anchoring. Clamps can be provided on the groin for anchoring. Magnetic forces can be used to hold the system in place. An attachment to tissue can be provided with suction. Each of these provide nonlimiting examples of anchoring means in accordance with the embodiments described herein.

Figure 35:
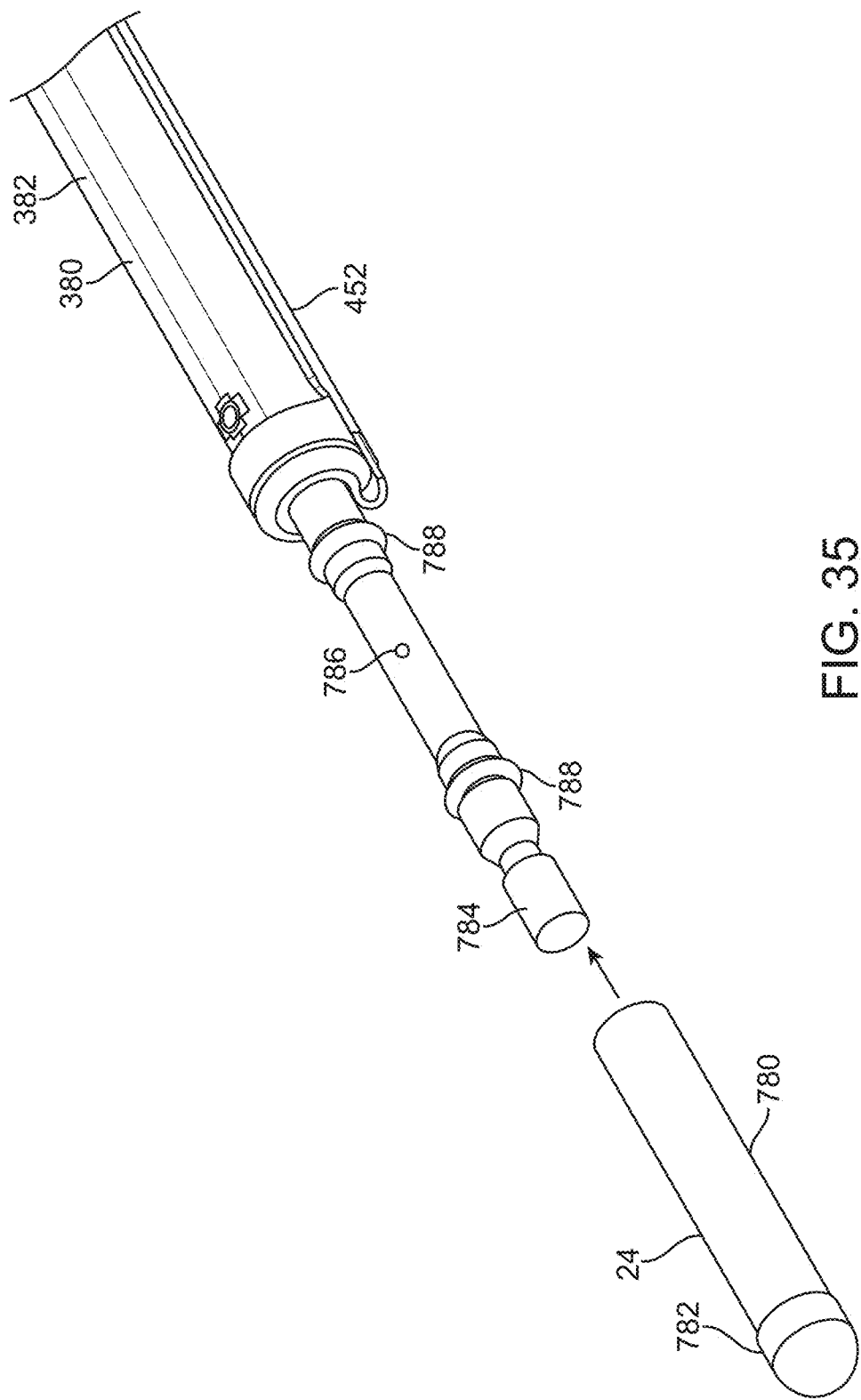
FIG. 35 shows a disposable balloon in accordance with embodiments.

FIG. 35 shows a disposable balloon in accordance with embodiments. The disposable balloon 780 can be threaded onto a distal end of the carrier 382. The disposable balloon may comprise internal threads in the tip of the balloon. Internal thread 782 can engage external thread 784. Threaded engagement between the balloon and the carrier can allow the balloon to be removed subsequent to treatment and the carrier 382 can be sterilized. An inflation hole can be provided. The inflation hole 786 allows inflation of the balloon 780 when the balloon 780 has been threadedly engaged on the distal tip. The disposable balloon can be sterilized individually. The threaded attachment of the balloon can be provided to a hand piece or to the carrier as described herein. Sealing can be achieved with the o ring and threaded engagement. A balloon capable of achieving a 1 to 7 collapsed to inflated ratio can be provided.

Figure 37:
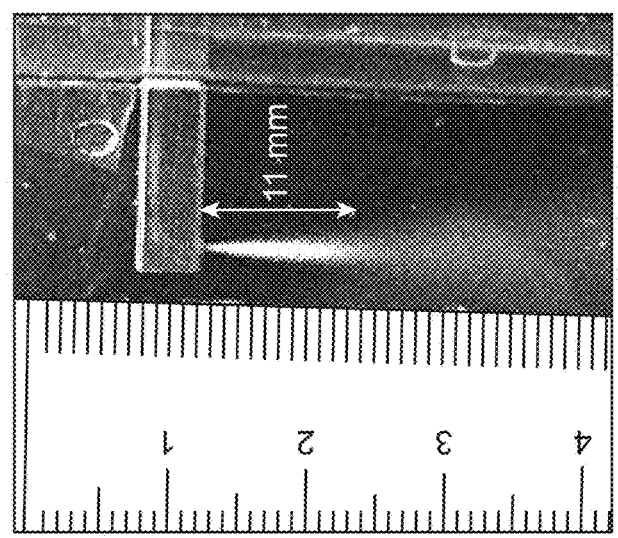
FIG. 37 shows the visible entrainment region at a first size as is shown in FIG. 36.
Figure 36:
FIG. 36 shows tissue resection and depth control in accordance with embodiments.

FIG. 36 shows tissue resection and depth control in accordance with embodiments. A live patient ultrasound image is shown. FIG. 37 shows a visible fluid flame in saline. The visible fluid flame in saline corresponds to the entrainment region of the jet as described herein. The visibility of the fluid flame of the entrainment region is provided with cavitation of small bubbles that can produce light scattering or acoustic scattering, so as to make the fluid flame of the entrainment region visible with imaging by ultrasound or optical imaging, for example. The benefit of the visible entrainment region can be for a physician to visualize the distance of the treatment and to compare this distance with ultrasound. FIG. 37 shows the visible entrainment region at 11 millimeters, the same size as is shown in FIG. 36. The substantial similarity of the distance of the entrainment region corresponds to the distance of tissue resection and removal. This experimental result showing the visualization of the entrainment region can provide for a safer treatment. Merely by way of example, the flow parameters used with the images shown in FIGS. 36 and 37 comprise a flow rate of approximately 130 milliliters per minute and a nozzle back pressure of approximately 2700 psi. The configuration of the nozzle on the carrier comprise a first liquid emitted with a divergent stream as described herein into a second fluid so as to provide the divergent stream. The second fluid comprises a liquid.

A physician when treating a patient, can use a live patient ultrasounds, for example, transrectal ultrasound (hereinafter "TRUS") as described herein. The physician can do the ultrasound in the entrainment region from the probe tip. This can be used to determine the appropriate parameters to treat the patient. For example, the physician can adjust the pressure so as to limit the depth of penetration of the probe tip such that the probe tip does not release energy to cause cutting outside of the organ, for example, beyond the sack of the organ such as the sack of the prostate. The image of FIG. 36 shows on the left hand side of the image a structure corresponding to an expandable balloon and the arrows show the 11 millimeter dimension. FIG. 37 is an optical image showing a similar distance of the entrainment region. The sweeping motion of the stream shown in FIG. 36 can be used to adjust the treatment to be contained within the prostate.

Figure 38:
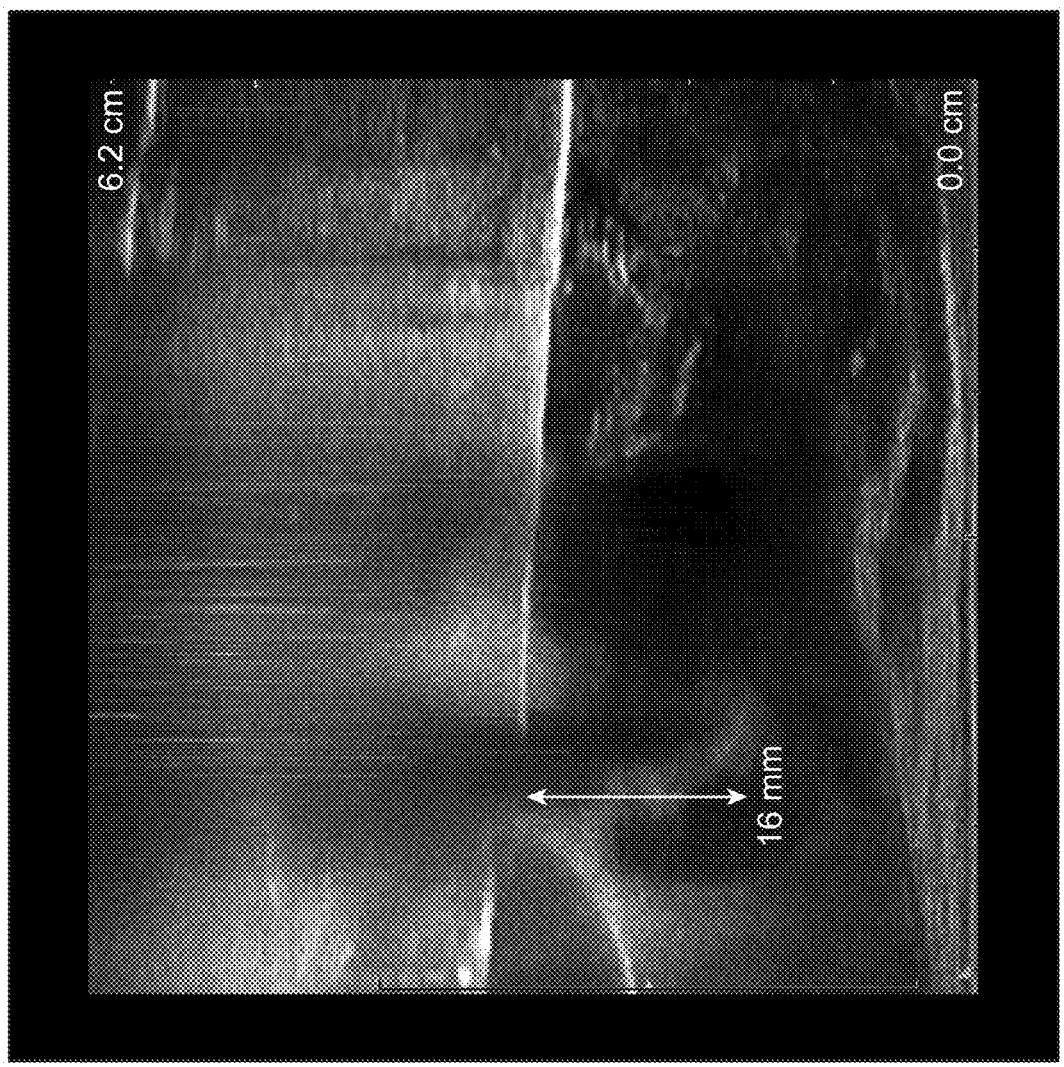
FIG. 38 shows tissue resection depth control in accordance with embodiments.

FIG. 38 shows tissue resection depth control in accordance with embodiments. Live patient ultrasound from the patient is shown in FIG. 38 similar to FIG. 37, but with increased back stream pressure to the nozzle.

Figure 39:
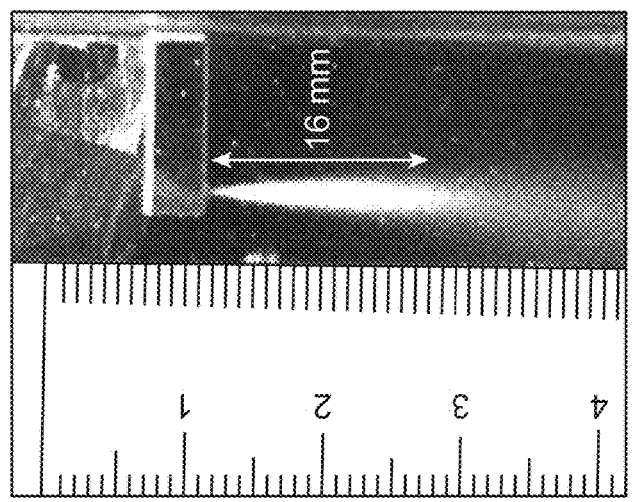
FIG. 39 shows an optical image of the entrainment region "flame" in saline as shown in FIG. 38 with a different pressure than is shown in FIGS. 36 and 37, in accordance with embodiments.

FIG. 39 shows an optical image of the fluid flame in saline showing the entrainment region with a different pressure. The pressure flow parameters for FIGS. 38 and 39 comprise an approximate flow rate of 205 milliliters per minute and the nozzle back pressure of approximately 5760 psi. The corresponding tissue resection depth is approximately 16 millimeters. The live patient ultrasound image shows an entrainment region of 16 millimeters similar to the entrainment region seen optically. The sweeping motion of the probe and the fluid stream emitted from the probe as seen on the left hand side of the image can be used to set the flow parameters and pressure so as to treat the patient safely with ultrasound images of the entrainment region.

Figure 40:
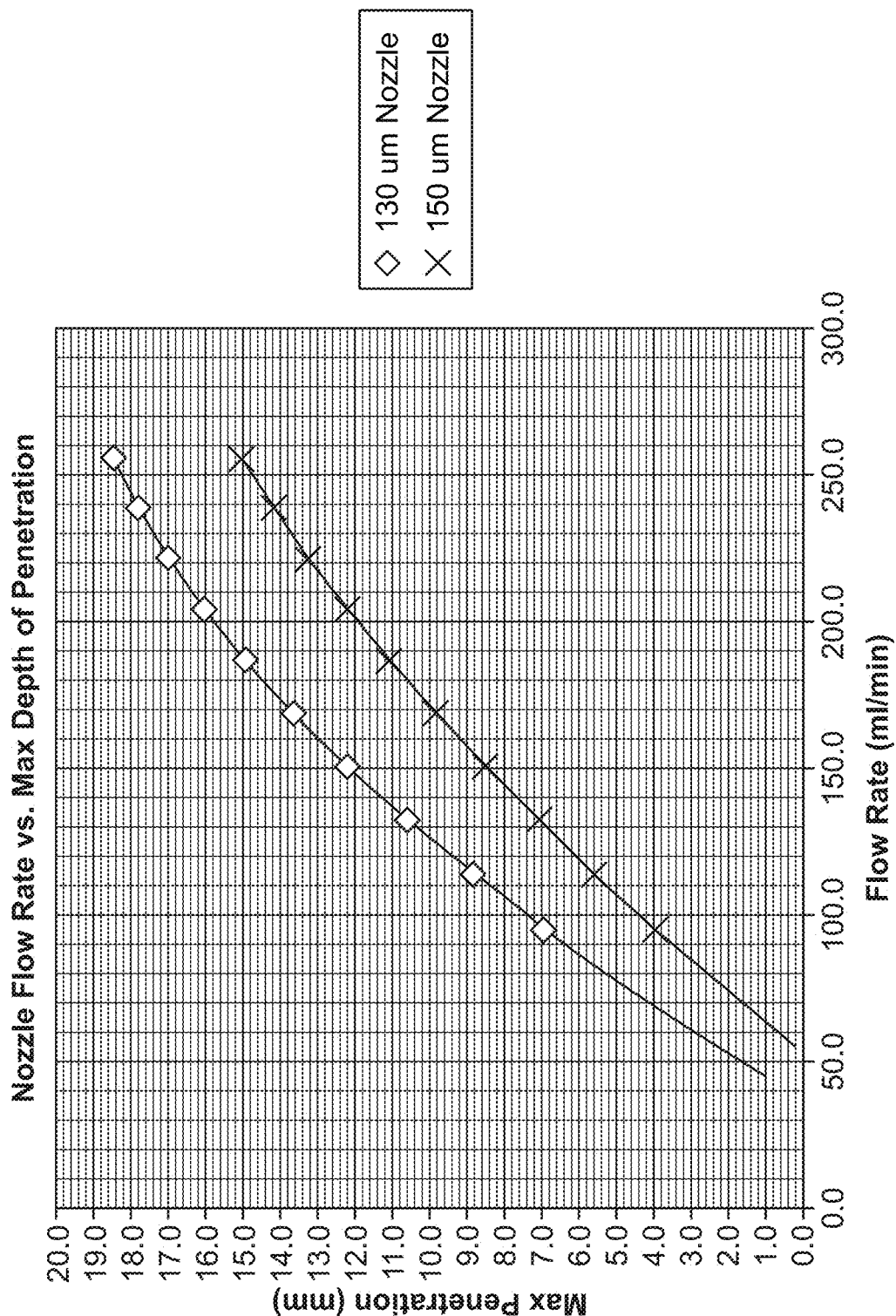
FIG. 40 shows nozzle flow rate versus maximum penetration depth for a plurality of pressures and nozzles in accordance with embodiments.

FIG. 40 shows nozzle flow rate versus maximum penetration depth for a plurality of pressures and nozzles. The flow rate in milliliters per minute is shown. The maximum penetration depth is also shown as a function of the flow rate. 130 micron nozzle shows a tissue penetration depth with diamonds and the 150 micron nozzle is shown with X's. The tissue penetration depth can be used based on the teachings described herein to set the flow rate parameters for treatment. For example, for a treatment to a maximum penetration depth of 12 millimeters or 130 micrometer nozzle, a flow rate of 150 milliliters per minute is selected. Similarly, for the 150 micron nozzle, a flow rate of 200 milliliters per minute is selected. A person of ordinary skill in the art can construct software to automatically identify a nozzle for treatment based on depth and also to identify a flow rate suitable for treatment based on depth. In addition, the flow rate can be varied based on the tissue profile as described herein. For example, tissue treatment profiles based on axial and sagittal images as described herein.

Figure 41:
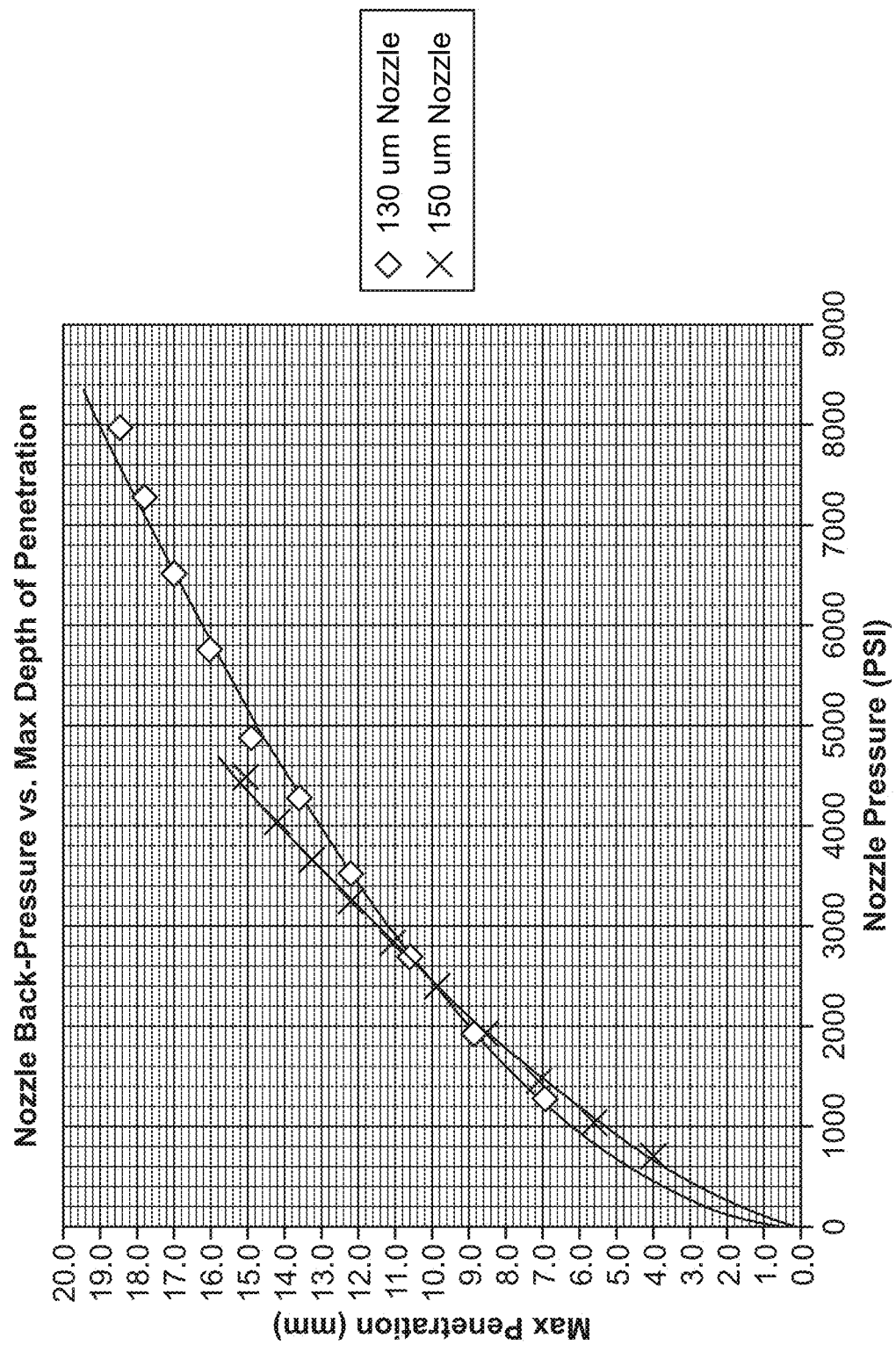
FIG. 41 shows nozzle back pressure versus maximum depth of penetration in accordance with embodiments.

FIG. 41 shows nozzle back pressure versus maximum depth of penetration. Maximum penetration in millimeters is shown as a function of nozzle pressure in psi for both 130 micron nozzle and 150 micron nozzle. Based on the identified nozzle size and tissue penetration depth, the software or user can identify an appropriate nozzle pressure to treat the patient.

Figure 42:
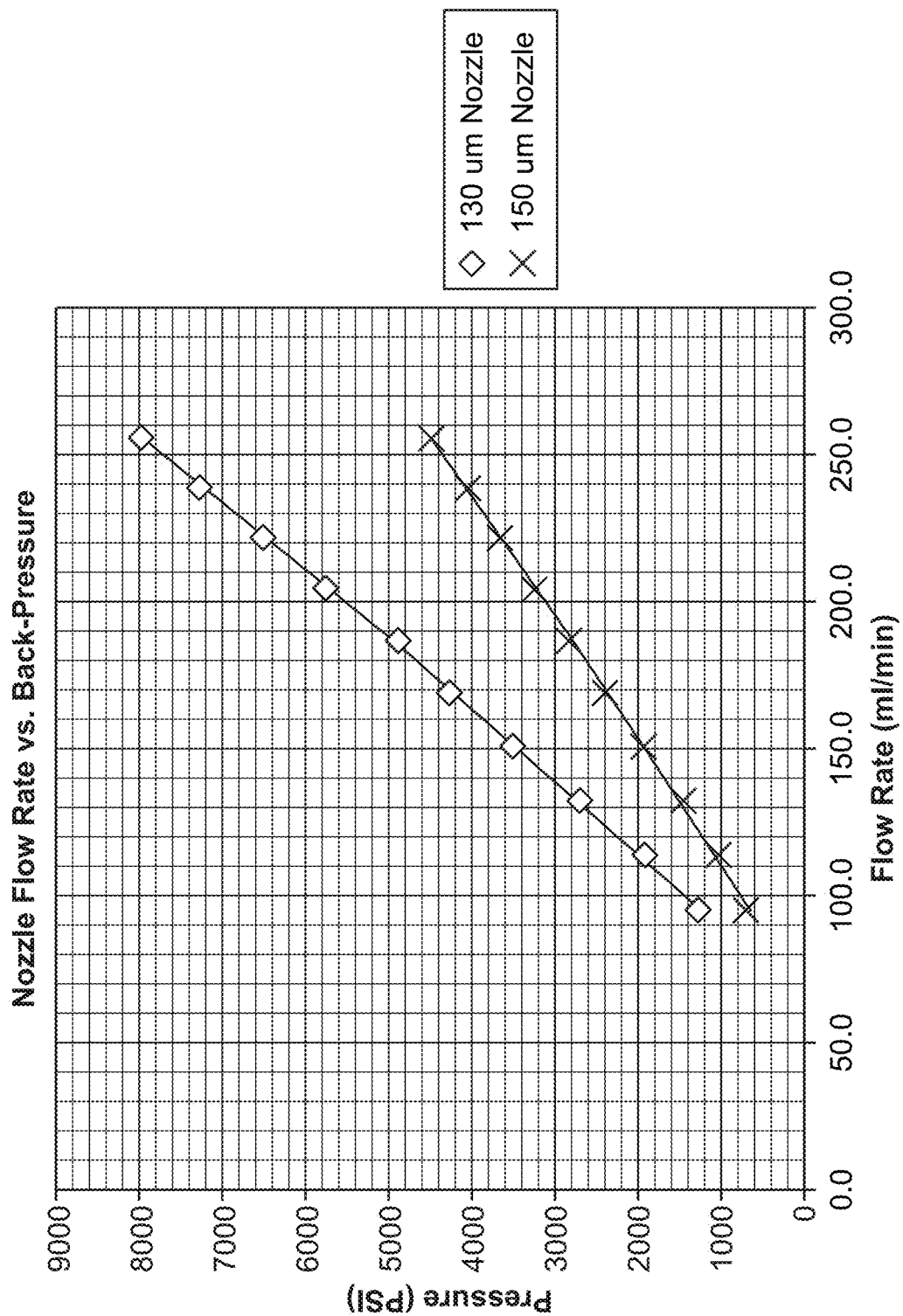
FIG. 42 shows nozzle flow rate versus back pressure for 130 micron nozzle and 150 micron nozzle in accordance with embodiments.

FIG. 42 shows nozzle flow rate versus back pressure for 130 micron nozzle and 150 micron nozzle. The pressure and flow rate are shown. For a flow rate, the flow rate is shown in milliliters per minute and the pressure is shown in psi. The flow rate can be from about 100 milliliters per minute to about 250 milliliters per minute, and the pressure can be from under 1000 psi to as high as 4000 psi or, for example, 8000 psi. In specific embodiments, the flow rate with a larger diameter nozzle is approximately linear with the pressure and the flow rate with the 130 micron nozzle is approximately linear with pressure. These relationships of flow rate and pressure can be used to appropriately set the pressure for treatment for desired flow rate. Furthermore, these flow rate pressure relationships can be non-linear when the range is expanded to lower values, or higher values, or both. Alternatively or in combination, the flow rate pressure relationships can be non-linear when different nozzles with different characteristics are used, for example.

A person of ordinary skill in the art can use the one or more of the nozzle pressure, cut depth and flow rates to resect tissue to a predefined profile and volume as described herein.

Ablation Monitoring with Acoustic Measurements

In many embodiments, an acoustic probe can be used to monitor the ablation. The probe can be coupled to the patient in one or more of many ways, for example placed on a limb or body of the patient and coupled to the skin of the patient with a gel.

In many embodiments, the ablation monitor comprises an acoustic sound analyzer. The sound analyze may comprise an acoustic sensor such as a hydrophone located in one or more of the Aquablation™ probe 450, the handpiece, the rectum of the patient or external to patient, such that sound emitted by the Aquablation™ system and the corresponding interaction with the prostate can be measured. The processor system may comprise instructions to determine one or more the following parameters:

a. Depth of tissue penetration
b. Volume removed (with a trend towards lower frequencies)
c. Flow rate (cavitation/fluid flame is extremely loud and can be characterized)
d. Perforation (a jet that is not contained emits a different sound)
e. Tissue densities (cancer, adenomatous tissue, surgical capsule)

Examples of actual decibel data are disclosed herein with reference to the following figures.

Figure 43:
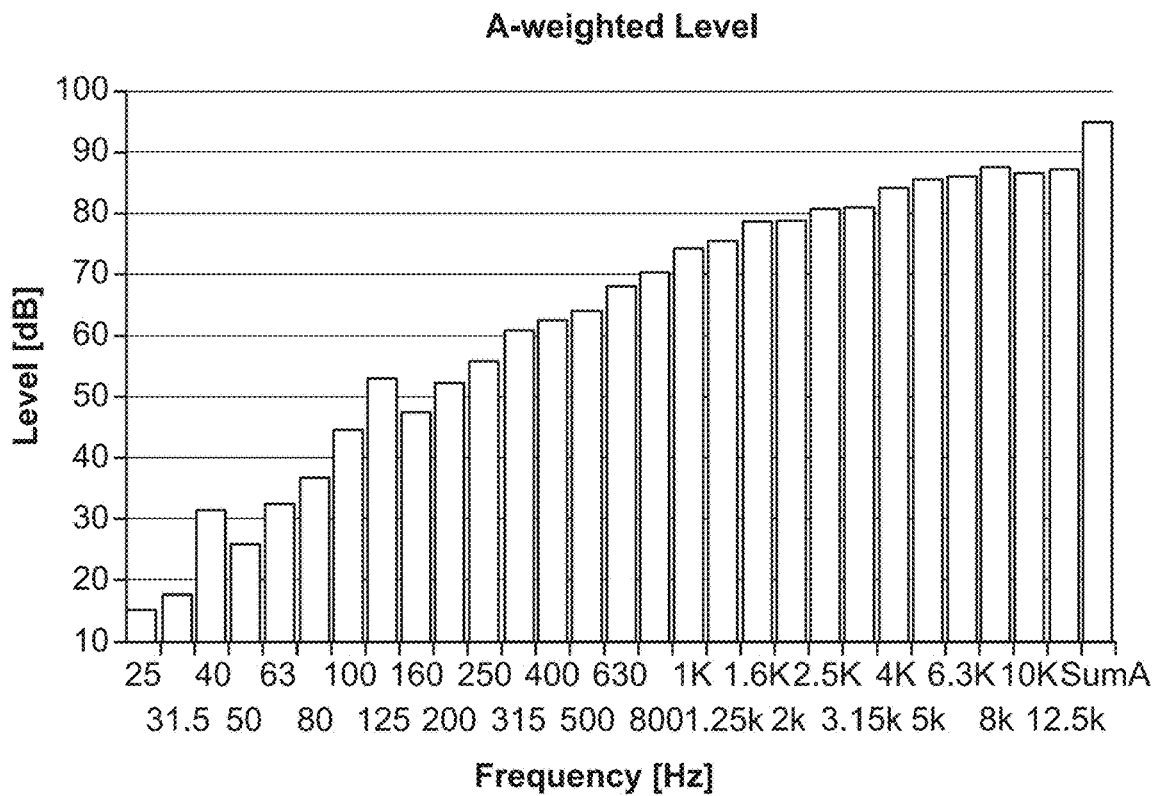
FIG. 43 shows a frequency spectrum of a jet configured to cut tissue in saline without striking tissue, in accordance with embodiments.

FIG. 43 shows a frequency spectrum of a jet configured to cut tissue in saline without striking tissue. FIG. 43 shows frequencies of sound from 25 Hz to 12.5 kHz, and a cumulative total. The cumulative total is approximately 95 dB. Frequencies up to the 80 Hz band are below 40 dB. Frequency bands from about 100 to 250 Hz are below 60 dB. Frequency bands of about 315 Hz and above are at least about 60 dB.

Figure 44:
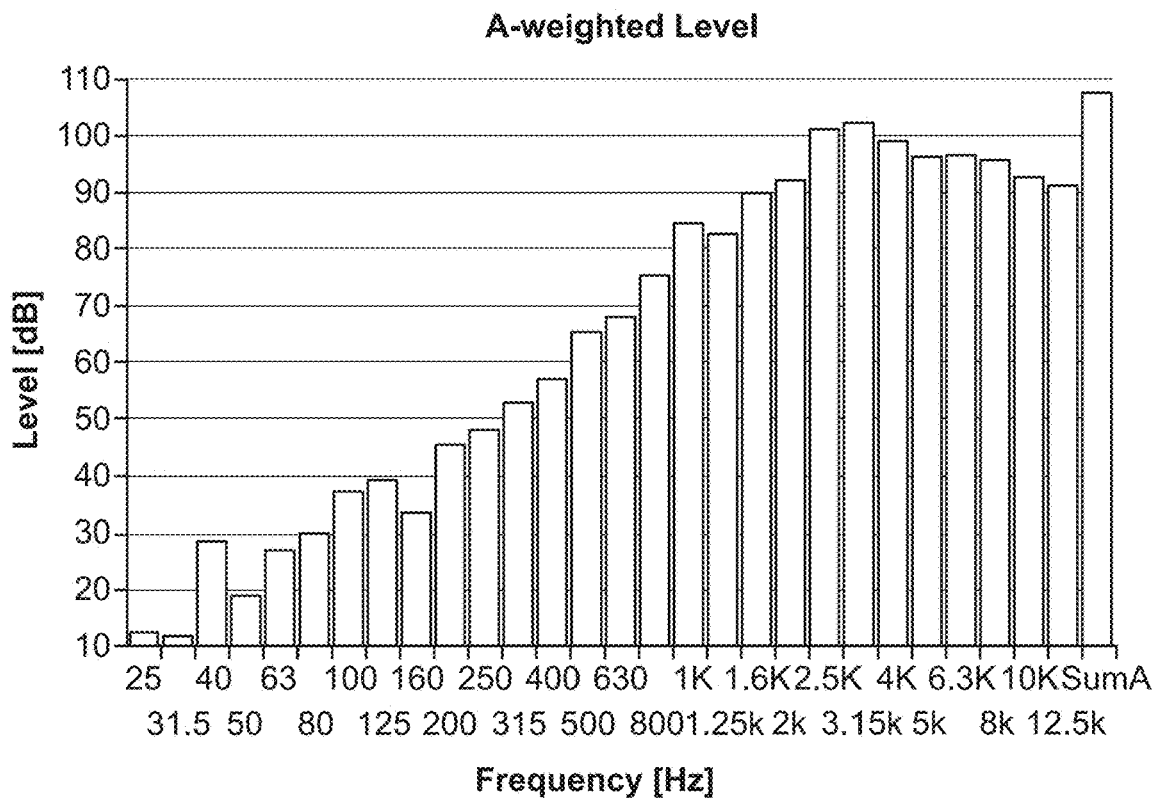
FIG. 44 shows a frequency spectrum of the jet as in FIG. 43 ablating tissue, in which the frequency spectrum has an increase in high frequency components corresponding to the ablation of tissue, in accordance with embodiments.

FIG. 44 shows a frequency spectrum of the jet as in FIG. 43 ablating tissue, in which the frequency spectrum has an increase in high frequency components corresponding to the ablation of tissue. The cumulative total is approximately 95 dB. The intensity increases of the frequency bands show a general trend of increasing with frequency, with greatest intensity around 4 to 12.5 kHz of about 85 dB. Frequencies up to the 80 Hz band are below 30 dB. Frequency bands from about 100 to 250 Hz are below 50 dB. Frequency bands of about 315 Hz and above are at least about 50 dB. An acoustic intensity peak is located within a range of frequencies from about 2 to 5 kHz, for example within a range from about 2.5 to 4 kHz, at about 3.15 kHz.

These data show trends suitable for incorporation in accordance with embodiments, which include one or more of: the intensity peak for tissue ablation located within a range of frequencies from about 2 to 5 kHz; decreased intensity of low frequencies near about 100 Hz during ablation; and a peak intensity over 100 dB, for example.

The measured frequencies may comprise one or more frequencies within a range from about 0 to 180 kHz, for example. The above frequency spectra are provided in accordance with some embodiments, and a person of ordinary skill in the art will recognize that many frequencies can be measured and the intensity of many frequency bins determined, for example for frequencies up to about 200 kHz.

The processor system as described herein may comprise one or more instructions to measure the acoustic signal during treatment. The processor system may comprise a frequency analyzer to measure frequency components of the acoustic spectrum. The acoustic signal comprises several frequencies with greater intensities. For example, each frequency band from 2 kHz to about 12.5 kHz has an intensity greater than 90 dB when the jet ablates tissue and each of these intensities is below 90 dB when the jet having the same flow parameters is placed in saline with cavitation to provide a cool flame as described herein. The cumulative acoustic intensity is about 95 dB when the jet is placed in saline and about 108 dB when the probe ablates tissue.

Based on the measurements disclosed herein, a person of ordinary skill in the art can configure to processor system to monitor for perforation of tissue based on a decrease in the intensity of the measured acoustic signal when the flow of the jet remains substantially constant.

Work in relation to embodiments suggests that different tissue types provide different frequency signatures, and a person of ordinary skill in the art can conduct experiments to determine the acoustic frequencies of each of a plurality of tissue types in response to the cutting jet in order to determine the type of tissue being ablated with real time monitoring. Types of tissue that can be monitored and for which ablation can be detected acoustically include one or more of: prostate tissue, benign prostate hyperplasia tissue, prostate capsule tissue, and carcinoma prostate tissue. A person of ordinary skill in the art can conduct experiments to determine the frequency characteristics of tissue as described herein in order to determine the type of tissue and one or more tissue removal parameters as described herein, such as:

a. Depth of tissue penetration
b. Volume removed (with a trend towards lower frequencies)
c. Flow rate (cavitation/fluid flame is extremely loud and can be characterized)
d. Perforation (a jet that is not contained emits a different sound)
e. Tissue densities (cancer)

Figure 45:
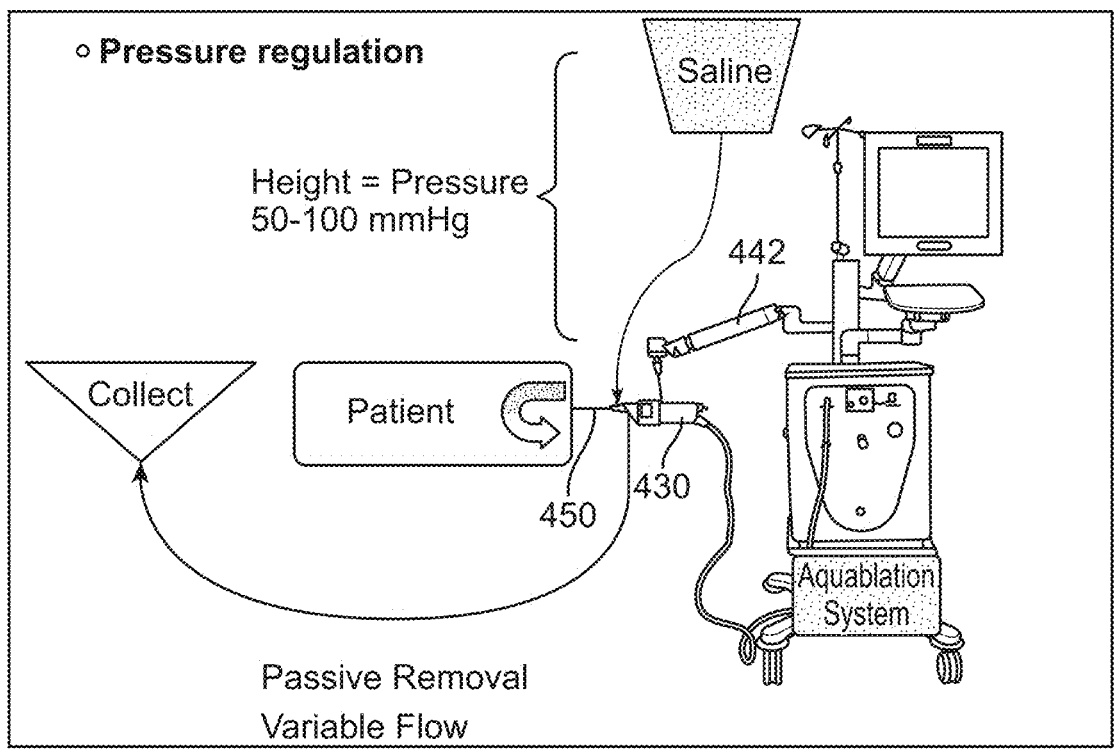
FIG. 45 shows pressure regulation of the surgical site with a substantially constant pressure and variable flow, in accordance with embodiments.

FIG. 45 shows pressure regulation of the surgical site with a substantially constant pressure and variable flow. The saline bag is placed at a height to provide substantially constant pressure regulation. The bag of saline can be placed at a height corresponding to about 50 to 100 mm of Mercury (hereinafter "mmHg"). The saline bag is coupled to the irrigation port as described herein. A collection bag is coupled to one or more of the irrigation port, the aspiration port, or the suction port as described herein. The collection bag collects tissue removed with the water jet ablation probe 450 as described herein.

Figure 46:
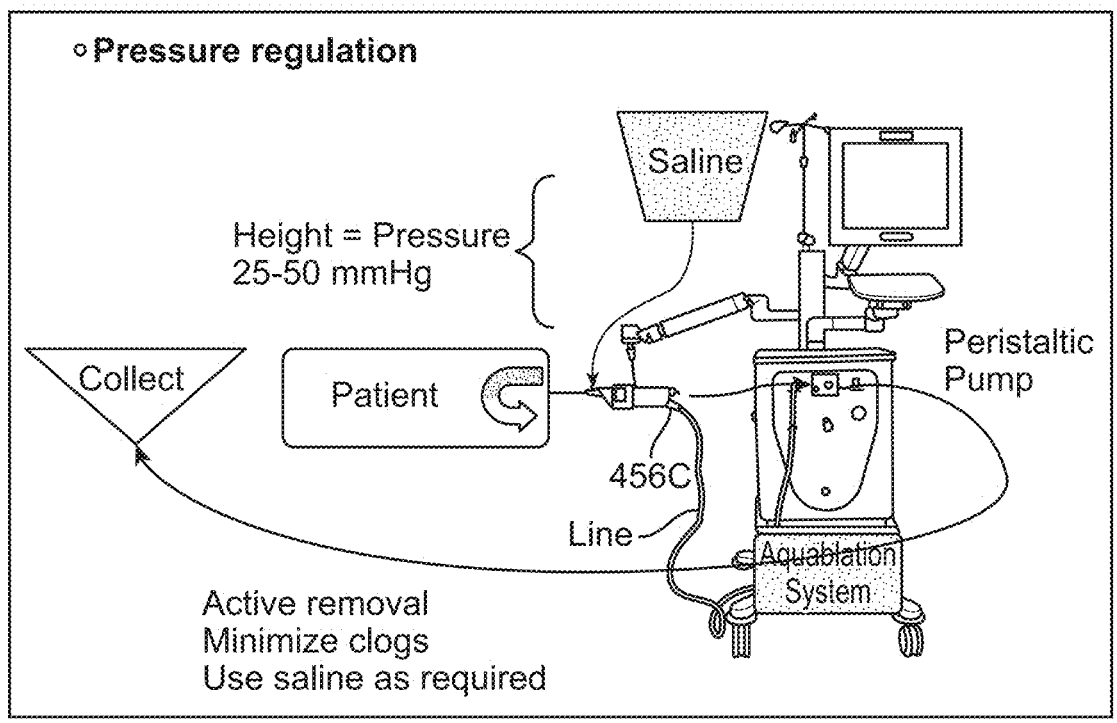
FIG. 46 shows flow regulation of the surgical site with a pump providing a substantially fixed fluidic flow and a substantially constant pressure, in accordance with embodiments.

FIG. 46 shows flow fluidic regulation of the surgical site with a pump providing a substantially fixed fluidic flow. A pump removes fluid from the surgical site at a substantially fixed flow rate. The pump may comprise a peristaltic pump, for example. The pump is configured to remove fluid at the substantially the same rate or greater than Aquablation™ saline flow rate, in order to inhibit pressure build up at the surgical site. The peristaltic pump can be coupled to the aspiration port of the manifold comprising tissue removal port 456C as described herein, for example. Providing the pump having the flow rate that is at least the flow rate of the tissue ablation jet provides improve suction as ablated tissue that might otherwise block the tissue removal openings and channel can be subjected to greater amounts of pressure when the pump maintains the substantially fixed flow rate in order to remove the material that would otherwise block the channel.

The irrigation flow from the saline bag may remain open in order to provide at least two functions: 1) maintain pressure based on the height of the saline bag; and 2) provide a safety check valve in case the peristaltic pump is not functioning correctly as visually a person would see flow entering the bag as a pink color.

In alternate embodiments, the flow of the pump comprises a variable rate in order to provide a substantially constant pressure within the patient near the surgical site. The active sensing of pressure of the treated organ and variable flow rate of the pump may comprise a closed loop pressure regulation system. The pump can be coupled to a sensor such as a pressure sensor, and the flow rate varied to maintain substantially constant pressure. The pressure sensor can be located in one or more of many places such as on the treatment probe, within the aspiration channel of the probe, in a recess of an outer surface the probe, on an inner surface of the probe coupled to the surgical site, or near the inlet to the pump on the console for example.

Imaging of the Treatment Site

Transrectal Ultrasound

Transrectal ultrasound as described herein can be used to probe images of the target tissue site. The images can be used for one or more of treatment planning or real time monitoring of the treatment site as described herein.

Transurethral Ultrasound

The transurethral ultrasound probe can be introduced into the patient through the urethra alongside or within the Aquablation™ treatment probe 450 for one or more of planning or real-time viewing of treatment as described herein. The ultrasound probe can be similar commercially available an intravascular ultrasound (hereinafter "IVUS") probe and an endobronchial ultrasound (hereinafter "EBUS") probe. The US probe can be placed in a working channel of the stiff sheath or ultrasound probe, for example. Alternatively or in combination, the US probe can be attached to the treatment probe 450 such that the US probe one or more of translates, rotates, or oscillates with the treatment probe 450, such that synchronous movement of the treatment probe 450 and US probe can be provided. These embodiments are not dependent on a separate TRUS probe whose images can be dependent on accurate and optimal user placement within the rectum. Work in relation to embodiments suggests that transrectal ultrasound can distorts the prostate and resulting images, both of which may be related to compression of tissue as the TRUS probe is advanced into the patient.

Figure 47A:
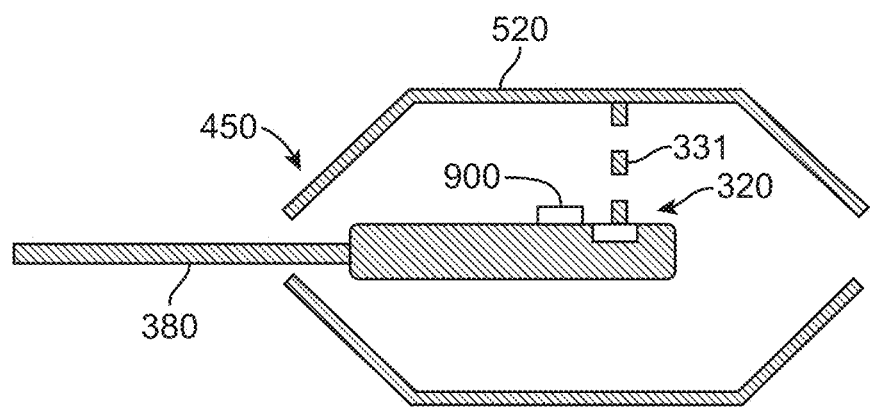
FIGS. 47A and 47B show a transurethral treatment probe having an ultrasound array located near the fluid release element to image the treatment site.
Figure 47B:
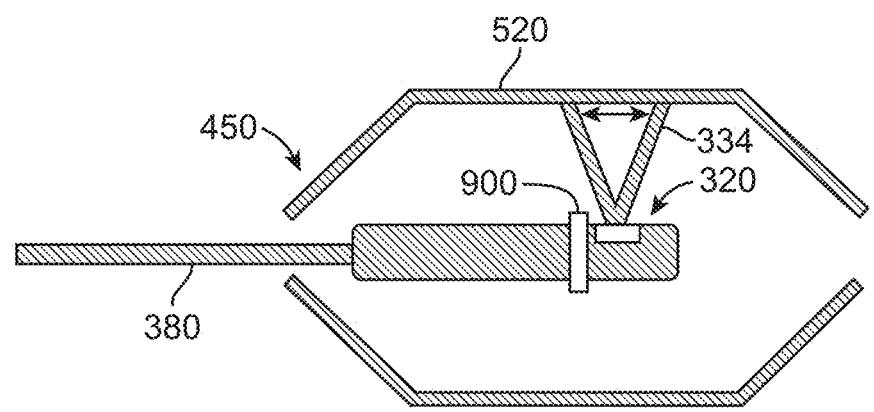

FIGS. 47A and 47B show a transurethral treatment probe 450 having an ultrasound array 900 located near the fluid release element 320 to image the treatment site with ultrasound. The treatment site can be imaged in real time as described herein, for example. The ultrasound array on carrier 380 moves with the fluid release element 320 such that the ultrasound image moves with the fluid release element comprising nozzle 322 as described herein. The ultrasound array can provide one or more of axial or sagittal images as described herein. For example, the array 900 may extend along an elongate axis of the carrier 380 to provide a B-scan slice radially outward from the probe and extending along the elongate axis as shown in FIG. 47A. The array 900 can be rotationally aligned with the fluid release element such that the array 900 is oriented toward the treatment site when the carrier 380 of probe 450 rotates. The carrier can be rotated around the elongate axis to provide tomographic images of the treatment site. Alternatively or in combination, the array 900 can extend circumferentially around the carrier 380 as shown in FIG. 47B, so as to provide axial images of the treatment site, and the probe can be translated along the elongate axis to provide 3D tomographic images of the target tissue as described herein.

Doppler Ultrasound

Doppler ultrasound can be used to provide a velocity measurement profile of the jet. Doppler ultrasound be could be used to see where the flow of the jet is slowing down or stopping in order to determine real-time depth of penetration. The Doppler ultrasound may comprise a spatially resolved Doppler ultrasound probe in order to determine the velocity distribution profile at each of a plurality of locations of the image. For example, the transaxial images as described herein may comprise two dimensional Doppler ultrasound images in which the pixels of the ultrasound image are color coded with the velocity of the jet, for example. Alternatively or in combination, the longitudinal (sagittal) images as described herein may comprise two dimensional Doppler ultrasound images in which the pixels of the ultrasound image are color coded with the velocity of the jet, for example.

Fluoroscopy

Fluoroscopic imaging can be used to visualize one or more of: the depth, shape of resected volume, or flow rate during Aquablation™ with probe 450, for example. A radiographic dye can be placed within the fluid jet saline, in order to clearly visualize depth, shape of resected volume, flow rate during Aquablation™, for example. If there is a perforation, the breach of the capsular portion of the prostate can be clearly visualized.

Thermal Imaging

Thermal imaging can be used to view the treatment site, as an alternative or in combination with endoscope viewing as described herein. During Aquablation™, the user may have difficulty visualizing that jet and the tissue penetration depth, in part related to the tissue removal of the fluid stream. In many embodiments, the water jet comprising the entrainment "flame" has a higher temperature than the surrounding fluid due to the high friction through the nozzle. Temperatures can range from about 90 to about 100 degrees Fahrenheit. Using thermal imaging, the flame comprising the entrainment region can be visualized as well as the tissue depth based on where the flame truncates and disappears upon contact with the surface of the tissue. As cancerous tissue may comprise a different tissue perfusion rates than non-cancerous tissues, cancerous regions of the prostate can be identified based on the differences in perfusion.

Figure 48A:
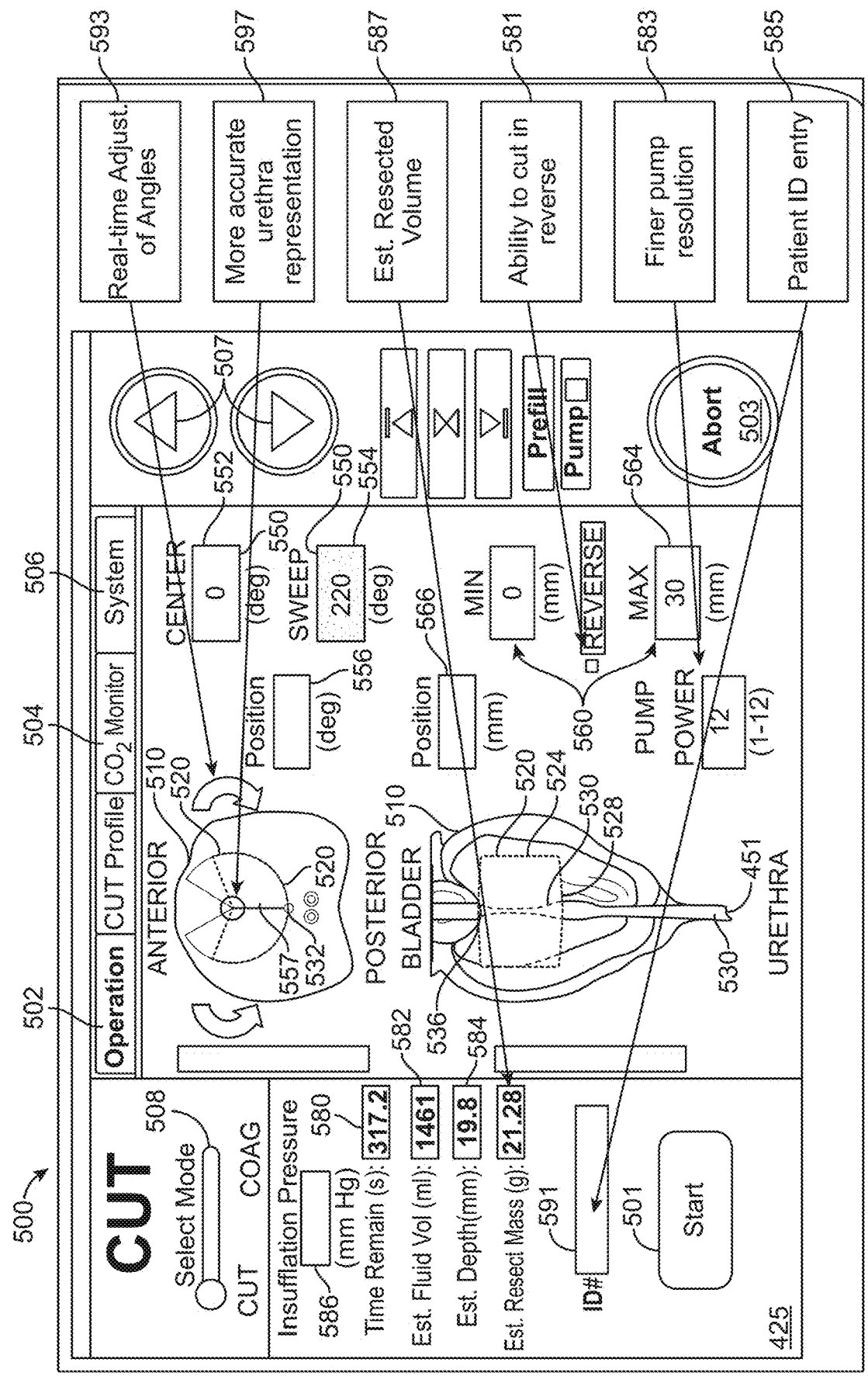
FIG. 48A shows a user interface screen with treatment input parameters and treatment monitoring parameters, in accordance with embodiments.

FIG. 48A shows a user interface 500 shown on a display screen with treatment input parameters and treatment monitoring parameters. The user interface 500 comprises one or more components as described herein, for example as described herein with reference to FIGS. 17A to 19A. The user interface 500 may provide a real time user adjustment of angles 593 of the treatment profile. The real time user adjustment of the treatment profile allows the physician to adjust the treatment in real time in response to real time images of the tissue at or near the treatment site. The image 510 of the treated organ such as the prostate may comprise a representation of the urethra of the patient, and the cross sectional size such as the diameter can be adjusted to represent the size of the urethra of the patient. The estimated volume of the resected tissue can be shown on the display. Alternatively or in combination, the estimated mass of the tissue to be resected can be shown on the display. The user interface 500 can be updated in real time to show the user the amount of tissue resected as the treatment proceeds and the amount can be expressed a percentage of the treatment completed. The user interface may comprise a user selectable input that allows the resection to proceed in reverse, for example if the treatment has not completed ablated the target tissue along a portion of the treatment profile, of if the physician believes additional tissue should be removed, for example in response to real-time ultrasound images.

The user interface may comprise a pump input parameter 583 related to the power of the pump that can be used to adjust the distance of the "cool flame" as described herein, for example. The pump input parameter may comprise a parameter related to one or more of a power, a flow rate, a depth (in mm), or a pressure of the pump, for example. The input may comprise a number, a letter, a level, a radial button or other input, for example.

The user interface may comprise a patient identifier (hereinafter "patient ID") input. The patient ID input can be used to identify the patient and may comprise data used to identify the patient, such as a name, hospital ID, or other data, for example.

Figure 48B:
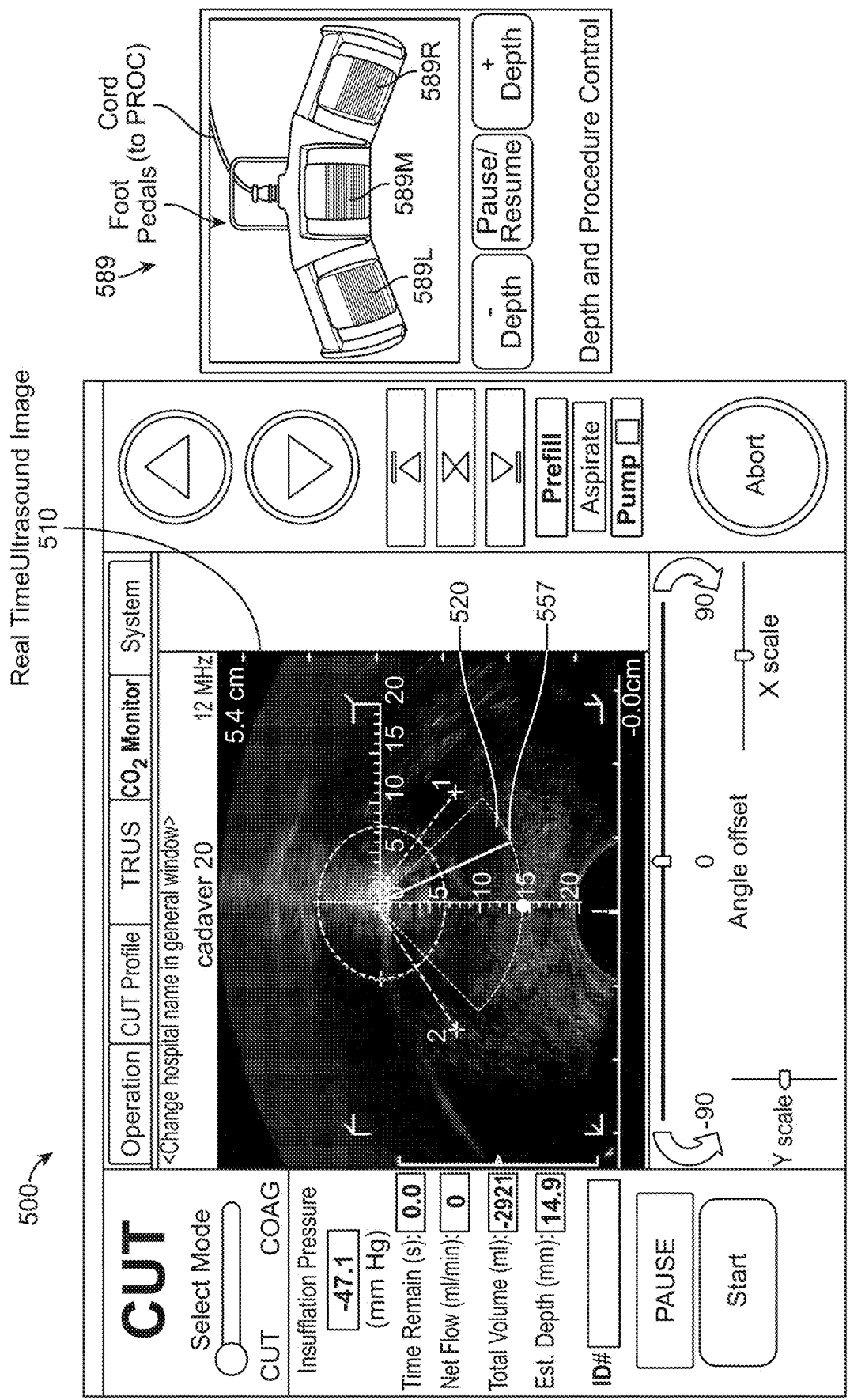
FIG. 48B shows a user interface as in FIG. 48A with a real-time ultrasound image of the treatment site, in accordance with embodiments.

FIG. 48B shows a user interface as in FIG. 48A with a real-time ultrasound image 510 of the treatment site, in which the treatment profile 520 is displayed with the real time ultrasound image. The treatment profile 520 can be aligned with the real time image 510 as shown on the display, in order to allow the physician to ensure that the treatment is correctly aligned with the patient.

The image 510 shown on the display may comprise a real time image as described herein, such as a real time ultrasound image as described herein, for example. The real time ultrasound image may comprise an image from a TRUS probe, in which the TRUS probe moves in synchrony with the treatment probe to align the TRUS probe axial section with the ablation site where the jet contacts tissue. Alternatively or in combination, the ultrasound probe can be mounted on the treatment probe and move rotationally and translationally with the probe.

The radial marker 557 is shown on the display in alignment with the location of the jet in real time, such that the position of radial marker 557 corresponds to the location of the jet shown in the image. The radial marker 557 can be seen to oscillate on the screen to and from left and right sides of the patient.

In many embodiments, the user interface 500 comprises an angle offset for the physician to align the axial ultrasound image with an axis of the patient such as a midline of the patient. In some embodiments, the probe can be inserted into the patient with an angular mis-alignment of the probe and the patient, and the angular offset can be adjusted to compensate for the errors in the angular alignment of the probe with the patient.

The user interface 500 may comprise a foot pedal assembly 589. The foot pedal assembly 589 comprises one or more foot pedals and may comprise a plurality of foot pedals. The plurality of foot pedals may comprise a left foot pedal 589L, a middle foot pedal 589M and right foot pedal 589R, for example. While the foot pedal assembly can be configured in one or more of many ways, in many embodiments the foot pedal assembly is configured with the left pedal to decrease the depth of penetration of the entrainment flame of the water jet, a right food pedal to increase the depth of penetration of the entrainment flame of the water jet, and a middle foot pedal to pause and resume the procedure in a toggle configuration. In many embodiments, the foot pedal assembly 589 comprises a cord that extends to an input of the processor. Alternatively or in combination, the foot pedal assembly may comprise a wireless interface to couple to the processor system as described herein.

Alignment of Treatment Probe for Embodiments without a Distal Anchor

In many embodiments, the treatment probe 450 can be provided without a distal anchor such as an anchoring balloon. This configuration allows fluid to flow into out of the bladder without increasing pressure and distension of the bladder. In many embodiments, the treatment reference location 536 corresponds to a location adjacent the bladder neck Reference location 536 corresponding to an end portion of the prostate adjacent the bladder neck. The end of the prostate can be aligned with the end 526 of the treatment profile 20, in which the treatment profile is shown aligned with the axis 451 of the treatment probe as described herein. Alternatively or in combination, real time imaging of the prostate can be used to align the treatment reference location with a reference location of the prostate.

Figure 49:
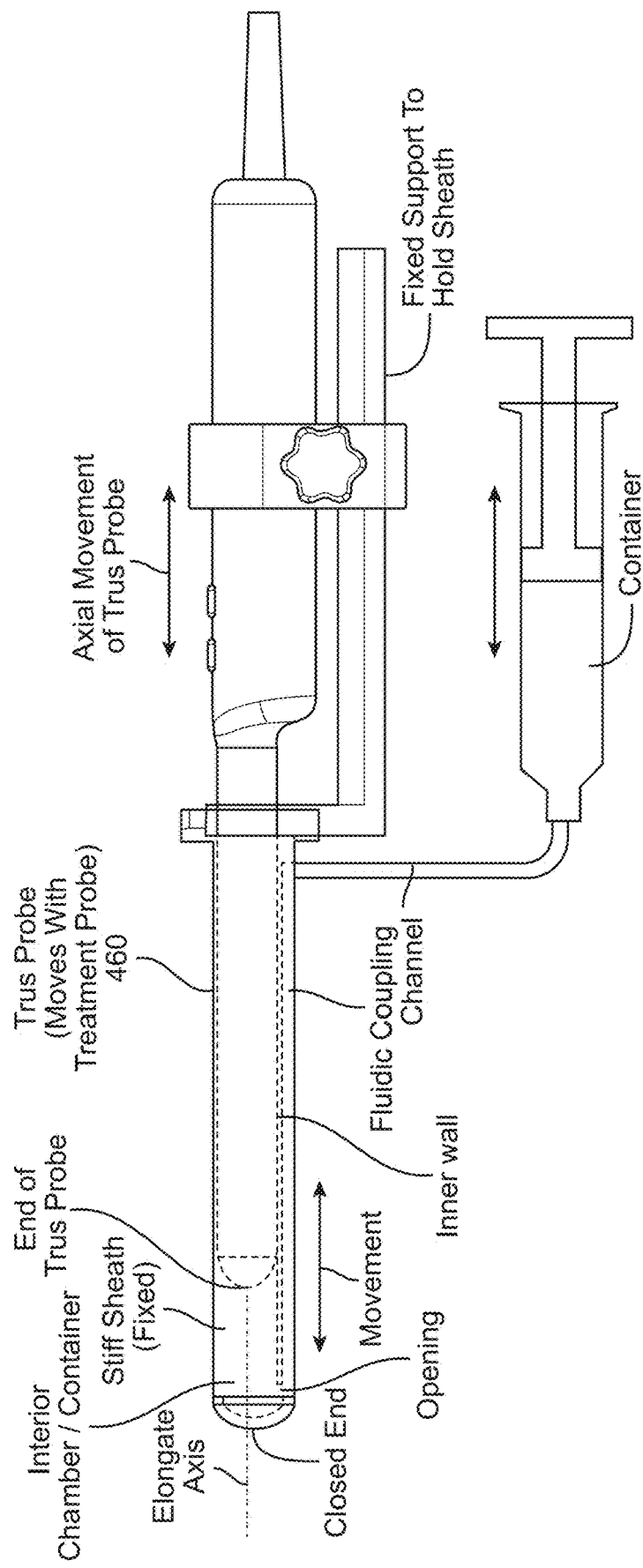
FIGS. 49 and 50 show a side view and an isometric view, respectively, of a stiff sheath over a transrectal ultrasound probe to inhibit changes in tissue shape as the elongate ultrasound probe moves along an elongate axis of the ultrasound probe, in accordance with embodiments.
Figure 50:
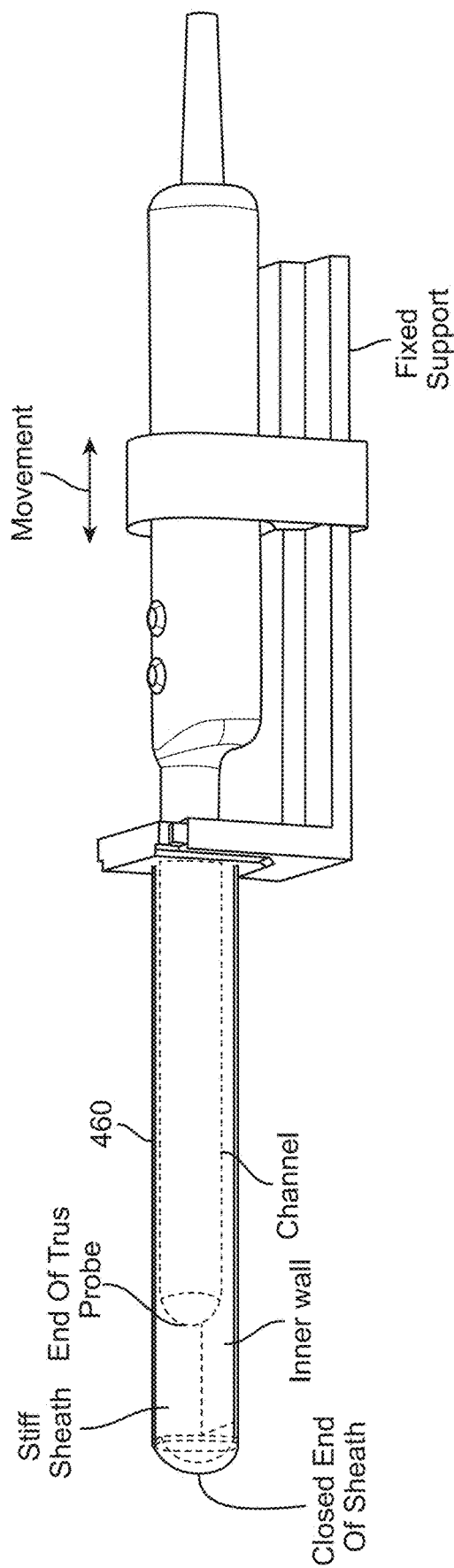

FIGS. 49 and 50 show a side view and an isometric view, respectively, of a stiff sheath over a transrectal ultrasound probe to inhibit changes in tissue shape as the elongate ultrasound probe moves along an elongate axis of the ultrasound probe. Insertion of the TRUS probe 460 into the patient can induce changes in the shape of the tissue when the probe is advanced. A stiff sheath can be provided on the TRUS probe such that the shape of the prostate and tissue near the prostate is not altered by axial movement of the TRUS probe along an elongate axis of the TRUS probe when the sheath remains substantially fixed. As the TRUS probe can be moved axially within the stiff sheath that engages the colon of the patient. As the stiff sheath engages the wall of the colon of the patient and separates the TRUS probe from the wall of the colon, the TRUS probe 460 can be moved axially without altering the shape of the patient tissue near the probe, such as the tissue of the prostate, for example.

The stiff sheath comprises a rounded distal end portion that can be spherical or oval in shape for advancement into the patient. The rounded distal end portion can be stiff, or deflect slightly when advanced, for example. The stiff sheath may comprise at least a tubular portion that has stiffness to add rigidity and define a chamber within the sheath when the distal end of the TRUS probe is away from the distal end of the sheath. The chamber extends axially between a distal end of the TRUS probe and a distal end of the stiff sheath, and radially between the cylindrical side of the sheath.

The elongate axis of the stiff sheath and the TRUS probe can be aligned with the elongate axis of the treatment probe 450. The stiff sheath can be fixed to a locking arm, and in many embodiments is provided in an assembly coupled to the transurethral sheath, such that the elongate axis of the TRUS probe is substantially parallel to the elongate axis of the treatment probe. The TRUS probe 460 can be moved axially with the treatment probe 450 such that the TRUS probe images the treatment site and the water jet striking tissue as the treatment probe moves along its own elongate axis. This spaced apart axial configuration of the sheath with the treatment probe 450 can inhibit changes in the shape of tissue as the treatment probe 450 and TRUS probe 460 move together axially and the sheath remains substantially fixed.

The stiff sheath can be configured to provide ultrasonic coupling material between the sheath and the TRUS probe to provide ultrasonic coupling of the TRUS probe to the prostate tissue with the stiff sheath extending therebetween. The stiff sheath comprises a closed end to inhibit deposition of fecal material in the chamber within the stiff sheath. The chamber of the sheath comprises a container having a variable volume as the TRUS probed is moved axially. As the TRUS probe is advanced distally, the volume of the container increases. As the TRUS probe is retracted proximally, the volume of the container defined with the sheath and the TRUS probe increases. A fluidic coupling channel is provided to couple fluid of the container within the sheath to a second container, such that US coupling fluid can be contained within the sheath as the volume changes. The second container comprises a sealed container such as a bag or syringe for example. The second container is configured to provide a variable volume and remain sealed, for example. The coupling channel may comprise an external channel outside the sheath, such as a tube, and an internal channel within the sheath such as an inner channel defined with an inner wall of the stiff sheath. The inner wall of the stiff sheath may comprise a stiff barrier material that defines the coupling channel, for example. Alternatively or in combination, the inner channel may comprise a groove on an inner surface of the stiff sheath to allow US coupling material to flow between the TRUS probe and the stiff sheath. The coupling channel extends to an opening near the distal end of the stiff sheath, such that the distal end of the TRUS probe can be placed near the distal end of the stiff sheath.

In many embodiments, axial movement of the TRUS probe is provided by axial movement of the linkage 430 as described herein. The axial movement of the TRUS probe provided by linkage 430 results in axial movement of the distal end of the TRUS probe in relation to the distal end of the stiff sheath. The stiff sheath can be fixedly coupled to a support that is coupled to an arm lock as described herein, such that the stiff sheath is locked with the sheath inserted transurethrally into the patient.

Sheath Docking System

FIGS. 51A and 51B shows a sheath docking system for positioning and fixating the sheath, such that a plurality of instruments and instrument delivery systems can be interchanged without the frame of reference changing as described herein. The docking mechanism attaches to commercially available articulating arm that mounts to a surgical bed rail or other support structure attached to the patient support.

FIG. 51A shows a docking structure 467 configured to engage a protrusion 461 extending from a manifold 468 in order to hold the stiff sheath 458 in place for the surgery. The protrusion 461 comprises a locking structure 463 on the distal end portion to engage the docking structure 467 which may comprise a docking mechanism. The locking structure 463 may comprise an annular channel extending circumferentially around the distal end portion of the protrusion. The mechanism of the locking structure 467 may comprise a ring shaped structure or protrusions to engage the annular ring of the locking structure 463.

FIG. 51B shows the docking structure engaging the stiff sheath 458 with the docking structure in order to support and inhibit movement of the stiff sheath during treatment, in which the docking structure is coupled to a lockable arm 442 as described herein. The lockable arm may comprise an arm lock 427 as described herein. The arm lock 427 may comprise a manually operated arm that can be manually locked by the user. Alternatively or in combination, the arm lock may comprise a computer controlled arm lock 427 that locks arm 442 in response to user input at user interface 500 as described herein.

The manual arm lock may comprise a user manipulated structure to release the docking structure 467 from the protrusion 461.

The imaging probe 460 may comprise a similar arm and locking structure as described herein.

Dynamic Probe Tip for Support with Tissue

FIGS. 52A and 52B show isometric and cross-sectional views, respectively, of a treatment probe 450 comprising an elongate support structure 840 having a dynamic tip 841. The treatment probe 450 comprises a carrier 380 as described herein contained within elongate support structure 840. The elongate support 840 is rotationally coupled to the manifold as described herein so as to allow rotation around an elongate axis of the support 840. The carrier 380 as described herein rotates the elongate support 840 in order to provide 360 degree rotational access while support structure 840 contacts tissue to support the probe. An aspiration opening 836 of channel 835 is provided on the tip of the support 840. The cross-sectional shape of support 840 can be one or more of many shapes and can be tubular, rectangular, square, oval or elliptical, for example. The lumen comprising channel 835 within support 840 provides aspiration distal to the jet from within the bladder, for example. In many embodiments, support 840 is sized to extend from a distal end of slot 842 to permit placement of the distal end comprising aspiration opening 836 within the bladder neck.

A distance from the distal tip of the support 840 to the stiff sheath 458 remains substantially constant when the support 840 rotates with rotation of carrier 380 about an elongate axis 848 in response to movement of linkage 430. A key 842 on probe carrier 380 fits within a slot 842 defined with support 840. The key 842 on the probe carrier 380 drives the dynamic tip of elongate support 840 in rotation around the elongate axis and partially occludes slot in order to reduce aspiration through the slot. The cross sectional area of the support 840 probe that defines channel 835 extending to distal opening 836 provides an aspiration path in order to aspirate material from the treatment site with the distal end of the probe. The slot 844 is sized to allow translation of carrier 380 along the elongate axis 848 with movement of linkage 380.

An irrigation channel can be provided to urge debris away from the viewing port in order to view the treatment site when tissue is ablated with the probe. In many embodiments, the irrigation channel comprises a channel 846 sized to receive a telescope or endoscope as described herein. The channel 846 can be coupled to the manifold and locking arm as described herein in order to fluidically couple the telescope channel with a source of irrigation fluid such as saline and hold the telescope in a substantially fixed configuration when the carrier 380 rotates and translates. In many embodiments, the channel 846 is size to receive the endoscope and provide a path for fluid. Alternatively or in combination, one or more channels 849 can be sized to pass irrigation fluid to an opening near the distal end of the endoscope.

Providing irrigation to the endoscope channel has the advantage of urging ablated material away from the treatment site toward the opening on the distal end of the support structure. The ablated material and can decrease visibility of the treatment site, and urging the material away from the endoscope and treatment site toward the distal end of the treatment probe 450 can substantially increase visibility of the treatment site as viewed by an operator through the endoscope.

Venturi Aspiration

Figure 53:
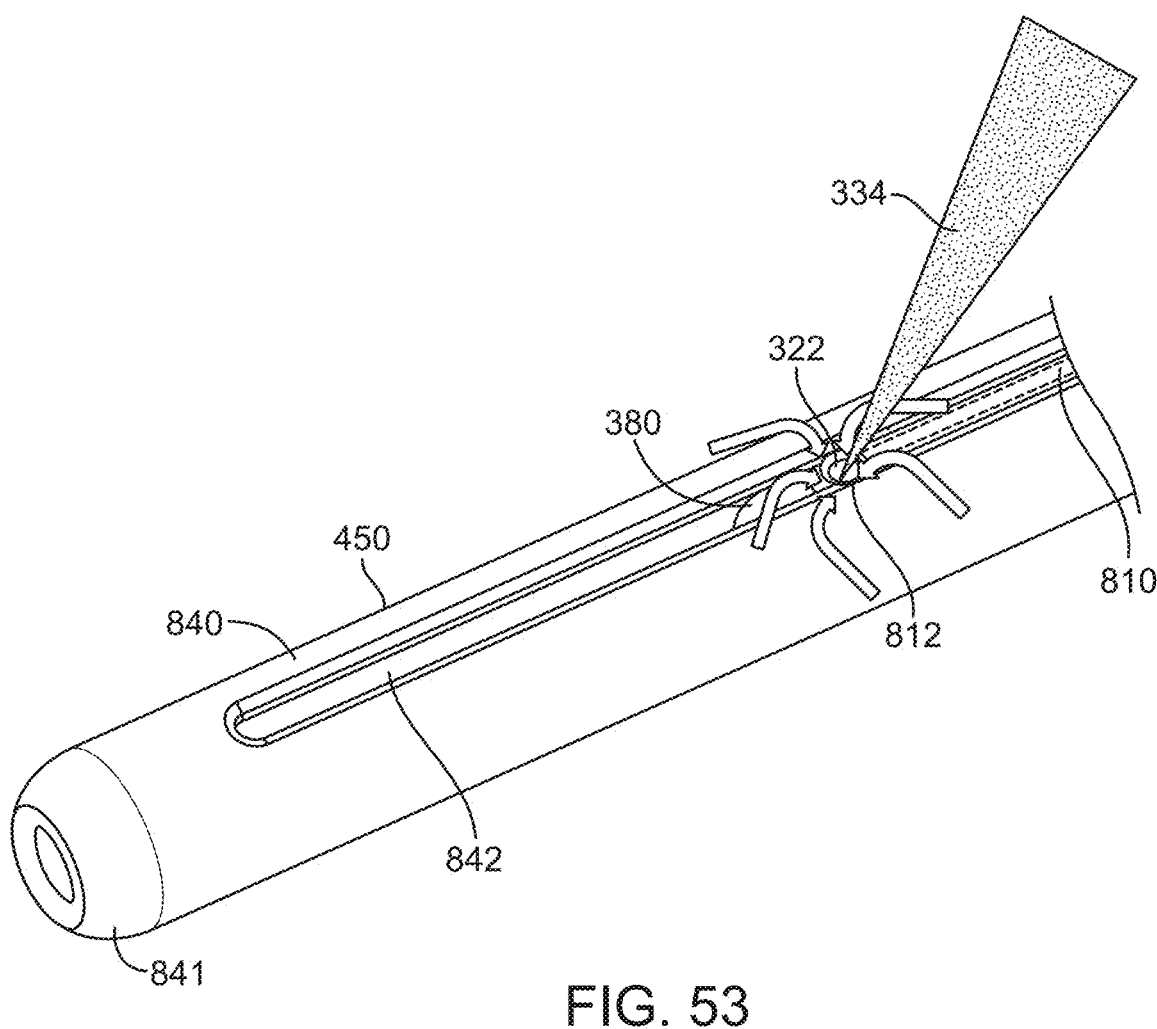
FIG. 53 shows venturi aspiration into the probe with a channel configured to receive fluid located on the moving probe near the nozzle of the ablative jet.

FIG. 53 shows venturi aspiration (with arrows) into the treatment probe 450 with an opening 812 of a venturi channel 810 configured to receive fluid. The venturi channel 810 may comprise an auxiliary channel located on the moving treatment probe 450 probe near the nozzle 322 of the fluid delivery element 320 that forms the ablative jet as described herein. High fluid stream velocity of the waterjet provides a local low pressure zone. The localized zone of low pressure can be used to provide or enhance aspiration flow into an opening 812 of an auxiliary channel 810. In many embodiments, the jet of the fluid stream can be directed proximally in order to increase effect. For example, with the jet oriented proximally and the venturi aspiration channel 810 extending proximally from opening 812 located near fluid delivery element 320 and nozzle 322, substantial amounts of fluid can be aspirated through venturi channel 810. The venturi channel 810 can be coupled to a tissue removal port of the manifold such as fluid removal port 456C as described herein, or another port of the manifold 468 as described herein, for example.

Cauterizing Treatment Probes

The plurality of treatment probes provided with the system as described herein may comprise one or more cautery probes configured for insertion along an interior of the sheath 468 as described herein.

FIG. 54 shows one or more radio frequency (hereinafter "RF") electrodes 820 on a cautery probe 825 configured to rotate around an elongate axis of the probe 825 in order to cauterize tissue. The one or more electrodes 820 can be connected to a source of electrical energy with wires extending along the elongate shaft of probe 825. The one or more RF electrodes can be rotated at least partially around the elongate axis to cauterize the tissue. The cautery can be performed subsequent to removal with one or more of the water jet or the light energy, for example.

FIG. 55 shows one or more electrodes 820 comprising one or more bipolar electrodes 824 configured to rotate around an elongate axis of a cautery probe in order to cauterize tissue.

The one or more electrodes as described herein comprise a resiliently deformable conductive material such that the electrodes can be advanced along the sheath in a narrow profile configuration and expand to a wide provide configuration when advanced beyond the distal end of the sheath. The resiliently deformable conductive material may comprise a metal such as stainless steel or nitinol, for example. Subsequent to cauterizing the tissue, the electrodes can be drawn away from the treatment site and urged to the narrow profile configuration in order to remove the electrodes from the probe.

The cautery treatment probe 825 can be coupled to the linkage 430 and configured to rotate under processor and software control as described herein, in a manner similar to the water jet probes, for example. Alternatively, the cautery treatment probe can be manually advanced and rotated when energized to cauterize tissue by the user such as a physician.

Integrated Irrigation and Aspiration Probes

In many embodiments, one or more of the irrigation or aspiration can be integrated into the treatment probe 450 comprising carrier 380 and corresponding components as described herein, for example. In many embodiments, the integrated irrigation and aspiration probes are used without an anchor, for example. Alternatively, the integrated probes can be used with an anchor as described herein.

Figure 56:
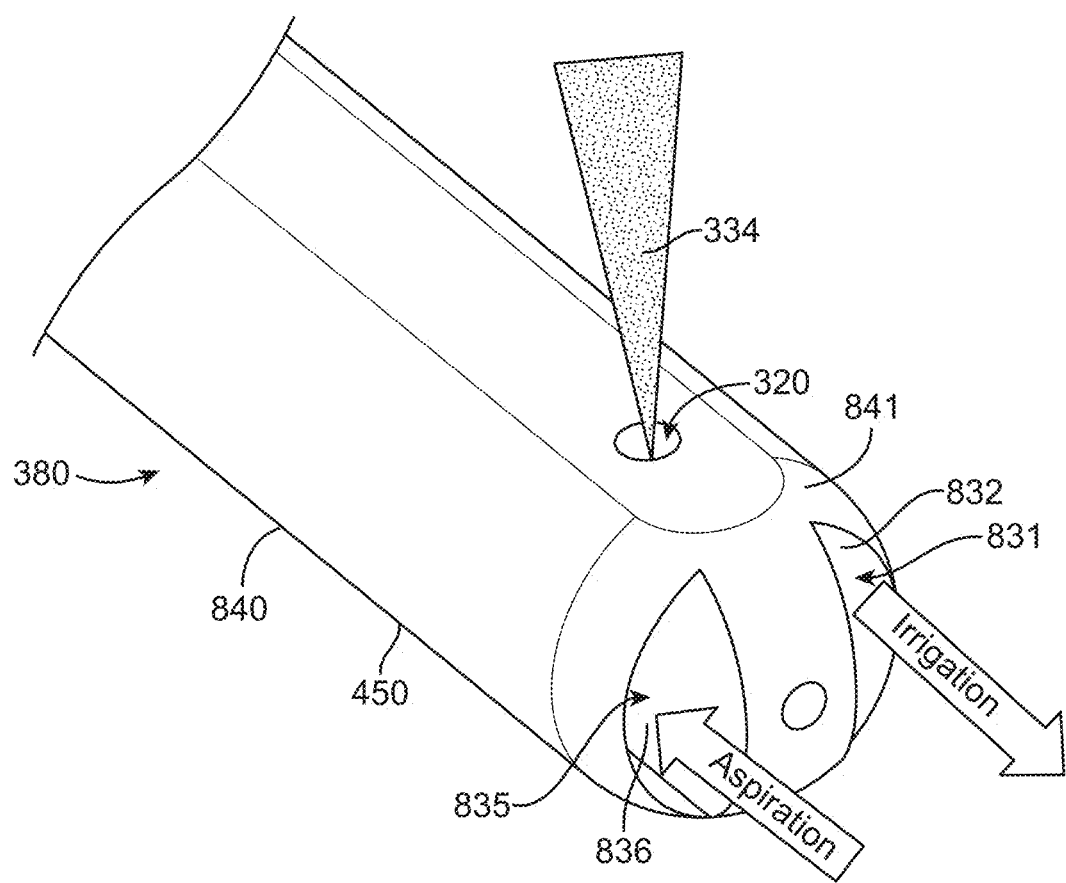
FIG. 56 shows an integrated tissue treatment probe having aspiration an irrigation integrated into the probe, in accordance with embodiments.

FIGS. 56 and 58 show an integrated tissue treatment probe 450 having aspiration and irrigation integrated into the probe.

FIG. 58 shows an integrated treatment probe having an aspiration opening and an irrigation opening on a distal end to aspirate through the aspiration opening and irrigate through the irrigation opening, in which the probe has been placed in a stiff sheath with an endoscope to view the treatment, in accordance with embodiments;

The treatment probe 450 may comprise an internal aspiration channel 835 and an internal irrigation channel 831. The internal irrigation channel 831 can extend to an irrigation opening 832 on the distal end of the probe 450. The internal aspiration channel 835 can extend to an aspiration opening 836 on the distal end of the probe 450, for example. The proximal end of treatment probe 450 and the distal end of the treatment probe can be moved with linkage 430 as described herein. The proximal end of the treatment probe 450 comprises an outlet 837 coupled to opening 836 with channel 835 to remove fluid and ablated material. The proximal end of the treatment probe 450 comprises an inlet 833 coupled to opening 832 with channel 831 to provide irrigation fluid. The proximal end of the probe comprises a high pressure inlet 830 to receive fluid for the cutting beam. The inlets, the outlet and the openings on the distal end and fluid delivery element 320 are driven together with linkage 430. The treatment probe 450 can be rapidly exchanged as described herein.

An irrigation port 830 can be coupled to the working channel that receives the endoscope as described herein. The irrigation along the working channel that receives the endoscope has the advantage of urging ablated material away from the distal end of the endoscope and away from the treatment site toward the distal end of the probe to improve visibility of the treatment site. The irrigation port 830 may comprise a port of manifold 468 as described herein, for example. The manifold can be fixed with an arm as described herein.

One or more optical fibers can extend to the fluid delivery element to couple light energy as described herein.

FIG. 57 shows an integrated treatment probe 450 with aspiration opening 836 for fluid suction on a distal end, in which the probe has been place in stiff sheath with an endoscope to view the treatment. The probe comprises one or more components of the treatment probe 450 as described herein. In many embodiments, the linkage 430, sheath 458, probe 450, and the endoscope are supported with a support 839 coupled to the lockable arm as described herein.

Plurality of Carriers and Probes Having Different Jet Angles

Figure 59A:
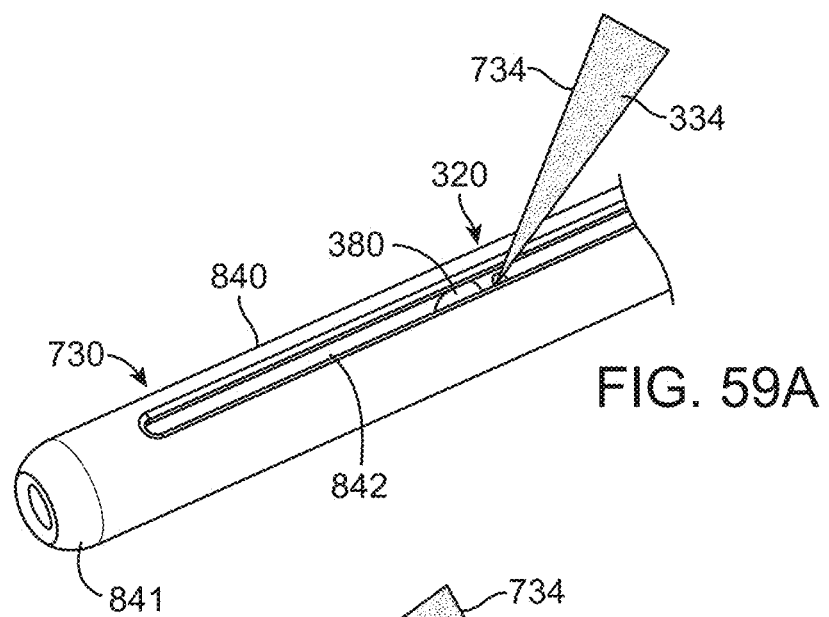
FIGS. 59A, 59B and 60 show nozzle angles of the probe, in accordance with embodiments.
Figure 59B:
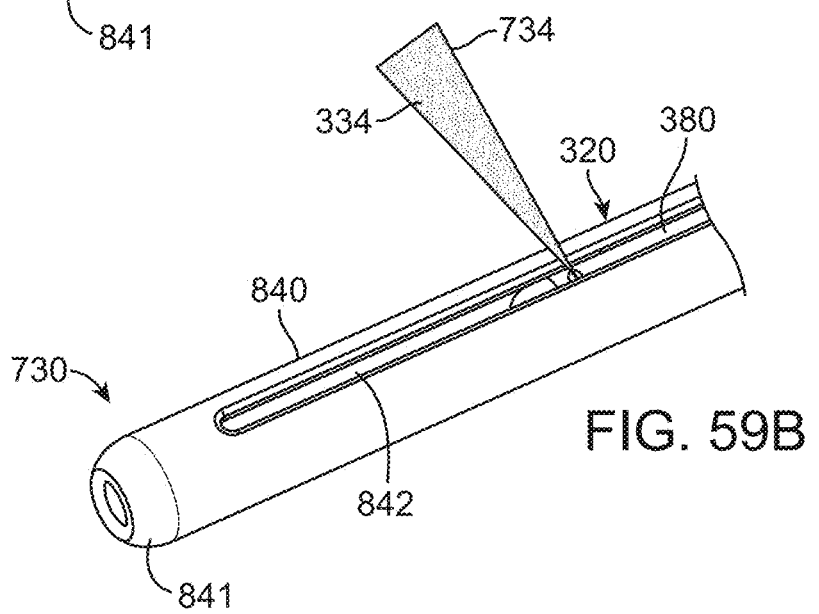
Figure 60:
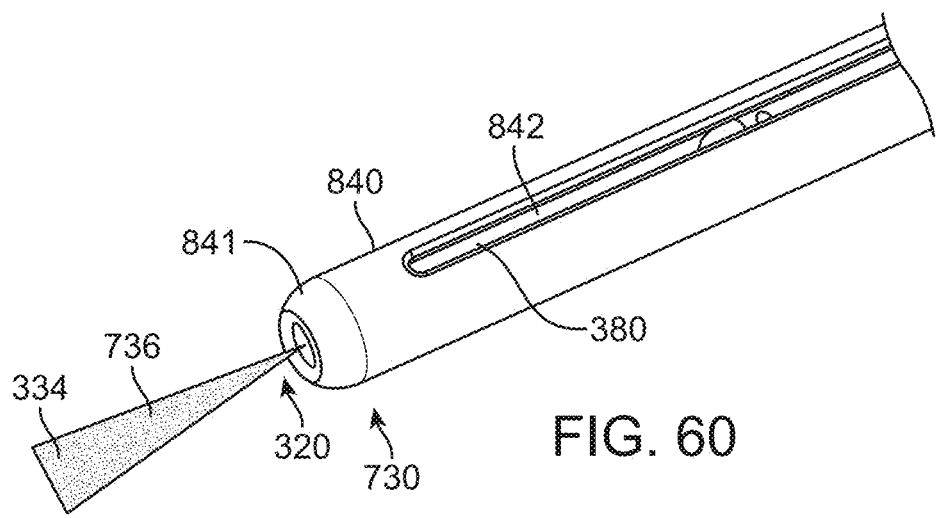

FIGS. 59A, 59B and 60 show nozzle angles of a plurality of treatment probes. The plurality of probes may comprise a plurality of carriers 730 as described herein, for example with reference to FIGS. 27A and 27B. Each of the plurality of carriers comprises a fluid delivery element 320 with nozzle 322 as described herein and can be configured to deliver light energy with an optical fiber as described herein. A first carrier 380 can deliver a first fluid stream at a first angle 732 to the elongate axis of the carrier 380 as shown in FIG. 59A. A second carrier 380 can deliver a second fluid stream at a second angle 734 to the elongate axis of the carrier 380 as shown in FIG. 59B. A third carrier 380 can deliver a third fluid stream at a third angle 737 to the elongate axis of the carrier 380, for example at an angle extending along the elongate axis of the third carrier 380 as shown in FIG. 60. Additional carriers can be provided having angles as described herein.

In many embodiments, the sheath 458 and treatment probe 450 are provided without a distal anchor. Each of the plurality of carriers 730 can be configured to extend from the distal end of the sheath without anchoring, for example. The treatment probe can be rotated around the elongate axis and translated as described herein in order to remove tissue. A probe 450 from among the plurality of probes comprising the plurality of carriers 730 can be selected by the treating physician to have an appropriate angle relative to the elongate axis of the shaft as described herein. The angle of the nozzle of the fluid delivery element can be oriented with respect to the elongate axis of the carrier to provide the fluid stream oriented at the angle with respect to the elongate axis of the carrier 380 and the elongate axis of the sheath 458.

Concentric Treatment Probe

Figure 61:
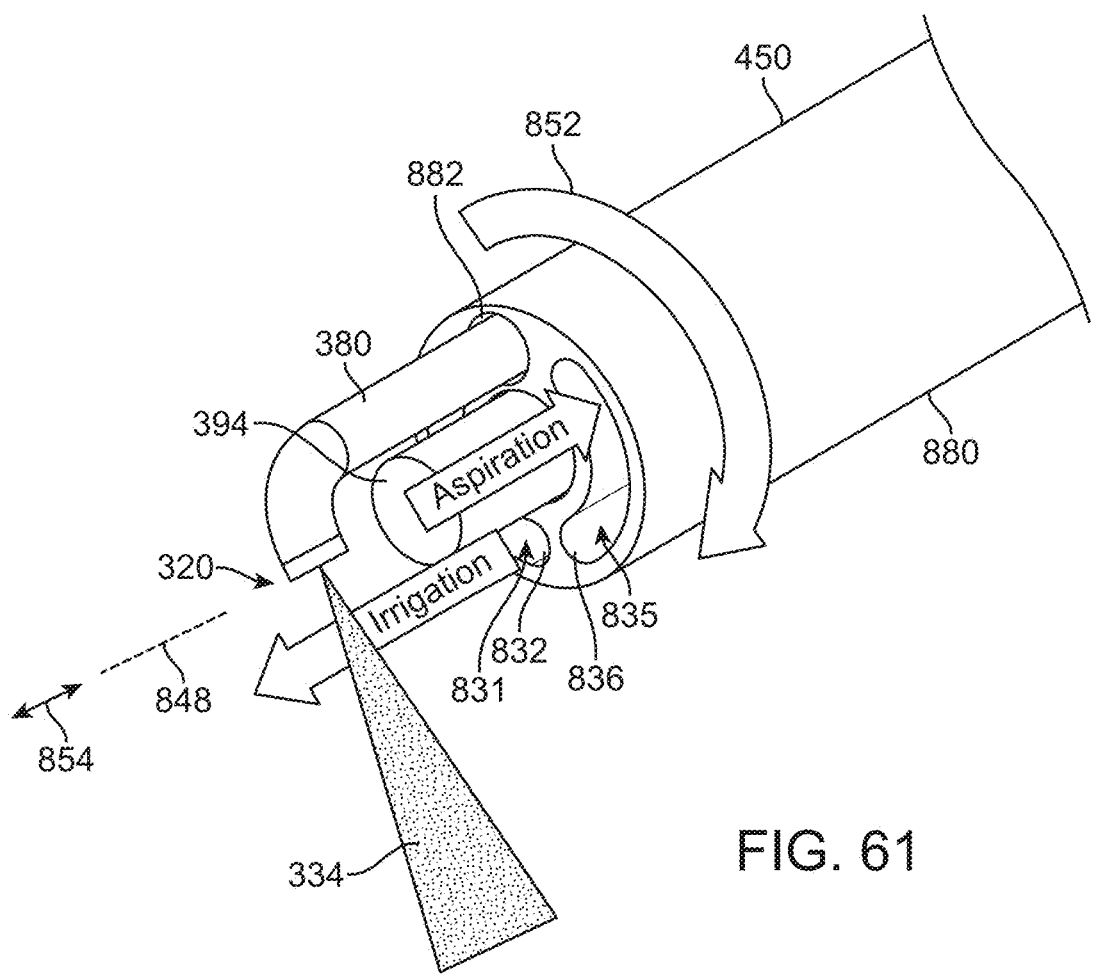

FIGS. 61, 62 and 63 isometric, side and cross-sectional views, respectively of a treatment probe 450 having a viewing path substantially concentric with rotation 852 of a nozzle of a treatment jet. In many embodiments, rotation of the endoscope viewing path around an elongate axis 848 of the endoscope and probe 450 is substantially inhibited when the jet rotates around the elongate axis 854 with rotation 852, in order to allow the user to view the treatment site when the probe rotates. In many embodiments, a round cross section of sheath 458 allows for full 360 degree viewing and treatment. Irrigation and aspiration can be incorporated into an intermediate carrier 880 as described herein. Motion can be provided with intermediate carrier 880 coupled to the linkage 430 as described herein. The endoscope viewing camera can be fixed or slidably coupled to the arm or other support structure to inhibit rotational movement of the endoscope around axis 848. Alternatively or in combination, the endoscope can be configured to slide along axis 848 with carrier 880 when rotation 852 about axis 848 is inhibited, for example. In many embodiments, the linkage 430 is decoupled from the endoscope such that the user can slide the endoscope to a desired location to view the treatment site or an anatomical landmark, for example.

The intermediate carrier 880 is configured to provide one or more of irrigation, aspiration, rotation of the fluid release element 320 about axis 848, or rotation of an optical fiber coupled to the fluid release element as described herein. The intermediate carrier 380 comprises channel 831 extending from inlet 833 to opening 832 for irrigation, and each of these structures may rotate about axis 848. The intermediate carrier 380 comprises channel 835 extending from outlet 837 to opening 836 for aspiration of ablated material from the treatment site, and each of these structures may rotate about axis 848.

In many embodiments, the intermediate carrier 880, supports the carrier 380 as described herein, for example with reference to FIGS. 30, 31A and 31B. The intermediate carrier 880 may comprise a longitudinal channel located away from axis 848 in order to hold the carrier 380 and provide rotation of carrier 380 about axis 848. In many embodiments, carrier 380 is rotationally fixed to channel 882 such that carrier 380 rotates with intermediate carrier 380, and the location the fluid release element 320 is maintained adjacent axis 848 as the intermediate carrier 880 and the carrier 380 rotate, for example.

The linkage 380 can be configured to move the probe 450 with rotational and translational motion as described herein. The linkage 380 can rotate probe 450 about axis 848 with rotation 852, and translate probe 450 along axis 848 with translation 854. The movements of the linkage are provided to the distal end of the probe for 450 and to the proximal components of the probe 450 such as the high pressure saline inlet 830 from the pump, the irrigation inlet 833, and the aspiration outlet 837 as described herein.

In many embodiments, the probe 450 comprises a rotating probe assembly 850. The rotating probe assembly 850 comprises the intermediate carrier 880 and corresponding structures as described herein, the carrier 380 and corresponding structures as described herein, and the proximal components such as the inlets and outlets as described herein. The rotating probe assembly 850 can be rapidly exchange with another probe as describe herein, for example. The endoscope viewing camera can be removed prior to exchanging the rotating probe assembly 850, or be removed with rotating probe assembly, for example.

Sliding Endoscope Support

Figure 64:
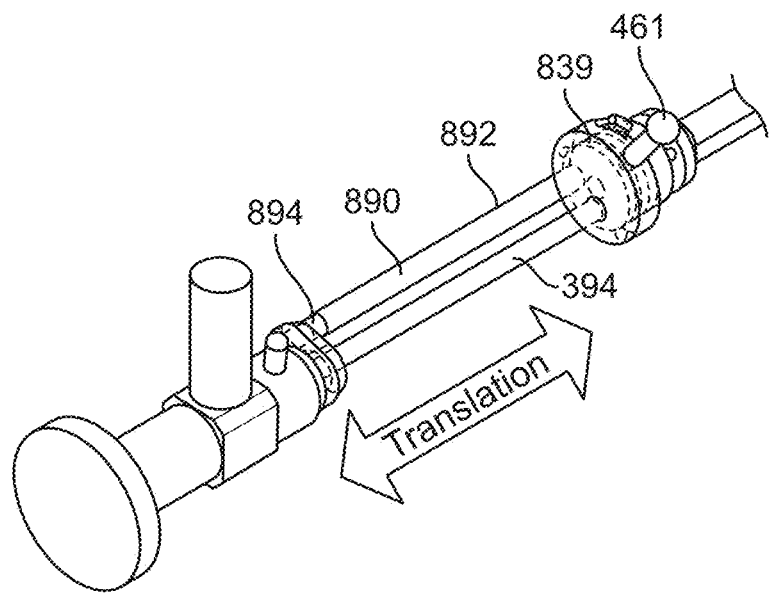
FIGS. 64 and 65 show an endoscope and a sliding telescopic structure to add stiffness and guide the endoscope into the stiff sheath, in accordance with embodiments.
Figure 65:
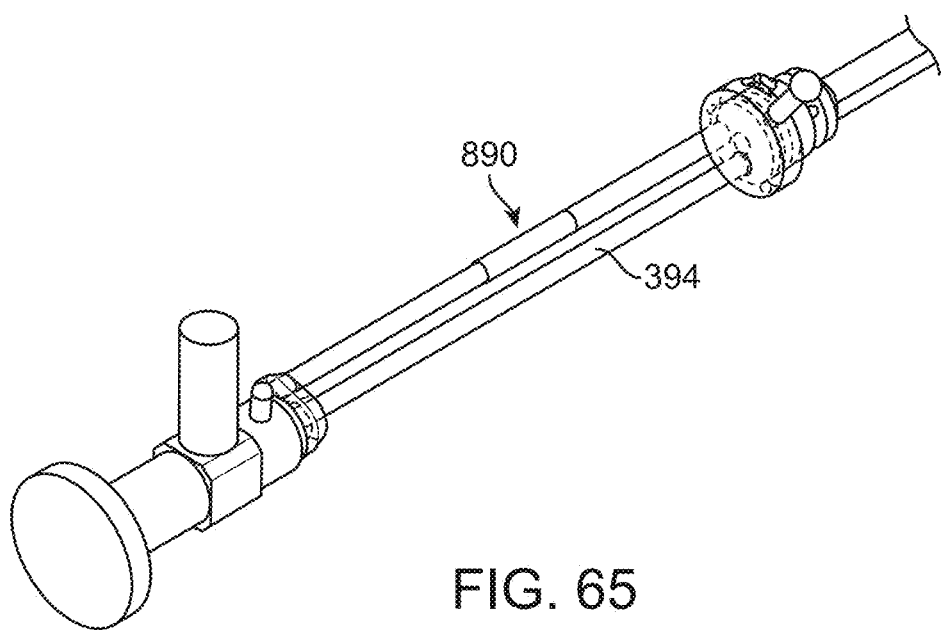

FIGS. 64 and 65 show an endoscope and a sliding support structure 890 to add stiffness and guide the endoscope into the stiff sheath. The sliding support structure 890 may comprise one or more of a sliding telescopic mechanism, a trombone, a rail or a receptacle 892 sized to receive an elongate structure 894, for example. In many embodiments, the receptacle 892 comprises a tubular support structure sized to receive an elongate tubular structure 894, so as to provide a telescope mechanism. The support structure 890 can be coupled to the support 839 and protrusion 461 such that the endoscope support structure 890 is coupled to the lockable arm 422 as described herein.

In many embodiments, support 890 comprises a telescopic structure that docks into tube that slides with respect to sheath. High temperature, autoclaveable seal keep fluids from leaking as the telescope slides back and forth. The auxiliary support structure 890 can provides rigidity to the telescope used to view the interior of the patient. The viewing telescope can be easily positioned close to cutting jet at any time during treatment by sliding the endoscope and elongate structure 894 of the support structure 890.

Weight Monitoring

The weight of the fluid removed from the surgical site can be monitored and compared with the weight of the fluid delivered to the surgical site. For example, the saline containers for delivery can be held by scales coupled to the processor system as described herein, and the containers that collect fluid can be held by scales coupled to the processor system to monitor the amount of fluid removed from the patient. The amount of fluid and overall fluid balance into and out of the surgical site can be shown on the display as described herein. In many embodiments, the saline bag for irrigation comprises a clear bag that can be monitored for the presence of blood if the fluid removal falls below a desired amount and blood and/or tissue enter the bag.

Single Use Structures

In many embodiments, the probe 450 comprises a single use probe. The probe 450 may comprise one or more structures to limit use of the probe. For example, the proximal end of the probe may comprise optically encoded data such a bar code, laser making or matrix two dimensional bar code such as an Aztec Code. The system may comprise one or more optical sensors coupled to the processor system to read the code and determine if the probe has been used previously, for example with a memory or database of previously used probes. Alternatively, the probe may comprise a radiofrequency identification (hereinafter "RFID") tag, and the processor may comprise an RFID reader to read the RFID tag on the probe. The processor may store in computer readable memory the amount of time that the probe has been used, and inhibit use if the probe has been used more than a predetermined amount of time. The probe 450 may comprise a breakable tubing where the probe connects to the pump, such that removal of the probe requires breaking the tubing, for example.

Partially Automated Manual Tissue Resection

In many embodiments, the ablative water jet can be configured with a combination of at least partially manual and at least partially automated tissue resection. For example, the linkage, sheath and probe assembly can be disconnected from the support arm, such that the user can manually move the probe with one or more of endoscope visualization or ultrasound visualization of the treatment site. The user can provide input the processor system to remove a predefined volume of tissue as described herein, and manually position and move the probe along the longitudinal axis in order to treat the target tissue based on visualization of the target area. Alternatively, the linkage can be configured to allow the user to manually slide the probe along the longitudinal axis to move and position the probe along the longitudinal axis in response to the progress of the treatment as viewed with the endoscope and/or ultrasound. The user may select this mode with input to the user interface as described herein. The linkage that allows the user to slide the probe axially has the advantage that the carrier probe can remain substantially parallel to the ultrasound probe as the user slides the probe axially.

In many embodiments, the longitudinal location of carrier 380 is determined and the TRUS probe moved into alignment with the carrier 380 in order to view the treatment site with ultrasound. In many embodiments, the TRUS probe is moved in synchrony with the carrier 380 such that movement of the TRUS probe tracks movement of the carrier 380 in order to image the treatment site when the ablated jet erodes tissue. The encoders or other position sensors of the linkage coupled to the treatment probe can be used to determine the location of the treatment jet along the longitudinal axis and this determine location can be used to drive the TRUS probe such that the TRUS probe remains substantially aligned with the longitudinal position of the treatment probe when the user moves the treatment probe. Alternatively or in combination, a detectable object such as a magnet can be placed near the end of the carrier 380 and the location of the detectable objected measured with a sensor on the TRUS probe such as a coil. In many embodiments, the carrier 380 comprises a magnet placed near the distal end of the probe, and the position of the magnet is determined in three dimensions (3D), and the location of the carrier 380 transmitted to the processor system. The processor system comprises instructions to determine the location of the TRUS probe along the elongate axis of the TRUS probe in order to align the TRUS probe with the fluid delivery element comprising the nozzle of the carrier 380 as described herein. While the location of the tip of the carrier 380 can be determined in one or more of many ways, in many embodiments the magnetic sensor comprises a commercially available Hall effect sensor known to persons of ordinary skill in the art. The components of the Hall effect sensor can be mounted on the carrier 380 and the TRUS probe, for example. In many embodiments, the TRUS probe senses the location of the carrier 380 along the urethra and is driven along the colon of the patient in order to align the TRUS probe in the colon with the nozzle of the fluid delivery element on the carrier 380 in the urethra in order to image the treatment site within the prostate of the patient. In many embodiments, the at least one transducer 392 as described herein may comprise a magnet on the carrier tube 380 in order to transmit a magnetic field signal to the Hall effect transducer on the TRUS probe, for example. In many embodiments, the at least one transducer 392 is located near the tip of the carrier 380 and the Hall effect sensor is located on the tip of the TRUS probe, for example.

FIG. 66 shows treatment probe 900 configured for at least partially manual treatment with one or more electrodes and at least partially automated treatment with a liquid jet. The probe 900 may comprise the carrier 380 as described herein, and one or more electrodes configured to move with the endoscope 394. The one or more electrodes may comprise a monopolar electrode 912, for example, and the monopolar electrode 912 may comprise a radiofrequency (hereinafter "RF") electrode. The carrier 380 can be configured to rotate with an automated rotation 854 about the elongate axis of the treatment probe 900 when the one or more electrodes and endoscope do not rotate, for example. The amount of rotational movement 852 can be user determined with adjustment of the user interface. The sheath 458 can be manually positioned in the patient as described herein, and the sheath 458 and one or more electrodes 910 manually rotated together and in combination with the automated rotation of the probe 380. In many embodiments, a handle is connected to the sheath to allow manual manipulation. The user can advance the sheath manually or actuate a sliding mechanism to move the carrier 380 with an axial movement 854. A torque cable can extend to the handle to automatically rotate the carrier 380 under computer control, for example. Alternatively or in combination, the user can rotate the sheath 458 in order to rotate the distal end of the carrier 380 with rotational movement 852.

FIG. 67 shows treatment probe 900 configured for at least partially manual treatment and at least partially automated treatment as described herein. In many embodiments the one or more electrodes 910 comprise bipolar electrodes 914, such as polar RF electrodes, for example.

Figure 68:
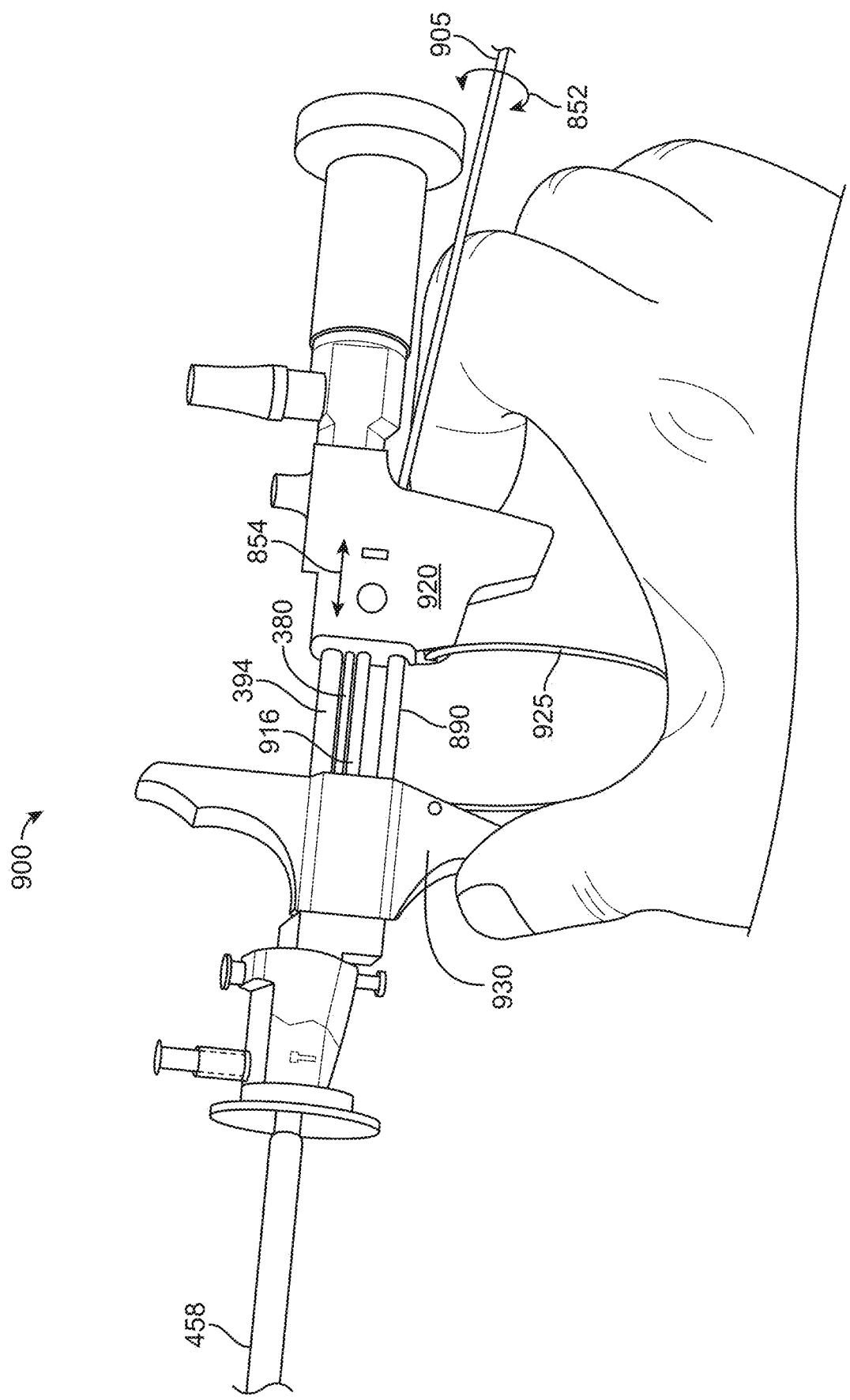
FIG. 68 shows a handpiece of the treatment probe as in FIGS. 66 and 67.

FIG. 68 shows a proximal handle 930 of treatment probe 900 of the treatment probes as in FIGS. 66 and 67. The handpiece comprise a handle 930 for the user to grasp. The handpiece comprises a movable carriage 920 slidable coupled to the handle. The sheath 458 is coupled to the handle 930 such that the rotation of the handle 930 results in corresponding rotation of the sheath 458. Alternatively, the handle can be rotated relative to sheath 458, for example with a slidable insert. A torque cable 905 extends from an actuator to carriage 920. The actuator coupled to the torque cable 905 may comprise a component of the console or a linkage as described herein, for example. The carriage 920 is configured to slide along one or more supports 890 with longitudinal movement 854. The one or more supports may comprise two sliding supports extending from the carriage 920 to the handle 930, for example. The sliding of the carriage 920 along one or more supports 890 results in longitudinal movement 854 of carriage 920.

The handle 930 combined with the carrier 380 comprising the fluid delivery element and one or more electrocautery electrodes 910 provides the user with substantial discretion when treating the patient. For example, the user can view the surgical site with endoscopy, remove tissue with water jet ablation, and additional cauterize the tissue where appropriate.

The one or more electrodes are shaped and arranged to treat tissue in combination with the jet. In many embodiments, electrical conductors such as wires extend along the elongate axis of the probe, and the electrodes are inclined at an angle to the portion of the conductors extending along the elongate axis in order to position the electrodes near the treatment site where the jet is directed to the tissue. In many embodiments, the tissue comprises invaginations, and the electrodes can be sized to fit in the invaginations to cauterize tissue. Alternatively or in combination, the electrodes may comprise a larger surface area such as a roller, for example.

The handle 930 and carriage 920 are arranged to advance and retract the carrier 380 and one or more electrodes 910 with longitudinal movement 854. The torque cable providing movement 905 can be coupled to the carriage 920 with a rotational bearing, such that the toque cable moves with the carrier 380 when the carriage 920 is advanced toward handle 930 and moved away from handle 930. The endoscope 394 can be connected to handle 930 with a retention structure, such that advancement of carriage 920 does not move the tip of the endoscope distally when the one or more electrodes 910 and carrier 380 are advanced distally with axial movement 907. Alternatively, the endoscope 394 can be connected to carriage 920 with a retention structure, such that advancement of carriage 920 moves the tip of the endoscope distally when the one or more electrodes 910 and carrier 380 are advanced distally with axial movement 854. A person of ordinary skill in the art will recognize many variations based on the teachings provided herein.

A resilient spring 925 can be provided between opposing surfaces of the handle 930 and carriage 920, such that the carriage 920 is urged away from the handle 930 in an unconstrained configuration. The resilient spring may comprise a leaf spring having a U-shape, which can be at least partially covered by the hand of the user.

The carriage 920 can be configured in one or more of many ways, and may comprise an insulating material to insulate the conductors that are coupled to the probe. In many embodiments, the cable extending to the handpiece comprises a torque cable and electrically conducting wires to transmit RF energy to the treatment site. The insulating material of the carriage can insulate the conductors to inhibit current leakage. The carriage 930 may comprise an insulated bearing traveler, providing both insulation and bearing surfaces, for example.

The handpiece portion may comprise one or more components of a commercially available device for transurethral resection of the prostatectomy (hereinafter "TURP"), for example.

Applicants note that the combination of water tissue ablation with the cautery can provide substantially improve the removal of tissue, as compared with removal based on cautery without water ablation, for example. Work in relation to embodiments has shown that the water jet can substantially remove a bulk portion of the tissue, and the remaining fibrous tissue can be removed with cautery in order to inhibit bleeding, for example.

Figure 69:
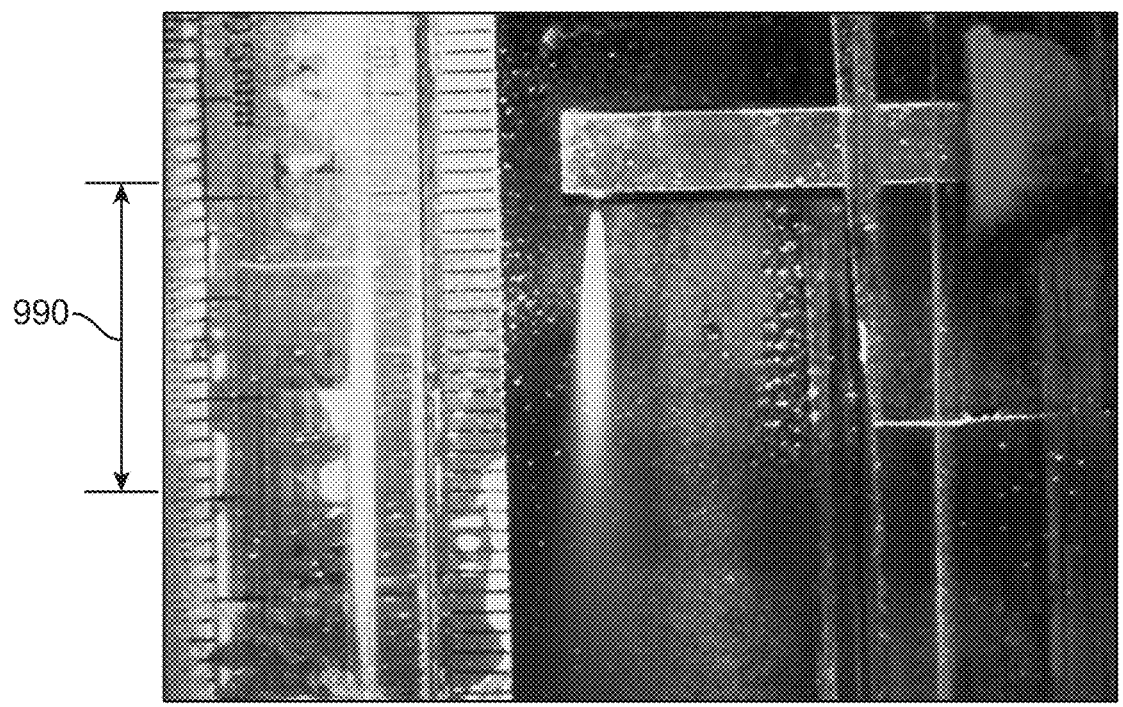
FIG. 69 shows an ablative flame visible to the human eye, in accordance with embodiments.

FIG. 69 shows an ablative flame visible to the human eye, in accordance with embodiments.

Figure 70:
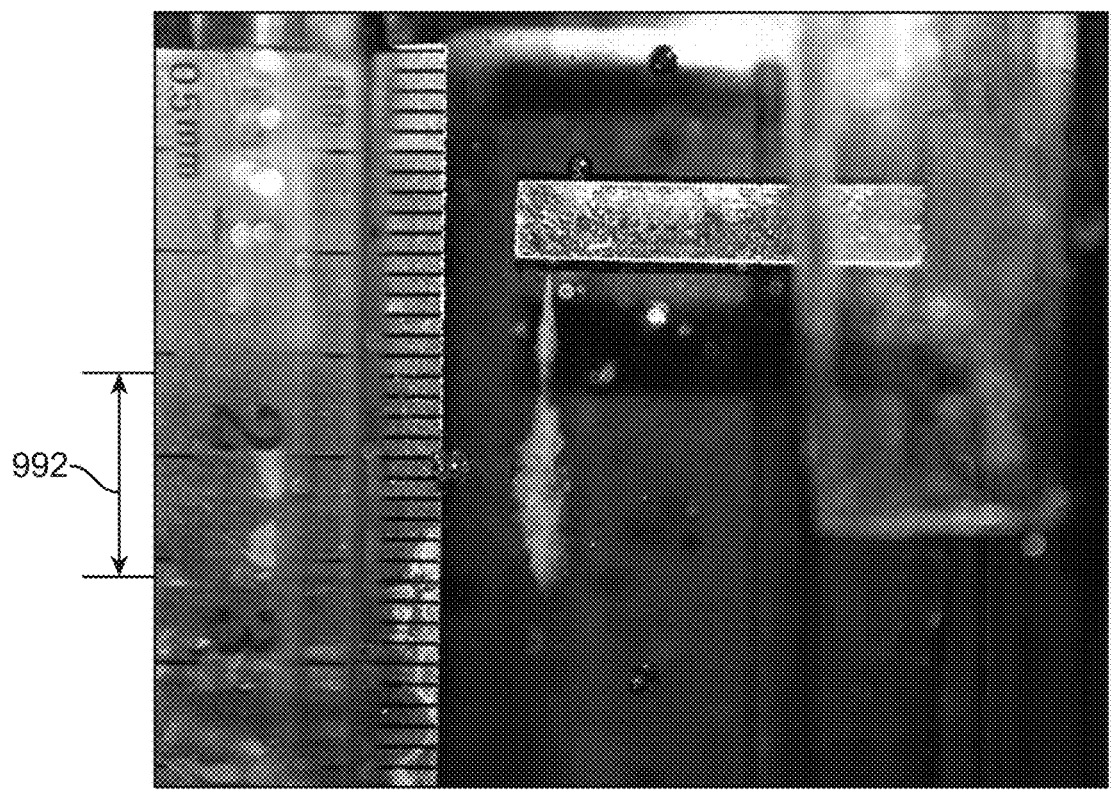
FIG. 70 shows a high speed image of the ablative flame as in FIG. 69.

FIG. 70 shows a high speed image of the ablative flame as in FIG. 69. The image was taken at a speed of about ¹⁄₄₀₀ of a second.

The data of FIGS. 69 and 70 show that the ablative flame comprises a plurality of white clouds generated with the ablative stream when released from the nozzle. Work in relation to embodiments has shown that the cavitating cloud can shed from the jet at a characteristic shedding frequency. A length 992 of each cloud is related to the shedding frequency and the velocity of the cloud. The relatively cool ablative flame of the jet comprises a length 990 corresponding to the cutting length of the jet which can be adjusted to cut tissue to controlled depth as described herein. In many embodiments, nozzle of the jet is placed at least about a quarter of the length 992 of a shed cloud in an non-cutting configuration as shown in FIG. 70, in order to allow the shedding cloud to substantially form prior to the cloud striking tissue. This divergence of the shed cloud to a larger cross sectional size can also provide improved tissue removal as the cloud can be distributed to a larger region of tissue and provide improved overlap among the pulses of the jet.

In addition to the impact pressure of the jet, the highly turbulent and aggressive region corresponding to the white cloud of the image contributes substantially to the ablation of tissue as described herein. The white cloud comprises a plurality of cavitation regions. When pressurized water is injected into water, small cavitations are generated in areas of low pressure in the shear layer, near the nozzle exit. The small cavitations may comprise cavitation vortices. The cavitation vortices merge with one another, forming large discrete cavitation structures that appear in the high speed images as cavitation clouds. These cavitation clouds provide effective ablation when interacting with tissue. Without being bound by any particular theory, it is believed that the cavitation clouds striking tissue cause substantial erosion of tissue related to the cavitations in combination of the high velocity fluid that defines the cavitations striking tissue.

The nozzle and pressure as described herein can be configured to provide the pulsatile clouds, for example with control of the angle of the nozzle, by a person of ordinary skill on the art based on the teachings provided herein. In many embodiments, the nozzle of the fluid delivery element comprises a cavitating jet in order to improve ablation of tissue.

The fluid delivery element nozzle and pressure can be arranged to provide a shedding frequency suitable for removal of tissue, and can be located on the probe to provide improved tissue resection.

In many embodiments, the "white cloud" of "flame" comprises an "entrainment" region where surrounding water is drawn in or "entrained" into the jet. Work in relation to embodiments suggests that the entrainment of fluid can be related to the shedding frequency.

The shedding frequency and size of the cloud shed from the jet can be used to provide tissue ablation in accordance with embodiments. The shedding frequency can be combined with the angular sweep rate of the probe around the longitudinal axis to provide overlap of the locations where each cloud interacts with the tissue.

The shedding pulses as described herein can be beneficially combined with the scanning of the jet as described herein, for example with reference to FIG. 21J.

Figure 71:
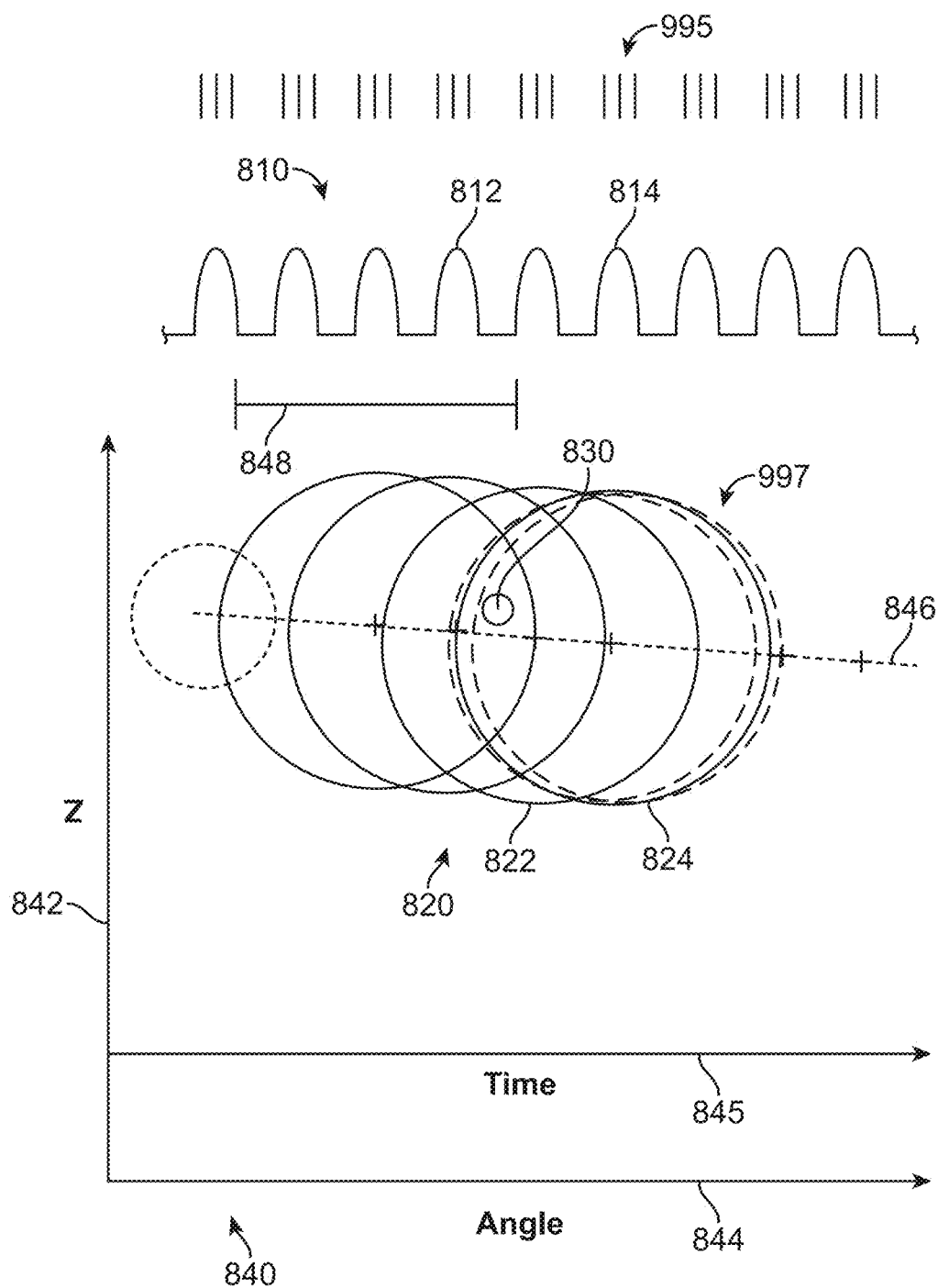
FIG. 71 shows a plurality of shedding pulses and sweeping of the ablative jet to provide smooth and controlled tissue erosion at a plurality of overlapping locations in accordance with embodiments.

FIG. 71 shows a plurality of shedding pulses 995 and sweeping of the ablative jet to provide smooth and controlled tissue erosion at a plurality of overlapping locations 997 in accordance with embodiments. This shedding frequency can be substantially faster than the pump frequency, when a pump is used, such that a plurality of shedding clouds are provided for each pulse of the pulsatile pump. The sweep rate of the probe can be related to shedding frequency to provide improved tissue removal, for example with the shedding clouds configured to provide overlapping pulses.

In many embodiments, the system comprises a pump having a frequency less than a frequency of the shedding pulses, in order to provide a plurality of shedding pulses for each pulse of the pump. The pump can have a pulse rate of at least about 50 Hz, for example within a range of about 50 Hz to about 200 Hz, and the shedding pulses comprise a frequency of at least about 500 Hz, for example within a range from about 1 kHz to about 10 kHz.

Although pulses of a pump are illustrated, similar scanning of pulsed clouds can be provided with a continuous flow pump.

While the nozzle can be configured in one or more of many ways, in many embodiments the nozzle comprises a Strouhal number (hereinafter "St") within a range from about 0.02 to about 0.3, for example within a range from about 0.10 to about 0.25, and in many embodiments within a range from about 0.14 to about 0.2.

In many embodiments, the Strouhal number is defined by:

$$St = (Fshed)*(W)/U$$

where Fshed is the shedding frequency, W is the width of the cavitating jet, and U is the velocity of the jet at the exit. A person of ordinary skill in the art can modify nozzles as described herein in order to obtain shedding frequencies suitable for combination in accordance with embodiments described herein, and experiments can be conducted to determine the cloud lengths and shedding frequencies suitable for tissue removal.

The nozzle configurations providing plurality of shedding clouds are suitable for use with one or more of the treatment probes as described herein.

Figure 72:
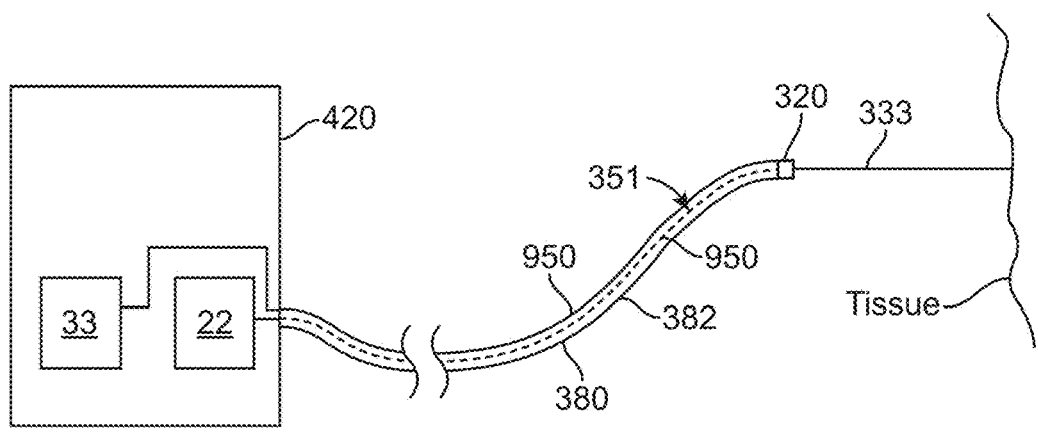
FIG. 72 shows a catheter 950 to treat a patient in accordance with embodiments.

FIG. 72 shows a catheter 950 to treat a patient in accordance with embodiments as described herein. The catheter 950 comprises an elongate tubular structure comprising a lumen 390 to pass a fluid from a source of fluidic energy to fluid delivery element 320 to release a divergent or collimated fluid stream 333 to treat tissue as described herein, for example. The catheter 950 is configured to be received with commercially available rigid or flexible endoscopes, or both, and may comprise a single tube as described herein. The catheter 950 can be coupled to console 420 comprising a light source 33 and energy source 22 as described herein, for example.

Figure 73:
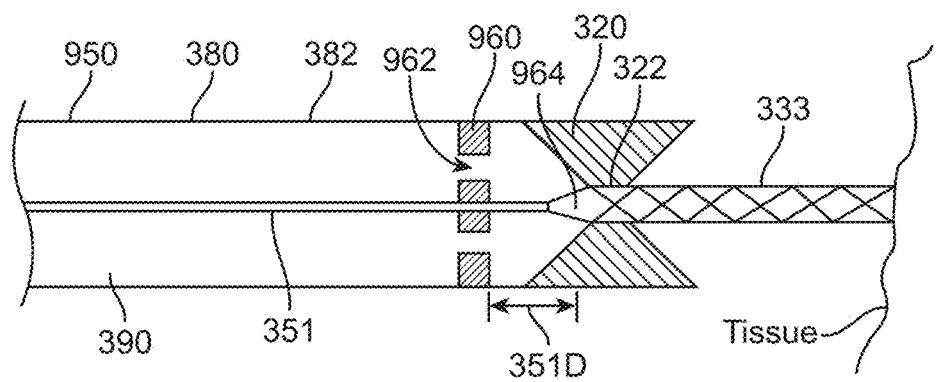
FIG. 73 shows the distal end of the catheter as in FIG. 72 in accordance with embodiments.

FIG. 73 shows the distal end of the catheter as in FIG. 72 in accordance with embodiments. The elongate tube comprising catheter 950 comprises fluid delivery element 320 comprising nozzle 322 as described herein. The distal end of the optical fiber is retained with an alignment structure 960 so as to align the optical fiber concentrically with the nozzle 322. The alignment structure may comprise a block, guide, annulus or other structure as described herein to holds the optical fiber in alignment with an orifice of the nozzle 322 as described herein. The alignment structure 960 comprises at least one aperture 962 to allow fluid to pass from the proximal end of the device to the nozzle. The distal end of the optical fiber is retained with the alignment structure 960 so as to align the optical fiber concentrically with the nozzle 322.

In many embodiments, the optical fiber 351 directs a divergent light beam 964 into the orifice of nozzle 322, so as to provide transmission of light energy through the nozzle as described herein. The light beam can be deflected with a mirror or other optical structure to deflect the divergent light beam into the nozzle, for example when the stream of energy is directed transverse to the axis of the carrier tube as described herein. Alternatively or in combination, the light beam can be focused with lenses, or mirrors, for example. The light beam can be transmitted along the fluid stream outside the nozzle with total internal reflection as described herein.

In many embodiments, the processor as described herein comprises instructions configured to provide a two stage illumination with the light source. With a first stage, the collimated stream from nozzle 332 comprises enough light energy to visualize the water jet contacting tissue. When the collimated light beam contacts tissue or becomes sufficiently proximate to the tissue, the collimation of the water stream is disrupted such that light energy scatters from the water stream and is no longer internally reflected, such that the location of the water stream contacting tissue is quite visible to the operator. The circuitry of the light source can be configured to provide a second power level for treatment. In many embodiments each of the first amount of light energy and the second amount of light energy is adjustable by the user. The first amount of light energy may comprise an amount of optical power of a visible wavelength of light, and the user can adjust the optical power to visualize the location of treatment. The second amount of energy may comprise sufficient optical power to treat the tissue, and may comprise similar wavelengths of light for the first amount of optical power, or different wavelengths of light. The light energy may comprise one or more of ultraviolet, visible, near infrared, mid infrared, or far infrared light energy, for example. The light source can be activated in one or more of many ways, for example with one or more of switches, buttons, dials or a two stage foot pedal of the user interface.

The display and endoscope can be configured in one or more of many ways. In many embodiments the substantially collimated stream of fluid contacts tissue within the field of view of the endoscope, such that the user can see the location of the fluid stream contacting the tissue.

Figure 74:
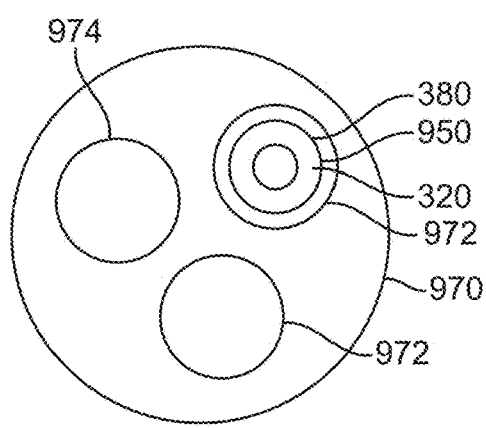
FIG. 74 shows a catheter placed in a working channel of a commercially available endoscope in accordance with embodiments.

FIG. 74 shows a catheter 950 placed in a working channel 972 of a commercially available endoscope 970. The commercially available endoscope may comprise a prior flexible introducer or scope, for example. The commercially available endoscope can be configured in one or more of many ways in accordance with the teachings described herein, and may comprise a viewing channel 974 comprising optics to view tissue of the patient. The endoscope 970 may comprise an additional working channel 972, for example.

Figure 75:
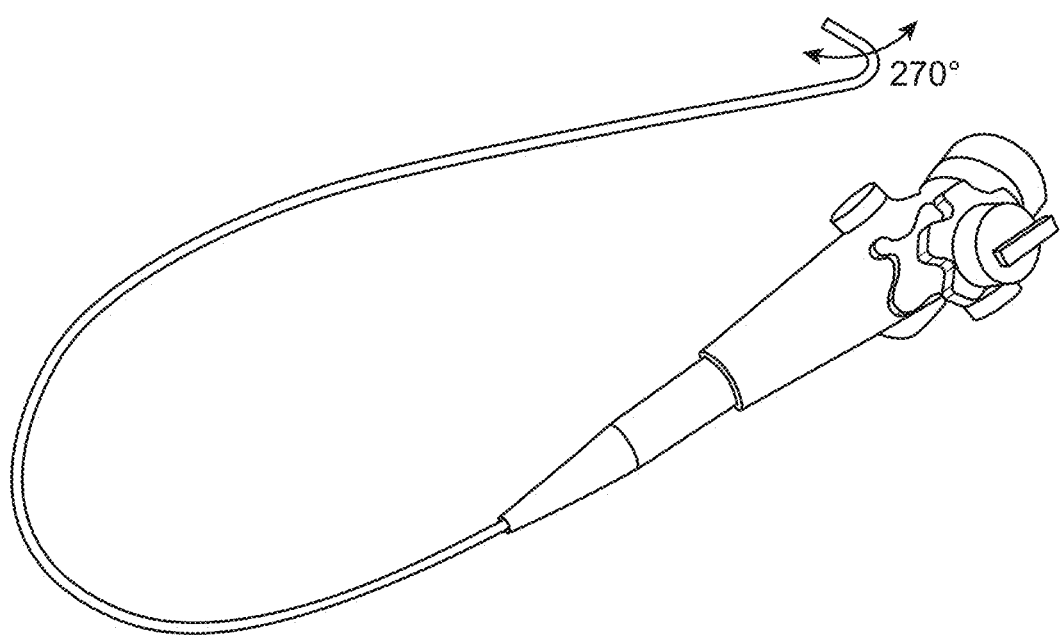
FIG. 75 shows a catheter as in FIGS. 72 and 73 placed an endoscope as in FIG. 74 and deflection of the distal end of the endoscope and catheter, in accordance with embodiments.

FIG. 75 shows a catheter as in FIGS. 72 and 73 placed an endoscope as in FIG. 74 and deflection of the distal end of the endoscope and catheter, in accordance with embodiments. In many embodiments, the catheter comprising the fiber and water jet nozzle as described herein is configured to deflect away from an axis, and can deflect at least about +/−20 degrees, for example at least about +/−90 degrees, and +/−135 degrees with a total range of deflection of about 270 degrees. The catheter may comprise an endoscope viewing channel that allows the optical channel to be deflected with the catheter comprising the one or more optical fibers and water nozzle. An additional channel can be used for biopsy sampling as described herein, for example.

The steerable catheter can be configured in one or more of many ways to deflect the distal end relative to the handle, for example. In many embodiments, the endoscope comprises a built-in mechanism such as pull wires, for example, and the catheter comprising the nozzle and optical fiber can be advanced along an internal channel of the endoscope. IN many embodiments, the endoscope comprising the optical fiber and water jet nozzle comprise an elongate flexible member comprising sufficient flexibility to bend along the internal channel of the endoscope, and sufficient stiffness to advance along the internal channel. Alternatively or in combination the catheter comprising the one or more optical fibers and nozzle for fluid delivery may comprise the built in steering mechanism and hand held control. The endoscope may comprise a commercially available endoscope endoscopes have an articulating distal tip. The user can guide the aquabeam catheter through the working channel and using one or more of levers or knobs, for example, and bend the last few centimeters of the scope in the desired direction. The endoscope scope may also be rotated, for example, so as to orient the tip at a desired target tissue when deflected, for example.

Cavitation

Cavitation is a phenomenon that occurs when a high pressure waterjet shoots through a nozzle into a liquid medium. Localized vapor pockets form as nuclei containing minute amounts of vapor and/or gas destabilize as they are subjected to drops in pressure rather than the commonly known method of addition of heat. Cavitation occurs when the local pressure drops below the vapor pressure, which occurs when the negative pressure coefficient ($-C_p$) is greater than cavitation number ($\sigma$), respectively governed by the equations below $$-C_p = \frac{p_{ref} - p}{\frac{1}{2}\rho v_{ref}^2} \quad (1)$$

$$\sigma = \frac{p_{ref} - p_v}{\frac{1}{2}\rho v_{ref}^2} \quad (2)$$

where pref is the hydrostatic pressure at the nozzle depth, p is the local pressure at the jet, ρ is the fluid density, vref is the exit velocity of the waterjet at the nozzle, and pv is the vapor pressure. When a liquid flows through a constricted region, its velocity increases to maintain continuity and there is a corresponding drop in pressure, known as the Venturi effect. Applying this to submerged waterjets, the velocity of water exiting through a nozzle is increased dramatically due to the constriction while the pressure of the jet stream is substantially reduced. When the pressure reduction is significant enough, it can drop below the vapor pressure, resulting in vapor cavity formation.

For a given flow dynamic, a cavitation number σ exists above which cavitation does not occur and below which cavitation will be present with increased cavitating region size. Several smaller pockets can combine to form a larger vapor cavity. As the momentum of the waterjet carries the vapor cloud further away from the nozzle into surrounding medium, viscous forces cause the jet velocity to drop and there is a corresponding rise in pressure. This rise causes the vapor cavity to collapse, resulting in a pressure pulse which further accelerates nearby water and causes localized microjets to form. Both the liquid microjets and pressure pulse can exceed the damage threshold energy of a material and cause erosion. Due to the rapid loss in velocity as the jet moves away from the nozzle, beyond a given distance the kinetic energy of the stream no longer exceeds the threshold energy and pressure waves and microjets from collapsed cavitation clouds becomes the primary modality for erosion.

In many embodiments, cavitation is dependent on local changes in pressure only, making it an isothermal phenomenon, meaning no thermal fluctuations are expected. Experimentally, as the vapor cavitation grows in size, latent heat is drawn from the surrounding liquid, and a very small drop in temperature (~0.35° C.) can be observed. Although in many embodiments, the process is not entirely isothermal, the almost negligible change in temperature is why waterjet cutting is useful for machining sensitive parts that demand no heat-affected zones.

In many embodiments, pressure pulse and microjet erosion becoming the primary modality of material removal is the limited erosion radius. Since cavitation occurs due to the pressure differential of the waterjet relative to the ambient liquid pressure, vapor cavities can only exist up to a maximum distance before the cavity collapses as the jet slows down and the pressure comes to equilibrium with the surrounding liquid. As a result, submerged waterjet cutting becomes substantially self-limiting due to the range of pressure pulses and microjets before they dissipate and is a very safe and high precision tool to cut with. In alternative embodiments, a gaseous waterjet will have high kinetic energy levels that exceed the threshold energy at much longer distances since there are relatively minimal forces acting on the jet to slow it down.

EXPERIMENTAL

Figure 76:
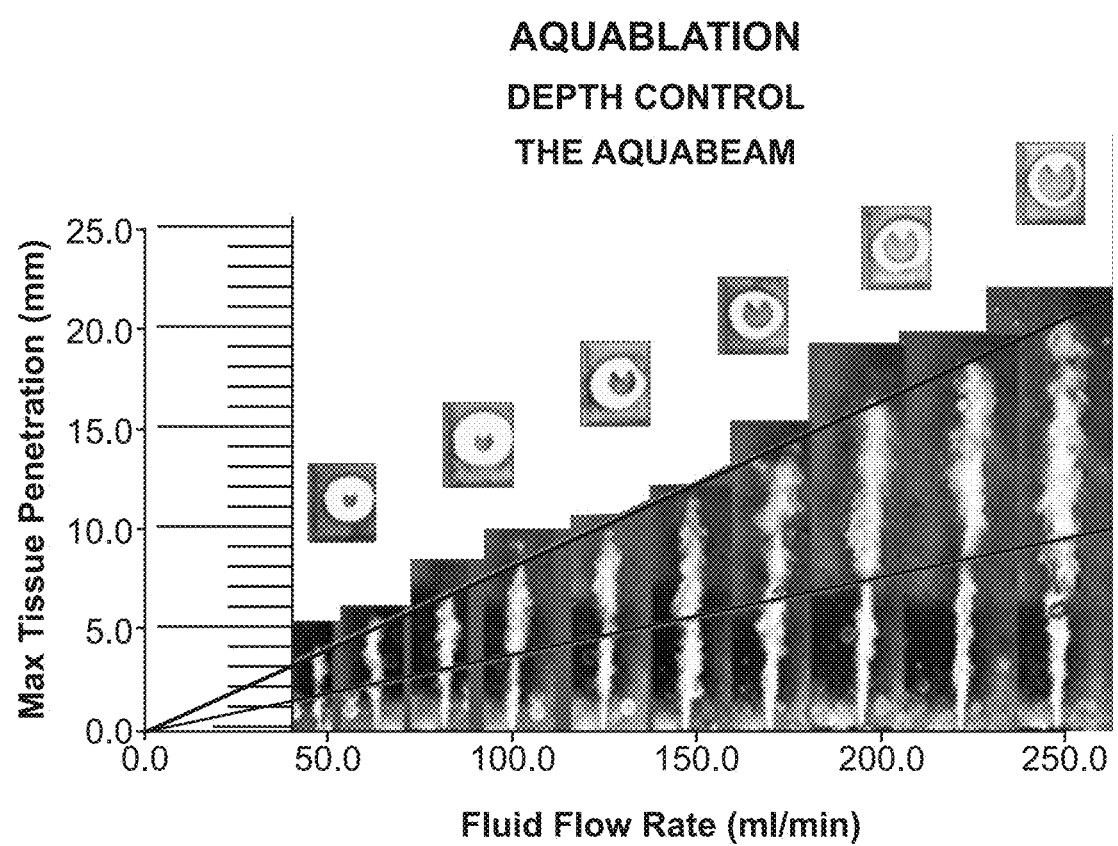
FIG. 76 shows maximum tissue penetration depth of cutting and flow rate through a nozzle in accordance with embodiments.

FIG. 76 shows maximum tissue penetration depth of cutting and flow rate through a nozzle in accordance with embodiments. The maximum penetration depth corresponds substantially to the length of the cavitation bubbles of the jet comprising the "cold" aquablation flame. The maximum tissue penetration depth of ablation corresponds directly to the flow rate and in many embodiments is linearly related to the flow rate.

The inset of FIG. 76 shows cut potato as a model of prostate BPH, in accordance with embodiments. The maximum penetration depth of potato corresponds closely to the maximum cut depth of BPH. The potato is shown cut with 10 different flow settings corresponding to rates within a range from about 50 ml/min to about 250 ml/min with a nozzle and rotating probe as described herein. The maximum penetration depth ranges from about 4 mm at 50 ml/min to about 20 mm at about 250 ml/min.

In many embodiments, the cavitation cloud growth and length comprises a function of flow rate, which is proportional to the injection pressure and vice versa, for an appropriately configured nozzle as described herein. As the pressure increases, the maximum erosive radius appears to increase linearly, which is shown as the maximum penetration depth of FIG. 76.

High velocity cavitating jets can be created by using a known high pressure pump to force the water through a nozzle in either a continuous or pulsatile flow. Despite the flow type produced by a pump, the cavitation phenomenon will be pulsatile due to the unsteady nature of vapor cavities and the cavity formation will be pulsatile even in a continuous flow jet as described herein. Without being bound to a particular theory, it is believed that both pulsatile and continuous flow waterjets will result in equivalent amounts of material erosion over a given amount of time. In many embodiments, nozzle geometry is configured to provide the flow dynamics and cavitation process as described herein. In many embodiments, the nozzle is configured to inhibit tight constriction at the waterjet exit, which can be related to cavitation occurring inside the nozzle itself. In many embodiments, the sharp corners cause the water to separate from the wall and converge towards the nozzle centerline, further constricting the waterjet pathway while simultaneously reducing frictional effects caused by the nozzle wall. This results in an increased velocity along with the corresponding pressure drop and the vapor cavities formation. Vapor cavity formation will impact the overall flow dynamics as their eventual collapse results in turbulence and can affect erosion depth. A person of ordinary skill in the art can conduct experiments to determine appropriate nozzle geometry and flow rate to provide tissue removal as described herein without undue experimentation.

Aquablation

Submerged waterjet cutting as described herein has the capability to take advantage of the cavitation phenomenon to treat patients with Benign Prostatic Hyperplasia (BPH). The jet removes the excess soft tissue growth seen in BPH through the pressure pulses and microjets caused by collapsed vapor cavities. The waterjet direction can be manipulated by changing the location and orientation of the devices nozzle, either by translating the nozzle along the anterior-posterior direction or by rotating the nozzle up to 180 degrees, for example.

As vapor cavity formation and its erosive strength is a function of both injection pressure and the flow dynamics, the depth of material can be controlled by configuring the pressure as well as nozzle geometry. A greater injection pressure will result in a faster exit velocity. As discussed herein, the nozzle geometry can further increase the velocity depending on the constriction and will affect the degree of pressure drop as the waterjet exits through the Venturi effect. These factors can result in longer distances the cavitation clouds can grow to and travel before collapsing and releasing pressure pulses and microjets. The nozzle geometry and pressure settings of the Aquablation system have been optimized to give the user precise control and ensure the cavitating jet removes only the desired benign tissue growth.

The images provided herein show the how tissue erosion depth is a function of pressure, in accordance with embodiments. The images show the smaller cavitation cloud length and corresponding tissue resection depth for a lower injection pressure as compared with other images.

In many embodiments, Aquablation as described herein is capable of removing the excess tissue growth, e.g. BPH, with inhibited removal and damage of arteries and veins. The pressure pulses and microjets caused by cavitation exceed the threshold energy required to erode the soft tissue growth, and may cause minimal damage to other structures like vessels which have a much higher threshold energy. Repeated and concentrated pressure pulses and microjets may cause fatigue stress on the vasculature and result in bleeding, but the Aquablation system algorithm and treatment instructions as described herein are configured designed to inhibit such damage.

In many embodiments, generation of harmful emboli are inhibited. Vapor cavity formation may benefit from a minute nucleus of air already present in the blood stream, for example. Cavitation can result in the growth of the nucleus without any additional air being introduced into the system. Furthermore, the cavity will collapse once the local jet pressure exceeds the vapor pressure, such that the air pockets may reduce back to their original nucleus size. In many embodiments, embolus formation is inhibited as cavitation depends on and can be limited to micro amounts of air native to the saline solution surrounding the urethra, and the vapor cavities quickly dissipate as the jet pressure begins to rise.

Aquablation as described herein takes advantage of this phenomenon. The naturally self-limiting erosive radius and unique ability to precisely ablate tissue with a low damage threshold energy while minimizing damage to nearby structures with a more dense cellular structure, such as arteries, make Aquablation as described herein a useful surgical tool for treating BPH. Coupled with the nearly isothermal property of cavitation as described herein, which can mitigate collateral damage and provide improved healing and an improved safety profile.

Figure 77:
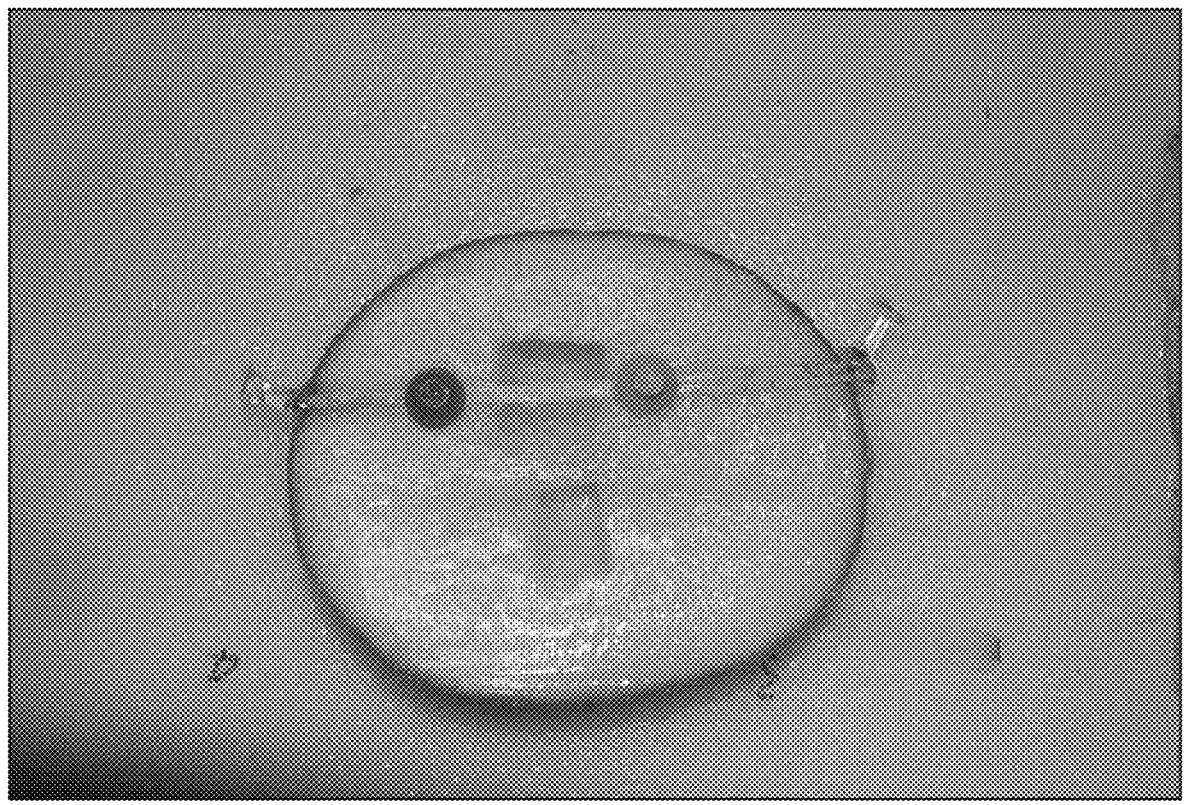
FIG. 77 shows selective removal of potato with a blood vessel positioned over the incision of the potato as a model for selective removal of tissue.

FIG. 77 shows selective removal of potato with a porcine blood vessel positioned over the incision of the potato as a model for selective removal of tissue. The porcine blood vessel was placed on the potato prior to the incision, such that the porcine blood vessel was exposed to the water jet with cavitation in order to remove the potato. Aquablation resected the soft potato tissue model, which is a close proxy for the benign tissue growth seen in BPH, without causing severe damage to the porcine vessel.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A method for tissue resection, said method comprising:
positioning a nozzle at a surgical site within tissue;
pressurizing the surgical site with a liquid;
directing a fluid stream outwardly from the nozzle at the surgical site while the surgical site is continuously pressurized with the liquid, the fluid stream directed toward the tissue to generate a plurality of shedding clouds comprising a characteristic length, wherein the nozzle is positioned at a distance from said tissue, in order to allow the plurality of shedding clouds to substantially form prior to said plurality of shedding clouds striking the tissue, wherein the distance comprises about one quarter of said characteristic length; and
moving the fluid stream such that the plurality of shedding clouds arrive at different overlapping locations and remove a volume of the tissue.

2. The method of claim 1, wherein the plurality of shedding clouds is shed from the fluid stream at a characteristic shedding frequency.

3. The method of claim 2, wherein the characteristic length of each of the plurality of shedding clouds is related to the characteristic shedding frequency and a velocity of said plurality of shedding clouds.

4. The method of claim 3, wherein the nozzle is positioned at the distance from said tissue, in order to allow the plurality of shedding clouds to substantially form prior to said plurality of shedding clouds striking the tissue.

5. The method of claim 4, wherein the distance is adjustable to distribute the plurality of shedding clouds over a desired region of said tissue.

6. The method of claim 5, wherein the distance is adjustable to a greater height from said tissue to distribute the plurality of shedding clouds over a larger region of said tissue, or adjustable to a lower height from said tissue to distribute the plurality of shedding clouds over a smaller region of said tissue.

7. The method of claim 1, wherein the fluid stream comprises a cavitating jet.

8. The method of claim 7, wherein the cavitating jet comprises a pulsed energy stream comprising a plurality of sequential pulses.

9. The method of claim 8, wherein the plurality of shedding clouds is provided for each of said plurality of sequential pulses.

10. The method of claim 8, wherein the plurality of shedding clouds is configured to overlap with the plurality of sequential pulses.

11. The method of claim 1, wherein a shedding frequency of the plurality of shedding clouds ranges from about 1 kHz to about 10 kHz.

12. The method of claim 7, wherein a shape of the plurality of shedding clouds is adjustable based on a shedding frequency of said clouds, a width of said cavitating jet, and a velocity of said cavitating jet at the nozzle.

13. The method of claim 8, wherein a shedding frequency of the plurality of shedding clouds is combined with an angular sweep rate of said nozzle around a longitudinal axis such that the plurality of shedding clouds overlaps with the pulsed energy stream comprising the plurality of sequential pulses.

14. The method of claim 1, wherein moving the fluid stream is at least partially controlled by an automated controller.

15. The method of claim 1, wherein the nozzle comprises a Strouhal number within a range from about 0.02 to about 0.3.

16. The method of claim 1, further comprising aspirating liquid from the pressurized surgical site.

* * * * *